United States Patent
Hogan et al.

(10) Patent No.: US 12,098,434 B2
(45) Date of Patent: *Sep. 24, 2024

(54) METHODS FOR DETECTING LOW LEVELS OF COVID-19 VIRUS

(71) Applicants: Michael Edward Hogan, Stony Brook, NJ (US); Benjamin Alan Katchman, Tucson, AZ (US); Frederick Henry Eggers, Sahuarita, AZ (US); Cory Scott Newland, Tucson, AZ (US)

(72) Inventors: Michael Edward Hogan, Stony Brook, NJ (US); Benjamin Alan Katchman, Tucson, AZ (US); Frederick Henry Eggers, Sahuarita, AZ (US); Cory Scott Newland, Tucson, AZ (US)

(73) Assignee: PathogenDx, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/950,171

(22) Filed: Nov. 17, 2020

(65) Prior Publication Data

US 2022/0195539 A1 Jun. 23, 2022

Related U.S. Application Data

(60) Provisional application No. 63/078,772, filed on Sep. 15, 2020, provisional application No. 63/000,844, filed on Mar. 27, 2020.

(51) Int. Cl.
C12Q 1/70 (2006.01)

(52) U.S. Cl.
CPC ........ *C12Q 1/701* (2013.01); *C12Q 2600/112* (2013.01)

(58) Field of Classification Search
CPC .......................... C12Q 1/701; C12Q 2600/112
See application file for complete search history.

(56) References Cited

U.S. PATENT DOCUMENTS

2018/0251758 A1* 9/2018 Hogan ................ C12Q 1/6837
2019/0032045 A1* 1/2019 Hogan ............... C12N 15/1086

OTHER PUBLICATIONS

Teo (Arch Virol (2011) 156:1371-1378).*
Veredus Laboratories (Vereduslab, 2020, pp. 1-2).*
Coiras (J Medical Virology, 2004, 72:484-495).*
Sun (Diagnostic Microbiology and Infectious Disease, 2011, 69, 432-439).*
Liu et al. (Clinical Chemistry, 2007, 53:2, 188-194).*
Liu (Chinese Science Bulletin, 2005, vol. 50, pp. 2896-2900).*
Wu (Anal. Chem, 2014, 86, 3461-3467).*
Yan (Oncotarget, 2017, vol. 8, No. 57, pp. 96913-96923).*
Emery (Emerging Infectious Diseases, 2004, vol. 10, p. 311-316).*
Li (Theranostics 2020, vol. 10, Issue 6, pp. 7150-7162).*
Lu (J Clin Microbiology, 2014, V 52, No. 1, pp. 67-75).*

* cited by examiner

*Primary Examiner* — Sarae L Bausch
(74) *Attorney, Agent, or Firm* — Benjamin Aaron Adler

(57) ABSTRACT

Provided herein is a method for detecting the presence of a COVID-19 virus in a human sample or an environmental sample having one or more viral and bacterial pathogens. Samples processed to obtain total nucleic acids. The nucleic acids are used as a template in a reverse transcription-amplification reaction to obtain cDNA, which is used in a PCR amplification reaction to obtain fluorescent COVID-19 virus specific amplicons. These amplicons are detected by microarray hybridization near the lowest limit of detection. Also provided is a method for detecting in addition to the COVID-19 virus, the presence of respiratory disease-causing pathogens including viruses, bacteria and fungus in a single assay using the above method.

16 Claims, 35 Drawing Sheets

Specification includes a Sequence Listing.

200 μm = Spacing between D= 100 μm microarray probes

DETECT$^X$-RV : Enhanced Content, Performance and Turnaround Time

DETECT$^X$-RV - V1
- SARS-CoV 2 (COVID-19)

Features
- N1, N2, N3 and RP
- 8 Built-in Controls
- 12 samples tested/slide
- Triplicate testing
- Sensitivity 99.9%
- Specificity 95%
- LLoD 50 genome copies/reaction

DETECT$^X$-RV – V2
- SARS-CoV 2 (COVID-19)
- S-D614G Variant

Features
- N1, N2, N3 and RP
- 8 Built-in Controls
- 96 samples tested/slide
- Triplicate testing
- Sensitivity 99.9%
- Specificity 95%
- LLoD 50 genome copies/reaction

DETECT$^X$-RV : Process Flow with Improved Turnaround Time

| Standard Swab/Saliva Workflow | |
|---|---|
| Sample Collection | Sample Processing |
| • Nares Swab<br>• Saliva Collection | • 1.5 hours<br>• Automated RNA extraction with magnetic beads<br>• Vortex/Lysis/Bind/ Wash and Release |

| DETECT$^X$-RV Process Flow | | |
|---|---|---|
| Enrich and Labeling PCR | Hybridization | Imaging & Analysis |
| • 1.5 hours<br>• PCR (DNA)<br>• RT-PCR (RNA)<br>• Fluorescent Tag<br>• Single Stranded | • 1.0 hours<br>• Tecan Automated Robot<br>• 96 arrays in parallel | • 30 minutes<br>• 96 arrays in parallel<br>• Autonomous data analysis |

FIG. 9

○ Negative probe control
○ SARS-CoV-2 N1 1.1
○ SARS-CoV-2 N2 1.3
○ SARS-CoV-2 N2 1.4
○ SARS-CoV-2 N3 1.1
○ RNAse P 1.1
○ Influenza A
○ Influenza B
▢ SARS-CoV-2 614D
▢ SARS-CoV-2 614G ○ Negative probe control
○ SARS-CoV-2 N1 1.1
○ SARS-CoV-2 N2 1.3
○ SARS-CoV-2 N2 1.4
○ SARS-CoV-2 N3 1.1
○ RNAse P 1.1
○ Influenza A
○ Influenza B
▢ SARS-CoV-2 614D
▢ SARS-CoV-2 614G

|   | 1  | 2   | 3   | 4   | 5   | 6   | 7   | 8   | 9   | 10  | 11  | 12  |
|---|----|-----|-----|-----|-----|-----|-----|-----|-----|-----|-----|-----|
| A | 1* | 9   | 17  | 25  | 33  | 41  | 49  | 57* | 65  | 73  | 81  | 89  |
| B | 2  | 10* | 18  | 26  | 34  | 42  | 50* | 58  | 66  | 74* | 82  | 90  |
| C | 3  | 11  | 19* | 27  | 35  | 43* | 51  | 59  | 67* | 75  | 83  | 91  |
| D | 4* | 12  | 20  | 28* | 36  | 44  | 52  | 60* | 68  | 76  | 84  | 92* |
| E | 5  | 13  | 21  | 29  | 37* | 45  | 53  | 61  | 69  | 77  | 85* | 93  |
| F | 6  | 14  | 22* | 30  | 38  | 46* | 54  | 62  | 70  | 78* | 86  | 94  |
| G | 7  | 15* | 23  | 31  | 39  | 47  | 55* | 63  | 71* | 79  | 87  | 95* |
| H | 8* | 16  | 24  | 32* | 40  | 48  | 56  | 64* | 72  | 80* | 88  | 96  |

SEQUENCE LISTING

```
<160> NUMBER OF SEQ ID NOS: 141

<210> SEQ ID NO 1
<211> LENGTH: 28
<212> TYPE: DNA
<213> ORGANISM: Artificial Sequence
<220> FEATURE:
<223> OTHER INFORMATION: Primer sequence for SARS CoV-2 Nucleocapsid

<400> SEQUENCE: 1
ttttgtctga taatggaccc caaaatca                                     28

<210> SEQ ID NO 2
<211> LENGTH: 28
<212> TYPE: DNA
<213> ORGANISM: Artificial Sequence
<220> FEATURE:
<223> OTHER INFORMATION: Primer sequence for SARS CoV-2 Nucleocapsid

<400> SEQUENCE: 2
tttgttctcc attctggtta ctgccagt                                     28

<210> SEQ ID NO 3
<211> LENGTH: 28
<212> TYPE: DNA
<213> ORGANISM: Artificial Sequence
<220> FEATURE:
<223> OTHER INFORMATION: Primer sequence for coronavirus Nucleocapsid

<400> SEQUENCE: 3
tttaggaact aatcagacaa ggaactga                                     28

<210> SEQ ID NO 4
<211> LENGTH: 28
<212> TYPE: DNA
<213> ORGANISM: Artificial Sequence
<220> FEATURE:
<223> OTHER INFORMATION: Primer sequence for coronavirus Nucleocapsid

<400> SEQUENCE: 4
tttgttcccg aaggtgtgac ttccatgc                                     28
```

```
<210> SEQ ID NO 5
<211> LENGTH: 28
<212> TYPE: DNA
<213> ORGANISM: Artificial Sequence
<220> FEATURE:
<223> OTHER INFORMATION: Primer sequence for coronavirus Nucleocapsid

<400> SEQUENCE: 5
tttcggcatc atatgggtyg caactgag                                      28

<210> SEQ ID NO 6
<211> LENGTH: 28
<212> TYPE: DNA
<213> ORGANISM: Artificial Sequence
<220> FEATURE:
<223> OTHER INFORMATION: Primer sequence for coronavirus Nucleocapsid

<400> SEQUENCE: 6
tttccttttg gcaatgttgt tccttgag                                      28

<210> SEQ ID NO 7
<211> LENGTH: 28
<212> TYPE: DNA
<213> ORGANISM: Artificial Sequence
<220> FEATURE:
<223> OTHER INFORMATION: Primer sequence for MERS coronavirus

<400> SEQUENCE: 7
ttttgtttcc actgttttcg tgcctgca                                      28

<210> SEQ ID NO 8
<211> LENGTH: 28
<212> TYPE: DNA
<213> ORGANISM: Artificial Sequence
<220> FEATURE:
<223> OTHER INFORMATION: Primer sequence for MERS coronavirus

<400> SEQUENCE: 8
tttctgtttt cgtgcctgca acgcgcga                                      28

<210> SEQ ID NO 9
<211> LENGTH: 28
<212> TYPE: DNA
<213> ORGANISM: Artificial Sequence
<220> FEATURE:
<223> OTHER INFORMATION: Primer sequence for human coronavirus 229E

<400> SEQUENCE: 9
ttttaatgca atcactgtca caaccgtg                                      28

<210> SEQ ID NO 10
<211> LENGTH: 28
<212> TYPE: DNA
<213> ORGANISM: Artificial Sequence
<220> FEATURE:
<223> OTHER INFORMATION: Primer sequence for human coronavirus 229E

<400> SEQUENCE: 10
tttaaaaccc agcctgtgct attttgtg                                      28

<210> SEQ ID NO 11
<211> LENGTH: 28
<212> TYPE: DNA
<213> ORGANISM: Artificial Sequence
<220> FEATURE:
<223> OTHER INFORMATION: Primer sequence for human coronavirus OC43
```

```
<400> SEQUENCE: 11
tttgtatgtt aggccgataa ttgaggac                                28

<210> SEQ ID NO 12
<211> LENGTH: 28
<212> TYPE: DNA
<213> ORGANISM: Artificial Sequence
<220> FEATURE:
<223> OTHER INFORMATION: Primer sequence for human coronavirus OC43

<400> SEQUENCE: 12
ttcaaacagc aaaaccacta gtatcgct                                28

<210> SEQ ID NO 13
<211> LENGTH: 28
<212> TYPE: DNA
<213> ORGANISM: Artificial Sequence
<220> FEATURE:
<223> OTHER INFORMATION: Primer sequence for human coronavirus NL63

<400> SEQUENCE: 13
ttattcctcc tccttcattt tacatgcc                                28

<210> SEQ ID NO 14
<211> LENGTH: 28
<212> TYPE: DNA
<213> ORGANISM: Artificial Sequence
<220> FEATURE:
<223> OTHER INFORMATION: Primer sequence for human coronavirus NL63

<400> SEQUENCE: 14
tttaatttaa ggtccttatg aggtccag                                28

<210> SEQ ID NO 15
<211> LENGTH: 28
<212> TYPE: DNA
<213> ORGANISM: Artificial Sequence
<220> FEATURE:
<223> OTHER INFORMATION: Primer sequence for human coronavirus HKU1

<400> SEQUENCE: 15
tttacacttc taytccctcc gatgtttc                                28

<210> SEQ ID NO 16
<211> LENGTH: 28
<212> TYPE: DNA
<213> ORGANISM: Artificial Sequence
<220> FEATURE:
<223> OTHER INFORMATION: Primer sequence for human coronavirus HKU1

<400> SEQUENCE: 16
tttaagatta gcratctcat cagccata                                28

<210> SEQ ID NO 17
<211> LENGTH: 28
<212> TYPE: DNA
<213> ORGANISM: Artificial Sequence
<220> FEATURE:
<223> OTHER INFORMATION: Primer sequence for Influenza A

<400> SEQUENCE: 17
tttatggcta aagacaagac cratcctg                                28

<210> SEQ ID NO 18
<211> LENGTH: 28
```

```
<212> TYPE: DNA
<213> ORGANISM: Artificial Sequence
<220> FEATURE:
<223> OTHER INFORMATION: Primer sequence for Influenza A

<400> SEQUENCE: 18
tttttaaggg cattytggac aaakcgtc                                              28

<210> SEQ ID NO 19
<211> LENGTH: 28
<212> TYPE: DNA
<213> ORGANISM: Artificial Sequence
<220> FEATURE:
<223> OTHER INFORMATION: Primer sequence for Influenza B

<400> SEQUENCE: 19
tttggatgaa gaagatggcc atcggatc                                              28

<210> SEQ ID NO 20
<211> LENGTH: 28
<212> TYPE: DNA
<213> ORGANISM: Artificial Sequence
<220> FEATURE:
<223> OTHER INFORMATION: Primer sequence for Influenza B

<400> SEQUENCE: 20
ttttctaatt gtctccctct tctggtga                                              28

<210> SEQ ID NO 21
<211> LENGTH: 28
<212> TYPE: DNA
<213> ORGANISM: Artificial Sequence
<220> FEATURE:
<223> OTHER INFORMATION: Primer sequence for human RNAse P control

<400> SEQUENCE: 21
tttacttcag catggcggtg tttgcaga                                              28

<210> SEQ ID NO 22
<211> LENGTH: 28
<212> TYPE: DNA
<213> ORGANISM: Artificial Sequence
<220> FEATURE:
<223> OTHER INFORMATION: Primer sequence for human RNAse P control

<400> SEQUENCE: 22
ttttgatagc aacaactgaa tagccaag                                              28

<210> SEQ ID NO 23
<211> LENGTH: 28
<212> TYPE: DNA
<213> ORGANISM: Artificial Sequence
<220> FEATURE:
<223> OTHER INFORMATION: Primer sequence for SARS CoV-2 Nucleocapsid

<400> SEQUENCE: 23
ttttaatgga ccccaaaatc agcgaaat                                              28

<210> SEQ ID NO 24
<211> LENGTH: 28
<212> TYPE: DNA
<213> ORGANISM: Artificial Sequence
<220> FEATURE:
<223> OTHER INFORMATION: Primer sequence for SARS CoV-2 Nucleocapsid
<220> FEATURE:
<221> NAME/KEY: modified_base
<222> LOCATION: 1
```

<223> OTHER INFORMATION: Thymidine at position 1 is modified with a
      fluorescent label

<400> SEQUENCE: 24
tttttctggt tactgccagt tgaatctg                                           28

<210> SEQ ID NO 25
<211> LENGTH: 28
<212> TYPE: DNA
<213> ORGANISM: Artificial Sequence
<220> FEATURE:
<223> OTHER INFORMATION: Primer sequence for coronavirus Nucleocapsid

<400> SEQUENCE: 25
tttactgatt acaaacattg gccgcaaa                                           28

<210> SEQ ID NO 26
<211> LENGTH: 29
<212> TYPE: DNA
<213> ORGANISM: Artificial Sequence
<220> FEATURE:
<223> OTHER INFORMATION: Primer sequence for coronavirus Nucleocapsid
<220> FEATURE:
<221> NAME/KEY: modified_base
<222> LOCATION: 1
<223> OTHER INFORMATION: Thymidine at position 1 is modified with a
      fluorescent label

<400> SEQUENCE: 26
ttttgccaat gcgycgacat tccraagaa                                          29

<210> SEQ ID NO 27
<211> LENGTH: 28
<212> TYPE: DNA
<213> ORGANISM: Artificial Sequence
<220> FEATURE:
<223> OTHER INFORMATION: Primer sequence for coronavirus Nucleocapsid

<400> SEQUENCE: 27
tttagggagc cttgaataca ccaaaaga                                           28

<210> SEQ ID NO 28
<211> LENGTH: 28
<212> TYPE: DNA
<213> ORGANISM: Artificial Sequence
<220> FEATURE:
<223> OTHER INFORMATION: Primer sequence for coronavirus Nucleocapsid

<400> SEQUENCE: 28
tttaagttgt agcacgattg cagcattg                                           28

<210> SEQ ID NO 29
<211> LENGTH: 28
<212> TYPE: DNA
<213> ORGANISM: Artificial Sequence
<220> FEATURE:
<223> OTHER INFORMATION: Primer sequence for MERS CoV

<400> SEQUENCE: 29
tttccatatg tccaaagaga gactaatg                                           28

<210> SEQ ID NO 30
<211> LENGTH: 28
<212> TYPE: DNA
<213> ORGANISM: Artificial Sequence
<220> FEATURE:
<223> OTHER INFORMATION: Primer sequence for MERS CoV

```
<220> FEATURE:
<221> NAME/KEY: modified_base
<222> LOCATION: 1
<223> OTHER INFORMATION: Thymidine at position 1 is modified with a
      fluorescent label

<400> SEQUENCE: 30
ttttagtagc gcagagctgc ttaaacga                                          28

<210> SEQ ID NO 31
<211> LENGTH: 28
<212> TYPE: DNA
<213> ORGANISM: Artificial Sequence
<220> FEATURE:
<223> OTHER INFORMATION: Primer sequence for HCoV-229E

<400> SEQUENCE: 31
tttacatact atcaacccat tcaacaag                                          28

<210> SEQ ID NO 32
<211> LENGTH: 28
<212> TYPE: DNA
<213> ORGANISM: Artificial Sequence
<220> FEATURE:
<223> OTHER INFORMATION: Primer sequence for HCoV-229E
<220> FEATURE:
<221> NAME/KEY: modified_base
<222> LOCATION: 1
<223> OTHER INFORMATION: Thymidine at position 1 is modified with a
      fluorescent label

<400> SEQUENCE: 32
tttctcggca cggcaactgt catgtatt                                          28

<210> SEQ ID NO 33
<211> LENGTH: 28
<212> TYPE: DNA
<213> ORGANISM: Artificial Sequence
<220> FEATURE:
<223> OTHER INFORMATION: Primer sequence for human coronavirus OC43

<400> SEQUENCE: 33
ttttcatacy ctgacggtca caataata                                          28

<210> SEQ ID NO 34
<211> LENGTH: 28
<212> TYPE: DNA
<213> ORGANISM: Artificial Sequence
<220> FEATURE:
<223> OTHER INFORMATION: Primer sequence for human coronavirus OC43
<220> FEATURE:
<221> NAME/KEY: modified_base
<222> LOCATION: 1
<223> OTHER INFORMATION: Thymidine at position 1 is modified with a
      fluorescent label

<400> SEQUENCE: 34
ttttaacctt agcaacagwc atataagc                                          28

<210> SEQ ID NO 35
<211> LENGTH: 28
<212> TYPE: DNA
<213> ORGANISM: Artificial Sequence
<220> FEATURE:
<223> OTHER INFORMATION: Primer sequence for human coronavirus NL63

<400> SEQUENCE: 35
ttatagttct gataaggcac catatagg                                          28
```

```
<210> SEQ ID NO 36
<211> LENGTH: 28
<212> TYPE: DNA
<213> ORGANISM: Artificial Sequence
<220> FEATURE:
<223> OTHER INFORMATION: Primer sequence for human coronavirus NL63
<220> FEATURE:
<221> NAME/KEY: modified_base
<222> LOCATION: 1
<223> OTHER INFORMATION: Thymidine at position 1 is modified with a
      fluorescent label

<400> SEQUENCE: 36 tttgaactttaggaggcaaatcaacacg                                          28

<210> SEQ ID NO 37
<211> LENGTH: 28
<212> TYPE: DNA
<213> ORGANISM: Artificial Sequence
<220> FEATURE:
<223> OTHER INFORMATION: Primer sequence for human coronavirus HKU1

<400> SEQUENCE: 37 tttgatcctactaytcaagaagctatcc                                          28

<210> SEQ ID NO 38
<211> LENGTH: 28
<212> TYPE: DNA
<213> ORGANISM: Artificial Sequence
<220> FEATURE:
<223> OTHER INFORMATION: Primer sequence for human coronavirus HKU1
<220> FEATURE:
<221> NAME/KEY: modified_base
<222> LOCATION: 1
<223> OTHER INFORMATION: Thymidine at position 1 is modified with a
      fluorescent label

<400> SEQUENCE: 38 tttcttaatgaacgaktattgggtccac                                          28

<210> SEQ ID NO 39
<211> LENGTH: 28
<212> TYPE: DNA
<213> ORGANISM: Artificial Sequence
<220> FEATURE:
<223> OTHER INFORMATION: Primer sequence for Influenza A

<400> SEQUENCE: 39 tttcaagaccratcctgtcacctctgac                                          28

<210> SEQ ID NO 40
<211> LENGTH: 28
<212> TYPE: DNA
<213> ORGANISM: Artificial Sequence
<220> FEATURE:
<223> OTHER INFORMATION: Primer sequence for Influenza A
<220> FEATURE:
<221> NAME/KEY: modified_base
<222> LOCATION: 1
<223> OTHER INFORMATION: Thymidine at position 1 is modified with a
      fluorescent label

<400> SEQUENCE: 40 tttaagggcattytggacaaakcgtcta                                          28

<210> SEQ ID NO 41
<211> LENGTH: 28
```

```
<212> TYPE: DNA
<213> ORGANISM: Artificial Sequence
<220> FEATURE:
<223> OTHER INFORMATION: Primer sequence for Influenza B

<400> SEQUENCE: 41
tttgcgtctc aatgaaggac attcaaag                                            28

<210> SEQ ID NO 42
<211> LENGTH: 28
<212> TYPE: DNA
<213> ORGANISM: Artificial Sequence
<220> FEATURE:
<223> OTHER INFORMATION: Primer sequence for Influenza B
<220> FEATURE:
<221> NAME/KEY: modified_base
<222> LOCATION: 1
<223> OTHER INFORMATION: Thymidine at position 1 is modified with a
      fluorescent label

<400> SEQUENCE: 42
ttttaatcgg tgctcttgac caaattgg                                            28

<210> SEQ ID NO 43
<211> LENGTH: 28
<212> TYPE: DNA
<213> ORGANISM: Artificial Sequence
<220> FEATURE:
<223> OTHER INFORMATION: Primer sequence for human RNAse P control

<400> SEQUENCE: 43
tttgtttgca gatttggacc tgcgagcg                                            28

<210> SEQ ID NO 44
<211> LENGTH: 27
<212> TYPE: DNA
<213> ORGANISM: Artificial Sequence
<220> FEATURE:
<223> OTHER INFORMATION: Primer sequence for human RNAse P control
<220> FEATURE:
<221> NAME/KEY: modified_base
<222> LOCATION: 1
<223> OTHER INFORMATION: Thymidine at position 1 is modified with a
      fluorescent label

<400> SEQUENCE: 44
tttaaggtga cggctgtctc cacaagt                                             27

<210> SEQ ID NO 45
<211> LENGTH: 30
<212> TYPE: DNA
<213> ORGANISM: Artificial Sequence
<220> FEATURE:
<223> OTHER INFORMATION: Probe sequence for SARS CoV-2 Nucleocapsid

<400> SEQUENCE: 45 ttttttttccg cattacgttt ggtgtttttt                                         30

<210> SEQ ID NO 46
<211> LENGTH: 30
<212> TYPE: DNA
<213> ORGANISM: Artificial Sequence
<220> FEATURE:
<223> OTHER INFORMATION: Probe sequence for SARS CoV-2 Nucleocapsid

<400> SEQUENCE: 46
tttttttatc agcgaaatgc acccttttt                                           30
```

```
<210> SEQ ID NO 47
<211> LENGTH: 30
<212> TYPE: DNA
<213> ORGANISM: Artificial Sequence
<220> FEATURE:
<223> OTHER INFORMATION: Probe sequence for SARS CoV-2 Nucleocapsid

<400> SEQUENCE: 47
tttttttttt gccccagcg cttctttttt                                    30

<210> SEQ ID NO 48
<211> LENGTH: 30
<212> TYPE: DNA
<213> ORGANISM: Artificial Sequence
<220> FEATURE:
<223> OTHER INFORMATION: Probe sequence for SARS CoV-2 Nucleocapsid

<400> SEQUENCE: 48 tttttacaa tttgccccca gcgtctttttt                                   30

<210> SEQ ID NO 49
<211> LENGTH: 30
<212> TYPE: DNA
<213> ORGANISM: Artificial Sequence
<220> FEATURE:
<223> OTHER INFORMATION: Probe sequence for SARS Nucleocapsid

<400> SEQUENCE: 49 ttttttttg ctccragtgc ctcttttttt                                    30

<210> SEQ ID NO 50
<211> LENGTH: 30
<212> TYPE: DNA
<213> ORGANISM: Artificial Sequence
<220> FEATURE:
<223> OTHER INFORMATION: Probe sequence for SARS Nucleocapsid

<400> SEQUENCE: 50
ttttttttgc tccragtgcc tctgtcctt                                    30

<210> SEQ ID NO 51
<211> LENGTH: 32
<212> TYPE: DNA
<213> ORGANISM: Artificial Sequence
<220> FEATURE:
<223> OTHER INFORMATION: Probe sequence for coronavirus Bat precursor

<400> SEQUENCE: 51 ttttgtttg cacctagtgc ttcagcccctt tt                                32

<210> SEQ ID NO 52
<211> LENGTH: 32
<212> TYPE: DNA
<213> ORGANISM: Artificial Sequence
<220> FEATURE:
<223> OTHER INFORMATION: Probe sequence for coronavirus Pangolin
      precursor

<400> SEQUENCE: 52 ttttatttg cwcctagcgc ttctgctctt tt                                 32

<210> SEQ ID NO 53
<211> LENGTH: 32
<212> TYPE: DNA
<213> ORGANISM: Artificial Sequence
<220> FEATURE:
```

<223> OTHER INFORMATION: Probe sequence for coronavirus Bat precursor-
      Yunnan 2013

<400> SEQUENCE: 53
tttttgtttg cacccagtgc ttctgctctt tt                                    32

<210> SEQ ID NO 54
<211> LENGTH: 30
<212> TYPE: DNA
<213> ORGANISM: Artificial Sequence
<220> FEATURE:
<223> OTHER INFORMATION: Probe sequence for coronavirus Bat precursor-
      Yunnan 2019

<400> SEQUENCE: 54 tttttacaa ttcgctccca gcgtctttt                                         30

<210> SEQ ID NO 55
<211> LENGTH: 30
<212> TYPE: DNA
<213> ORGANISM: Artificial Sequence
<220> FEATURE:
<223> OTHER INFORMATION: Probe sequence for coronavirus Nucleocapsid

<400> SEQUENCE: 55
tttttctggc acccgcaatc ctgtctttt                                        30

<210> SEQ ID NO 56
<211> LENGTH: 30
<212> TYPE: DNA
<213> ORGANISM: Artificial Sequence
<220> FEATURE:
<223> OTHER INFORMATION: Probe sequence for coronavirus Nucleocapsid

<400> SEQUENCE: 56 ttttayca cattggcacc cgcatctttt                                         30

<210> SEQ ID NO 57
<211> LENGTH: 30
<212> TYPE: DNA
<213> ORGANISM: Artificial Sequence
<220> FEATURE:
<223> OTHER INFORMATION: Probe sequence for MERS coronavirus

<400> SEQUENCE: 57
ttttatctct tcacataatc gcccttttt                                        30

<210> SEQ ID NO 58
<211> LENGTH: 30
<212> TYPE: DNA
<213> ORGANISM: Artificial Sequence
<220> FEATURE:
<223> OTHER INFORMATION: Probe sequence for MERS coronavirus

<400> SEQUENCE: 58 tttttataa tcgccccgag ctcgtctttt                                        30

<210> SEQ ID NO 59
<211> LENGTH: 32
<212> TYPE: DNA
<213> ORGANISM: Artificial Sequence
<220> FEATURE:
<223> OTHER INFORMATION: Probe sequence for human coronavirus 229E

<400> SEQUENCE: 59
tttttttgct ttacgttgac ggacatttt tt                                     32

```
<210> SEQ ID NO 60
<211> LENGTH: 32
<212> TYPE: DNA
<213> ORGANISM: Artificial Sequence
<220> FEATURE:
<223> OTHER INFORMATION: Probe sequence for human coronavirus 229E

<400> SEQUENCE: 60
tttttttcag gtgttcaggt tcataatctt tt                                    32

<210> SEQ ID NO 61
<211> LENGTH: 32
<212> TYPE: DNA
<213> ORGANISM: Artificial Sequence
<220> FEATURE:
<223> OTHER INFORMATION: Probe sequence for human coronavirus OC43

<400> SEQUENCE: 61
tttttcatct ttacattcaa ggtataattt tt                                    32

<210> SEQ ID NO 62
<211> LENGTH: 32
<212> TYPE: DNA
<213> ORGANISM: Artificial Sequence
<220> FEATURE:
<223> OTHER INFORMATION: Probe sequence for human coronavirus OC43

<400> SEQUENCE: 62
ttttctgcta ttctttggca gatttgcttt tt                                    32

<210> SEQ ID NO 63
<211> LENGTH: 32
<212> TYPE: DNA
<213> ORGANISM: Artificial Sequence
<220> FEATURE:
<223> OTHER INFORMATION: Probe sequence for human coronavirus NL63

<400> SEQUENCE: 63
tttttctaag agcgttggcg tatgcttttt tt                                    32

<210> SEQ ID NO 64
<211> LENGTH: 32
<212> TYPE: DNA
<213> ORGANISM: Artificial Sequence
<220> FEATURE:
<223> OTHER INFORMATION: Probe sequence for human coronavirus NL63

<400> SEQUENCE: 64 tttttttaaga tgagcagatt ggttaccttt tt                                   32

<210> SEQ ID NO 65
<211> LENGTH: 32
<212> TYPE: DNA
<213> ORGANISM: Artificial Sequence
<220> FEATURE:
<223> OTHER INFORMATION: Probe sequence for human coronavirus HKU1

<400> SEQUENCE: 65 tttttttcagg ttcacgttct caatcatttt tt                                   32

<210> SEQ ID NO 66
<211> LENGTH: 32
<212> TYPE: DNA
<213> ORGANISM: Artificial Sequence
<220> FEATURE:
```

-continued

<223> OTHER INFORMATION: Probe sequence for human coronavirus HKU1

<400> SEQUENCE: 66
ttttctgtac gattytgcct caaggccttt tt                         32

<210> SEQ ID NO 67
<211> LENGTH: 30
<212> TYPE: DNA
<213> ORGANISM: Artificial Sequence
<220> FEATURE:
<223> OTHER INFORMATION: Probe sequence for Influenza A

<400> SEQUENCE: 67
tttttttcgt gcccagtgag cgagtttttt                           30

<210> SEQ ID NO 68
<211> LENGTH: 30
<212> TYPE: DNA
<213> ORGANISM: Artificial Sequence
<220> FEATURE:
<223> OTHER INFORMATION: Probe sequence for Influenza A

<400> SEQUENCE: 68
tttttttcgt gcccagtgag cgagtttttt                           30

<210> SEQ ID NO 69
<211> LENGTH: 30
<212> TYPE: DNA
<213> ORGANISM: Artificial Sequence
<220> FEATURE:
<223> OTHER INFORMATION: Probe sequence for Influenza B

<400> SEQUENCE: 69 tttttteccaa ttcgagcagc tgaatttttt                          30

<210> SEQ ID NO 70
<211> LENGTH: 30
<212> TYPE: DNA
<213> ORGANISM: Artificial Sequence
<220> FEATURE:
<223> OTHER INFORMATION: Probe sequence for Influenza B

<400> SEQUENCE: 70 tttttttagca gctgaaactg cggtttttt                           30

<210> SEQ ID NO 71
<211> LENGTH: 34
<212> TYPE: DNA
<213> ORGANISM: Artificial Sequence
<220> FEATURE:
<223> OTHER INFORMATION: Probe sequence for human RNAse P control

<400> SEQUENCE: 71
tttttttcct gacctgaagg ctctgcgcgt tttt                      34

<210> SEQ ID NO 72
<211> LENGTH: 30
<212> TYPE: DNA
<213> ORGANISM: Artificial Sequence
<220> FEATURE:
<223> OTHER INFORMATION: Probe sequence for human RNAse P control

<400> SEQUENCE: 72
tttttcttga cctgaaggct ctgctttttt                           30

```
<210> SEQ ID NO 73
<211> LENGTH: 34
<212> TYPE: DNA
<213> ORGANISM: Artificial Sequence
<220> FEATURE:
<223> OTHER INFORMATION: Probe sequence for Negative Control

<400> SEQUENCE: 73 tttttctac tacctatgct gattcactct tttt                               34

<210> SEQ ID NO 74
<211> LENGTH: 28
<212> TYPE: DNA
<213> ORGANISM: Artificial Sequence
<220> FEATURE:
<223> OTHER INFORMATION: Primer sequence for ?-coronavirus Nucleocapsid
<220> FEATURE:
<221> NAME/KEY: modified_base
<222> LOCATION: 1
<223> OTHER INFORMATION: Thymidine at position 1 is modified with a
      fluorescent label

<400> SEQUENCE: 74
ttttgccaat gcgcgacatt ccgaagaa                                     28

<210> SEQ ID NO 75
<211> LENGTH: 28
<212> TYPE: DNA
<213> ORGANISM: Artificial Sequence
<220> FEATURE:
<223> OTHER INFORMATION: Primer sequence for SARS-CoV-2 Spike Gene

<400> SEQUENCE: 75
tttagtgtta taacaccagg aacaaata                                     28

<210> SEQ ID NO 76
<211> LENGTH: 28
<212> TYPE: DNA
<213> ORGANISM: Artificial Sequence
<220> FEATURE:
<223> OTHER INFORMATION: Primer sequence for SARS-CoV-2 Spike Gene
<220> FEATURE:
<221> NAME/KEY: modified_base
<222> LOCATION: 1
<223> OTHER INFORMATION: Thymidine at position 1 is modified with a
      fluorescent label

<400> SEQUENCE: 76
ttttgcatga atagcaacag ggacttct                                     28

<210> SEQ ID NO 77
<211> LENGTH: 30
<212> TYPE: DNA
<213> ORGANISM: Artificial Sequence
<220> FEATURE:
<223> OTHER INFORMATION: Primer sequence for Pan-coronavirus
      RNA-dependent RNA polymerase

<400> SEQUENCE: 77 tttttaata agtattttaa gcaytggagt                                   30

<210> SEQ ID NO 78
<211> LENGTH: 29
<212> TYPE: DNA
<213> ORGANISM: Artificial Sequence
<220> FEATURE:
<223> OTHER INFORMATION: Primer sequence for Pan-coronavirus
      RNA-dependent RNA polymerase
<220> FEATURE:
```

```
<221> NAME/KEY: modified_base
<222> LOCATION: 1
<223> OTHER INFORMATION: Thymidine at position 1 is modified with a
      fluorescent label

<400> SEQUENCE: 78
tttaagagtg tgttaaaatt tgaacaatg                                    29

<210> SEQ ID NO 79
<211> LENGTH: 30
<212> TYPE: DNA
<213> ORGANISM: Artificial Sequence
<220> FEATURE:
<223> OTHER INFORMATION: Primer sequence for Pan-coronavirus
      RNA-dependent RNA polymerase

<400> SEQUENCE: 79
ttttgtttaa gaagtatttt aartattggg                                   30

<210> SEQ ID NO 80
<211> LENGTH: 29
<212> TYPE: DNA
<213> ORGANISM: Artificial Sequence
<220> FEATURE:
<223> OTHER INFORMATION: Primer sequence for Pan-coronavirus
      RNA-dependent RNA polymerase
<220> FEATURE:
<221> NAME/KEY: modified_base
<222> LOCATION: 1
<223> OTHER INFORMATION: Thymidine at position 1 is modified with a
      fluorescent label

<400> SEQUENCE: 80
tttaatagtg tattraaatt agcacaatg                                    29

<210> SEQ ID NO 81
<211> LENGTH: 28
<212> TYPE: DNA
<213> ORGANISM: Artificial Sequence
<220> FEATURE:
<223> OTHER INFORMATION: Primer sequence for Influenza B

<400> SEQUENCE: 81
tttggatcct caactcactc ttcgagcg                                     28

<210> SEQ ID NO 82
<211> LENGTH: 28
<212> TYPE: DNA
<213> ORGANISM: Artificial Sequence
<220> FEATURE:
<223> OTHER INFORMATION: Primer sequence for Influenza A
<220> FEATURE:
<221> NAME/KEY: modified_base
<222> LOCATION: 1
<223> OTHER INFORMATION: Thymidine at position 1 is modified with a
      fluorescent label

<400> SEQUENCE: 82
tttgggcatt ytggacaaak cgtctacg                                     28

<210> SEQ ID NO 83
<211> LENGTH: 28
<212> TYPE: DNA
<213> ORGANISM: Artificial Sequence
<220> FEATURE:
<223> OTHER INFORMATION: Primer sequence for human respiratory syncytial
      virus

<400> SEQUENCE: 83
```

```
tttaaaratg gctcttagca aagtcaag                                    28
```

<210> SEQ ID NO 84
<211> LENGTH: 28
<212> TYPE: DNA
<213> ORGANISM: Artificial Sequence
<220> FEATURE:
<223> OTHER INFORMATION: Primer sequence for human respiratory syncytial
      virus
<220> FEATURE:
<221> NAME/KEY: modified_base
<222> LOCATION: 1
<223> OTHER INFORMATION: Thymidine at position 1 is modified with a
      fluorescent label

<400> SEQUENCE: 84

```
tttcgttgra trgtrtattt gctggatg                                    28
```

<210> SEQ ID NO 85
<211> LENGTH: 30
<212> TYPE: DNA
<213> ORGANISM: Artificial Sequence
<220> FEATURE:
<223> OTHER INFORMATION: Probe sequence for coronavirus Bat precursor
<220> FEATURE:
<221> NAME/KEY: modified_base
<222> LOCATION: 1
<223> OTHER INFORMATION: Thymidine at position 1 is modified with a
      fluorescent label

<400> SEQUENCE: 85

```
tttttttgttt gcacctagtg cttccttttt                                 30
```

<210> SEQ ID NO 86
<211> LENGTH: 30
<212> TYPE: DNA
<213> ORGANISM: Artificial Sequence
<220> FEATURE:
<223> OTHER INFORMATION: Probe sequence for coronavirus Pangolin
      precursor

<400> SEQUENCE: 86

```
ttttttttttg ctcctagcgc ttcttttttt                                 30
```

<210> SEQ ID NO 87
<211> LENGTH: 34
<212> TYPE: DNA
<213> ORGANISM: Artificial Sequence
<220> FEATURE:
<223> OTHER INFORMATION: Probe sequence for Pan SARS-CoV-2 614

<400> SEQUENCE: 87

```
tttttctctt tatcaggrtg ttaactgctt tttt                             34
```

<210> SEQ ID NO 88
<211> LENGTH: 30
<212> TYPE: DNA
<213> ORGANISM: Artificial Sequence
<220> FEATURE:
<223> OTHER INFORMATION: Probe sequence for SARS-CoV-2 614 variant

<400> SEQUENCE: 88

```
tttttttccta tcagggtgtt aacttttttt                                 30
```

<210> SEQ ID NO 89
<211> LENGTH: 30
<212> TYPE: DNA

```
<213> ORGANISM: Artificial Sequence
<220> FEATURE:
<223> OTHER INFORMATION: Probe sequence for SARS-CoV-2 614 variant

<400> SEQUENCE: 89
tttttcttat caggatgtta actttttttt                                    30

<210> SEQ ID NO 90
<211> LENGTH: 35
<212> TYPE: DNA
<213> ORGANISM: Artificial Sequence
<220> FEATURE:
<223> OTHER INFORMATION: Probe sequence for human coronavirus OC43

<400> SEQUENCE: 90
tttttatatc atcctaacac tgttgattgt ttttt                              35

<210> SEQ ID NO 91
<211> LENGTH: 35
<212> TYPE: DNA
<213> ORGANISM: Artificial Sequence
<220> FEATURE:
<223> OTHER INFORMATION: Probe sequence for human coronavirus NL63

<400> SEQUENCE: 91
tttttttatc atcctaattg tagtgactgt ttttt                              35

<210> SEQ ID NO 92
<211> LENGTH: 35
<212> TYPE: DNA
<213> ORGANISM: Artificial Sequence
<220> FEATURE:
<223> OTHER INFORMATION: Probe sequence for human coronavirus HKU1

<400> SEQUENCE: 92
tttttgtatc atcctaatac tgtggattgt ttttt                              35

<210> SEQ ID NO 93
<211> LENGTH: 35
<212> TYPE: DNA
<213> ORGANISM: Artificial Sequence
<220> FEATURE:
<223> OTHER INFORMATION: Probe sequence for human coronavirus 229E

<400> SEQUENCE: 93
tttttttatc atcctgattg tgttgattgc ttttt                              35

<210> SEQ ID NO 94
<211> LENGTH: 35
<212> TYPE: DNA
<213> ORGANISM: Artificial Sequence
<220> FEATURE:
<223> OTHER INFORMATION: Probe sequence for MERS

<400> SEQUENCE: 94
tttttaattg cgttaattgt actgatgacc ttttt                              35

<210> SEQ ID NO 95
<211> LENGTH: 36
<212> TYPE: DNA
<213> ORGANISM: Artificial Sequence
<220> FEATURE:
<223> OTHER INFORMATION: Probe sequence for Influenza B

<400> SEQUENCE: 95
ttttccaatt cgagcagctg aaactgcggt gttttt                             36
```

<210> SEQ ID NO 96
<211> LENGTH: 36
<212> TYPE: DNA
<213> ORGANISM: Artificial Sequence
<220> FEATURE:
<223> OTHER INFORMATION: Probe sequence for human respiratory syncytial
      virus-A

<400> SEQUENCE: 96
tttttcacac tcaacaaaga tcaacttctt cttctt                               36

<210> SEQ ID NO 97
<211> LENGTH: 35
<212> TYPE: DNA
<213> ORGANISM: Artificial Sequence
<220> FEATURE:
<223> OTHER INFORMATION: Probe sequence for human respiratory syncytial
      virus-B

<400> SEQUENCE: 97
tttttcgata cattaaataa ggatcagctt ttttt                                35

<210> SEQ ID NO 98
<211> LENGTH: 48
<212> TYPE: DNA
<213> ORGANISM: Artificial Sequence
<220> FEATURE:
<223> OTHER INFORMATION: Sequence for SARS CoV-2

<400> SEQUENCE: 98
ttcttcggaa tgtcgcgcat tggcaaaaca tggtcatagc tgtttcct                  48

<210> SEQ ID NO 99
<211> LENGTH: 52
<212> TYPE: DNA
<213> ORGANISM: Artificial Sequence
<220> FEATURE:
<223> OTHER INFORMATION: Sequence for discordant SARS CoV-2
<220> FEATURE:
<221> NAME/KEY: misc_feature
<222> LOCATION: 5, 6, 10, 16, 27, 32, 38, 39, 40, 41, 47
<223> OTHER INFORMATION: n is any nucleotide

<400> SEQUENCE: 99
ttccnncggn aggccngcca ttgggcnaaa cntggacnnn ngcgtgnttt cc             52

<210> SEQ ID NO 100
<211> LENGTH: 50
<212> TYPE: DNA
<213> ORGANISM: Artificial Sequence
<220> FEATURE:
<223> OTHER INFORMATION: Sequence for discordant SARS CoV-2
<220> FEATURE:
<221> NAME/KEY: misc_feature
<222> LOCATION: 16, 26
<223> OTHER INFORMATION: n is any nucleotide

<400> SEQUENCE: 100
ttcttcggga gggcgngcat tgggcnaaac atgggtcata gctgtttcct                50

<210> SEQ ID NO 101
<211> LENGTH: 54
<212> TYPE: DNA
<213> ORGANISM: Artificial Sequence
<220> FEATURE:
<223> OTHER INFORMATION: Sequence for discordant SARS CoV-2
<220> FEATURE:

```
<221> NAME/KEY: misc_feature
<222> LOCATION: 12, 23,48
<223> OTHER INFORMATION: n is any nucleotide

<400> SEQUENCE: 101
ttcttcggga angtcgcggc atnggcaaaa catggggtca taggctgntt        50
tcct                                                          54

<210> SEQ ID NO 102
<211> LENGTH: 55
<212> TYPE: DNA
<213> ORGANISM: Artificial Sequence
<220> FEATURE:
<223> OTHER INFORMATION: Sequence for discordant SARS CoV-2
<220> FEATURE:
<221> NAME/KEY: misc_feature
<222> LOCATION: 17, 37, 46
<223> OTHER INFORMATION: n is any nucleotide

<400> SEQUENCE: 102
ttcttcggga aggtcgnggc attggcaaaa catgggntca taggcntgat        50
ttcct                                                         55

<210> SEQ ID NO 103
<211> LENGTH: 50
<212> TYPE: DNA
<213> ORGANISM: Artificial Sequence
<220> FEATURE:
<223> OTHER INFORMATION: Sequence for discordant SARS CoV-2
<220> FEATURE:
<221> NAME/KEY: misc_feature
<222> LOCATION: 12, 22, 32
<223> OTHER INFORMATION: n is any nucleotide

<400> SEQUENCE: 103
ttcttcggga angtcgcgca tnggcaaaac anggtcatag ctggtttcct        50

<210> SEQ ID NO 104
<211> LENGTH: 53
<212> TYPE: DNA
<213> ORGANISM: Artificial Sequence
<220> FEATURE:
<223> OTHER INFORMATION: Sequence for discordant SARS CoV-2
<220> FEATURE:
<221> NAME/KEY: misc_feature
<222> LOCATION: 44, 47
<223> OTHER INFORMATION: n is any nucleotide

<400> SEQUENCE: 104
ttcttcggga aggtcgcggc attggcaaaa catggatcat agtntgnttt        50
cct                                                           53

<210> SEQ ID NO 105
<211> LENGTH: 49
<212> TYPE: DNA
<213> ORGANISM: Artificial Sequence
<220> FEATURE:
<223> OTHER INFORMATION: Sequence control for Positive SARS CoV-2
<220> FEATURE:
<221> NAME/KEY: misc_feature
<222> LOCATION: 41
<223> OTHER INFORMATION: n is any nucleotide

<400> SEQUENCE: 105
ttcttcggaa tgtcgcgcat tggcaaaaca tggtcatagc ntgtttcct         49
```

<210> SEQ ID NO 106
<211> LENGTH: 28
<212> TYPE: DNA
<213> ORGANISM: Artificial Sequence
<220> FEATURE:
<223> OTHER INFORMATION: Primer sequence for Influenza B.8.univ-RE1.3

<400> SEQUENCE: 106
ttttccctct tctggtgata atcggtgc                                28

<210> SEQ ID NO 107
<211> LENGTH: 60
<212> TYPE: DNA
<213> ORGANISM: Artificial Sequence
<220> FEATURE:
<223> OTHER INFORMATION: Sequence for human respiratory syncytial
      virus-A

<400> SEQUENCE: 107
gatggctctt agcaaagtca agttgaatga tacactcaac aaagatcaac          50
ttctgtcatc                                                      60

<210> SEQ ID NO 108
<211> LENGTH: 60
<212> TYPE: DNA
<213> ORGANISM: Artificial Sequence
<220> FEATURE:
<223> OTHER INFORMATION: Sequence for human respiratory syncytial
      virus-B

<400> SEQUENCE: 108
gatggctctt agcaaagtca agttaaatga tacattaaat aaggatcagc          50
tgctgtcatc                                                      60

<210> SEQ ID NO 109
<211> LENGTH: 60
<212> TYPE: DNA
<213> ORGANISM: Artificial Sequence
<220> FEATURE:
<223> OTHER INFORMATION: Sequence for human respiratory syncytial
      virus-A

<400> SEQUENCE: 109
cagcaaatac accatccaac ggagcacagg agatagtatt gatactccta          50
attatgatgt                                                      60

<210> SEQ ID NO 110
<211> LENGTH: 60
<212> TYPE: DNA
<213> ORGANISM: Artificial Sequence
<220> FEATURE:
<223> OTHER INFORMATION: Sequence for human respiratory syncytial
      virus-B

<400> SEQUENCE: 110
cagcaaatac actattcaac gtagtacagg agataatatt gacactccca          50
attatgatgt                                                      60

<210> SEQ ID NO 111
<211> LENGTH: 26
<212> TYPE: DNA
<213> ORGANISM: Artificial Sequence
<220> FEATURE:
<223> OTHER INFORMATION: Probe sequence for human respiratory syncytial
      virus

```
<400> SEQUENCE: 111
gctcttagca aagtcaagtt gaatga                                          26

<210> SEQ ID NO 112
<211> LENGTH: 21
<212> TYPE: DNA
<213> ORGANISM: Artificial Sequence
<220> FEATURE:
<223> OTHER INFORMATION: Probe sequence for human respiratory syncytial
      virus

<400> SEQUENCE: 112
tgctccgttg gatggtgtat t                                               21

<210> SEQ ID NO 113
<211> LENGTH: 33
<212> TYPE: DNA
<213> ORGANISM: Artificial Sequence
<220> FEATURE:
<223> OTHER INFORMATION: Probe sequence for human respiratory syncytial
      virus

<400> SEQUENCE: 113
acactcaaca aagatcaact tctgtcatcc agc                                  33

<210> SEQ ID NO 114
<211> LENGTH: 26
<212> TYPE: DNA
<213> ORGANISM: Artificial Sequence
<220> FEATURE:
<223> OTHER INFORMATION: Probe sequence for human respiratory syncytial
      virus

<400> SEQUENCE: 114
gatggctctt agcaaagtca agttaa                                          26

<210> SEQ ID NO 115
<211> LENGTH: 30
<212> TYPE: DNA
<213> ORGANISM: Artificial Sequence
<220> FEATURE:
<223> OTHER INFORMATION: Probe sequence for human respiratory syncytial
      virus

<400> SEQUENCE: 115
tgtcaatatt atctcctgta ctacgttgaa                                      30

<210> SEQ ID NO 116
<211> LENGTH: 35
<212> TYPE: DNA
<213> ORGANISM: Artificial Sequence
<220> FEATURE:
<223> OTHER INFORMATION: Probe sequence for human respiratory syncytial
      virus

<400> SEQUENCE: 116
tgatacatta aataaggatc agctgctgtc atcca                                35

<210> SEQ ID NO 117
<211> LENGTH: 25
<212> TYPE: DNA
<213> ORGANISM: Artificial Sequence
<220> FEATURE:
<223> OTHER INFORMATION: Probe sequence for human respiratory syncytial
      virus
```

```
<400> SEQUENCE: 117
aaaratggct cttagcaaag tcaag                                          25

<210> SEQ ID NO 118
<211> LENGTH: 25
<212> TYPE: DNA
<213> ORGANISM: Artificial Sequence
<220> FEATURE:
<223> OTHER INFORMATION: Probe sequence for human respiratory syncytial
      virus

<400> SEQUENCE: 118
cgttgratrg trtatttgct ggatg                                          25

<210> SEQ ID NO 119
<211> LENGTH: 23
<212> TYPE: DNA
<213> ORGANISM: Artificial Sequence
<220> FEATURE:
<223> OTHER INFORMATION: Probe sequence for human respiratory syncytial
      virus

<400> SEQUENCE: 119
acactcaaca aagatcaact tct                                            23

<210> SEQ ID NO 120
<211> LENGTH: 23
<212> TYPE: DNA
<213> ORGANISM: Artificial Sequence
<220> FEATURE:
<223> OTHER INFORMATION: Probe sequence for human respiratory syncytial
      virus

<400> SEQUENCE: 120
acattaaata aggatcagct gct                                            23

<210> SEQ ID NO 121
<211> LENGTH: 27
<212> TYPE: DNA
<213> ORGANISM: Artificial Sequence
<220> FEATURE:
<223> OTHER INFORMATION: Primer sequence for human coronavirus NL63 and
      OC43

<400> SEQUENCE: 121
tttaataagt attttaagca ytggagt                                        27

<210> SEQ ID NO 122
<211> LENGTH: 27
<212> TYPE: DNA
<213> ORGANISM: Artificial Sequence
<220> FEATURE:
<223> OTHER INFORMATION: Primer sequence for MERS and human coronavirus
      229E and HKU1

<400> SEQUENCE: 122
tgtttaagaa gtattttaar tattggg                                        27

<210> SEQ ID NO 123
<211> LENGTH: 26
<212> TYPE: DNA
<213> ORGANISM: Artificial Sequence
<220> FEATURE:
<223> OTHER INFORMATION: Primer sequence for human coronavirus 299E

<400> SEQUENCE: 123
```
aagagtgtgt taaaatttga acaatg                                    26

<210> SEQ ID NO 124
<211> LENGTH: 26
<212> TYPE: DNA
<213> ORGANISM: Artificial Sequence
<220> FEATURE:
<223> OTHER INFORMATION: Primer sequence for MERS and human coronavirus
      NL63, human coronavirus OC43 and human coronavirus HKU1

<400> SEQUENCE: 124
aatagtgtat traaattagc acaatg                                    26

<210> SEQ ID NO 125
<211> LENGTH: 25
<212> TYPE: DNA
<213> ORGANISM: Artificial Sequence
<220> FEATURE:
<223> OTHER INFORMATION: Probe sequence for human coronavirus NL63

<400> SEQUENCE: 125
ttatcatcct aattgtagtg actgt                                     25

<210> SEQ ID NO 126
<211> LENGTH: 25
<212> TYPE: DNA
<213> ORGANISM: Artificial Sequence
<220> FEATURE:
<223> OTHER INFORMATION: Probe sequence for human coronavirus 229E

<400> SEQUENCE: 126
ttatcatcct gattgtgttg attgc                                     25

<210> SEQ ID NO 127
<211> LENGTH: 25
<212> TYPE: DNA
<213> ORGANISM: Artificial Sequence
<220> FEATURE:
<223> OTHER INFORMATION: Probe sequence for human coronavirus OC43

<400> SEQUENCE: 127
atatcatcct aacactgttg attgt                                     25

<210> SEQ ID NO 128
<211> LENGTH: 25
<212> TYPE: DNA
<213> ORGANISM: Artificial Sequence
<220> FEATURE:
<223> OTHER INFORMATION: Probe sequence for human coronavirus HKU1

<400> SEQUENCE: 128
gtatcatcct aatactgtgg attgt                                     25

<210> SEQ ID NO 129
<211> LENGTH: 25
<212> TYPE: DNA
<213> ORGANISM: Artificial Sequence
<220> FEATURE:
<223> OTHER INFORMATION: Probe sequence for MERS

<400> SEQUENCE: 129
aattgcgtta attgtactga tgacc                                     25

<210> SEQ ID NO 130
<211> LENGTH: 27
<212> TYPE: DNA

```
<213> ORGANISM: Artificial Sequence
<220> FEATURE:
<223> OTHER INFORMATION: Primer sequence for human coronavirus NL63 and
      human coronavirus OC43

<400> SEQUENCE: 130
ttyaataagt aytttaagca ytggagt                                           27

<210> SEQ ID NO 131
<211> LENGTH: 27
<212> TYPE: DNA
<213> ORGANISM: Artificial Sequence
<220> FEATURE:
<223> OTHER INFORMATION: Primer sequence for MERS and human coronavirus
      229E and human coronavirus HKU1

<400> SEQUENCE: 131
tstttrabaa gtaytttaar tattggg                                           27

<210> SEQ ID NO 132
<211> LENGTH: 26
<212> TYPE: DNA
<213> ORGANISM: Artificial Sequence
<220> FEATURE:
<223> OTHER INFORMATION: Primer sequence for human coronavirus 299E

<400> SEQUENCE: 132
aagagtgtgt taaaatttga acaatg                                            26

<210> SEQ ID NO 133
<211> LENGTH: 26
<212> TYPE: DNA
<213> ORGANISM: Artificial Sequence
<220> FEATURE:
<223> OTHER INFORMATION: Primer sequence for MERS and human coronavirus
      NL63, human coronavirus OC43 and human coronavirus HKU1

<400> SEQUENCE: 133
aahartryrt traaattagc acaatg                                            26

<210> SEQ ID NO 134
<211> LENGTH: 25
<212> TYPE: DNA
<213> ORGANISM: Artificial Sequence
<220> FEATURE:
<223> OTHER INFORMATION: Primer sequence for human coronavirus NL63

<400> SEQUENCE: 134
ttatcatcct aattgtagtg actgt                                             25

<210> SEQ ID NO 135
<211> LENGTH: 25
<212> TYPE: DNA
<213> ORGANISM: Artificial Sequence
<220> FEATURE:
<223> OTHER INFORMATION: Primer sequence for human coronavirus 229E

<400> SEQUENCE: 135
ttatcatcct gattgtgttg attgc                                             25

<210> SEQ ID NO 136
<211> LENGTH: 25
<212> TYPE: DNA
<213> ORGANISM: Artificial Sequence
<220> FEATURE:
<223> OTHER INFORMATION: Primer sequence for human coronavirus OC43
```

<400> SEQUENCE: 136
atatcatcct aacackgttg attgt 25

<210> SEQ ID NO 137
<211> LENGTH: 25
<212> TYPE: DNA
<213> ORGANISM: Artificial Sequence
<220> FEATURE:
<223> OTHER INFORMATION: Primer sequence for human coronavirus HKU1

<400> SEQUENCE: 137
gtatcatcct aatactgtgg attgt 25

<210> SEQ ID NO 138
<211> LENGTH: 24
<212> TYPE: DNA
<213> ORGANISM: Artificial Sequence
<220> FEATURE:
<223> OTHER INFORMATION: Primer sequence for MERS

<400> SEQUENCE: 138
attgcgttaa ttgtactgat gacc 24

<210> SEQ ID NO 139
<211> LENGTH: 24
<212> TYPE: DNA
<213> ORGANISM: Artificial Sequence
<220> FEATURE:
<223> OTHER INFORMATION: Sequence for SARS?CoV?2 Wuhan-Hu-1
<220> FEATURE:
<221> NAME/KEY: misc_feature
<222> LOCATION: 7
<223> OTHER INFORMATION: n is any nucleotide

<400> SEQUENCE: 139
ccctagnttc aactggcagt aacc 24

<210> SEQ ID NO 140
<211> LENGTH: 25
<212> TYPE: DNA
<213> ORGANISM: Artificial Sequence
<220> FEATURE:
<223> OTHER INFORMATION: Sequence for SARS?CoV?2 Wuhan-Hu-1

<400> SEQUENCE: 140
ccctcagatt caactggcag taacc 25

<210> SEQ ID NO 141
<211> LENGTH: 76
<212> TYPE: DNA
<213> ORGANISM: Artificial Sequence
<220> FEATURE:
<223> OTHER INFORMATION: Sequence for SARS?CoV?2 Wuhan-Hu-1
<220> FEATURE:
<221> NAME/KEY: misc_feature
<222> LOCATION: 20,29,61,62,63
<223> OTHER INFORMATION: n is any nucleotide

<400> SEQUENCE: 141
ctgactggga ctggtgacgn cgccctagnt tcaactggca gtaacccgta 50
gaaaacatgg nnntagctgt ttccta 76

METHODS FOR DETECTING LOW LEVELS OF COVID-19 VIRUS

CROSS-REFERENCE TO RELATED APPLICATIONS

This non-provisional application claims the benefit of priority under 35 U.S.C. § 119(e) of provisional applications U.S. Ser. No. 63/078,772, filed Sep. 15, 2020, and U.S. Ser. No. 63/000,844, filed Mar. 27, 2020, both of which are hereby incorporated by reference in their entireties.

BACKGROUND OF THE INVENTION

Field of the Invention

The present invention relates to the field of multiplex based viral pathogen detection and analysis. More particularly, the present invention relates to detecting the presence of COVID-19 virus in patient and environmental samples.

Description of the Related Art

The COVID-19 pandemic has increased awareness that viral infection can be an existential threat to health, public safety and the US economy. More fundamentally, there is a recognition that the viral risks are more dangerous and more complex than had been thought and will require new approaches to diagnostics and screening.

The next pandemic wave is expected to have more pronounced flu-like symptoms (seasonal influenza A and/or B) coupled with the COVID-19, or COVID-19 variants that will coexist with the Coronavirus already responsible for the common cold. These complexities are expected to pose significant challenges to public health and the healthcare system in diagnosing multi-symptom conditions accurately and efficiently.

The COVID-19 pandemic has also led to the realization of an additional level of complexity that the realization that human health and environmental contamination are linked in a fundamental way that affects collection efficiency and increases risk to the healthcare workers (1, 2). Alternatives to nasopharyngeal collection methods such as for example, saliva collection are needed to enable scalability among millions of individuals.

Q-RT-PCR technology has dominated COVID-19 diagnostics and public health screening. Independent of the test developer, Q-RT-PCR has been shown to have an unusually high false negative rate (15% up to 30%). As of May 2020, the CDC has recorded 613,041 COVID-19 tests. With a 15% false negative rate, approximately 91,956 people would thus be falsely classified as free of infection. Meta-analysis has shown that the false negative rate for Q-RT-PCR is high below day 7 of infection when viral load is still low. This renders Q-RT-PCR ineffective as a tool for early detection of weak symptomatic carriers while also lessening its value in epidemiology.

Thus, there is a need in the art for superior tools to not only administer and stabilize sample collection for respiratory viruses from millions of samples in parallel obtained from diverse locations including, clinic, home, work, school and in transportation hubs, but also to test multiple respiratory markers at the highest levels of sensitivity and specificity.

SUMMARY OF THE INVENTION

The present invention is further directed to a method for detecting a Coronavirus disease 2019 (COVID-19) virus in a sample. A sample is obtained and total RNA isolated. At least one amplification reaction is performed using the COVID-19 virus RNA as template and at least one fluorescent labeled primer pair selective for COVID-19 virus RNA to generate fluorescent labeled COVID-19 virus specific amplicons. These amplicons are hybridized to a plurality of nucleic acid probes, each attached at specific positions on a solid microarray support. The sequence of the nucleic acid probes corresponds to a sequence determinant in the COVID-19 virus RNA. The microarray is washed and at least one fluorescent signal from the hybridized fluorescent labeled COVID-19 virus amplicons is detected, thereby detecting the COVID-19 virus in the sample. The present invention is also directed to a related method further comprising calculating an intensity of the fluorescent signal that correlates with the number of COVID-19 virus genomes in the sample. The present invention is further directed to a related method further comprising detecting at least one other, non-COVID-19 virus in the sample by performing the at least one amplification reaction with at least two pairs of fluorescently labeled primers selective for the COVID-19 virus and at least one of the other viruses to generate the fluorescent labeled virus specific cDNA amplicons and hybridizing the fluorescent labeled virus specific amplicons to the plurality of nucleic acid probes each having a sequence corresponding to a sequence determinant in the COVID-19 virus and the at least one of the other viruses.

The present invention is also directed to a method for detecting a respiratory disease-causing pathogen in a sample. A sample is obtained, and total nucleic acid is isolated. A combined, reverse transcription reaction and a first PCR amplification reaction (RT-PCR) is performed on the isolated total nucleic acids using at least one first primer pair selective for at least one respiratory disease-causing pathogen to generate at least one pathogen specific cDNA amplicons. A second amplification is performed using the pathogen specific cDNA amplicons as template and at least one fluorescent labeled second primer pair selective for at least one target nucleotide sequence in the pathogen specific cDNA amplicons to generate at least one fluorescent labeled pathogen specific amplicons. These amplicons are hybridized to a plurality of nucleic acid probes each attached at specific positions on a solid microarray support. The nucleic acid probes have sequence corresponding to sequence determinants in the pathogen. The microarray is washed at least once and imaged to detect a fluorescent signal corresponding to the fluorescent labeled pathogen specific amplicons. The present invention is also directed to a related method further comprising calculating an intensity of the fluorescent signal for the fluorescent labeled pathogen specific amplicons, correlating with the number of pathogen specific genomes in the sample.

The present invention is further directed to a method for detecting a Coronavirus disease 2019 (COVID-19) virus in a sample. A sample is obtained, and a total nucleic acid is isolated to obtain a test sample. A combined, reverse transcription reaction and a first PCR amplification reaction (RT-PCR) is performed on the test sample using at least one first primer pair selective for the COVID-19 virus RNA to generate COVID-19 virus cDNA amplicons. A second amplification is performed using the COVID-19 virus cDNA amplicons as template and at least one fluorescent labeled second primer pair selective for a target nucleotide sequence in the COVID-19 virus cDNA to generate at least one fluorescent labeled COVID-19 virus amplicons. These amplicons are hybridized to a plurality of nucleic acid probes each attached at specific positions on a solid microarray support. The nucleic acid probes have a sequence corresponding to sequence determinants in the COVID-19 virus. The microarray is washed at least once and imaged to detect at least one fluorescent signal from the hybridized fluorescent labeled COVID-19 virus amplicons thereby detecting the COVID-19 in the sample. The present invention is also directed to a related method comprising detecting at least one non-COVID-19 virus in the test sample. The combined reverse transcription and the first PCR amplification reaction on the test sample is performed using at least two first primer pairs selective for the COVID-19 virus and the non-COVID-19 virus to generate the COVID-19 virus specific cDNA amplicons and non-COVID-19 virus specific cDNA amplicons. The second amplification is then performed using the COVID-19 virus specific cDNA amplicons and the at least one non-COVID-19 virus specific cDNA amplicons as templates and at least two fluorescent labeled second primer pairs selective for a target nucleotide sequence in the COVID-19 virus specific cDNA and in the non-COVID-19 virus specific cDNA to generate the at least one fluorescent labeled COVID-19 virus specific amplicon and at least one fluorescent labeled non-COVID-19 virus specific amplicon, which are hybridized to the plurality of nucleic acid probes each having a sequence corresponding to the sequence determinant in the COVID-19 virus and the at least one non-COVID-19 virus. The present invention is also directed to a related method comprising detecting at least one bacterium in the test sample. The combined reverse transcription and the first PCR amplification reaction on the test sample is performed using at least two first primer pairs selective for the COVID-19 virus and the bacterium to generate the COVID-19 virus specific cDNA amplicons and bacterium specific cDNA amplicons. The second amplification is then performed using the COVID-19 virus specific cDNA amplicons and the at least one bacterium specific cDNA amplicons as templates and at least two fluorescent labeled second primer pairs selective for a target nucleotide sequence in the COVID-19 virus specific cDNA and in the bacterium specific cDNA to generate the at least one fluorescent labeled COVID-19 virus specific amplicon and at least one fluorescent labeled bacterium specific amplicon, which are hybridized to the plurality of nucleic acid probes each having a sequence corresponding to the sequence determinant in the COVID-19 virus and the at least one bacterium. The present invention is also directed to a related method comprising detecting at least one fungus in the test sample. The combined reverse transcription and the first PCR amplification reaction on the test sample is performed using at least two first primer pairs selective for the COVID-19 virus and the fungus to generate the COVID-19 virus specific cDNA amplicons and fungus specific cDNA amplicons. The second amplification is then performed using the COVID-19 virus specific cDNA amplicons and the at least one fungus specific cDNA amplicons as templates and at least two fluorescent labeled second primer pairs selective for a target nucleotide sequence in the COVID-19 virus specific cDNA and in the fungus specific cDNA to generate the at least one fluorescent labeled COVID-19 virus specific amplicon and at least one fluorescent labeled fungus specific amplicon, which are hybridized to the plurality of nucleic acid probes each having a sequence corresponding to the sequence determinant in the COVID-19 virus and the at least one fungus.

BRIEF DESCRIPTION OF THE FIGURES

FIG. 3A shows Q-RT-PCR signal-to-noise in the limit of (1) vs (0) Genomes per Reaction. FIG. 3B shows the amount of DNA amplicons produced as a function of PCR cycle number. FIG. 3C shows microarray detection limit as a function of copy number of viral genome.

FIG. 4A shows the probability of RT-PCR positive detection in samples from SARS-CoV2 infected patients. FIG. 4B shows the probability of samples identified as infected when RT-PCR reports negative detection.

FIG. 6A shows a box and whiskers plot of relative fluorescent values for hybridization-based SARS-CoV2 detection in nasal samples. FIG. 6B shows sensitivity of DETECTX-RV in detecting SARS-CoV2 RNA. FIG. 6C shows sensitivity of Q-RT-PCR in detecting SARS-CoV2 RNA.

FIG. 7A shows the workflow, based on an Asymmetric, Tandem, Two-Step Labelling PCR reaction, for the automated DETECTX-RV-V2 platform used for detecting SARS-CoV2 RNA. FIG. 7B shows the related workflow, based on the corresponding Asymmetric, One-Step RT-PCR reaction, for the automated DETECTX-RV-V2 platform used for detecting SARS-CoV2 RNA. FIG. 7C shows a 96-well automation-friendly microarray format for DETECTX-RV-V2.

FIG. 9 shows the enhanced content DETECTX-RV pan respiratory pathogen diagnostic platform roadmap.

FIG. 13A shows a representative image a printed 96-well DETECTX-RV plate. FIG. 13B shows a printed 384-well Mini-RV plate comprising 13,824 probe spots with no printing errors.

FIG. 16A is a CY5 image showing initial SARS-CoV2 hybridization feasibility. FIG. 16A is a CY3 image showing initial SARS-CoV2 hybridization feasibility. FIG. 16C is a CY5-color analysis of the Cy-5 image shown in FIG. 16A showing probe identification. FIG. 16D is a CY3-color analysis of the Cy-3 image shown in FIG. 17B showing probe identification.

FIG. 17A shows an imaging matrix for 1 hour hybridization with mixing. FIG. 17B shows the imaging matrix in FIG. 17A after spin drying. FIG. 17C shows the benefit of a low salt wash buffer incubation prior to spin-drying on background. where the arrow signifies the benefit associated with the low salt wash prior to spin drying. FIG. 17D shows an imaging matrix for 30 hour hybridization with intermittent pipette mixing of the hybridization solution. FIG. 17E shows the imaging matrix in FIG. 17D after spin drying. FIG. 17F shows Optimization of hybridization in 96-well format.

FIG. 18A shows optimization data for SARS-CoV2 containing samples at a primer ratio of 4:1. FIG. 18A shows optimization data for SARS-CoV2 containing samples at a primer ratio of 8:1.

FIG. 19A shows gel analysis for samples PATHO-003, PATHO-005, PATHO-008 and PATHO-012. FIG. 19B shows gel analysis for samples PATHO-015 and Positive sample-215981.

FIG. 22A show a representative (well A1) automated hybridization and wash in 96-well format. FIG. 22B show a representative (well G1) manual hybridization and wash in 96-well format.

FIG. 23A compares the hybridization analysis for RNA from SARS-COV2-N1-RE1, amplified using 4 different protocols. FIG. 23B compares the hybridization analysis for RNA from SARS-COV2-N2-RE1.4, amplified using 4 different protocols. FIG. 23C compares the hybridization analysis for RNA from SARS-COV2-N3-RE1.1, amplified using 4 different protocols.

FIG. 24A compares static, shaking and pipetting hybridization methods in analysis of SARS-COV2-N1-RE1 samples. FIG. 24B compares static, shaking and pipetting hybridization methods in analysis of SARS-COV2-N2-RE1.4 samples. FIG. 24C compares static, shaking and pipetting hybridization methods in analysis of SARS-COV2-N3-RE1.1 samples.

FIG. 27A shows one microarray images from samples processed using the CERES NANOTRAP method. FIG. 27B shows a second microarray images from samples processed using the CERES NANOTRAP method. FIG. 27C shows a third microarray images from samples processed using the CERES NANOTRAP method. FIG. 27D shows a fourth microarray images from samples processed using the CERES NANOTRAP method.

FIG. 30A shows the RFU versus Ct value plot for RNase P probe. FIG. 30B shows the RFU versus Ct value plot for SARS-COV-2 N2-RE1.1 probe FIG. 30C shows the RFU versus Ct value plot for SARS-COV-2 N2-RE1.4 probe. FIG. 30D shows the RFU versus Ct value plot for SARS-COV-2 N3-RE1.1 probe.

FIG. 31A LoD analysis for the SARS-COV-2 N1 probe. FIG. 31B LoD analysis for the SARS-COV-2 N2 probe FIG. 31C LoD analysis for the SARS-COV-2 N3 probe.

FIG. 32A shows the results of probe signal versus threshold for SARS-COV-2 N1-RE1.1 probe. FIG. 32B shows the results of probe signal versus threshold for SARS-COV-2 N2-RE1.3 probe. FIG. 32C shows the results of probe signal versus threshold for SARS-COV-2 N2-RE1.4 probe. FIG. 32D shows the results of probe signal versus threshold for SARS-COV-2 N3-RE1.1 probe. FIG. 32E is an additional dataset showing the results of probe signal versus threshold for probes SARS-COV-2 N1-RE1.1, SARS-COV-2 N2-RE1.4 and SARS-COV-2 N3-RE1.1.

FIG. 33A shows the results of probe signal versus threshold for SARS-COV-2 N1-RE1.1 probe. FIG. 33B shows the results of probe signal versus threshold for SARS-COV-2 N2-RE1.4 probe.

FIG. 37A is a background analysis showing low thresholds for Inf A and Inf B. FIG. 37B is a representative LoD analysis for Inf A samples. FIG. 37C is a representative LoD analysis for Inf B samples.

FIG. 38A is a background analysis showing low thresholds for Inf A and Inf B. FIG. 38B is a representative LoD analysis for Inf A samples. FIG. 38C is a representative LoD analysis for Inf B samples.

FIG. 40A shows a representative plot of LoD threshold determination for SARS-CoV-2 N1 probe. FIG. 40B shows a representative plot of LoD threshold determination for SARS-CoV-2 N2 probe.

DETAILED DESCRIPTION OF THE INVENTION

Figure 1:
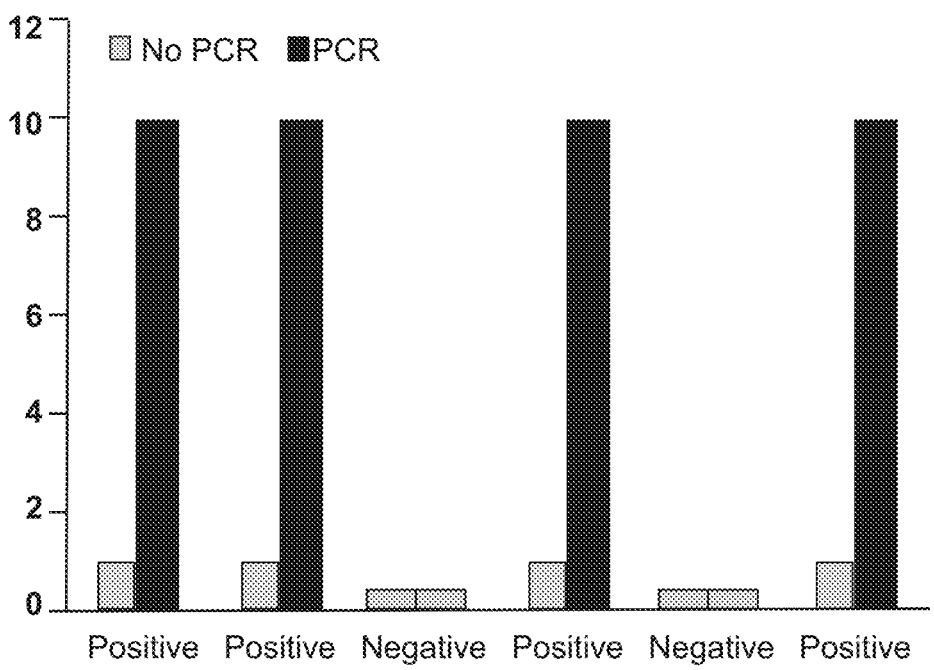
FIG. 1 shows that random fluid aliquot sampling can deliver "positive" and "negative" aliquots and that amplification by tandem PCR for subsequent hybridization testing does not after lowest limit of detection (LLoD) counting statistics.

As used herein, the term "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method described herein can be implemented with respect to any other method described herein.

As used herein, the term "or" in the claims is used to mean "and/or" unless explicitly indicated to refer to alternatives only or the alternatives are mutually exclusive, although the disclosure supports a definition that refers to only alternatives and "and/or."

As used herein, "comprise" and its variations, such as "comprises" and "comprising," will be understood to imply the inclusion of a stated item, element or step or group of items, elements or steps but not the exclusion of any other item, element or step or group of items, elements or steps unless the context requires otherwise. Similarly, "another" or "other" may mean at least a second or more of the same or different claim element or components thereof.

As used herein the phrase "lowest limit of detection (LLoD)" corresponds to the lowest number of genome copies capable of generating a measurable signal in the assay under consideration. For example, the LLoD corresponds to an analytical sensitivity of ~0.3 copies/reaction and post extraction sensitivity of ~3 copies/reaction.

As used herein, the term "about" refers to a numeric value, including, for example, whole numbers, fractions, and percentages, whether or not explicitly indicated. The term "about" generally refers to a range of numerical values (e.g., ±5-10% of the recited value) that one of ordinary skill in the art would consider equivalent to the recited value (e.g., having the same function or result). In some instances, the term "about" may include numerical values that are rounded to the nearest significant figure. For example, a fold excess of 3.6-fold to 8.8-fold is encompassed by about 4-fold to about 8-fold.

In one embodiment of the present invention, there is provided a method detecting a Coronavirus disease 2019 (COVID-19) virus in a sample, comprising, obtaining the sample; isolating from the sample, a total RNA; amplifying in at least one amplification reaction using COVID-19 virus RNA as template and at least one fluorescently labeled primer pair selective for COVID-19 virus RNA to generate fluorescent labeled COVID-19 virus specific amplicons; hybridizing the fluorescent labeled COVID-19 virus specific amplicons to a plurality of nucleic acid probes each having a sequence corresponding to a sequence determinant in the COVID-19 virus RNA, each of said nucleic acid probes attached at a specific position on a solid microarray support: washing the microarray at least once; and imaging the microarray to detect at least one fluorescent signal from the hybridized fluorescent labeled COVID-19 virus specific amplicons, thereby detecting the COVID-19 virus in the sample.

In this embodiment, in one aspect, the sample is any sample obtained from a subject including, but not limited to a nasopharyngeal swab, nasal swab, mouth swab, and mouthwash (sample obtained by rinsing the subject's buccal cavity). A pooled sample obtained by combining two or more of these samples or by combining samples from multiple subjects may also be used. In another aspect of this embodiment, the sample is an environmental sample obtain from inanimate sources including but is not limited to an aerosol and a hard surface. In this embodiment, the aerosol samples are obtained using commercial air samplers such as for example a Coriolis Micro Air Sampler. In this embodiment, a sample from a hard surface is obtained using a swab. In either aspect of this embodiment, the viruses from samples obtained on swabs are dispersed in a liquid such as phosphate buffered saline. Aerosol samples are transferred into a volume of a liquid such as phosphate buffered saline.

In this embodiment, the COVID-19 virus is a Severe Acute Respiratory Syndrome Coronavirus 2 (SARS-CoV 2) or a mutated form thereof. In this embodiment, in some aspects, the sample is mixed with an RNA stabilizer such as for example, a chemical stabilizer that would protect the RNA from degradation during storage and transportation, prior to the RNA isolating step.

In this embodiment, a total RNA potentially comprising RNA from COVID-19 virus and other contaminating pathogens and human cells is isolated. Commercially available RNA isolation kits such as for example, a Quick-DNA/RNA Viral MagBead Kit from Zymo Research are used for this purpose. The total RNA thus isolated is used without further purification. Alternatively, intact virus may be captured with magnetic beads, using kits such as that from Ceres Nanosciences (e.g. CERES NANOTRAP technology), or by first precipitating the virus with polyethylene glycol (PEG), followed by lysis of the enriched virus by heating with a "PCR-Friendly" lysis solution such as 1% NP40 in TE buffer and then used without additional purification.

In this embodiment, the COVID-19 virus RNA in the total RNA isolate is used as a template for amplifying a COVID-19 virus specific sequence. This comprises, first performing a combined reverse transcriptase enzyme catalyzed reverse transcription reaction and a first amplification reaction using at least one unlabeled primer pair selective for the virus to generate COVID-19 virus specific amplicons. In this embodiment, the unlabeled primer pairs (or first primer pairs) have forward (odd numbers) and reverse (even number) sequences shown in SEQ ID: to SEQ ID: 6 (Table 1). SEQ ID: 121 to SEQ ID: 124 (Table 39) and SEQ ID: 130 to SEQ ID: 137 (Table 40). Commercially available reverse transcriptase enzyme and buffers are used in this step. Controls including, but not limited to a RNAse P control having first primer pair (forward primer SEQ ID: 21, reverse primer SEQ ID: 22) are also used herein (Table 1).

TABLE 1

Primer sequences used for PCR

| SEQ ID NOS. | Target | Gene | Primer Sequence (5 to 3') |
|---|---|---|---|
| First amplification primers (Unlabeled Primers) ||||
| SEQ ID: 1 | SARS CoV2 Nucleocapsid | $N_1$ | TTTTGTCTGATAATGGACCCCAAAATCA |
| SEQ ID: 2 | SARS CoV2 Nucleocapsid | $N_1$ | TTTGTTCTCCATTCTGGTTACTGCCAGT |
| SEQ ID: 3 | CoV Nucleocapsid* | $N_2$ | TTTAGGAACTAATCAGACAAGGAACTGA |
| SEQ ID: 4 | CoV Nucleocapsid* | $N_2$ | TTTGTTCCCGAAGGTGTGACTTCCATGC |
| SEQ ID: 5 | CoV Nucleocapsid* | $N_3$ | TTTCGGCATCATATGGGTYGCAACTGAG |
| SEQ ID: 6 | CoV Nucleocapsid* | $N_3$ | TTTCCTTTTGGCAATGTTGTTCCTTGAG |
| SEQ ID: 7 | MERS CoV | upE | TTTTGTTTCCACTGTTTTCGTGCCTGCA |
| SEQ ID: 8 | MERS CoV | upE | TTTCTGTTTTCGTGCCTGCAACGCGCGA |
| SEQ ID: 9 | HCoV-229E | M | TTTTAATGCAATCACTGTCACAACCGTG |
| SEQ ID: 10 | HCoV-229E | M | TTTAAAACCCAGCCTGTGCTATTTTGTG |
| SEQ ID: 11 | HCoV-OC43 | M | TTTGTATGTTAGGCCGATAATTGAGGAC |
| SEQ ID: 12 | HCoV-OC43 | M | TTCAAACAGCAAAACCACTAGTATCGCT |
| SEQ ID: 13 | NHCoV-NL63 | N | TTATTCCTCCTCCTTCATTTTACATGCC |
| SEQ ID: 14 | NHCoV-NL63 | N | TTTAATTTAAGGTCCTTATGAGGTCCAG |
| SEQ ID: 15 | NHCoV-HKU1 | N | TTTACACTTCTAYTCCCTCCGATGTTTC |
| SEQ ID: 16 | NHCoV-HKU1 | N | TTTAAGATTAGCRATCTCATCAGCCATA |
| SEQ ID: 17 | Influenza A | M | TTTATGGCTAAAGACAAGACCRATCCTG |
| SEQ ID: 18 | Influenza A | M | TTTTTAAGGGCATTYTGGACAAAKCGTC |
| SEQ ID: 19 | Influenza B | NS1 | TTTGGATGAAGAAGATGGCCATCGGATC |
| SEQ ID: 20 | Influenza B | NS1 | TTTTCTAATTGTCTCCCTCTTCGGTGA |
| SEQ ID: 21 | Human RNAse RNAse P control | P | TTTACTTCAGCATGGCGGTGTTTGCAGA |
| SEQ ID: 22 | Human RNAse RNAse P control | P | TTTTGATAGCAACAACTGAATAGCCAAG |
| Second amplification primers ||||
| SEQ ID: 23 | SARS CoV2 Nucleocapsid | $N_1$ | TTTTAATGGACCCCAAAATCAGCGAAAT |
| SEQ ID: 24 | SARS CoV2 Nucleocapsid | $N_1$ | (FL)TTTTTCTGGTTACTGCCAGTTGAATCTG |
| SEQ ID: 25 | CoV Nucleocapsid* | $N_2$ | TTTACTGATTACAAACATTGGCCGCAAA |
| SEQ ID: 26 | CoV Nucleocapsid* | $N_2$ | (FL)TTTTGCCAATGCGYCGACATTCCRAAGAA |
| SEQ ID: 27 | CoV Nucleocapsd* | $N_3$ | TTTAGGGAGCCTTGAATACACCAAAAGA |
| SEQ ID: 28 | CoV Nucleocapsid* | $N_3$ | (FL)TTTAAGTTGTAGCACGATTGCAGCATTG |
| SEQ ID: 29 | MERS CoV | upE | TTTCCATATGTCCAAAGAGAGACTAATG |

TABLE 1-continued

Primer sequences used for PCR

| SEQ ID NOS. | Target | Gene | Primer Sequence (5 to 3') |
|---|---|---|---|
| SEQ ID: 30 | MERS CoV | upE | (FL)TTTTAGTAGCGCAGAGCTGCTTARACGA |
| SEQ ID: 31 | HCoV-229E | M | TTTACATACTATCAACCCATTCAACAAG |
| SEQ ID: 32 | HCoV-229E | M | (FL)TTTCTCGGCACGGCAACTGTCATGTATT |
| SEQ ID: 33 | HCoV-OC43 | M | TTTTCATACYCTGACGGTCACAATAATA |
| SEQ ID: 34 | HCoV-OC43 | M | (FL)TTTTAACCTTAGCAACAGWCATATAAGC |
| SEQ ID: 35 | NHCoV-NL63 | N | TTATAGTTCTGATAAGGCACCATATAGG |
| SEQ ID: 36 | NHCoV-NL63 | N | (FL)TTTGAACTTTAGGAGGCAAATCAACACG |
| SEQ ID: 37 | NHCoV-HKU1 | N | TTTGATCCTACTAYTCAAGAAGCTATCC |
| SEQ ID: 38 | NHCoV-HKU1 | N | (FL)TTTCTTAATGAACGAKTATTGGGTCCAC |
| SEQ ID: 39 | Influenza A | M | TTTCAAGACCRATCCTGTCACCTCTGAC |
| SEQ ID: 40 | Influenza A | M | (FL)TTTAAGGGCATTYTGGACAAAKCGTCTA |
| SEQ ID: 41 | Influenza B | NS1 | TTTGCGTCTCAATGAAGGACATTCAAAG |
| SEQ ID: 42 | Influenza B | NS1 | (FL)TTTTAATCGGTGCTCTTGACCAAATTGG |
| SEQ ID: 43 | Human RNAse RNAse P control | P | TTTGTTTGCAGATTTGGACCTGCGAGCG |
| SEQ ID: 44 | Human RNAse RNAse P control | P | (FL)TTTAAGGTGAGCGGCTGTCTCCACAAGT |

*Amplifies SARS-CoV2, SARS, Bat_SARS-like CoV, Pangolin CoV (S. China), Bat precursor CoV (Yunnan 2013) and New Bat CoV (Yunnan 2019).
(FL) = fluorescent label.

Also in this embodiment, the virus specific amplicons generated in the first amplification reaction are used as a template for a second amplification that employs at least one fluorescent labeled primer pair selective for a target nucleotide sequence in the COVID-19 virus cDNA to generate fluorescent labeled COVID-19 virus specific amplicons. In this embodiment, the fluorescent labeled primer pairs have forward (odd numbers) and reverse (even number) sequences shown in SEQ ID: 23 to SEQ ID: 28 (Table 1) and SEQ ID: 74 to SEQ ID: 80 (Table 37). Controls including, but not limited to a RNAse P control having primer pair (forward primer SEQ ID: 43, reverse primer SEQ ID: 44) are also used herein (Table 1). Any fluorescent label may be used, including, but not limited to CY3, a CY5, SYBR Green, a DYLIGHT™ DY647, a ALEXA FLUOR 647, a DYLIGHT™ DY547 and a ALEXA FLUOR 550.

Further in this embodiment, the fluorescent labeled COVID-19 virus amplicons generated are hybridized to the plurality of nucleic acid probes. The nucleic acid probes have a sequence corresponding to sequence determinants in the COVID-19 virus and have sequences SEQ ID: 45 to SEQ ID: 48 (Table 2). SEQ ID: 85 to SEQ ID: 93 (Table 38) and SEQ ID: 125 to SEQ ID: 129 (Table 39). Controls including, but not limited to a RNAse P control nucleic acid probe (SEQ ID: 71 and SEQ ID: 72) and a negative control nucleic acid probe (SEQ ID: 73) are also used herein (Table 2). In this embodiment, the fluorescent labeled COVID-19 virus amplicons hybridize to the nucleic acid probes, which are attached at specific positions on a microarray support including a 3-dimensional lattice microarray support. Further in this embodiment, after hybridization, the microarray is washed at least once to remove unhybridized amplicons. Washed microarrays are imaged to detect a fluorescent signal corresponding to the fluorescent labeled COVID-19 virus specific amplicons to detect presence of the COVID-19 virus in the sample.

TABLE 2

Nucleic acid probe sequences used for hybridization

| SEQ ID NOS. | Target | Gene | Probe Sequence |
|---|---|---|---|
| SEQ ID: 45 | SARS CoV2 Nucleocapsid | $N_1$ | TTTTTTTCCGCATTACGTTTGGTGTTTTT |
| SEQ ID: 46 | SARS CoV2 Nucleocapsid | $N_1$ | TTTTTTTATCAGCGAAATGCACCCTTTTT |

TABLE 2-continued

Nucleic acid probe sequences used for hybridization

| SEQ ID NOS. | Target | Gene | Probe Sequence |
|---|---|---|---|
| SEQ ID: 47 | SARS CoV2 Nucleocapsid | $N_2$ | TTTTTTTTTGCCCCCAGCGCTTCTTTTTT |
| SEQ ID: 48 | SARS CoV2 Nucleocapsid | $N_2$ | TTTTTTACAATTTGCCCCCAGCGTCTTTTT |
| SEQ ID: 49 | SARS Nucleocapsid | $N_2$ | TTTTTTTTTGCTCCRAGTGCCTCTTTTTTT |
| SEQ ID: 50 | SARS Nucleocapsid | $N_2$ | TTTTTTTTGCTCCRAGTGCCTCTGTCCTTT |
| SEQ ID: 51 | CoV Bat precursor | $N_2$ | TTTTTGTTTGCACCTAGTGCTTCAGCCCTTTT |
| SEQ ID: 52 | CoV Pangolin precursor | $N_2$ | TTTTTATTTGCWCCTAGCGCTTCTGCTCTTTT |
| SEQ ID: 53 | CoV Bat precursor-Yunnan 2013 | $N_2$ | TTTTTGTTTGCACCCAGTGCTTCTGCTCTTTT |
| SEQ ID: 54 | CoV Bat precursor-Yunnan 2019 | $N_2$ | TTTTTTACAATTCGCTCCCAGCGTCTTTTT |
| SEQ ID: 55 | CoV Nucleocapsid* | $N_3$ | TTTTTCTGGCACCCGCAATCCTGTCTTTTT |
| SEQ ID: 56 | CoV Nucleocapsid* | $N_3$ | TTTTTTAYCACATTGGCACCCGCATCTTTT |
| SEQ ID: 57 | MERS CoV | upE | TTTTATCTCTTCACATAATCGCCCTTTTTT |
| SEQ ID: 58 | MERS | upE | TTTTTTATAATCGCCCCGAGCTCGTCTTTT |
| SEQ ID: 59 | HCoV-229E | M | TTTTTTTGCTTTACGTTGACGGACATTTTTT |
| SEQ ID: 60 | HCoV-229E | M | TTTTTTTCAGGTGTTCAGGTTCATAATCTTTT |
| SEQ ID: 61 | HCoV-OC43 | M | TTTTTCATCTTTACATTCAAGGTATAATTTTT |
| SEQ ID: 62 | HCoV-OC43 | M | TTTTCTGCTATTCTTTGGCAGATTTGCTTTTT |
| SEQ ID: 63 | NHCoV-NL63 | N | TTTTTCTAAGAGCGTTGGCGTATGCTTTTTT |
| SEQ ID: 64 | NHCoV-NL63 | N | TTTTTTAAGATGAGCAGATTGGTTACCTTTTT |
| SEQ ID: 65 | NHCoV-HKU1 | N | TTTTTTCAGGTTCACGTTCTCAATCATTTTTT |
| SEQ ID: 66 | NHCoV-HKU1 | N | TTTTCTGTACGATTYTGCCTCAAGGCCTTTTT |
| SEQ ID: 67 | Influenza A | M | TTTTTTTCGTGCCCAGTGAGCGAGTTTTTT |
| SEQ ID: 68 | Influenza A | M | TTTTTTAGTGAGCGAGGACTGCATTTTTTT |
| SEQ ID: 69 | Influenza B | NS1 | TTTTTTCCAATTCGAGCAGCTGAATTTTTT |
| SEQ ID: 70 | Influenza B | NS1 | TTTTTTAGCAGCTGAAACTGCGGTTTTTTT |
| SEQ ID: 71 | Human RNAse P control | RNAse P | TTTTTTTTCTGACCTGAAGGCTCTGCGCGTTTTT |
| SEQ ID: 72 | Human RNAse P control | RNAse P | TTTTTCTTGACCTGAAGGCTCTGCTTTTTT |
| SEQ ID: 73 | Negative Control | — | TTTTTTCTACTACCTATGCTGATTCACTCTTTTT |

*Hybridizes with SARS-CoV2, SARS, Bat-SARS-like CoV, Pangolin CoV (S. China), Bat precursor CoV (Yunnan 2013), New Bat CoV (Yunnan 2019)

Further to this embodiment, the method further comprises calculating an intensity for the fluorescent signal. The calculated intensity is correlated with the number of COVID-19 virus specific genomes in the sample. The measured intensity is a function of the number of COVID-19 virus specific genomes in the sample. Based on analysis of virus-free samples, an experimentally determined intensity threshold is established for the hybridization to each probe on the microarray, such that a fluorescent intensity above that threshold signifies the presence of SARS-CoV-2 viral RNA, while fluorescence intensities below the threshold signifies that SARS-CoV-2 was not detected.

Further to this embodiment, the method further comprises detecting at least one other non-COVID-19 virus comprising a Respiratory Syncytial Virus, a Middle East Respiratory Syndrome coronavirus (MERS-CoV), a Severe Acute Respiratory Syndrome Coronavirus (SARS-CoV), a 229E Coronavirus, a OC43 Coronavirus, a NL63 Coronavirus, a HKU1 Coronavirus an Influenza A virus and an Influenza B virus in the sample, wherein the amplifying step comprises performing the at least one amplification reaction with at least two pairs of fluorescently labeled primers selective for the COVID-19 virus and at least one of the other viruses to generate the fluorescent labeled virus specific cDNA amplicons; and wherein the hybridizing step comprises hybridizing the fluorescent labeled virus specific amplicons to the plurality of nucleic acid probes each having a sequence corresponding to a sequence determinant in the COVID-19 virus and the at least one of the other viruses.

In this embodiment, the unlabeled primer pair has forward (odd numbers) and reverse (even number) sequences shown in SEQ ID: 1 to SEQ ID: 20 (Table 1), SEQ ID: 121 to SEQ ID: 124 (Table 39) and SEQ ID: 130 to SEQ ID: 138 (Table 40), the fluorescent labeled primer pairs have forward (odd numbers) and reverse (even number) sequences shown in SEQ ID: 23 to SEQ ID: 42 (Table 1) and SEQ ID: 74 to SEQ ID: 84 (Table 37), and nucleic acid probe sequences SEQ ID: 45 to SEQ ID: 70 (Table 2), SEQ ID: 111 to SEQ ID: 120 (Table 29), SEQ ID: 85 to SEQ ID: 97 (Table 38) and SEQ ID: 125 to SEQ ID: 129 (Table 39). Controls including, but not limited to a RNAse P control having unlabeled primer pair (forward primer SEQ ID: 21, reverse primer SEQ ID: 22), fluorescent labeled primer pair (forward primer SEQ ID: 43, reverse primer SEQ ID: 44) and nucleic acid probe (SEQ ID: 71 and SEQ ID: 72) and, a negative control nucleic acid probe (SEQ ID: 73) are also used herein.

In another embodiment of the present invention, there is provided a method for detecting a respiratory disease-causing pathogen in a sample, comprising obtaining a sample; isolating total nucleic acids from the sample; performing a combined reverse transcription and a first PCR amplification reaction on the isolated total nucleic acids using at least one first primer pair selective for at least one respiratory disease-causing pathogen to generate at least one pathogen specific cDNA amplicons; performing a second amplification using the pathogen specific cDNA amplicons as template and at least one fluorescent labeled second primer pair selective for at least one target nucleotide sequence in the pathogen specific cDNA amplicons to generate at least one fluorescent labeled pathogen specific amplicons; hybridizing the fluorescent labeled pathogen specific amplicons to a plurality of nucleic acid probes each having a sequence corresponding to sequence determinants in the pathogen, each of said nucleic acid probes attached at a specific position on a solid microarray support; washing the microarray at least once; and imaging the microarray to detect a fluorescent signal corresponding to the fluorescent labeled pathogen specific amplicons, thereby detecting the respiratory disease-causing pathogen in the sample.

In this embodiment, in one aspect, the sample is any sample obtained from a subject including, but not limited to a nasopharyngeal swab, nasal swab, mouth swab, and mouthwash (sample obtained by rinsing the subject's buccal cavity). A pooled sample obtained by combining two or more of these samples or by combining samples from multiple subjects may also be used. In another aspect of this embodiment, the sample is an environmental sample obtain from inanimate sources including but is not limited to an aerosol and a hard surface. In this embodiment, the aerosol samples are obtained using commercial air samplers such as for example a Coriolis Micro Air Sampler. In this embodiment, a sample from a hard surface is obtained using a swab. In either aspect of this embodiment, the viruses from samples obtained on swabs are dispersed in a liquid such as phosphate buffered saline. Aerosol samples are transferred into a volume of a liquid such as phosphate buffered saline.

In this embodiment, the respiratory disease-causing pathogen is a virus, a bacteria, a fungi, or a combination of these. The sample may also comprise mutated forms of these pathogens. Examples of respiratory disease-causing viruses include, but are not limited to, Severe Acute Respiratory Syndrome Coronavirus 2 (COVID-19 virus), a Respiratory Syncytial Virus, a Middle East Respiratory Syndrome coronavirus (MERS-CoV), or a Severe Acute Respiratory Syndrome Coronavirus (SARS-CoV), or a 229E Coronavirus, or a OC43 Coronavirus, or a NL63 Coronavirus, or a HKU1 Coronavirus or an Influenza A virus or an Influenza B virus, an adenovirus, a bocavirus, a metapneumovirus, a parainfluenza and a rhinovirus. Examples of respiratory disease-causing bacteria include, but are not limited to, a *Mycobacterium* species (e.g. *Mycobacterium tuberculosis*), a *Streptococcus* species (e.g. *Streptococcus pneumoniae*), a *Mycoplasma* species, an *Enterococcus* species, a *Haemophilus* species, a *Klebsiella* species, a *Moraxella* species and a *Corynebacterium* species. Examples of respiratory disease-causing fungus include, but are not limited to, a *Histoplasma* species, a *Coccidioides* species, a *Blastomyces* species, a *Rhizopus* species, an *Aspergillus* species, a *Pneumocystis* species and a *Cryptococcus* species. In this embodiment, in some aspects, the sample is mixed with an nucleic acid stabilizer such as for example, a chemical stabilizer that would protect the nucleic acids from degradation during storage and transportation, prior to the isolating step.

In this embodiment, a total nucleic acids potentially comprising nucleic acids from the pathogen and contaminating human cells is isolated. Commercially available nucleic acid isolation kits such as for example, a Quick-DNA/RNA MagBead Kit from Zymo Research are used for this purpose. The total nucleic acids thus isolated is used without further purification. Alternatively, the pathogens may be captured using hydrogel chemistry (Ceres Nanosciences) or enriched using methods including, but not limited to centrifugation and polyethylene glycol (PEG), followed by lysis of the enriched pathogens by heating with a "PCR-Friendly" lysis solution such as 1% NP40 in TE buffer and the total nucleic acids used without additional purification.

In this embodiment, a combined reverse transcriptase enzyme catalyzed reverse transcription reaction, and a first PCR amplification reaction is performed using the isolated nucleic acids as template and at least one first primer pair selective for the pathogens to generate pathogen specific cDNA amplicons.

In this embodiment, when the pathogen is a virus, the unlabeled primer pairs (or first primer pairs) have forward (odd numbers) and reverse (even number) sequences shown in SEQ ID: 1 to SEQ ID: 6 (Table 1), SEQ ID: 121 to SEQ ID: 124 (Table 39) and SEQ ID: 130 to SEQ ID: 137 (Table 40). Commercially available reverse transcriptase enzyme and buffers are used in this step. Controls including, but not limited to a RNAse P control having first primer pair (forward primer SEQ ID: 21, reverse primer SEQ ID: 22) are also used herein (Table 1) Also in this embodiment, the pathogen specific cDNA amplicons generated in the first amplification reaction are used as a template for a second amplification that employs at least one fluorescent labeled primer pair selective for a target nucleotide sequence in the pathogen specific cDNA to generate fluorescent labeled pathogen specific amplicons. Any fluorescent label may be used, including, but not limited to CY3, a CY5, SYBR Green, a DYLIGHT™ DY647, an ALEXA FLUOR 647, a DYLIGHT™ DY547 and a ALEXA FLUOR 550.

In this embodiment, when the pathogen is a virus, the fluorescent labeled primer pairs have forward (odd numbers) and reverse (even number) sequences shown in SEQ ID: 23 to SEQ ID: 28 (Table 1) and SEQ ID: 74 to SEQ ID: 80 (Table 37). Controls including, but not limited to a RNAse P control having primer pair (forward primer SEQ ID: 43, reverse primer SEQ ID: 44) are also used herein (Table 1).

Further in this embodiment, the fluorescent labeled pathogen specific amplicons generated are hybridized to the plurality of nucleic acid probes. The nucleic acid probes have a sequence corresponding to sequence determinants in the pathogens.

In this embodiment, when the pathogen is a virus, the nucleic acid probes have sequences SEQ ID: 45 to SEQ ID: 48 (Table 2), SEQ ID: 85 to SEQ ID: 93 (Table 38) and SEQ ID: 125 to SEQ ID: 129 (Table 39). Controls including, but not limited to a RNAse P control nucleic acid probe (SEQ ID: 71 and SEQ ID: 72) and a negative control nucleic acid probe (SEQ ID: 73) are also used herein (Table 2).

In this embodiment, the fluorescent labeled pathogen specific amplicons hybridize to the nucleic acid probes, which are attached at specific positions on a microarray support including a 3-dimensional lattice microarray support. Further in this embodiment, after hybridization, the microarray is washed at least once to remove unhybridized amplicons. Washed microarrays are imaged to detect a fluorescent signal corresponding to the fluorescent labeled pathogen specific amplicons to detect presence of the pathogens in the sample.

Further to this embodiment, the method further comprises calculating an intensity for the fluorescent signal. The calculated intensity is correlated with the number of pathogen specific genomes in the sample. The measured intensity is a function of the number of pathogen specific genomes in the sample. Based on analysis of pathogen-free samples, an experimentally determined intensity threshold is established for the hybridization to each probe on the microarray, such that a fluorescent intensity above that threshold signifies the presence of pathogen nucleic acid, while fluorescence intensities below the threshold signifies that the pathogen was not detected.

In yet another embodiment of the present invention, there is provided a method for detecting a Coronavirus 2019 disease (COVID-19) virus in a sample, comprising obtaining a sample; isolating a total nucleic acid from the sample to obtain a test sample; performing a combined reverse transcription and a first PCR amplification reaction on the test sample using at least one first primer pair selective for the COVID-19 virus RNA to generate COVID-19 virus cDNA amplicons; performing a second amplification using the COVID-19 virus cDNA amplicons as template and at least one fluorescent labeled second primer pair selective for a target nucleotide sequence in the COVID-19 virus cDNA to generate at least one fluorescent labeled COVID-19 virus amplicons; hybridizing the fluorescent labeled COVID-19 virus amplicons to a plurality of nucleic acid probes each having a sequence corresponding to a sequence determinant in the COVID-19 virus, each of said nucleic acid probes attached at a specific position on a solid microarray support; washing the microarray at least once; and imaging the microarray to detect at least one fluorescent signal from the hybridized fluorescent labeled COVID-19 virus amplicons, thereby detecting the COVID-19 in the sample.

In this embodiment, in one aspect, the sample is any sample obtained from a subject including, but not limited to a nasopharyngeal swab, nasal swab, mouth swab, and mouthwash (sample obtained by rinsing the subject's buccal cavity). A pooled sample obtained by combining two or more of these samples or by combining samples from multiple subjects may also be used. In another aspect of this embodiment, the sample is an environmental sample obtain from inanimate sources including but is not limited to an aerosol and a hard surface. In this embodiment, the aerosol samples are obtained using commercial air samplers such as for example a Coriolis Micro Air Sampler. In this embodiment, a sample from a hard surface is obtained using a swab. In either aspect of this embodiment, the viruses from samples obtained on swabs are dispersed in a liquid such as phosphate buffered saline. Aerosol samples are transferred into a volume of a liquid such as phosphate buffered saline.

In this embodiment, the COVID-19 virus is a Severe Acute Respiratory Syndrome Coronavirus 2 (SARS-CoV 2) or a mutated form thereof. In this embodiment, in some aspects, the sample is mixed with an RNA stabilizer such as for example, a chemical stabilizer that would protect the RNA from degradation during storage and transportation, prior to the RNA isolating step.

In this embodiment, a total nucleic acids potentially comprising nucleic acids from pathogens including the COVID-19 virus, and contaminating human cells is isolated. Commercially available nucleic acid isolation kits such as for example, a Quick-DNA/RNA MagBead Kit from Zymo Research are used for this purpose. The total nucleic acids thus isolated is used without further purification. Alternatively, the pathogens may be captured using hydrogel chemistry (Ceres Nanosciences) or enriched using methods including, but not limited to centrifugation and polyethylene glycol (PEG), followed by lysis of the enriched pathogens by heating with a "PCR-Friendly" lysis solution such as 1% NP40 in TE buffer and the total nucleic acids used without additional purification.

In this embodiment, the COVID-19 virus RNA in the total RNA isolate is used as a template for amplifying a COVID-19 virus specific sequence. This comprises, first performing a combined reverse transcriptase enzyme catalyzed reverse transcription reaction and a first amplification reaction using at least one unlabeled primer pair selective for the virus to generate COVID-19 virus specific amplicons. In this embodiment, the unlabeled primer pairs (or first primer pairs) have forward (odd numbers) and reverse (even number) sequences shown in SEQ ID: 1 to SEQ ID: 6 (Table 1), SEQ ID: 121 to SEQ ID: 124 (Table 39) and SEQ ID: 130 to SEQ ID: 137 (Table 40). Commercially available reverse transcriptase enzyme and buffers are used in this step. Controls including, but not limited to a RNAse P control having first primer pair (forward primer SEQ ID: 21, reverse primer SEQ ID: 22) are also used herein (Table 1)

Also in this embodiment, the virus specific amplicons generated in the first amplification reaction are used as a template for a second amplification that employs at least one fluorescent labeled primer pair selective for a target nucleotide sequence in the COVID-19 virus cDNA to generate fluorescent labeled COVID-19 virus specific amplicons. In this embodiment, the fluorescent labeled primer pairs have forward (odd numbers) and reverse (even number) sequences shown in SEQ ID: 23 to SEQ ID: 28 (Table 1) and SEQ ID: 74 to SEQ ID: 80 (Table 37). Controls including, but not limited to a RNAse P control having primer pair (forward primer SEQ ID: 43, reverse primer SEQ ID: 44) are also used herein (Table 1). Any fluorescent label may be used, including, but not limited to CY3, a CY5, SYBR Green, a DYLIGHT™ DY647, a ALEXA FLUOR 647, a DYLIGHT™ DY547 and a ALEXA FLUOR 550.

Further in this embodiment, the fluorescent labeled COVID-19 virus amplicons generated are hybridized to the plurality of nucleic acid probes. The nucleic acid probes have a sequence corresponding to sequence determinants in the COVID-19 virus and have sequences SEQ ID: 45 to SEQ ID: 48 (Table 2), SEQ ID: 85 to SEQ ID: 93 (Table 38) and SEQ ID: 125 to SEQ ID: 129 (Table 39). Controls including, but not limited to a RNAse P control nucleic acid probe (SEQ ID: 71 and SEQ ID: 72) and a negative control nucleic acid probe (SEQ ID: 73) are also used herein (Table 2). In this embodiment, the fluorescent labeled COVID-19 virus amplicons hybridize to the nucleic acid probes, which are attached at specific positions on a microarray support including a 3-dimensional lattice microarray support. Further in this embodiment, after hybridization, the microarray is washed at least once to remove unhybridized amplicons. Washed microarrays are imaged to detect a fluorescent signal corresponding to the fluorescent labeled COVID-19 virus specific amplicons to detect presence of the COVID-19 virus in the sample.

Further to this embodiment, the method further comprises detecting at least one non-COVID-19 virus in the test sample, wherein the step of performing the combined reverse transcription and the first PCR amplification reaction on the test sample comprises using at least two first primer pairs selective for the COVID-19 virus and the at least one non-COVID-19 virus to generate the COVID-19 virus specific cDNA amplicons and non-COVID-19 virus specific cDNA amplicons; wherein the step of performing the second amplification comprises using the COVID-19 virus specific cDNA amplicons and the at least one non-COVID-19 virus specific cDNA amplicons as templates and at least two fluorescent labeled second primer pairs selective for a target nucleotide sequence in the COVID-19 virus specific cDNA and in the non-COVID-19 virus specific cDNA to generate the at least one fluorescent labeled COVID-19 virus specific amplicon and at least one fluorescent labeled non-COVID-19 virus specific amplicon; and wherein the step of hybridizing comprises hybridizing the at least one fluorescent labeled COVID-19 virus specific amplicon and the at least one fluorescent labeled non-COVID-19 virus specific amplicon to the plurality of nucleic acid probes each having a sequence corresponding to the sequence determinant in the COVID-19 virus and the at least one non-COVID-19 virus.

In this embodiment, the non-COVID-19 virus is any virus including, but not limited to a respiratory disease-causing RNA or DNA virus. Examples of RNA viruses include, and are not limited to a Respiratory Syncytial Virus, a Middle East Respiratory Syndrome coronavirus (MERS-CoV), a Severe Acute Respiratory Syndrome Coronavirus (SARS-CoV), a 229E Coronavirus, a OC43 Coronavirus, a NL63 Coronavirus, a HKU1 Coronavirus an Influenza A virus, an Influenza B virus, a metapneumovirus, a parainfluenza, and a rhinovirus. In this embodiment, the fluorescent labeled primer pairs have forward (odd numbers) and reverse (even number) sequences shown in SEQ ID: 23 to SEQ ID: 42 (Table 1) and SEQ ID: 74 to SEQ ID: 84 (Table 37). and nucleic acid probe having sequences SEQ ID: 45 to SEQ ID: 70 (Table 2) and SEQ ID: 85 to SEQ ID: 97 (Table 38). Controls including, but not limited to a RNAse P control having primer pair (forward primer SEQ ID: 43, reverse primer SEQ ID: 44) and nucleic acid probe (SEQ ID: 71 and SEQ ID: 72) and, a negative control nucleic acid probe (SEQ ID: 73) are also used herein. Examples of DNA viruses include and are not limited to an adenovirus and a bocavirus.

Further to this embodiment, the method comprises detecting at least one bacterium in the test sample, wherein the step of performing the combined reverse transcription and the first PCR amplification reaction on the test sample comprises using at least two first primer pairs selective for the COVID-19 virus and the at least one bacterium to generate the COVID-19 virus specific cDNA amplicons and the bacterium specific cDNA amplicons; wherein the step of performing the second amplification comprises using the COVID-19 virus specific cDNA amplicons and the bacterium specific cDNA amplicons as templates and at least two fluorescent labeled second primer pairs selective for a target nucleotide sequence in the COVID-19 virus specific cDNA and in the bacterium specific cDNA to generate the at least one fluorescent labeled COVID-19 virus specific amplicon and at least one fluorescent labeled bacterium specific amplicon; and wherein the step of hybridizing comprises hybridizing the at least one fluorescent labeled COVID-19 virus specific amplicon and the at least one fluorescent labeled bacterium specific amplicon to the plurality of nucleic acid probes each having a sequence corresponding to the sequence determinant in the COVID-19 virus and the at least one bacterium.

In this embodiment, the bacterium is any bacterium including, but not limited to a respiratory disease-causing bacterium. Examples of bacteria include, and are not limited to a *Mycobacterium* species (e.g. *Mycobacterium tuberculosis*), a *Streptococcus* species (e.g. *Streptococcus pneumoniae*), a *Mycoplasma* species, an *Enterococcus* species, a *Haemophilus* species, a *Kebsiella* species, a *Moraxella* species and a *Corynebacterium* species.

Further to this embodiment, the method comprises detecting at least one fungus in the test sample, wherein the step of performing the combined reverse transcription and the first PCR amplification reaction on the test sample comprises using at least two first primer pairs selective for the COVID-19 virus and the at least one fungus to generate the COVID-19 virus specific cDNA amplicons and the fungus specific cDNA amplicons; wherein the step of performing the second amplification comprises using the COVID-19 virus specific cDNA amplicons and the fungus specific cDNA amplicons as templates and at least two fluorescent labeled second primer pairs selective for a target nucleotide sequence in the COVID-19 virus specific cDNA and in the fungus specific cDNA to generate the at least one fluorescent labeled COVID-19 virus specific amplicon and at least one fluorescent labeled fungus specific amplicon; and wherein the step of hybridizing comprises hybridizing the at least one fluorescent labeled COVID-19 virus specific amplicon and the at least one fluorescent labeled fungus specific amplicon to the plurality of nucleic acid probes each having a sequence corresponding to the sequence determinant in the COVID-19 virus and the at least one fungus.

In this embodiment, the fungus is any virus including, but not limited to a respiratory disease-causing fungus. Examples of fungus include, and are not limited to a *Histoplasma* species, a *Coccidioides* species, a *Blastomyces* species, a *Rhizopus* species, an *Aspergillus* species, a *Pneumocystis* species and a *Cryptococcus* species.

In any of the above embodiments, the method steps for detecting the virus, the bacterium and the fungus are performed in a single assay with the COVID-19 virus detection steps described above. This is advantageous since it enables streamlined detection of COVID-19 virus and the other pathogens in a one assay. Further in this embodiment, the methods described above may be used to concurrently detect in any combination, a COVID-19 virus, a non-COVID-19 virus, a bacterium, or a fungus.

Also, in any of the above embodiments, the imaging step further comprises calculating an intensity for the fluorescent signal. The calculated intensity is correlated with the number of genomes of the virus, bacterium, and fungus in the sample. The measured intensity is a function of the number of such genomes in the sample. Based on analysis of pathogen-free samples, an experimentally determined intensity threshold is established for the hybridization to each probe on the microarray, such that a fluorescent intensity above that threshold signifies the presence of nucleic acids for the virus, bacterium or fungus, while fluorescence intensities below the threshold signifies that the virus, bacterium or fungus was not detected respectively.

Described herein is a method for detecting a COVID-19 disease in a sample such as a nasopharyngeal swab, a nasal swab, a mouth swab, a mouthwash, an aerosol, or a swab from a hard surface. The sample is mixed with a chemical stabilizer after sample collection. The stabilizer prevents RNA degradation during storage and transportation prior to RNA isolation. The isolated RNA is a total RNA preparation comprising viral and non-viral RNA including COVID-19 virus RNA that is used without further purification. This RNA preparation is used in a combined reverse transcription and first amplification reaction (RT-PCR) to generate COVID-19 virus cDNA amplicons. These amplicons are used as template in a second amplification reaction that uses fluorescent labeled second primer pair selective for a target nucleotide sequence in the COVID-19 virus to generate fluorescent labeled COVID-19 virus amplicons. The fluorescent labeled COVID-19 virus amplicons are hybridized to nucleic acid probes attached at specific positions on a microarray. This method allows positive hybridization signals to be validated on each sample tested based on internal "mismatched" and "sequence specific" controls. Also described herein is a method for detecting presence of a respiratory virus disease-causing virus, bacterium and fungus in the sample using pathogen specific primers and nucleic acid probes and the same method steps described above. The method steps may be performed concurrently performed in a single assay, which is beneficial since it enables streamlined detection of COVID-19 virus and the other pathogens in a single assay. Any combination of COVID-19 virus, non-COVID-19 virus, bacterium, and fungus may be detected using this method.

In the embodiments described above, the microarray is made of any suitable material known in the art including but not limited to borosilicate glass, a thermoplastic acrylic resin (e.g., poly(methyl methacrylate-VSUVT) a cycloolefin polymer (e.g. ZEONOR 1060R), a metal including, but not limited to gold and platinum, a plastic including, but not limited to polyethylene terephthalate, polycarbonate, nylon, a ceramic including, but not limited to $TiO_2$, and Indium tin oxide (ITO) and engineered carbon surfaces including, but not limited to graphene. A combination of these materials may also be used. The solid support has a front surface and a back surface and is activated on the front surface by chemically activatable groups for attachment of the nucleic acid probes. In this embodiment, the chemically activatable groups include but are not limited to epoxysilane, isocyanate, succinimide, carbodiimide, aldehyde and maleimide. These materials are well known in the art and one of ordinary skill in this art would be able to readily functionalize any of these supports as desired. In a preferred embodiment, the solid support is epoxysilane functionalized borosilicate glass support.

The nucleic acid probes are attached either directly to the microarray support, or indirectly attached to the support using bifunctional polymer linkers. In this embodiment, the bifunctional polymer linker has a top domain and a bottom end. On the bottom end is attached a first reactive moiety that allows covalent attachment to the chemically activatable groups in the solid support. Examples of first reactive moieties include but are not limited to an amine group, a thiol group and an aldehyde group. In one aspect the first reactive moiety is an amine group. On the top domain of the bifunctional polymer linker is provided a second reactive moiety that allows covalent attachment to the oligonucleotide probe. Examples of second reactive moieties include but are not limited to nucleotide bases like thymidine, adenine, guanine, cytidine, uracil and bromodeoxyuridine and amino acid like cysteine, phenylalanine, tyrosine glycine, serine, tryptophan, cystine, methionine, histidine, arginine and lysine. The bifunctional polymer linker may be an oligonucleotide such as OLIGOdT, an amino polysaccharide such as chitosan, a polyamine such as spermine, spermidine, cadaverine and putrescine, a polyamino acid, with a lysine or histidine, or any other polymeric compounds with dual functional groups which can be attached to the chemically activatable solid support on the bottom end, and the nucleic acid probes on the top domain. Preferably, the bifunctional polymer linker is OLIGOdT having an amine group at the 5' end.

In this embodiment, the bifunctional polymer linker may be unmodified with a fluorescent label. Alternatively, the bifunctional polymer linker has a fluorescent label attached covalently to the top domain, the bottom end, or internally. The second fluorescent label is different from the fluorescent label in the fluorescent labeled primers. Having a fluorescent label (fluorescent tag) attached to the bifunctional polymer linker is beneficial since it allows the user to image and detect the position of the individual nucleic acid probes ("spot") printed on the microarray. By using two different fluorescent labels, one for the bifunctional polymer linker and the second for the amplicons generated from the viral RNA being queried, the user can obtain a superimposed image that allows parallel detection of those nucleic acid probes which have been hybridized with amplicons. This is advantageous since it helps in identifying the virus comprised in the sample using suitable computer and software, assisted by a database correlating nucleic acid probe sequence and microarray location of this sequence with a known RNA signature in viruses. Examples of fluorescent labels include, but are not limited to CY5, DYLIGHT™ DY647, ALEXA FLUOR 647, CY3, DYLIGHT™ DY547, or ALEXA FLUOR 550. The fluorescent labels may be attached to any reactive group including but not limited to, amine, thiol, aldehyde, sugar amido and carboxy on the bifunctional polymer linker. In one aspect, the bifunctional polymer linker is CY5-labeled OLIGOdT having an amino group attached at its 3' terminus for covalent attachment to an activated surface on the solid support.

Further in this embodiment, when the bifunctional polymer linker is also fluorescently labeled a second fluorescent signal image is detected in the imaging step. Superimposing the first fluorescent signal image and second fluorescent signal image allows identification of the virus by comparing the sequence of the nucleic acid probe at one or more superimposed signal positions on the microarray with a database of signature sequence determinants for a plurality of viral RNA. This embodiment is particularly beneficial since it allows identification of more than one type of virus in a single assay.

DETECTX-RV enables screening for COVID-19 in nasopharyngeal swabs. The microarray has the capacity to test for multiple viral analytes in parallel DETECTX-RV is based on endpoint PCR (rather than qPCR) and is coupled to concurrent analysis of up to 144 distinct nucleic acid probes (rather than just 4 probes for qPCR). This enhanced test capacity enables concurrent testing of 3 different sites (N1, N2, N3) in the SARS CoV2 genome and further, include a human RNA control (RNAse P). The testing may be performed in triplicate along with a panel of 8 viral controls, enabling confirmation of COVID-19 at a level of experimental specificity of over 10× compared to Q-RT-PCR. The DETECTX-RV-V2 microarray differs from DETECTX-RV in the additional inclusion of the newly discovered S-D614G variant in the same assay and an additional amplification step. This microarray is suitable for fully automated testing capable of processing samples in a 96-well array plate format, or the higher throughput 384-well microarray plate format.

The following examples are given for the purpose of illustrating various embodiments of the invention and are not meant to limit the present invention in any fashion.

Example 1

Tandem PCR (or RT-PCR, then Asymmetric PCR) Reactions to Enhance the Ability to Accurately Detect the Population Density (i.e. Molecules/μL) Near the Lowest Limit of Detection (LLoD)

The first of the two tandem reactions coverts segments of RNA genome into an abundance of amplified DNA. It is a type of Endpoint PCR reaction, such that the original RNA input is amplified 35 cycles, to form an Endpoint PCR product, wherein the input RNA target segments have been amplified to generate a maximal number of DNA amplicons.

The second PCR reaction, which may be a real-time or an endpoint PCR reaction, builds upon the first reaction such that if one or more molecules of DNA or RNA are input into the first reaction, that first PCR reaction produces an amplified DNA segment which has been amplified to yield a sample that may display up to a $10^{+6}$ fold increase in strand concentration within the amplicon product (FIG. 1).

The second PCR reaction additionally tags the PCR amplified product with a Dye (e.g. CY-3), which enables amplicon detection after microarray hybridization. The second reaction is performed as an asymmetric PCR reaction, such that upon completion of this second "Endpoint" PCR reaction, the product is >90% single stranded (due to the asymmetry of the PCR reaction) with the single strand of interest being the only strand bearing the CY-3 dye probe. This asymmetry allows the product to be used for hybridization without the need for heat denaturation and avoids hybridization artifacts which are otherwise common.

If no RNA (or DNA) were input into the first reaction, none will be amplified (FIG. 1). Having received that amplified input into the second PCR reaction, the quantitative distinction between (0) copies of original genomic nucleic acid. i.e. a "negative Aliquot", vs (1, >1) copies of genomic nucleic acid in an aliquot, that is, "positive" aliquot is thus greatly amplified. Thus, in the context of the tandem reactions of the present invention, the first PCR (or RT-PCR) reaction can be thought of as a method of signal amplification to increase signal "gain" (FIG. 1) to be of benefit to the second PCR reaction or similar amplification reaction. Equation 1. PCR Reaction #1. Amplifies mass distinction between sample aliquots with (0) vs (>0)

DNA Copies in the Original:

1 copy of genomic DNA Target→at $1 \times 2^M$ Copies of Product Targets (M=number of PCR Cycles).

0 copy of genomic DNA Target→at $0 \times 2^M$ Copies of Product Targets (M=number of PCR Cycles).

DNA target signal strength increases after PCR. 1 Copy→1× $2^M$ copies.

Statistical occurrence of "Negative" events (Pr0) in aliquots of the original sample does not change as a result of PCR Reaction #1.

$$Pr(0) = \exp(-\langle N \rangle) \text{ before and after PCR}$$

In medical diagnostics, food safety and other demanding applications, the LLoD is a crucial test parameter, which is defined by, and directly measured, in the context of samples where, for nucleic acids, the number of microbial or viral genomes in fluid solution are introduced as small (typically 1 μL) aliquots into the PCR reaction at levels so dilute that such single 1 μL aliquots will, via ordinary random sampling statistics, be expected to capture a significant number of "negative" aliquots, i.e. (0) copies of the original nucleic acid genome in each (see FIG. 1).

The present invention serves to greatly increase the amplitude of the signal associated with the "positive" events (≥1 genomes per aliquot) relative to the "negative" events where, lacking a template for PCR, PCR does not occur (see Equation 1 and FIG. 1). Thus, without altering the relative frequency of "positive" vs "negative" sampling events, the signal associated with the "positive" signals is greatly amplified, making subsequent analysis of such positives more accurate, while still providing an accurate determination of the original nucleic acid sample density, as manifest in the "positive/negative" sampling frequency ratio.

For example, in the context of Poisson statistics, LLoD can be measured by counting the statistical likelihood of "negative" signals derived from the "negative" (N=0) aliquot events, relative to statistical occurrence of all "positive" events, i.e. signals obtained when (N=1+N>1). Using Poisson statistics, that (positive/negative) event ratio can be used to calculate the average population density ($\langle N \rangle$) of nucleic acid target molecules in the original sample aliquot size. For instance, in an ideal assay near the LLOD, where $\langle N \rangle = 1$ per sample aliquot (e.g. 1 genome per 1 μL) Poisson statistics specify that the statistical likelihood of "positive" vs "negative" signals on repeat 1 μL aliquoting will approach $1-e^1/e^1 \approx 2$. Alternatively, when $\langle N \rangle = 3$ per aliquot, the ratio of (positive vs "negative) signals on repeat measurement would approach $1-e^{-3}/e^{-3} \approx 20$ which is the standard definition of the LLoD defined by the FDA and the USDA food safety and medical diagnostics.

Thus, as seen in Equation #1 and FIG. 1, the first PCR reaction of the present invention does not change the statistical likelihood of introducing an aliquot of fluid sample which, by chance had no genomic DNA or RNA in it to support PCR, or RT-PCR, respectively. Thus, determination of original sample density (genomes/μL) is not altered by PCR #1 (FIG. 1). The substantial signal amplification afforded by the use of that first PCR reaction (FIG. 1) greatly increases the number of amplified DNA molecules in those samples which, by chance, contained one or more nucleic target strands (FIG. 1) thus improving the sensitivity of single molecule detection near LLoD.

Figure 2:
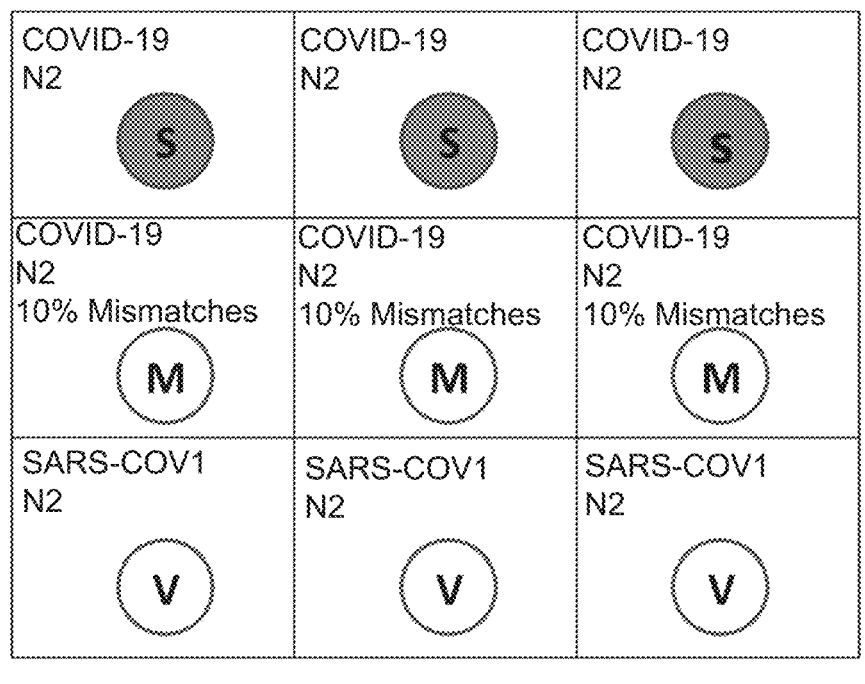
FIG. 2 shows that DNA microarray-based hybridization near the lowest limit of detection allows "positive" hybridization signals to be validated on each sample tested based on internal "mismatched" and "sequence specific" controls.

Use of a Panel of Multiple DNA Hybridization Reactions to Enhance Authentication of "Bona Fide" PCR-Amplified "Positive" Hybridization Signals The present invention describes the use of a first PCR or RT-PCR reaction (as in FIG. 1) in the context of a second PCR reaction coupled to DNA hybridization analysis on a microarray, rather than the use of a second real time PCR reaction as the second PCR step. The reason for such a choice is based on the capacity of a microarray to introduce a very large number of control measurements on a microarray, such that any hybridization signal obtained from a "positive" aliquot of amplified RNA or DNA to its cognate surface bound probe, can be verified as being a bona fide (specific) signal by means of direct comparison of that hybridization signal to multiple control probes on the same array (FIG. 2). Such control probes can be readily introduced into each microarray test and can be "mismatched" probes which have been altered by a simple physical change (i.e. to produce mismatched base pairings) or by the use of probes specific to other closely-related organisms, i.e. "species specific" probes. The ability to use a panel of multiple control probes to independently validate the data quality for a "positive" hybridization signal in the LLoD limit, on every sample being analyzed via the microarray test, is a unique property of microarray analysis in the present invention and is not generally possible with real time PCR.

More formally, and in the context of the present invention, when the (n) nucleic acid target sites are distributed throughout the pathogen genome, each can be interrogated by a set ($P_n$) of at least 9 microarray probes, comprising at least three types of probe (in triplicate). The first probe type ($s_n$) is perfectly matched to a sequence in target site (n) which is chosen to be unique to the pathogen. A second probe type ($m_n$) is identical to ($s_n$) but altered to include at least 10% of base changes to induce mismatches. In addition, there is created at least a third probe type ($v_n$) which is intentionally made to be identical to a sequence in a closely related species variant and to differ in sequence relative to ($s_n$) by at least 10% of base changes (See FIG. 2).

The aggregated signal from all three probe types can be compared to each other to define a numerical value for the certainty that the hybridization signal (S) obtained from the pathogen (on probe $s_n$) is statistically different from the hybridization signal (M) obtained on $m_n$ and also the signal (V) on $v_n$; and wherein one such representative numerical value could comprise the relationship "Merit"=$[S/(M+V)/2]$ where based on previous analysis of manufacturing and other sources of variance, "Merit" values at >10 would be significant of validated detection of the pathogen in any sample and values for "Merit" at <2 would indicate that the pathogen signal is not detected.

Nucleic acid-based microarray technology is based on the ability to mass produce DNA microarrays in a low cost a 1"×3" glass slide format. This platform is used for DETECTX-RV and is scalable to 100,000 DETECTX-RV tests per month.

Briefly, viral RNA is extracted from a swab sample (see below) and taken through two Endpoint PCR reactions performed in tandem. The first PCR performs endpoint RT-PCR reactions on COVID-19 RNA to generate a set of primary DNA amplicons, each directed to one of several important regions of the COVID-19 genome N1, N2, N3. The primary DNA amplicons are used as a template for a second PCR reaction which additionally amplifies the primary product, while also applying a CY-3 fluorescent label to it. The second PCR is set-up as asymmetric PCR, a specialized version of Endpoint PCR, which produces a large excess of the CY-3 dye tagged strand of interest. The second PCR product is single stranded and can be used directly for microarray hybridization without clean-up or thermal denaturation. The workflow enables generation of 576 samples of microarray data/shift, which can be doubled with doubling upfront automation of RNA extraction.

The data is analyzed via AUGURY (Augury Technology company New York N.Y.), cloud-based automated software developed at PathogenDx, which can be implemented with modifications as appropriate. The software uses a basic logarithmic analysis to determine the results and is automatically processed and reported without any user interaction. Further, the cloud-based network capability enables data sharing with any number of testing labs needed to support national screening.

Example 2

A Microarray to Measure Very Low Levels of a Virus Such as COVID-19

Based on the general principles described in background, a microarray test is described with a LLoD at about 1 viral genome per assay and as such more than 10× more sensitive than Q-RT-PCR. Such a >10× sensitivity enhancement enables the ability to detect and speciate COVID-19 at 100 virus particles per swab, which according to the literature is roughly 10× greater sensitivity than any known Q-RT-PCR reaction. Such LLoD performance is a direct result of 3 fundamental principles of tandem PCR coupled to microarray analysis.

Two 30 Cycle PCR Reactions Performed Serially, which Deliver, De Facto, 60 Cycles of Endpoint RT-PCR Amplification Prior to Microarray Analysis RNA template input held constant, such a 2-step tandem RT-PCR+PCR reaction produces DNA amplicon (to support microarray hybridization) at a concentration that is >3 orders of magnitude greater than the amount of PCR amplified DNA which generates the Cq metric in Q-RT-PCR.

Analysis of Multiple COVID-19 Loci to Reduce the LLoD

Nucleic acid analysis becomes more sensitive when interrogating multiple copy loci, e.g. rDNA in bacteria or fungi, because one genome becomes represented by (n) identical target nucleic acid strands. In the present microarray test, (n)=6 independent COVID-19 test loci were configured, distributed throughout the genome.

Near the LLoD, where aliquot sampling becomes stochastic (see Equations 1 and FIG. 1) ordinary FDA standards specify that the LLOD be defined as the point where the assay generates at least 19/20 positives (due to aliquot sampling statistics). If a single PCR based assay is performed on each COVID-19 genome, such ordinary (Poisson) counting statistics specify that 19/20 positives would result from a population average of N=3 COVID-19 "events" in each sample aliquot being tested, typically 1 μL of an RNA extract. Thus, at n=1 target loci per genome, the practical limit of COVID-19 detection is about 3 genomes of purified RNA per μL.

Equation #2. The Analysis of Multiple Loci per Genome. The Effect on LLoD. $Pr(0)=e^{-<N>}$, where $<N>=$the population average of events per sample aliquot$=(n\times<g>)$, where $<g>$ is the average number of genomes per sample and n is the number of loci analyzed per genome.

LLoD is defined by the FDA as $Pr(0)=1/20=e^{-<N>}$, thus at LLoD $<N>=3$ (3 average events per aliquot).

For 1 Locus analyzed per genome, (n)=1 and $<N>=<g>$ and LLoD=3 genomes per aliquot ($<N>=3$).

For 6 Loci analyzed independently per genome, (n)=6 and $<N>=6\times<g>$ and LLoD=3/6=0.5 genomes per aliquot (n=6). (n)=6 independent target loci per genome is easily obtained in a microarray test. In that important case, due to the multiple sampling (n=6) per genome, Equation #2 shows that the same 19/20 LLoD limit would be satisfied by a population average of 3/6=0.5 COVID-19 genomes per test. Thus, simultaneous measurement of (n)=6 independent target loci per COVID-19 test (each being an independent assay of the same genome) can be seen to reduce the LLOD 6-fold from about 3 COVID-19 genomes/assay to about 0.5 COVID-19 genomes/assay.

Multiple, "Built-In" Hybridization Probe Controls to Define "Threshold" Internally for Every Sample The widely used TaqMan qPCR technology, like all similar Molecular Beacon technologies, is based on deployment of PCR Primers (to amplify the RNA target) and the use of a Probe, to detect by hybridization, the PCR amplicon. Therefore, TaqMan Q-RT-PCR or its various Molecular Beacon equivalents are formally analogous to microarray hybridization analysis, which also relies on deployment of PCR amplification, then detection by hybridization.

Near the LLoD, the sensitivity of all nucleic acid tests (Q-RT-PCR and microarray hybridization included) become limited by the ability to distinguish "positive" signals from background, via the knowledge of a Threshold value to distinguish them from each other. In Q-RT-PCR, the analytical parameter of interest to define a "positive" signal is Cq. In microarrays, the analytical parameter is Relative Fluorescence Units (RFU).

For Q-RT-PCR, background discrimination is based on the setting of a "Threshold" which is based on accumulated historical data, or external "no template controls" run in the same batch, along with actual samples, but external to the sample aliquots themselves. Thus in Q-RT-PCR, in nearly all cases, including the current COVID-19 Q-RT-PCR assays, the crucial calculation of "positive" Cq values vs "negative" signals is performed by extrapolation of an external Threshold and not by direct reference to internal standards within the same sample aliquot (FIG. 3).

As such, the capacity to detect positive signals, near the LLoD, where Cq values are typically at or greater than 35, becomes subject to sample-to-sample variation extrapolated from other measurements, rather than from the sample itself. Such extrapolation is a source of systematic calculational error to reduce the statistical certainty of distinguish "positive" from "negative" signals.

In the present Example, the DNA microarray test performs 144 individual hybridization tests in parallel for each sample aliquot tested. For each of the (n)=6 hybridization tests being used to detect COVID-19, 3 different "specific" probes are used to detect the presence of each of the (n)=6 viral cDNA targets/genome, along with 3 "mismatched" hybridization probes for each of the 6 target loci.

Thus, for the seminal parameter of importance to LLoD in microarray analysis ("positive" probe hybridization) the threshold, which defines the signal as being distinct from a "negative" is obtained for every sample by direct experimental numerical comparison. This is achieved by comparing a set of three "specific" vs three "mismatched" probes vs 3 or more species specific probes (FIG. 2). This set defines the magnitude of a "negative" signal and thus the threshold, via multiple independent methods in the same sample. Consequently, the LLoD for the present DNA microarray based test is much less sensitive to systematic (sample-sample) error in Threshold determination because the crucial comparison between "positive" and "negative" signal is not based on extrapolation, but is based on direct experimental analysis within each sample.

Testing of the microarray in this Example is focused on demonstrating that the LLoD for COVID-19 analysis is superior by an order of magnitude relative to that obtained by any of the known Q-RT-PCR assays. Such demonstration is done by third party testing on matched sample aliquots near the LLoD for microarray analysis relative to multiple commercial Q-RT-PCR COVID-19 tests.

Lowest Limit of Detection

Figure 4A:
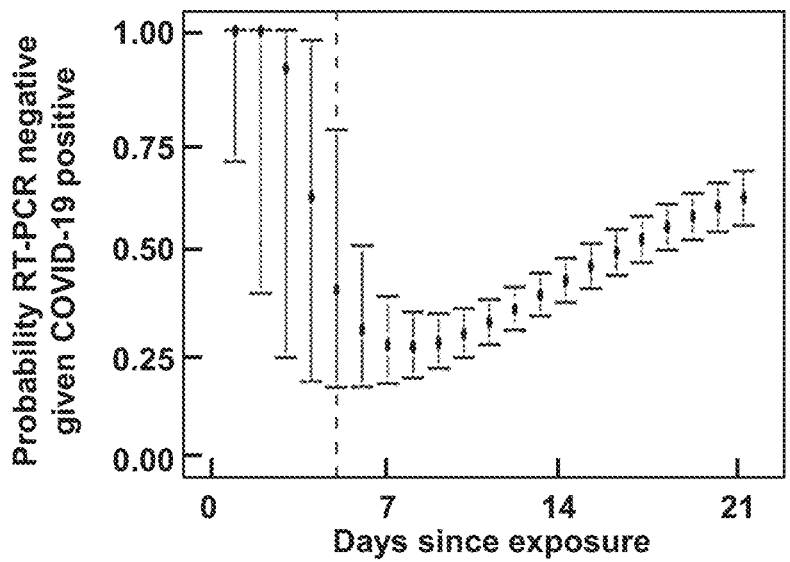
FIGS. 4A and 4B shows the probability of RT-PCR.
Figure 4B:
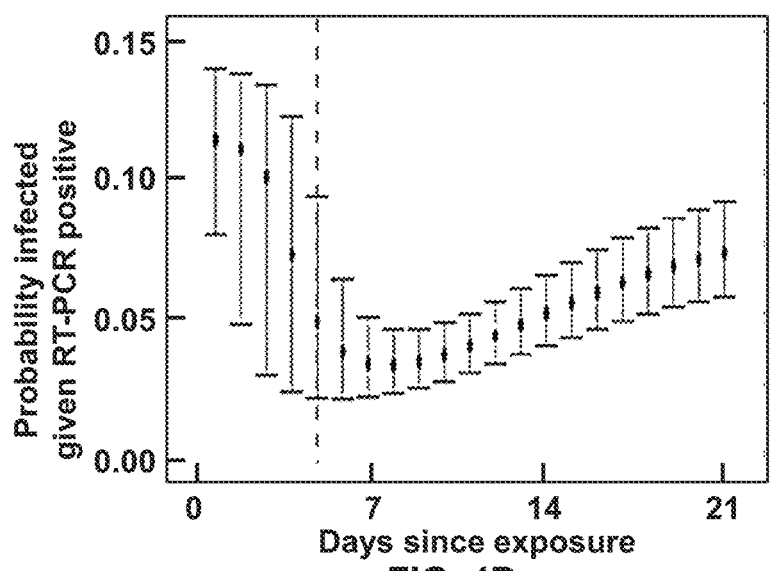

Q-RT-PCR technology has been widely implemented to test for COVID-19 among patients. Q-RT-PCR has been shown to have significantly high false negative rates in the range of 15% up to 48%, requiring re-testing (with the same level of inaccuracy). Therefore, it is challenging to detect low viral loads for patients who are asymptomatic or pre-symptomatic (3,4). FIG. 4A shows the probability of being RT-PCR negative among SARS-CoV2 infected patients and the FIG. 4B shows the probability of being infected, given RT-PCR positive (3)

False negative rates seen for Q-RT-PCR is due in part to the poor signal/noise ratio associated with Q-RT-PCR when it is implemented in the limit of low viral load and may be due to the nature of the principal Q-RT-PCR observable (Cq). It may also be due to poor control of RNA stability during and after collection.

Figure 3A:
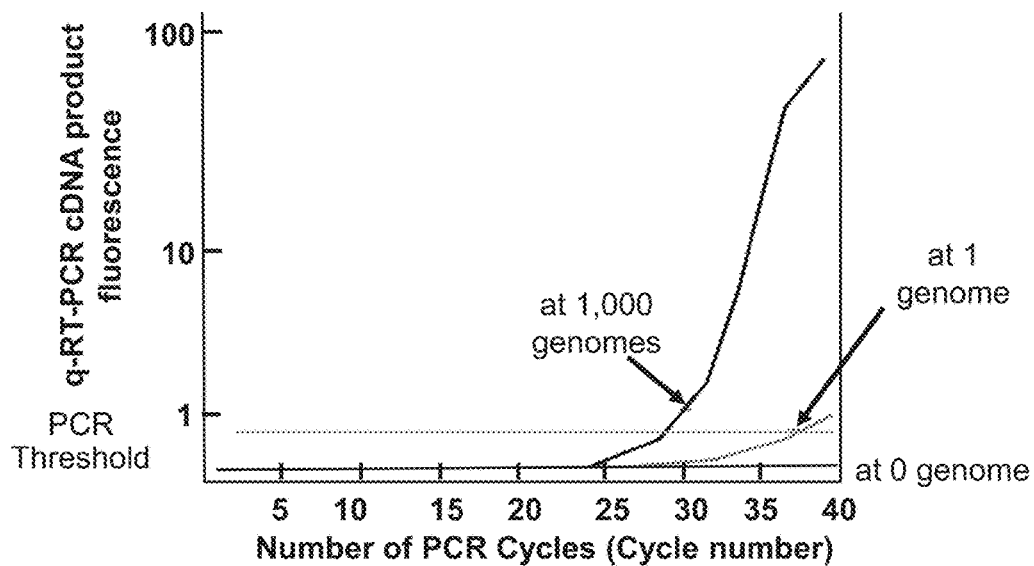
FIGS. 3A-3C shows signal to noise near the lowest limit of detection.
Figure 3B:
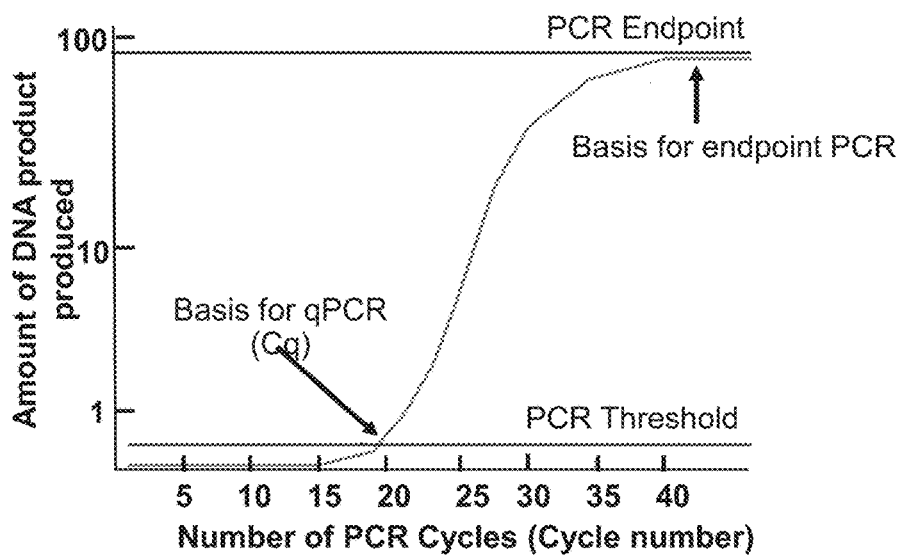
Figure 3C:
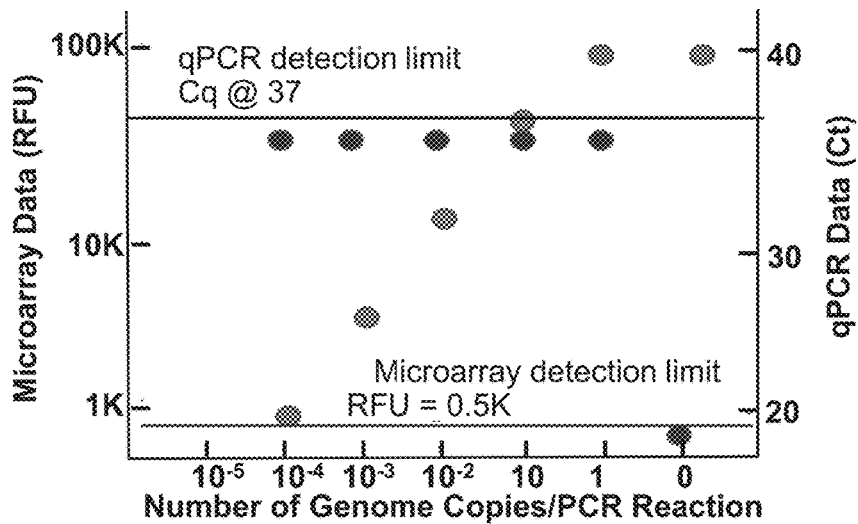

Cq refers to the point at which PCR amplification of the COVID-19 genome produces enough product to be resolved from background (FIG. 3B). In that limit, the signal for (1) genome (Cq=35) is not well-resolved from signal associated with (0) genomes at 40 Cq (FIG. 3A). While that distinction may seem esoteric, in the processing of low viral load samples (swabs or saliva) no more than 10 uL of the RNA extracted from such a sample can be introduced into the Q-RT-PCR reaction. The ability to resolve >1 genome from (0) genomes per PCR reaction is a requirement to set the useful LLoD. If as is ordinarily the case, the processed COVID-19 RNA delivered into Q-RT-PCR constitutes 5% of the viral RNA collected in the original sample to detect viral load of a hundred virion/swab, the LLoD must approach that nearly-theoretical detection limit of 1 genome/reaction, which may be more than 10× lower than the present LLoD for Q-RT-PCR.

The LLoD (Solution): DETECTX-RV, an Alternative Technology Platform. The problems associated with LLoD is well known in the detection of other pathogens. The nucleic acid-based microarray technology of the present invention obviates LLoD limitations. The nucleic acid-based microarray technology is based on the ability to mass produce DNA microarrays in a low cost a 1"×3" glass slide format.

Deployment of Tandem PCR Prior to Microarray Hybridization Increases the Difference Between "Positive" and "Negative" Hybridization Signal Amplitude By inspection of typical Q-RT-PCR data (FIG. 3) vs typical microarray data (FIG. 5) is can be seen that the signal size which distinguishes a "positive from a "negative signal in Q-RT-PCR (typically Cq=37 vs Cq=40) comprises a signal change that is generally small. For comparison, it can be seen that the signal size that distinguishes a "positive from a "negative" signal after tandem PCR then microarray hybridization (typically RFU 60,000 vs RFU=500) comprises a signal change that is almost 20× greater than that for Q-RT-PCR. Given that the ability to discriminate "positive" vs "negative" signal is the basis for the determination of LLoD for such testing, these data demonstrate that the signal strength (i.e. the positive-negative signal differential) is more than 10× greater for the present microarray technology, than is the case for Q-RT-PCR. Such representative differences are summarized in Table 3.

TABLE 3

Typical Microarray Hybridization Data vs Q-RT-PCR Data, Limit near 0

| Copy Number per reaction | Q-RT-PCR Signal (Cq) | Q-RT-PCR signal change relative to zero | Tandem PCR + Microarray Signal (RFU/1 000) | Microarray Signal change relative to zero |
|---|---|---|---|---|
| 100,000 | 30 | 20 | 60 | 59.5 |
| 10,000 | 34 | 16 | 60 | 59.5 |
| 1,000 | 27 | 13 | 60 | 59.5 |
| 100 | 30 | 10 | 60 | 59.5 |
| 10 | 33 | 7 | 60 | 59.5 |
| 1 | 36 | 4 | 60 | 59.5 |
| 0 | 40 | 0 | about 0.5 | 0 |

Epidemiological Pooling is Enabled by Tandem Endpoint PCR

Figure 5:
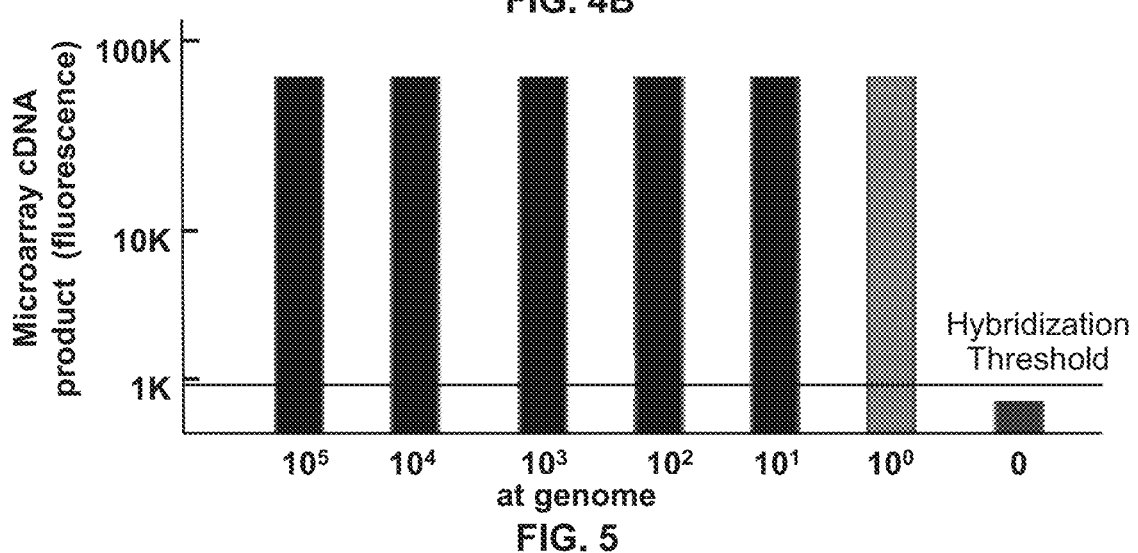
FIG. 5 shows that near the lowest limit of detection tandem PCR then microarray hybridization distinguishes "positive" from a "negative" signal relative to internal controls and "binary" over significant dilution.

FIG. 5 shows that an additional important attribute of the present invention is that the data of importance, i.e. a positive" vs a "negative" signal in a sample aliquot, is binary in the sense that positive signals quickly converge to a limiting hybridization signal value (about 60,000 in FIG. 5) over about a 4-log dynamic range. Such a binary signal saturation is intentional in the present invention and is a direct result of the fact that both of the tandem PCR reactions (RT-PCR #1 or PCR #1+PCR #2) have been designed to proceed to completion during their execution, and thus are each a type of "Endpoint PCR". The defining feature of Endpoint PCR (FIG. 3, right) is that the final amount of PCR product obtained after 30 or more cycles of PCR, often reaches a common plateau, independent of the amount of original pathogen input in a sample aliquot. This saturation is used to the benefit of the invention, to create a tandem PCR product, and in turn microarray hybridization data which remains constant (and large) over many factors of sample dilution.

A direct practical result of such saturation is that in many cases, such saturation allows samples to be pooled, as might be useful to expedite very large-scale epidemiological screening. See for instance, representative data as in FIG. 5, where it can be concluded that a sample containing 1,000 genome equivalents could easily be diluted with 10 samples, each lacking any pathogen, to yield a "pooled" sample, at 100 copies per aliquot in the present example, that would still be expected to demonstrate the presence of one or more contaminated samples within the pooled sample cohort.

Exemplary Microarray Test, to Detect COVID-19 and Other Respiratory Viruses Test Content In this example, COVID-19 is the primary analyte, plus multiple coronavirus targets [SARS-CoV, MERS-CoV, CoV 229E, CoV OC43, CoV NL63, CoV HKU1] plus Influenza [type A and B] as species variants (Table 4).

TABLE 4

DETECTX-RV Content. PCR Primers and Microarray Probes

| Viral Target | Target Sites/Virus | Microarray Probes | PCR Primers |
|---|---|---|---|
| SARS-CoV2 | N1, N2, N3 | 12 ($S_n$) 12 ($m_n$) | 3 sets |
| SARS-CoV | N, 1ab | 4 ($V_n$) | |
| SARS-CoV2 (Mutation) | S-D614G | 2 | 1 set |
| MERS-CoV | N, 1ab | 2 ($V_n$) | 2 sets |
| CoV 229E | N, 1ab | 2 ($V_n$) | 2 sets |
| CoV OC43 | N, 1ab | 2 ($V_n$) | 2 sets |
| CoV NL63 | N, 1ab | 2 ($V_n$) | 2 sets |
| CoV HKU1 | N, 1ab | 2 ($V_n$) | 2 sets |
| Pan Influenza A-type | M, NS1 | 2 | 2 sets |
| Pan Influenza B-type | M, NS1 | 2 | 2 sets |
| Internal RNA Control | RNAse P | 2 | 1 set |

The extra content available in the microarray format allows a very large panel of COVID-19 target sites (n=6) to be measured in parallel and in triplicate. The other six coronavirus targets and two influenza targets are included and are being used as both controls and as a universal screening tool for coronavirus and influenza.

Specificity

For each of the n=6 unique SARS-CoV2 target loci [N1, N2, N3, ORF1ab, RNA-dependent RNA polymerase (RdRP), E] there are (2) microarray probes ($S_n$), 12 specific probes in total, and 2 mismatched probes ($m_n$) for each, with 10% of intentional base mismatching (i.e. there are 12 mismatched specificity probes). Relative to the twelve COVID-19 specific probes ($S_n$), the 14 species specific controls ($v_n$) are distributed among other coronavirus (SARS-CoV, MERS-CoV, CoV 229E, CoV OC43, CoV NL63, CoV HKU1). In that format, a Positive COVID-19 signal for any one of the set of six loci, deemed valid if it possesses a fluorescence signal strength of >10× background (>10,000 RFU) while at the same time and in the same microarray, the mismatched specificity probe ($m_n$) generates a signal less than 2× background (<2,000 RFU).

DETECTX-RV Assay Improves the LLoD for Viral Detection

The serial application of two PCR Endpoint reactions (RT-PCR, with Asymmetric PCR) creates a type of analysis which is "Binary" in the sense that, an aliquot of specimen which lacks RNA produces no measurable hybridization signal, under conditions where any input with at least 1 genome copy produces a signal of nearly constant, very large signal amplitude. Such behavior is shown graphically in FIGS. 6A-6C, where during the course of microarray analysis only two classes of hybridization signal are detected namely, "Positives" resulting from samples with one or more copies of viral RNA target (producing fluorescent signals in excess of about 40,000 RFU) vs "Negatives" resulting from samples with (0) copies of viral RNA target, which produce no hybridization signal above background.

"Binary" Hybridization Principles

For LLoD analysis, the highly characterized COVID-19 standards (BEI) have been doped into N=30 separate pooled human nasal secretion samples (Lee Bioscience) along with 20 matched (negative) nasal secretion controls. Subsequent to RNA purification (Zymo kit) the resulting 50 RNA samples were subjected to PCR-Microarray.

Figure 6A:
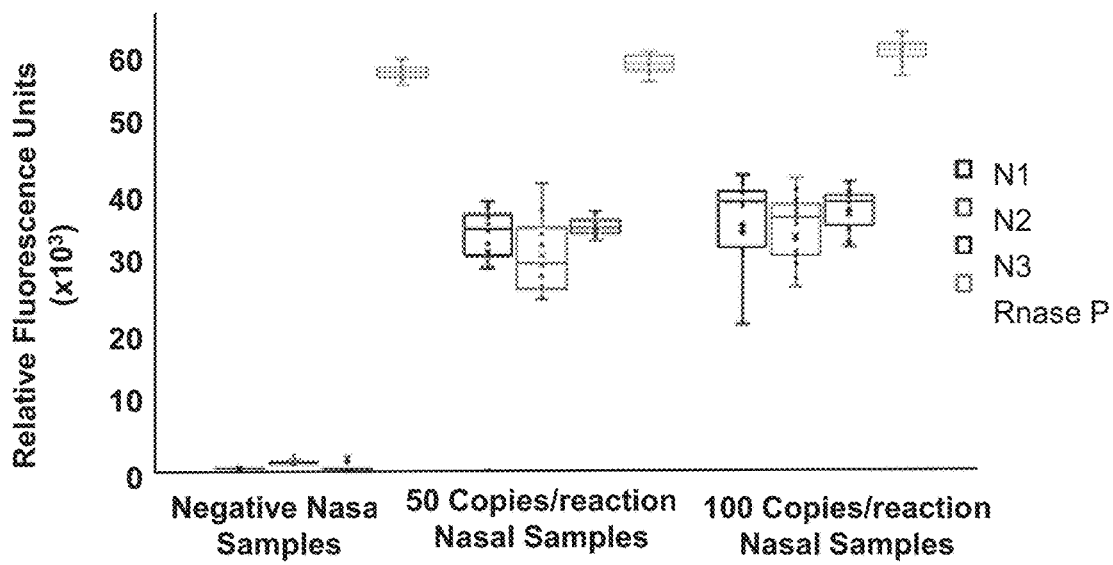
FIGS. 6A-6C shows relative fluorescent values for hybridization-based SARS-CoV2 detection in nasal samples.
Figure 6B:
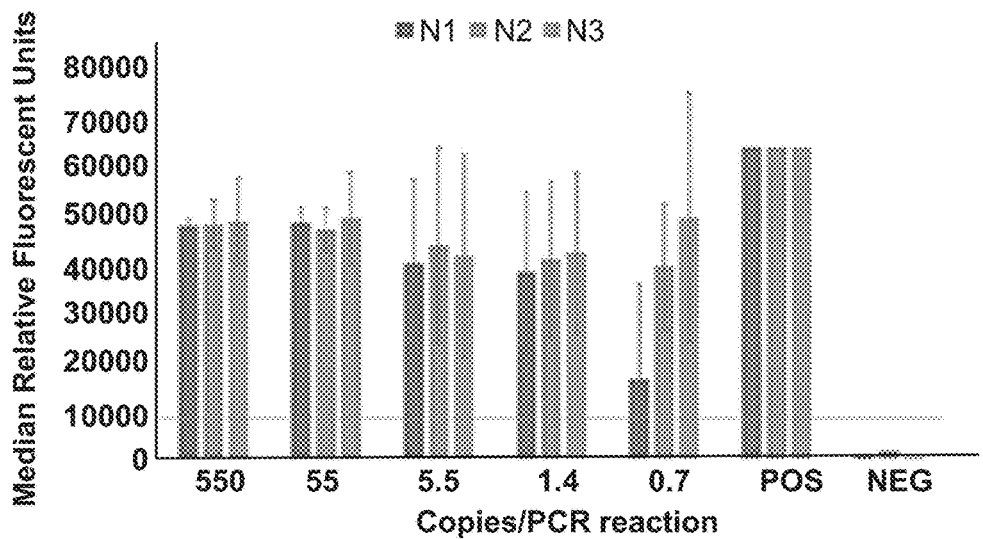
Figure 6C:
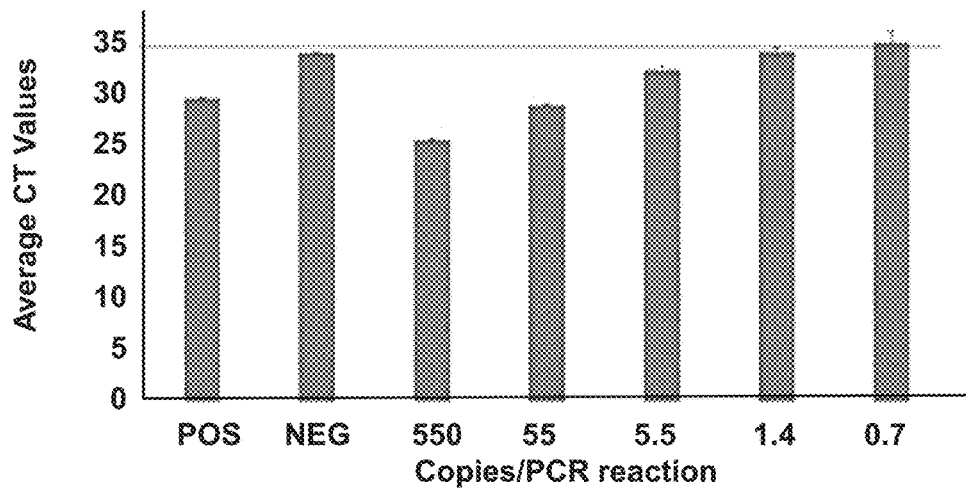

As seen from FIGS. 6A-6C, all three COVID-19 targets N1, N2, N3 and the human RNA internal control (P) each display clustered signals that are independent of viral load and which give a (+)/(−) ratio of about 20-110, which is approximately 20× the signal strength typically obtained by Q-RT-PCR in the same range of viral load (FIGS. 6B and 6C). That log increase in Signal-Background is central to the detection power of the DETECTX-RV technology. It should be noted that only 20% of the original 1 ml sample is subjected to RNA preparation, and in turn only 20% of that is used for microarray analysis. Thus, assuming 100% recovery from RNA extraction, the data shown in FIG. 6A comprise at most, signal from 2 copies and 4 copies per test (that is, ½5th of the original 50 and 100 copies doped into the pre-processed sample).

To confirm the intrinsic detection limit inferred from the LLoD analysis (FIG. 6A, <<5 copies/reaction) a simple dilution series was performed (FIGS. 6B, 6C), where well-characterized purified SARS-CoV2 RNA (ATCC/BEI) is titrated into PBS followed by DETECTX-RV analysis (FIG. 6B) or in parallel, Q-RT-PCR (FIG. 6C) using kits from RayBiotech (gift from RevolutionDx Labs, Dayton Ohio). In all cases, the data shown comprise n=10 determinations at each dilution level, measured in units of copies added/PCR reaction. The DETECTX-RV data (FIG. 6B) displays the "Binary" Characterization described above, especially for N2 and N3 SARS-COV2 target sequences. Within experimental accuracy, the measured signal strength does not diminish with dilution over the range from 550 to 0.7 genome copies/PCR reaction and retains a signal strength of about 20× to negative controls at (0) copy per reaction. Thus, consistent with the LLoD data (FIG. 6A) the detection limit for DETECTX-RV is <1 genome copy per reaction, becoming limited by the stochastic nature of such "copy counting" rather than by diminishment of signal strength as the 1 genome/reaction limit is approached. By comparison, signal from the N1 target diminishes marginally at the lowest level (0.7 copies/reaction). This observed N1 behavior at about 1 copy/reaction can be mitigated by increase of its PCR primer concentration.

Comparison to matched Q-RT-PCR data (N1 target) shows performance typical of all such Q-RT-PCR tests. The data obtained below 5.5 copies per reaction becomes indistinguishable from the detection threshold (Ct≈35) as defined by negative controls. Thus, the detection limit for DETECTX-RV (<1 genome copy per reaction, is more than 5× lower than that of the present Q-RT-PCR assay. A summary of COVID-19 hybridization statistics is shown in Table 5.

TABLE 5

COVID-19 Hybridization Statistics

| SARS-CoV2 Targets N1, N2, and N3 RNase P Control | | Average | Standard Deviation | Signal Divided by Negative Background |
|---|---|---|---|---|
| Negative Nasal Samples | N1 | 273 | 63 | — |
| | N2 | 1189 | 287 | — |
| | N3 | 1726 | 6601 | — |
| | RNase P | 56479 | 5531 | — |
| 50 copies/reaction Nasal Samples | N1 | 31199 | 11194 | 114 |
| | N2 | 30904 | 5507 | 26 |
| | N3 | 35181 | 1372 | 20 |
| | RNase P | 58614 | 1317 | — |
| 100 copies/reaction Nasal Samples | N1 | 34781 | 9650 | 127 |
| | N2 | 33740 | 8224 | 28 |
| | N3 | 37647 | 3459 | 22 |
| | RNase P | 60586 | 1604 | — |

Sample Pooling

Based on the substantial Signal/Background ratio obtained with DETECTX-RV near the LLoD (FIGS. 6A-6C), it was determined whether positive samples containing COVID-19 copies near the LLoD could be "pooled" with samples that were also in nasal matrix, but lacked COVID-19 RNA. As previously calculated, the benefit of such pooling appears to reach a maxim at N=10, especially in the limit of a low population infection rate (at 1%).

Such 10-fold pooling is shown in Table 6, wherein a single sample near the LLoD (50 copies/ml) is mixed with an equal volume of 9 samples lacking COVID-19 RNA, yielding a net viral load of about 5 copies/ml. As seen in Table 6, all 3 COVID-19 markers are detected in each of the pooled samples tested. The data show both of the important attributes of "Binary" sample Collection. The signal strength at 5 copies/mi, is about 30,000 RFU, which is identical within experimental accuracy to the 50 copies/ml sample used for pooling (Table 6) and in turn identical within experimental accuracy to identical un-pooled samples at 100 copies/ml (FIGS. 6A-6C). Both the unpooled sample (at 50 copies/ml) and the pooled sample (at 5 copies/ml) are near to the range where simple counting statistics begin to contribute to the data.

TABLE 6

Pooling of Contrived nasopharyngeal Samples

| Specimen No. | N1 | | | N2 | | | N3 | | | RNase P | | |
|---|---|---|---|---|---|---|---|---|---|---|---|---|
| | Pooled | Original (un-pooled) | RFU Difference | Pooled | Original (un-pooled) | RFU Difference | Pooled | Original (un-pooled) | RFU Difference | Pooled | Original (un-pooled) | RFU Difference |
| | | | | | | Copies/PCR | | | | | | |
| 1 | 28372 | 37941 | 9569 | 52162 | 37535 | 14627 | 54474 | 34875 | 19599 | 63708 | 59477 | 4231 |
| 2 | 1901 | 35502 | 33601 | 7051 | 34064 | 27013 | 43202 | 35692 | 7510 | 63822 | 58669 | 5154 |
| 3 | 7096 | 36504 | 29408 | 7772 | 30066 | 22294 | 491 | 34769 | 34278 | 63590 | 56065 | 7525 |
| 4 | 54097 | 35026 | 19071 | 52847 | 24796 | 28050 | 55732 | 37250 | 18481 | 63369 | 58476 | 4893 |
| 5 | 53035 | 34549 | 18486 | 55302 | 32452 | 22850 | 55422 | 34985 | 20437 | 63288 | 59814 | 3474 |
| 6 | 42780 | 29158 | 13622 | 53682 | 27965 | 25718 | 56635 | 35545 | 21090 | 63535 | 57633 | 5902 |
| 7 | 61250 | 38769 | 22481 | 58258 | 41392 | 16866 | 56104 | 37459 | 18645 | 63464 | 59929 | 3535 |

TABLE 6-continued

Pooling of Contrived nasopharyngeal Samples

| Specimen No. | N1 | | | N2 | | | N3 | | | RNase P | | |
|---|---|---|---|---|---|---|---|---|---|---|---|---|
| | Pooled | Original (un-pooled) | RFU Difference | Pooled | Original (un-pooled) | RFU Difference Copies/PCR | Pooled | Original (un-pooled) | RFU Difference | Pooled | Original (un-pooled) | RFU Difference |
| 8 | 57968 | 440 | 57528 | 56086 | 26561 | 29525 | 54116 | 33214 | 20901 | 63670 | 60348 | 3322 |
| 9 | 45702 | 31467 | 14236 | 56951 | 24634 | 32316 | 55258 | 34304 | 20954 | 63565 | 57664 | 5901 |
| 10 | 51537 | 32639 | 18898 | 55067 | 29572 | 25495 | 52673 | 33719 | 18953 | 63656 | 58067 | 5589 |

Test Content

The Problem: The platform limit of Q-RT-PCR can be multiplexed to resolve four analytes in parallel, based on the four principal emission channels on most devices including CDC, LabCorp, Quest (N1, N2, N3, P). This limit may be exceeded as evidenced for Abbott (RdRp, N), Cepheid (E, N2, P) and Eurofins (N,P). However, the "maxed" capacity suggests that the known Q-RT-PCR assays will not be able to accommodate additional testing complexity, such as might arise if alternative COVID-19 clade variants were to emerge. A recent publication has suggested however, that a stable variant has been detected comprising a mutation in the spike protein S-D614G, which has been hypothesized to be more virulent.

Based on test content capacity alone, detection of both SARS-CoV2 and the S-D614G spike protein mutant will prove difficult to detect on the same q-RT-PCR test. Thus Q-RT-PCR might not be useful as a tool to screen for both variants.

The Solution. The process by which new coronavirus content can be added to DETECTX-RV is very efficient. It is based on the robust probe capacity of the arrays (144) and on the highly standardized methods of PCR primer design and microarray probe design (at one base pair hybridization specificity). As an example, the presumed importance of the S-D614G mutant was only recently published (Apr. 29, 2020). The variant comprises a SNP G-A transition converting Asp to Gly. New probes specific for the wild type and new variant along with a set of mismatched control probes were designed within a day, and submitted for fabrication, and were completed May 11, 2020. Microarray fabrication with these new probes was added to an otherwise identical DETECTX-RV microarray and were completed on May 15, 2020. In parallel, a pair of test amplicons were designed and produced by SGI methods possessing the wild type and new COVID-19 SNP. In parallel, 4 candidate PCR primer pairs have been designed. Probe selectivity was confirmed with the SGI template, and in parallel, inclusivity and exclusivity confirmed experimentally with the full panel of coronavirus research standards in-house from ATCC-BEI.

Specificity

The Problem. While Q-RT-PCR can deliver adequate test specificity it is well-known that the TaqMan probe-template interaction does not adequately resolve SNPs in many cases (6.7) due to the fact that in a TaqMan assay, primer binding, probe binding and the Taq exonuclease activity must all occur at the same time and thus cannot be optimized independently. The problem is exacerbated in the present case (S-D614G) because the SNP generates a "run" of 3G's, which are difficult to accommodate.

The Solution. In this respect, the microarray technology of the present invention is beneficial as it has the capability of routinely generating "all or none" SNP discrimination due to uncoupling of probe binding from PCR. Further, a separate washing step is included for improved specificity. Here, a first set of hybridization tests are shown on a set of probe candidates to detect and resolve the SNP variants which define SARS-CoV2 Clade variation at the Spike protein (D-614G). Methods of probe design were used. Array manufacture was performed in the standard 12-well format, but all other aspects of probe formulation and deposition were identical to those deployed in the 96 and 384 well Plate formats. Six PCR primer pairs were designed and optimized for the standard Tandem PCR (RT-PCR+Labeling PCR) amplification process. Since both "sense" and "antisense" probes were tested, different asymmetric Labelling PCR reactions were deployed, which differed in which of the 2 PCR primers had the 5'-CY3 label in the second PCR reaction (labeling PCR).

Hybridization in 12-Well Slide Format

To evaluate hybridization feasibility in 12-well slides, 50 probes candidates were printed on the slides to detect and resolve the 2 SNP variants which define SARS-CoV2 Clade variation at the Spike protein (D-614G). Proprietary methods of probe design developed at PDx (PathogenDx. Scottsdale, AZ) were used in the design. All aspects of probe formulation and deposition were identical to those used for 96-well and 384-well plates.

A PCR primer pair was designed and optimized for standard (tandem) 2-Step RT-PCR and labeling PCR. Since both "sense" and "antisense" probes were tested, different asymmetric labelling PCR reactions were deployed, which differed in which of the 2 PCR primers had the 5'-CY3 label. The template for this study was a pair of synthetic templates. Each template contained the defining SNP (A or G) embedded in the Wuhan reference sequence for the Spike protein.

Subsequent to standard hybridization and washing in the slide format (similar to 96-well and 384-well plate format), the two SNP variants were resolved with signal (relative fluorescence units, RFU) strength differences in the range from 15-40 (see Table 7) which approaches the theoretical limit for resolving SNPs by hybridization. For expediency, two "Sense Strand" and Two "Antisense Strand" candidates from the probe set were chosen for inclusion in the 384-well Plate "Mini-RV" print content. All four of these probes displayed very good sensitivity and SNP specificity. This Example conforms that the present tandem PCR (RT-PCR+ labeling PCR) reaction coupled to microarray hybridization can cleanly resolve two SARS-Cov2 variants which differ by a single RNA base change the Spike protein.

Scalability

The Problem. Scalability of test capacity is a huge challenge particularly during a pandemic. Assuming 1000 COVID-19 test sites throughout the US, this would require the ability for each site to support at least 10.000 tests/shift/site. At present Roche and Abbott lead the pack with Q-RT-PCR capacity, amounting to 250-900 tests/shift and 150 tests/shift respectively. This microarray technology supports population scale nucleic acid screening.

The Solution. In the present deployment of DETECTX-RV, the core array format (12×12) is deployed as 12 tests per slide. Eight such slides are routinely processed in parallel with ordinary fluid handling, thus allowing multiples of 96 tests in parallel.

TABLE 7

Preliminary Spike Hybridization on Multiple Probes Reveals SNP Resolution

| | 614 "D" Gene fragment used as template for PCR PCR primer | | | | | | 614 "G" Gene fragment used as template for PCR PCR primer | | | | | | Summary | | |
|---|---|---|---|---|---|---|---|---|---|---|---|---|---|---|---|
| | Set 1 | Set 2 | Set 3 | Set 4 | Set 5 | Set 6 | Set 1 | Set 2 | Set 3 | Set 4 | Set 5 | Set 6 | Average "on" signal | Average "off" signal | Specificity ratio |
| Negative control probe | 818 | 1378 | 1306 | 933 | 1079 | 1414 | 1353 | 1667 | 1754 | 681 | 1182 | 1506 | N/A | 1256 | N/A |
| Universal sense probe (1.1) | 62680 | 62844 | 62585 | 62792 | 62846 | 62966 | 62692 | 62739 | 59582 | 62912 | 62980 | 62382 | 62500 | not shown | N/A |
| 614D sense probe (1.1)* | 44032 | 43713 | 27743 | 40724 | 43321 | 40221 | 937 | 992 | 785 | 1070 | 788 | 1117 | 39959 | 948 | 42:1 |
| 614G sense probe (1.1) | 2910 | 2293 | 1344 | 4040 | 2936 | 2742 | 57171 | 54694 | 41786 | 51479 | 52386 | 47918 | 50906 | 2711 | 19:1 |
| 614D sense probe (1.2) | 32106 | 26908 | 15862 | 26590 | 29157 | 29425 | 782 | 464 | 244 | 464 | 493 | 436 | 26675 | 480 | 32:1 |
| 614G sense probe (1.2)* | 1684 | 1238 | 284 | 743 | 1130 | 897 | 38030 | 40558 | 30402 | 38493 | 38089 | 38909 | 37413 | 996 | 38:1 |
| 614D sense probe (1.3) | 23244 | 26480 | 9676 | 27537 | 26787 | 19197 | 734 | 691 | 782 | 704 | 842 | 668 | 22153 | 737 | 30:1 |
| 614G sense probe (1.3) | 1663 | 1335 | 1372 | 1592 | 1778 | 1584 | 12536 | 13520 | 7302 | 13813 | 12849 | 11782 | 11967 | 1554 | 8:1 |
| 614D sense probe (1.4) | 62650 | 62275 | 51469 | 62764 | 62758 | 60077 | 12087 | 14478 | 7047 | 12071 | 11956 | 9954 | 60332 | 11266 | 5:1 |
| 614G sense probe (1.4) | 4570 | 4528 | 2530 | 3930 | 4856 | 4415 | 62112 | 61074 | 46297 | 55602 | 53042 | 55918 | 55674 | 4138 | 13:1 |
| Negative control probe | 1084 | 1319 | 1276 | 996 | 1565 | 1356 | 1018 | 1417 | 1767 | 675 | 1124 | 1918 | N/A | 1293 | N/A |
| Universal sense probe (1.1) | 62556 | 62369 | 62425 | 62448 | 62356 | 62579 | 62441 | 62311 | 62164 | 62398 | 62360 | 62466 | 62406 | not shown | N/A |
| 614D sense probe (1.1)* | 62556 | 62369 | 62390 | 62448 | 59860 | 60257 | 11481 | 14199 | 15072 | 11668 | 12673 | 14795 | 61646 | 13314 | 5:1 |
| 614G sense probe (1.1)* | 2025 | 2770 | 2440 | 2719 | 2387 | 3645 | 62441 | 62311 | 62164 | 62398 | 62360 | 62466 | 62356 | 2664 | 23:1 |

TABLE 7-continued

| | | | | | | | | | | | | | | | | |
|---|---|---|---|---|---|---|---|---|---|---|---|---|---|---|---|---|
| 614D sense probe (1.2) | 44098 | 44683 | 43784 | 47299 | 43836 | 43526 | 5681 | 2628 | 3668 | 1717 | 2241 | 2750 | 44538 | | 3114 | 14:1 |
| 614G sense probe (1.2) | 1319 | 1444 | 1352 | 1516 | 1393 | 1071 | 50541 | 52272 | 46864 | 52110 | 46551 | 49087 | 49571 | | 1349 | 37:1 |
| 614D sense probe (1.3) | 25571 | 28872 | 21946 | 29427 | 25272 | 26117 | 1474 | 1745 | 2490 | 1749 | 1821 | 2893 | 26200 | | 2029 | 13:1 |
| 614G sense probe (1.3) | 1208 | 1513 | 1042 | 1183 | 1297 | 1300 | 25524 | 26758 | 20659 | 27328 | 28548 | 34719 | 27256 | | 1257 | 22:1 |
| 614D sense probe (1.4) | 62556 | 62369 | 62425 | 62448 | 62356 | 62579 | 37925 | 37274 | 30141 | 36901 | 34103 | 37302 | 62455 | | 35607 | 2:1 |
| 614G sense probe (1.4) | 4597 | 7848 | 4909 | 5042 | 5793 | 6225 | 62441 | 62311 | 62164 | 62398 | 62360 | 62466 | 62356 | | 5736 | 11:1 |

*Currently on 12-probe 384-well array

At present, coupled to ordinary 96-well magnetic bead RNA purification, the hybridization steps are in all cases faster than the RNA preparation. Automation and system integration are deployed with industry leading partners. Technologies, which have been integrated for DETECTX-RV (FIG. 7A) are each already approved for invitro diagnostic (IVD) use for workflow required for DETECTX-RV testing viz, RNA preparation via magnetic beads ("Tecan", Tecan Trading AG) RT-PCR and PCR (Thermo) Open Architecture, Ambient Temperature Binding and washing (Tecan) and microarray imaging (Sensovation). The AUGURY software discussed in Example 1 was developed at PathogenDx and has all functionalities in place to support DETECTX-RV data acquisition and analysis and has been modified to process both 96-well and 384-well plates. Its capacity to manage and upload such data into a secure Cloud Network is also complete and fully validated for RUO use. AUGURY is in place among 100 Regulated Testing Labs. Additionally, AUGURY may be operated on a customer's slide imager or computer. This is an advantage as it obviates the requirement for uploading large size images to the cloud which may be time consuming. Smaller size dot score files and output reports may continue to be uploaded to the data repository in the cloud.

Example 3

DETECTX-RV-V2

The full content of the original DETECTX-RV assay is described in Example 2 and Table 4. Table 8 shows a variant (DETECTX-RV-V2) of that Pan Coronavirus format. It is based on SARS-CoV2 analysis at (N1,N2) as in the original assay and differs in the inclusion of 2 new microarray probes and an additional RT-PCR primer pair to interrogate the recently described novel S-D614G mutant (5) in the same assay.

TABLE 8

Streamlined COV1D-19 Analysis, DETECTX-RV-V2

| Row # | Viral Target | Target Sites/ Virus | Microarray Probes | PCR Primers |
|---|---|---|---|---|
| 1 | SARS-CoV2 (hCoV-19) | N2 | 2 | 1 set |
| 2 | SARS-CoV | N2 | 1 | |
| 3 | hCoV-19/pangolin (groups 1 and 2) | N2 | 1 | |
| 4 | hCoV-19/bat/Yunnan/RaTG13 (2013) | N2 | 1 | |
| 5 | Bat_SARS-like_CoVZC45 and XC21 | N2 | 1 | |
| 6 | hCoV-19/bat/Yunnan/RmYN02 | N2 | 1 | |
| 7 | SARS-CoV2 (hCoV-19) | N1 | 2 | 1 set |
| 8 | SARS-CoV2 (Mutation) | S-D614G | 2 | 1 set |
| 9 | Internal Control | RNAse P | 1 | 1 set |

Figure 7A:
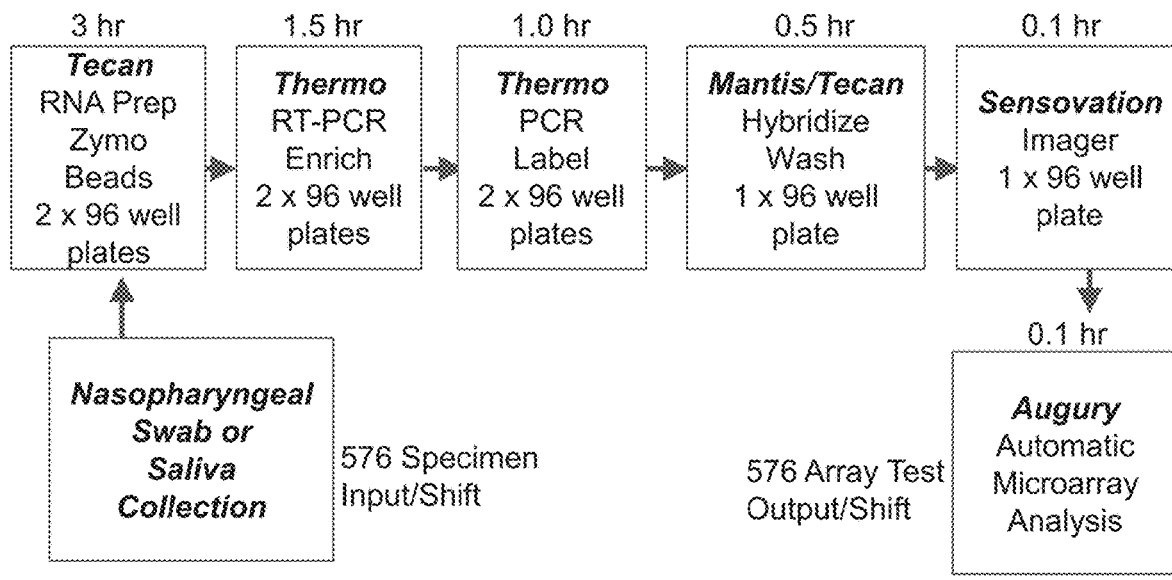
FIGS. 7A-7C shows the DETECTX-RV-V2 platform.
Figures 7B, 7C:
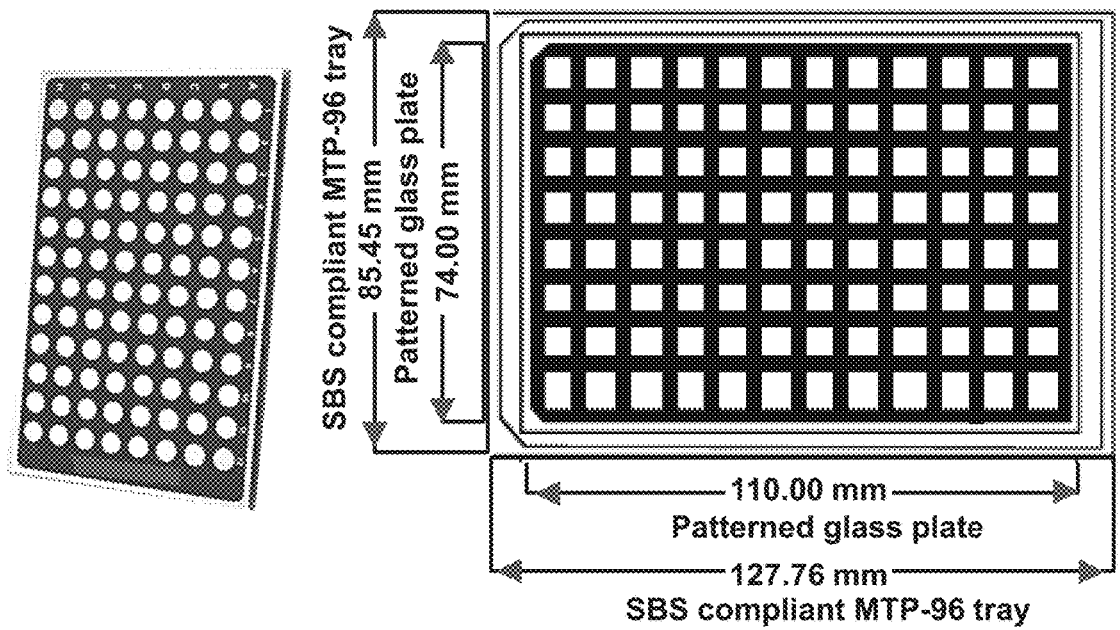

The streamlined DETECTX-RV-V2 assay deploys 12 microarray probes, which when printed in N=12 multiplicity, become a highly redundant 144 probe array suitable for printing in the present 12-well slide format, and in the more automation-friendly 96-well Society for Biomolecular Screening (SBS) format (FIGS. 7B-7C). DETECTX-RV-v2 additionally contains a set of 4 other coronavirus (rows 3-6, Table 8), which have been previously identified by cluster analysis (GISAID—Initiative) as being the closest SARS-CoV2 homologues. These targets provide functionally relevant "species specificity" controls that help confirm that the signals obtained from SARS-CoV2 (COVID-19) or its S-D614G mutant are specific. It must be noted that although the DETECTX-RV-V2 test variant is simpler in design and execution than the original DETECTX-RV prototype (Table 4) its test content is at least 3× greater than any Q-RT-PCR assay.

Structure of the 96-Well Format for DETECTX-RV-V2

The 96-well late format (FIGS. 7B-7C) for COVID-19 testing, developed by Schott glass (NEXTERION) uses epoxy-silane coated, Teflon masked slides. They serve as an excellent substrate for microarrays. The 96-well plate SBS format is better suited for large scale, COVID-19 testing. Although the plate format is slightly more expensive than the slide format at small scale, the COGS for arrays in plates are less than on slides, at production >714,240 arrays/month.

The 96-well DETECTX-RV-V2 workflow has been integrated into off-the-shelf Tecan automation (Freedom Evo-2 100 Base) beginning with magnetic bead-based RNA extraction (Zymo) and ending with automated microarray hybridization and washing. The intervening PCR reactions are mediated by Tandem Thermo-ABI cyclers and imaging is performed on a Sensovation CCD based imager. Data generated is fed into AUGURY software discussed in Example 2 for autonomous plate reading, microarray data compilation and analysis.

The major strength of the DETECTX-RV-V2 technology is its large-scale public health application in any setting including at-home, at-work, healthcare institutions and transportation hub sample collection for diagnosis and detection of active and asymptomatic individuals. Current use of nasopharyngeal swabs is not suitable for such collection, due in most cases to the difficulty of sample collection and the instability of RNA on such swabs, using the currently used transport media of the day.

High Throughout Automation

The Tecan robot or other commercial equivalents can process multiple 96-well plates in parallel, thus sample throughput of (6) 96-well microarray plates/shift is possible (FIGS. 7A-7C). Upon transition to a 384 well format, the Tecan and related commercial robots can be reprogrammed for the higher-throughput 384-well format.

DETECTX-RV-V3

Deployment of DETECTX-RV-V2 enables 12,000 arrays/day in a 96-well array plate format providing a 360,000 arrays/month capacity. While DETECTX-RV-V2 will retain its 12×12=144 element structure (in 7 mm wells), the 384-well structure (3.5 mm wells) will accommodate a 6×6=36 probe array. The core probe content for SARS-CoV2 (N1, N2)S-D614G variant and Human RNase-P (P) internal control can all be included along with SARS CoV and MERS CoV as species specificity controls as 12 probes, printed in triplicate. The DETECTX-RV-V2 format may be modified to include pan Influenza A and Influence B probes to generate a targeted pan-respiratory virus test (DETECTX-RV-V3). The DETECTX-RV-V3 format has substantial benefits since it readily adapts to increase system testing throughput to more than 2,104 tests/shift, which exceeds existing commercial testing technologies and at the same time achieves a 3× reduction in test cost, from manufacturing & reagent economies of scale.

Manufacturing

DETECTX-RV-V2 & DETECTX-RV-V3 are each manufacturable in 24 hours with a single printer in batches of 62 plates, comprising 6,000 arrays/day (96-well plate) 24,000 arrays/batch/day (384-well plate). Each printer completes two batches per 24-hour day.

Example 4

Development of a Fully Featured Pan-Coronavirus-Influenza Test

DETECTX-RV System Architecture.

The entire suite of Pan-Coronavirus content (Table 4) has been designed, developed and manufactured and is resident in the DETECTX-RV version of the assay. The full Pan-Corona Respiratory Virus content suite is validated using standardized viral reagents from ATCC-BEI, which are spiked into the same matrices (nasal and saliva). The test format employed for such expanded validation uses the LLoD and N=30 repeats testing protocols.

Figure 8:
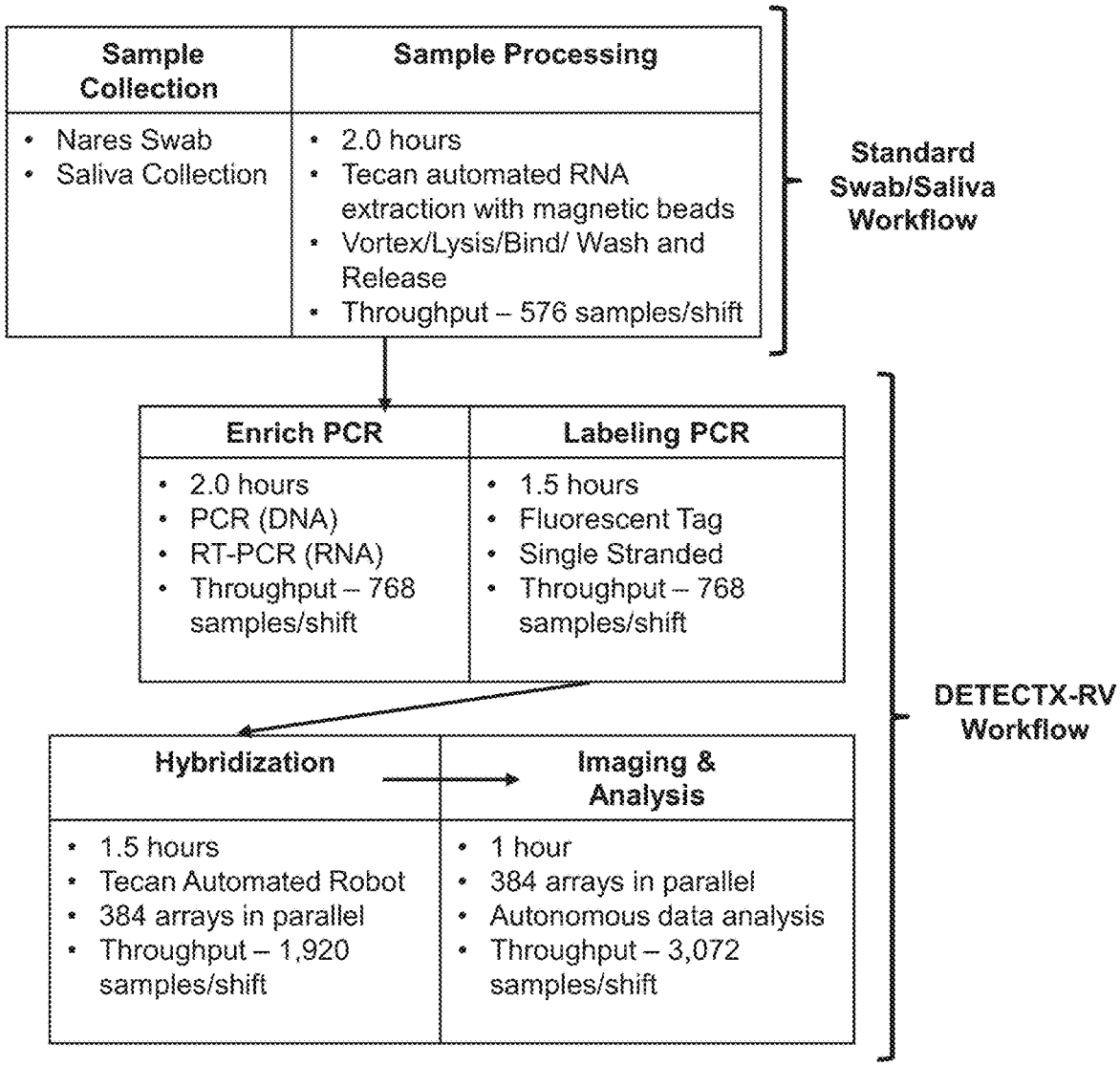
FIG. 8 shows a DETECTX-RV pan respiratory pathogen diagnostic platform roadmap.

Early stages of COVID-19 clade development are in progress, which could be selected for stable changes in environmental durability, virulence or acute symptomology. PathogenDx monitors such data on a daily basis. At such time that solid evidence emerges for development of stable COVID-19 clade variants, new content was immediately added to DETECTX-RV (FIG. 8).

The process by which new coronavirus content can be added to DETECTX-RV is very efficient due to the robust probe capacity of the arrays (144), and the highly standardized methods of PCR primer design and microarray probe design (at one base pair hybridization specificity).

If a new SARS-CoV2 subtype were identified in the literature, based on one or more regions with local sequence change in one of the domains already Interrogated in DETECTX-RV (N1. N2 or N3), PCR primer design would not change. The only modification is design of one or more new probes specific for the new variant added to the existing DETECTX-RV microarray. In parallel, a test amplicon would be produced by ordinary SGI methods possessing the new COVID-19 sequence markers. Probe selectivity would be confirmed with the SGI template, and in parallel, inclusivity and exclusivity confirmed experimentally with the full panel of coronavirus research standards in-house from ATCC-BEI.

On the other hand, if the new content were in regions not yet being interrogated, the process remains the same, with the added task of designing and fabricating a primer pair to amplify the COVID-19 region of interest. The primer design process occurs in parallel to probe design with a 2-week turnaround for the desired DETECTX-RV test modification.

DETECTX-RV Enhanced Content (DETECTX-RV-V2)

The DETECTX-RV assay coupled to nasopharyngeal swab collection is presently being launched into CLIA certified labs for human diagnostics screening. Its oligonucleotide probe content (Table 4) comprises a 12×12 array, at present, with RNA targets comprising sites within a set of 10 respiratory viruses and a human RNA control (RNase P). Of these, SARS CoV2, SARS-CoV and SARS COV2 (mutation) support pandemic testing. The remainder of the test content (other coronaviruses and Influenza) are present as probes within the present 12×12 array and used as specificity controls.

In the Tandem, Asymmetric, Two-Step implementation of the present invention, DETECTX-RV workflow begins with viral RNA that had been extracted from a nasopharyngeal Swab Sample followed by two Endpoint PCR reactions in tandem. The first PCR, an "Enrich" PCR (FIG. 9) performs (N=4 multiplex) endpoint RT-PCR reactions on COVID-19 RNA to generate a set of primary DNA amplicons, each directed to one of several important regions of the COVID-19 genome N1, N2, N3 (Table 4). The primary DNA amplicon product serves as the template for a second PCR reaction The second PCR reaction is set-up using CY-3 fluorescent labeled primers ("Labelling" PCR) in 4-fold or 8-fold excess over unlabeled reverse primers which are not dye labelled. The second PCR is set-up as asymmetric PCR—a specialized version of endpoint PCR and produces a large excess of the CY-3 dye tagged strand of interest. The second PCR product is single stranded and therefore can be used directly for microarray hybridization without clean-up or thermal denaturation. This technology is robust for large scale respiratory virus screening of clinical samples in at-home, at-work and healthcare institutional settings.

The DETECTX-RV workflow shown in FIG. 9 can generate 576 samples-worth of microarray data/shift; which can be doubled with doubling up-front automation of RNA extraction. The data is analyzed autonomously via AUGURY software.

Example 5

Sample Collection

The COVID-19 pandemic has confirmed what many had known from field study of zoonotic disease: namely that the "Viral Transport Media" (VTM) used to collect virus on swabs, are poor stabilizers of viral RNA. To address this, a novel chemical stabilizer from GENTEGRA LLC (GTR) as well as inexpensive polymer stabilizers (PVS) along with well-known lab-based RNAse inhibitor (RNA-Shield) are used to allow for stable field collection of respiratory virus samples on swabs without refrigeration. Stabilized swab collection (COVID-19, Coronavirus and Influenza stability over one week at 30° C.) enables better clinical collection of nares swabs and saliva fluid also enables at-home nasal swab collection for population scale screening in centralized labs. Emphasis is to support very large-scale clinical collection (nares) plus at-home (lower nasal) collection.

Modified Swab Design

A modified swab design that includes chemical stabilizers of viral RNA initiated in collaboration with GENTEGRA LLC enables samples to be transported at ambient temperature. This improved collection design may be employed with the DETECTX-RV-V2 platform to support very large-scale clinical collection and at-home collection.

Modified Sample Processing Hardware and Software for System Integration

The technologies for integration into DETECTX-RV are approved for in vitro diagnostics use for the type of workflow required for DETECTX-RV testing—RNA preparation via magnetic beads (Tecan) RT-PCR and PCR (Thermo Fisher Scientific), open architecture, ambient temperature binding and washing (Tecan) and microarray imaging (Sensovation AG). The AUGURY software has all functionalities in place to support DETECTX-RV data acquisition and analysis. Its capacity to manage and upload such data into a secure cloud network is also complete and fully validated for RUO use.

Modified Saliva Collection by Chemical Stabilization of Viral RNA.

A "mouthwash" based saliva collection technology (QUIKSAL) is employed for collecting saliva samples. In a separate set of studies, 200 nasopharyngeal swabs are collected per the standard RevolutionDx and Lucid Lab protocols along with matched QuiKSal mouthwash collection from the same individual (400 matched swabs and Saliva). The swab and half of the mouthwash is analyzed in accordance with standard Q-RT-PCR workflow, while the remainder of the mouthwash was split and shipped at ambient temperature and −20 C in transport medium for analysis at PathogenDx on the DETECTX-RV-V2 microarray. The samples analyzed at PathogenDx have no associated personal identifiers or medical information other than the Cq values obtained from Q-RT-PCR testing at RevolutionDx.

Feasibility of Sample Pooling from Swabs and Saliva for Population Scale Screening Pooling of swab and saliva samples among pre-symptomatic individuals is a powerful tool to enable contact tracing. This is established by the findings that demonstrated pooling of specimens with the highest COVID-19 load from at least 64 nasopharyngeal swab samples via Q-RT-PCR is free of false negatives when the input (positive) sample used for pooling is a clear, "strong positive" and characterized by a Cq value <30 (FIGS. 3A-3C, 4A and 4B). Specifically, the threshold for determination of "COVID-19 Positive" is Cq<35 for most Q-RT-PCR assays. At this threshold, the intrinsic "False Negative" rate is about 20% to about 40%.

Sample pooling is a powerful public health screening tool. However, for the most useful pooling levels (N≥10) for many COVID-19 positive samples (those with Cq >30) Q-RT-PCR generates an unacceptably high "Pooled False Negative Rate". If that occurs, sample pooling in combination with Q-RT-PCR would not be adopted as a routine public health or industrial hygiene tool.

As shown in Table 6, data with contrived nasopharyngeal samples near the LLoD (at 50 genome copies/ml) suggests that DETECTX-RV may have the sensitivity needed to enable expanded pooling (N=10) with a reduced risk of false (pooled) negatives. Therefore, contrived samples are used to refine the sensitivity and specificity of N=10 pooling similar to that shown in Table 6, with technical emphasis on increasing cycle number from 30-35 in the Enrichment RT-PCR reaction. Pooling is then performed prior to RNA extraction, on the same swab and saliva samples freshly obtained. Raw samples (unstabilized swabs or stabilized swabs or stabilized saliva) are measured immediately by both DETECTX-RV-V2 and by Q-RT-PCR. Immediately upon identification of "true "positives", the set is divided into quartiles, based on the semi-quantitative Q-RT-PCR data (that is, Very High. High, Medium. Low) for viral load based on the Cq value associated with each. 20 uL of each such positive sample are immediately mixed with 20 uL of 9 of the many "negatives" to yield 200 μL of pooled sample and transferred directly into Zymo RNA lysis buffer for freezing prior to RNA extraction. This approach permits the nasopharyngeal swab or saliva studies to yield up 40-80 unique N=10 pooled samples, where data for each pooled sample (Table 8) is directly compared to the "positive" from which it originated.

Example 6

Analysis of Clinical Samples (Nasopharyngeal Swabs)

Clinical Sample Evaluation:

PathogenDx received 50 blinded nasopharyngeal swab samples in flash frozen Abbott Transport Media from Testing Matters Laboratory (TM Labs—Sunrise, FL, CLIA certified) to evaluate the performance of the PathogenDx DETECTX-RV assay in comparison to the FDA-EUA approved Abbott Real-Time SARS-CoV2 qPCR assay.

Each of the 50 samples were collected on the same day/same time, one sample was collected from the right nostril and one from the left nostril. The two separate samples (each separately labelled and stored identically in transport medium) were taken back to TM Labs where one sample was flash frozen and shipped to PathogenDx and the second sample was processed and screened according to the Abbott Real-Time SARS-CoV2 qPCR assay FDA-EUA protocol. The results from the Abbott testing at TM Labs were shared after PathogenDx had screened the 50 samples using the DETECTX-RV assay.

The 50 matched samples that were sent to PathogenDx, arrived frozen on dry ice and were stored at −80° C. until use. The samples were thawed on ice and 400 μL of the 2 mL sample was used as the input for the Zymo Quick-DNA/RNA Viral MagBead purification. The purified RNA was then used to screen for SARS-CoV2 in these patient samples according to the PathogenDx product insert using the Promega AccessQuick RT-PCR system coupled to the PathogenDx PCR and the corresponding microarray test.

There were 50 total samples tested as well as the PathogenDx external positive and negative controls. Table 9 shows the results of the analysis.

ments were repeated for all 9 samples of the samples that were identified as positive using the DETECTX-RV assay.

Run 2—The DETECTX-RV assay demonstrated 86% concordance (6 DETECTX-RV/7 Abbott) with the samples called positive (N=7) using the Abbott system. The one

TABLE 9

Comparison of Q-RT-PCR and DETECTX-RV analysis

| Sample ID | Abbott Q-RT-PCR COVID-19 Ct Value | Abbott Q-RT-PCR COVID-19 POS/NEG | PathogenDx DETECTX-RV SARS-COV-2 (Run 1) RFU Value N1 | N2 | N3 | POS/NEG | PathogenDx DETECTX-RV SARS-COV-2 (Run 2) RFU Value N1 | N2 | N3 | POS/NEG |
|---|---|---|---|---|---|---|---|---|---|---|
| 18997 | — | NEG | — | — | — | NEG | | | | |
| 18977 | — | NEG | — | — | — | NEG | | | | |
| 18955 | 15.4 | POS | 43951 | 42054 | 45570 | POS | 45156 | 41096 | 52115 | POS |
| 18902 | — | NEG | — | — | — | NEG | | | | |
| 18907 | 24.21 | POS | 16988 | 18392 | 40621 | POS | 11354 | — | 41910 | POS |
| 18943 | — | NEG | — | — | — | NEG | | | | |
| 18974 | — | NEG | — | 11452 | 40725 | POS | — | — | — | NEG |
| 18913 | 25.67 | POS | 37474 | 37443 | 47522 | POS | 31044 | 34238 | 51157 | POS |
| 19032 | — | NEG | — | — | — | NEG | | | | |
| 18962 | — | NEG | — | — | — | NEG | | | | |
| 18969 | — | NEG | — | — | — | NEG | | | | |
| 18994 | — | NEG | — | — | — | NEG | | | | |
| 18983 | — | NEG | — | — | — | NEG | | | | |
| 19029 | — | NEG | — | — | — | NEG | | | | |
| 18989 | — | NEG | — | — | — | NEG | | | | |
| 18935 | 11.56 | POS | 42479 | 40111 | 42063 | POS | 46701 | 40965 | 52325 | POS |
| 19026 | — | NEG | — | — | — | NEG | | | | |
| 18906 | 26.13 | POS | 8858 | 15329 | 45827 | POS | 11021 | 8272 | 46969 | POS |
| 18958 | — | NEG | — | — | — | NEG | | | | |
| 18963 | — | NEG | — | — | — | NEG | | | | |
| 19005 | — | NEG | — | — | — | NEG | | | | |
| 19016 | — | NEG | — | — | — | NEG | | | | |
| 18993 | — | NEG | — | — | — | NEG | | | | |
| 18986 | — | NEG | — | — | — | NEG | | | | |
| 19014 | — | NEG | — | — | — | NEG | | | | |
| 19027 | — | NEG | — | — | — | NEG | | | | |
| 18928 | — | NEG | — | — | — | NEG | | | | |
| 18867 | — | NEG | 30246 | 34971 | 51303 | POS | 18297 | 21713 | 48564 | POS |
| 19020 | — | NEG | — | — | — | NEG | | | | |
| 18871 | — | NEG | — | — | — | NEG | | | | |
| 19030 | 26.25 | POS | 16515 | 18861 | 46116 | POS | — | — | 39022 | RERUN |
| 18953 | — | NEG | — | — | — | NEG | | | | |
| 19022 | — | NEG | — | — | — | NEG | | | | |
| 18927 | — | NEG | — | — | — | NEG | | | | |
| 18972 | — | NEG | — | — | — | NEG | | | | |
| 19003 | — | NEG | — | — | — | NEG | | | | |
| 18870 | — | NEG | — | — | — | NEG | | | | |
| 18978 | — | NEG | — | — | — | NEG | | | | |
| 19024 | — | NEG | — | — | — | NEG | | | | |
| 18910 | — | NEG | — | — | — | NEG | | | | |
| 18981 | — | NEG | — | — | — | NEG | | | | |
| 19017 | — | NEG | — | — | — | NEG | | | | |
| 18990 | — | NEG | — | — | — | NEG | | | | |
| 19000 | — | NEG | — | — | — | NEG | | | | |
| 19007 | — | NEG | — | — | — | NEG | | | | |
| 19025 | — | NEG | — | — | — | NEG | | | | |
| 19019 | — | NEG | — | — | — | NEG | | | | |
| 18937 | 25.3 | POS | 27209 | 26359 | 31789 | POS | 28012 | 31267 | 50736 | POS |
| 18967 | — | NEG | — | — | — | NEG | | | | |
| 19009 | — | NEG | — | — | — | NEG | | | | |

Run 1—The DETECTX-RV assay demonstrated 100% concordance with the samples called positive (N=7) using the Abbott system and 93% concordance with the samples called negative (N=43) using the Abbott system. The PathogenDx, DETECTX-RV assay identified 2 additional samples as positive, that were identified as negative by Abbott testing and one additional sample as needing to be rerun. Measure-sample that was discordant was identified as a rerun on the second run. The rerun confirmed the positive signal from Run 1 for the two samples that were identified as negative by Abbott testing. The one previous sample that was identified as a rerun came back as negative on the second run. Table 10 summarizes the results from Run 1 and Run 2.

TABLE 10

Summary of results from Run 1 and Run 2

|  | POS (N = 7) | NEG (N = 43) |
|---|---|---|
| Run 1 | 100% POS | 95% NEG + 2 POS |
| Run 2 | 86% POS + 1 RERUN | 97% NEG + 1 POS |

Example 7

Analysis of Environmental Samples (Surface Swabs and Air)

One of the greatest challenges in performing environmental monitoring of air and surfaces for viral contamination is the collection and stabilization of the viral RNA prior to analysis. To overcome this challenge, the strategy of utilizing a dilute RNA stabilization solution (from GENTEGRA LLC) called "ATA" here was evaluated at 1:40 dilution in 1×PBS and/or DNase/RNase Free Water for stabilization of COVID-19 RNA collected from surfaces on swabs or from the air into a fluid collection solution, using a device from Bertin Corporation, as an example.

Environmental Monitoring of Air

Figure 10:
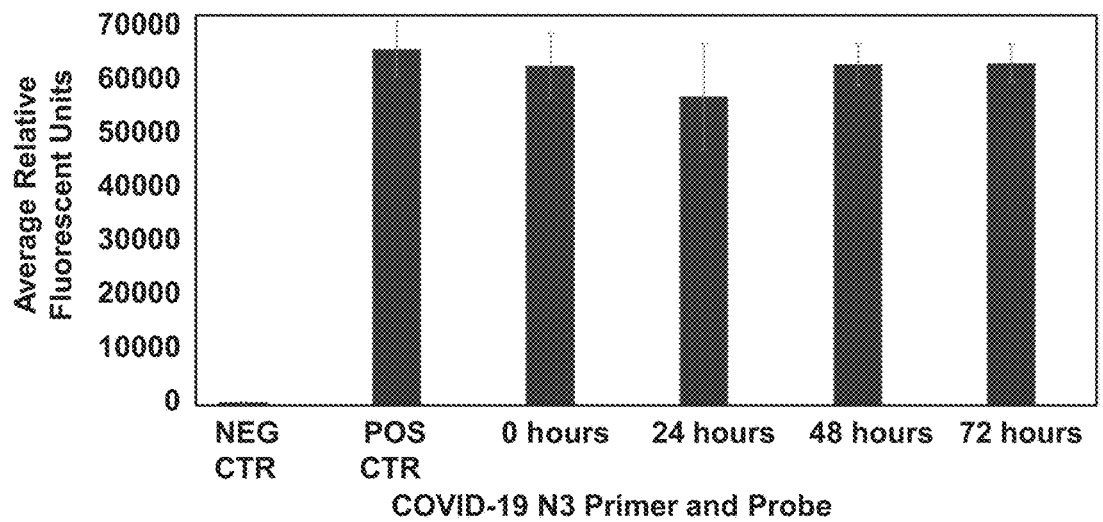
FIG. 10 shows the results of RNA stability analysis during environmental air analysis.

To determine if the air is contaminated with bacteria, fungi, and/or virus air was collected using the Coriolis Micro Air Sampler from Bertin. In this utilization, the stability of viral RNA was evaluated during and up to 72 hours post collection. In this demonstration the GENTEGRA RNA stabilizer ("ATA") was diluted at 1:40 dilution in 5 mL of 1×PBS, pH 7.2 or molecular grade water. Purified 5 µL of SARS-CoV2 RNA was spiked at 200,000 copies/µL directly into the collection cone and ran the instrument to dryness, which took ~30 min, during which the spiked sample was exposed to the particulate contamination resulting from @2 m3 of collected air input. Post air collection the dry viral RNA plus dried stabilizer and accumulated airborne contaminants were resuspended in 1 mL of molecular grade water and stored the samples at room temperature (0, 24, 48, and 72 hours) until RNA purification was performed. The RNA was extracted and purified using the Zymo Quick DNA/RNA Viral MagBead collection kit and the samples were ran on the DETECTX-RV assay by PathogenDx. RNA collection and stability for the entire 72 hour period as demonstrated in the FIG. 10, which presents signals obtained from the N3 region of COVID-19 as measured on the DETECTX-RV assay produced via the present invention. Data are presented as raw microarray hybridization signals obtained from probes for the N3 region, as a function of post-collection storage time at RT (in hours). The positive control constitutes an identical matched, unprocessed spiked COVID-19 sample that had not gone through air collection, air drying or storage. The data show that the 30 minutes of air collection (0 hours) did not give rise to measurable RNA loss, nor did up to 72 hours of RT storage of the dried air-collection sample prior to analysis.

Environmental Monitoring of Surfaces by Swabbing

Figure 11:
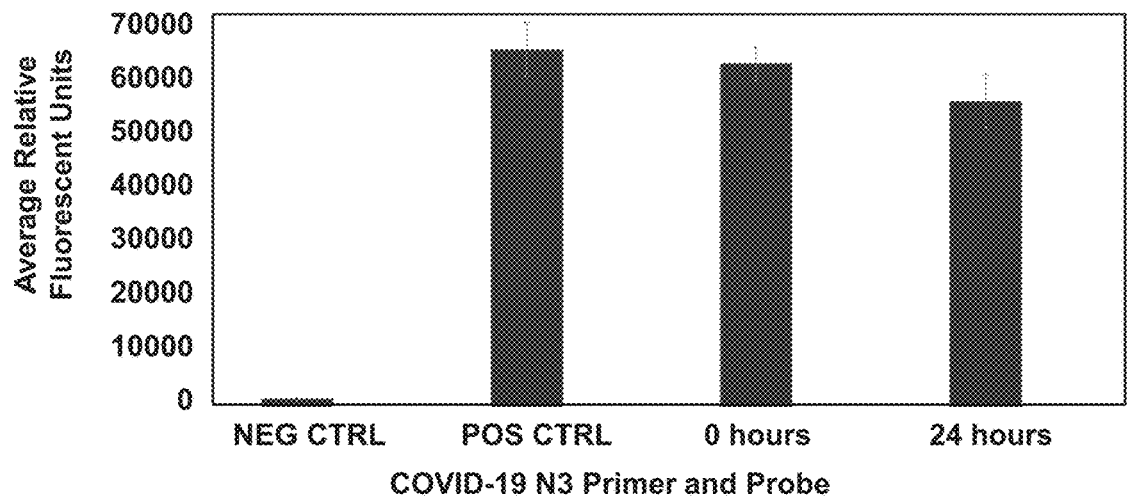
FIG. 11 shows the results of RNA stability analysis during environmental monitoring of surfaces by swabbing.

To determine if the surface is contaminated with a microbe (COVID-19 virus in the present example) surface swab samples were collected using nylon flocculated and rayon swabs. In this utilization, the stability of viral RNA during and up to 24 hours post collection was evaluated. In this demonstration, the "ATA" RNA stabilizer was diluted 1:40 in 5 mL of 1×PBS, pH 7.2 or molecular grade water. Purified 5 µL of SARS-CoV2 RNA was spiked at 200,000 copies/µL then applied it directly onto a stainless-steel surface. The swab was removed from its sterile case and three drops of the dilute "ATA" stabilizer were placed onto the swab to moisten it. The surface was swabbed to collect the viral RNA. The swab was placed directly back into the sterile container and allowed to sit at room temperature for 24 hours. Post surface collection and either (0 hrs) or (24 hrs) of ambient temperature swab storage, 1 mL of 1×PBS, pH 7.2 was added to the swab in the container and vortexed for 10 seconds. 400 µL of the resuspended viral RNA was removed for viral RNA preparation. The RNA was extracted and purified using the Zymo Quick DNA/RNA Viral MagBead collection kit and the samples were run on the DETECTX-RV assay, monitoring the fluorescence signal from the COVID-19 (N3) region. The positive control constitutes an identical matched, unprocessed spiked COVID-19 samples that had not been applied to the surface or gone through swabbing or storage. The data demonstrate RNA recovery and stability from a surface swab, subsequent to ordinary ambient storage of the swab for 24 hrs, as assessed by analysis via the present invention, as demonstrated in FIG. 11.

Example 8

Analysis of Mouthwash Samples

The purpose of this study was to demonstrate that the present invention could be used to detect COVID-19 RNA in a novel oral rinse solution (QuiKSal from CLC Corporation) which had been spiked into it at clinically meaningful levels, then analyzed subsequent to several days of unrefrigerated ambient temperature storage, to emulate overnight shipping from point of collection to a central lab for COVID-19 analysis by the present invention. Two versions of QuiKSal were tested. One possessed a tracking Dye (SOW+) and one without the dye (SOW−).

The QuiKSal procedure asks the patient to swish 1 mL of the QuiKSal and spit the QuiKSal into the sterile storage container. The collection procedure was mimicked by spiking in a high and a low SARS-CoV2 RNA into 1 mL of QuiKSal. Eight 1 mL aliquots of Oral Rinse Solution were created, with and without SARS-CoV2 RNA spike. Two of the spiked sampled aliquots had 200,000 copies/mL (high) of a SARS-CoV2 standard (Integrated DNA Technologies) while the other six aliquots were spiked to 20,000 copies/mL (low). Following the addition of the RNA to the samples the samples were stored from 0 to 72 hours at room temperature to evaluate the stability of the RNA in the QuiKSal mouthwash. Following incubation, the RNA was isolated using the Zymo Quick-DNA/RNA Viral MagBead kit by removing 400 µL of the QuiKSal for sample preparation per the manufacturer's instructions. Following sample preparation, the samples were analyzed using the PathogenDx DETECTX-RV test, based on the teaching of the present invention.

Figure 12:
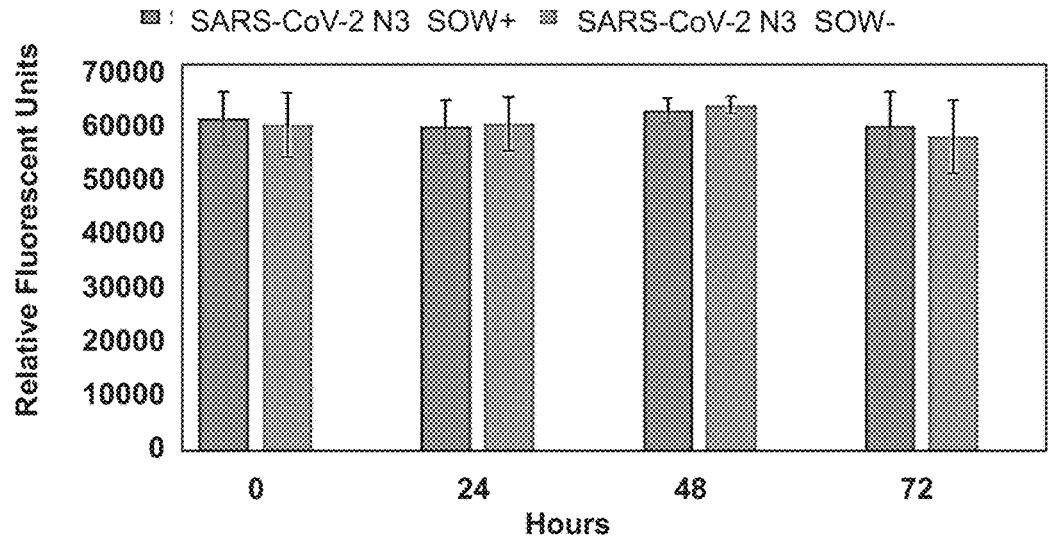
FIG. 12 shows microarray data for detection of SARS-CoV2 N3 target gene at various time points after spiking into SOW+ (with dye) and SOW− (minus dye).

Array data (FIG. 12) showing detection of SARS-CoV2 N3 target gene relative fluorescent units (RFU) at various time points after spike into SOW+ (with dye) and SOW− (minus dye). No signal was obtained from the no template control oral rinse (not shown). Signals above 10,000 RFU are considered positive.

The present invention was capable of detecting COVID-19 RNA from the QuiKSal oral rinse with or without dye. COVID-19 RNA in that stabilized mouthwash was detectable via the present invention for up to 72 hours at room temperature.

Example 9

Figure 13A:
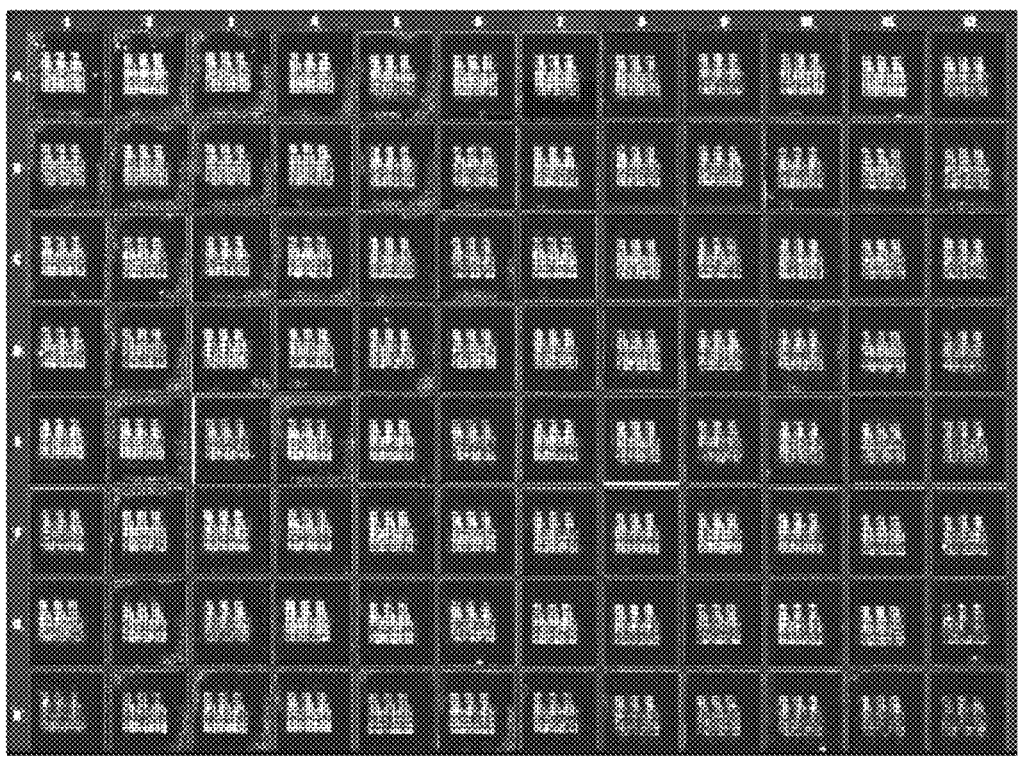
FIGS. 13A-13B show quality control images for printed microarray plates.
Figure 13B:
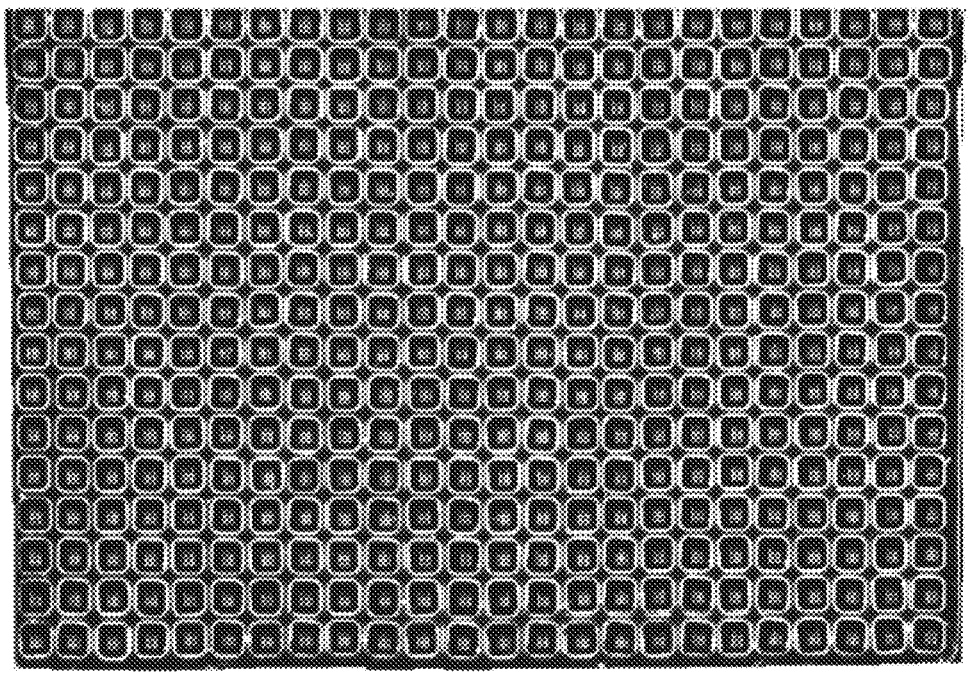
Figure 14:
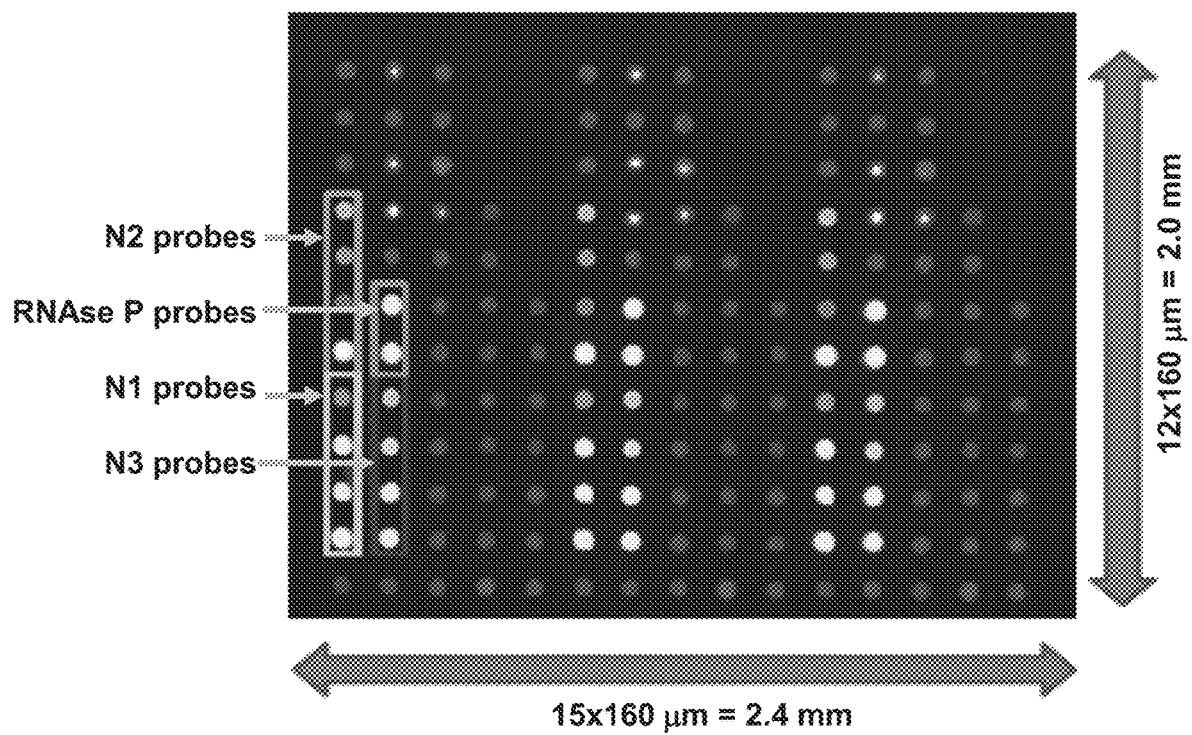
FIG. 14 shows a representative DETECTX-RV hybridization data for clinical nasopharyngeal swab samples in 96-well format.

Printing and Quality Control 96-well plates were printed with the hybridization probes under conditions optimized to eliminate dust and fiber contamination in the wells. Optical Inspection suggested that there are no measurable failures in printing (FIG. 13A, pate #9901005001). Similarly. 384-well plates were printed with the hybridization probes. The plates were inspected using Sensation Imaging and reveal no measurable failures (FIG. 13B, plate #1 9980001001). Therefore, no further changes to printing parameters and slide processing (UV and well mounting) are required. The array structure and probe layout for the 96 well plate (FIG. 13A) are shown in FIGS. 8 and 14. The probes and probe layout for the 384-well printing (FIG. 13B) are exactly as displayed in FIGS. 16A-16D and as described in Table 12.

Hybridization Analysis

A small number of validated clinical nasopharyngeal swab samples obtained from Boca Biolistics having 11 positives and 1 validated nasopharyngeal negative control were subjected to standard 2-step tandem RT-PCR (RT-PCR+PCR). Standard hybridization and washing were performed with an increase in hybridization (136 µL) and wash (200 µL) volumes, followed by imaging from the bottom of the fully assembled 96-well plate (plate #9901005001). FIG. 14 shows one of the positive samples from one well of the 96-well plate. A gradient of probe affinity was used for each of the locus analyzed using N1, N2, N3 and RNAse P probes. Four of the loci (N1, N2, N3, RNAse P) are for COVID, while the rest are species controls including other coronavirus, Influenza A and Influenza B. As seen, the array structure has well-characterized sample signals for all targets (N1, N2, N3, RNAse P probes). Negligible cross hybridization is observed among the various controls.

Pilot Study on Clinical Nasopharyngeal Isolates on Identical DETECTX-RV Arrays in 96-Well Vs 12-Well Slide Format A small number of validated clinical nasopharyngeal samples obtained from Boca Biolistics having 11 positives and 1 validated nasopharyngeal negative control were subjected to standard 2-step tandem RT-PCR (RT-PCR+PCR). Samples were analyzed on the 96-well slide format with direct comparison to match samples on the 12-well slide format and are shown in Table 11. Signal intensity was optimized by increasing labelling PCR reaction volume and sample volume.

TABLE 11

Comparison of DETECTX-RV data on 96-well plates and 12-well slides.

| 384-well plate Sample # → | 17 | 18 | 19 | 20 | 21 | 22 | 25 | 26 | 27 | 28 | 29 | 30 |
|---|---|---|---|---|---|---|---|---|---|---|---|---|
| H-RNAse P positive control | D | D | D | D | D | D | D | D | D | D | D | D |
| Negative RT-PCR control | ND | ND | ND | ND | ND | ND | ND | ND | ND | ND | ND | ND |
| SARS-CoV2 N3 | D | D | D | D | ND | D | D | D | D | D | D | D |
| SARS-CoV2 N1 | D | D | D | D | ND | D | D | D | D | ND | D | D |
| SARS-CoV2 N2 | D | D | D | D | ND | ND | D | D | D | ND | D | D |

TABLE 11-continued

Comparison of DETECTX-RV data on 96-well plates and 12-well slides.

| 12-well slide Sample # → | 1 | 2 | 3 | 4 | 5 | 6 | 7 | 8 | 9 | 10 | 11 | 12 |
|---|---|---|---|---|---|---|---|---|---|---|---|---|
| H-RNAse P positive control | D | D | D | D | D | D | D | D | D | D | D | D |
| Negative RT-PCR control | ND | ND | ND | ND | ND | ND | ND | ND | ND | ND | ND | ND |
| SARS-CoV2 N3 | D | D | D | D | ND | D | D | D | D | D | D | D |
| SARS-CoV2 N1 | D | D | D | D | ND | D | D | D | D | ND | D | D |
| SARS-CoV2 N2 | D | D | D | D | ND | D | D | D | D | D | D | D |

D = detected, signal above threshold; ND = not detected, signal below threshold

Probe Design and Probe Material Assembly of Mini-RV 384-Well Microarray

Figure 15:
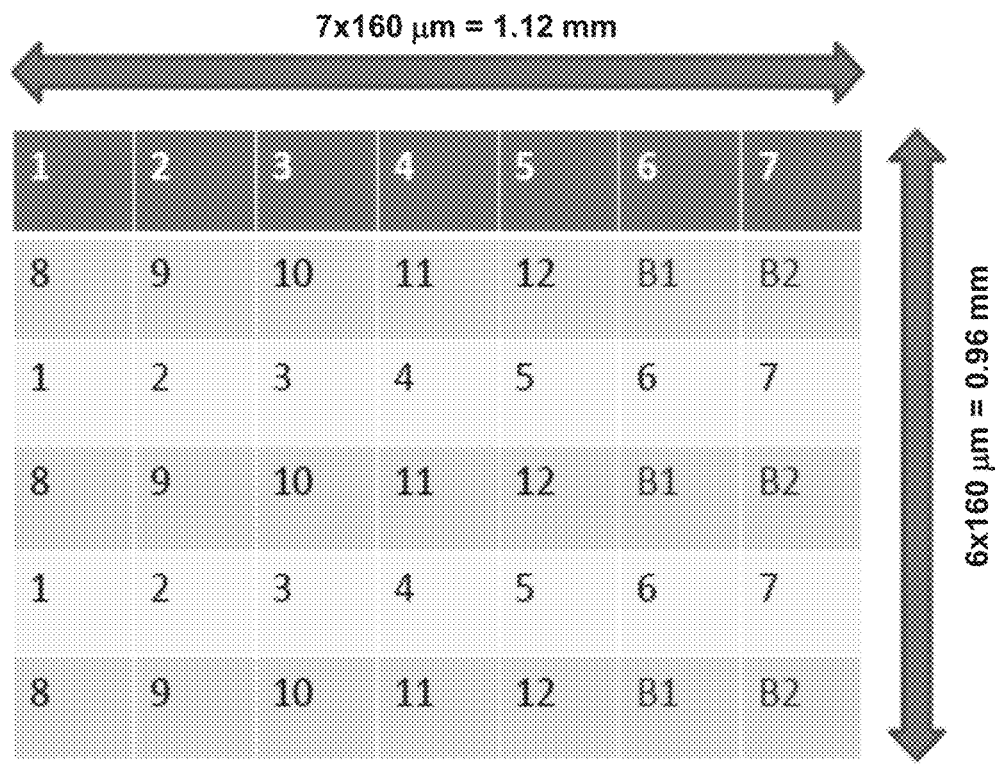
FIG. 15 is a microarray layout for 384-well printing showing triplicates for 12 probes (D=100-110 μm, P=160 μm) and two "make-up" slots, where "D" refers to average spot diameter and "P" refers to the pitch. i.e. the average separation.

The probe content for the smaller version of DETECTX-RV (Mini-RV V1) was designed and is shown in Table 12. FIG. 15 shows a 6×7 probe layout for the Mini-RV 384-well microarray where the contents are printed in triplicate.

TABLE 12

Probe content in Mini-RV, 384-well plate format

| 1 | Negative hybridization control probe |
| 2 | SARS-CoV2 N1 probe |
| 3 | SARS-CoV2 N2 probe |
| 4 | SARS-CoV2 N2 probe alternate |
| 5 | SARS-CoV2 N3 probe |
| 6 | RNAse P probe |
| 7 | Influenza A probe segment (M) |
| 8 | Influenza B probe segment (NS) |
| 9 | SARS-CoV2 (S) 614D probe antisense |
| 10 | SARS-CoV2 (S) 614G probe antisense |
| 11 | SARS-CoV2 (S) 614D probe sense |
| 12 | SARS-CoV2 (S) 614G probe sense |
| B1 | Blank (for make-up/manufacturer error correction) |
| B2 | Blank (for make-up/manufacturer error correction) |

Example 10

Mini-RV Hybridization in 384-Well Format

SARS-CoV2 probe specificity and characteristics of probe prints were evaluated for clinical nasopharyngeal swab samples.

Materials:

384-well test print—9980001001

DETECTX-RV Kit

SARS-CoV2 Standard at 200 Copies/Reaction (Exact Diagnostics LLC)

Figure 16A:
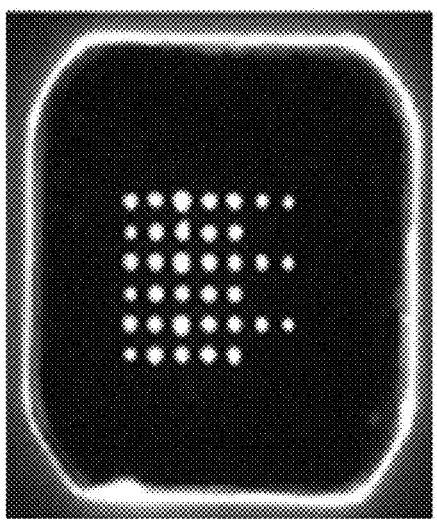
FIGS. 16A-16D show hybridization data for a clinical nasopharyngeal swab sample in one well of the 384-well Mini-RV plate, shown magnified.
Figure 16B:
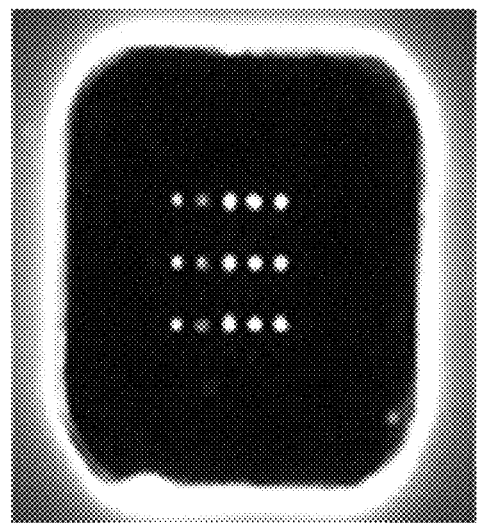
Figure 16C:
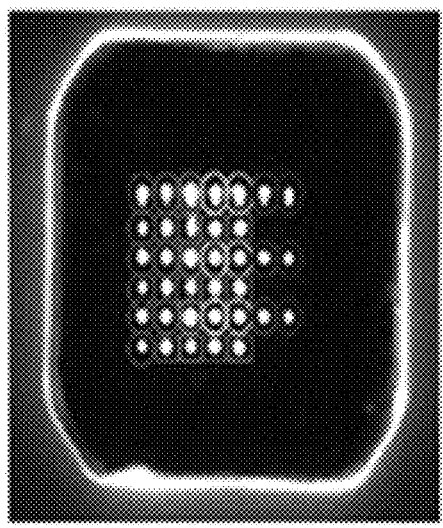
Figure 16D:
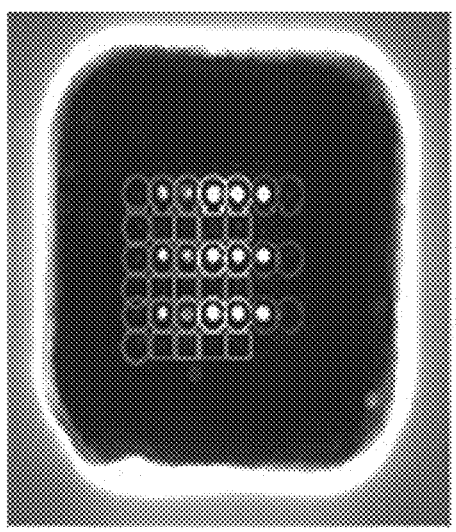

Probes were printed in triplicate and amplified at 200 copies/reaction. A pooled PCR sample was created from 24 individual PCR reactions amplifying SARS-CoV2. FIGS. 16A-16D shows data for a representative well. A clear replicate fluorescent signal was obtained between wells for RNAse P, SARS-CoV2 N1. N2 and N3 probes (FIGS. 16A, 16B). FIGS. 16C and 16D show the results of imaging analysis for the CY5 (Probe label) and CY3 (amplicon) label. These data demonstrate feasibility of the 2-step labeling protocol and functionality of the 384-well plate.

Example 11

Optimization of Microarray Manufacture

By increasing the amount of UV cross linking from 300 mJ to 500 mJ, the signal strength obtained for COVID-19 microarray analysis in the 96-well and 384-well plate format was comparable (Tables 13 and 14) to that obtained with 12-well slide hybridization as assessed by LLoD and clinical specimen analysis.

TABLE 13

Comparison of SARS-CoV2 Hybridization Signals on 12-well, 96-well and 384-well plates for 30 Contrived LLoD Samples. (62.5 copies/ml in Boca nasopharyngeal negatives using the 2-Step method)

|  | Average | Standard Deviation |
|---|---|---|
| 12-Well | | |
| SARS.COV2-N1-RE1.1 | 48543 | 9553 |
| SARS.COV2-N2-RE1.3 | 51253 | 11844 |
| SARS.COV2-N3-RE1.1 | 57398 | 12004 |
| RNAse.P.Probe-pub1.1 | 60697 | 11038 |
| 96-Well | | |
| 62-Negcont-B | 537 | 508 |
| SARS.COV2-N1-RE1.1 | 38377 | 25385 |
| SARS.COV2-N2-RE1.3 | 48524 | 13774 |
| SARS.COV2-N3-RE1.1 | 56905 | 11754 |
| RNAse.P.Probe-pub1.1 | 60312 | 11108 |
| 384-Well | | |
| 62-Negcont-B | 2328 | 872 |
| SARS.COV2-N1-RE1.1 | 48919 | 10759 |
| SARS.COV2-N2-RE1.3 | 37186 | 7833 |
| SARS.COV2-N2-RE1.4 | 54071 | 10080 |
| SARS.COV2-N3-RE1.1 | 54087 | 9993 |
| RNAse.P.Probe-pub1.1 | 55129 | 4339 |

TABLE 14

Comparison of SARS-CoV2 Hybridization on 12-well, 96-well and 384-well plates for 30 positive and 30 negative clinical samples (Boca/NP/VTM using the 2-Step method)

|  | Average Positive | Positive Standard Deviation | Average Negatives | Negative Standard Deviation |
|---|---|---|---|---|
| 12-Well | | | | |
| 62-Negcont-B | 1640 | 312 | 1711 | 209 |
| SARS.COV2-N1-RE1.1 | 32850 | 19701 | 1322 | 2343 |
| SARS.COV2-N2-RE1.3 | 38570 | 15524 | 2980 | 6620 |
| SARS.COV2-N2-RE1.4 | 43670 | 16656 | 3779 | 6748 |
| SARS.COV2-N3-RE1.1 | 59723 | 5485 | 5182 | 10348 |
| RNAse.P.Probe-pub1.1 | 62532 | 319 | 63073 | 165 |
| 96-Well | | | | |
| 62-Negcont-B | 122 | 351 | 347 | 336 |
| SARS.COV2-N1-RE1.1 | 35577 | 20782 | 251 | 1474 |
| SARS.COV2-N2-RE1.3 | 26098 | 15252 | 1383 | 1220 |
| SARS.COV2-N2-RE1.4 | 54771 | 13048 | 1852 | 8090 |
| RNAse.P.Probe-pub1.1 | 62475 | 298 | 62611 | 788 |
| 384-Well | | | | |
| 62-Negcont-B | 2233 | 761 | 2512 | 510 |
| SARS.COV2-N1-RE1.1 | 30764 | 16572 | 1354 | 1698 |
| SARS.COV2-N2-RE1.3 | 28451 | 15541 | 2781 | 2658 |
| SARS.COV2-N2-RE1.4 | 51946 | 11150 | 5203 | 10023 |
| SARS.COV2-N3-RE1.1 | 54192 | 6684 | 5224 | 8237 |
| RNAse.P.Probe-pub1.1 | 57343 | 1681 | 57494 | 1496 |

Example 12

Performance Optimization

Figure 17A:
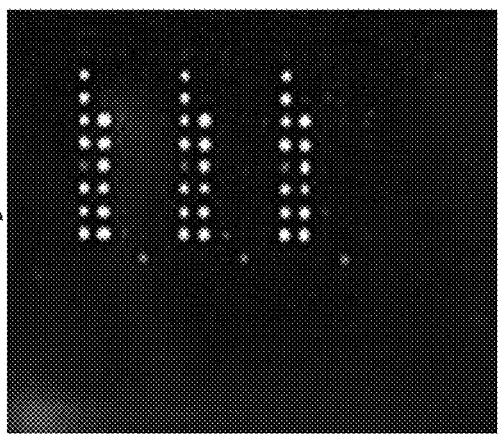
FIGS. 17A-17F shows the effects of parameters such as hybridization time, washing and spin-drying on signal strength.
Figure 17B:
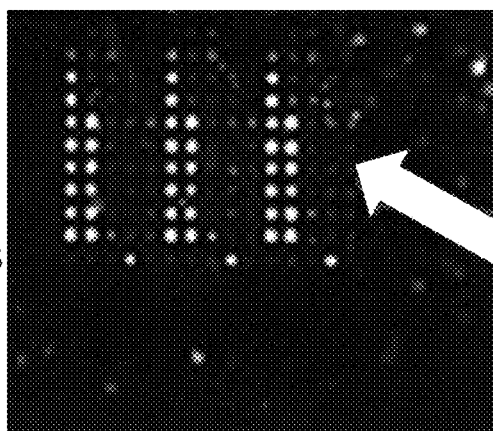
Figure 17C:
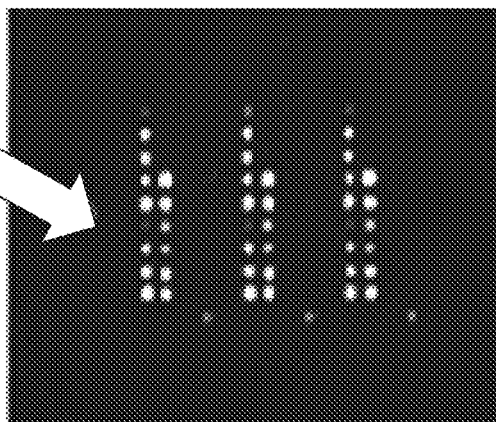
Figure 17D:
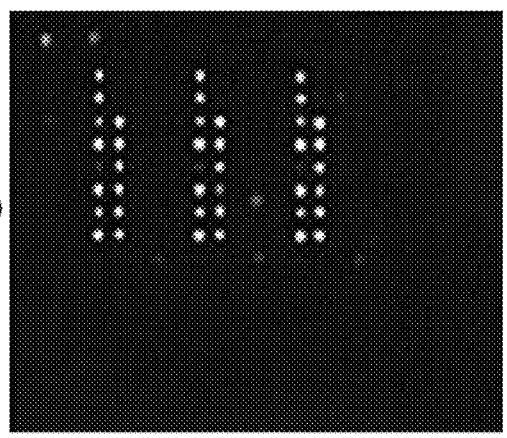
Figure 17E:
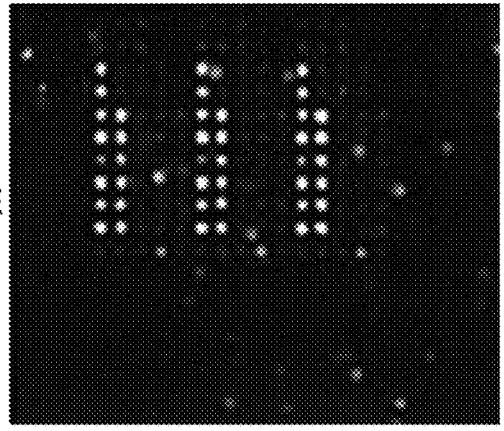
Figure 17F:
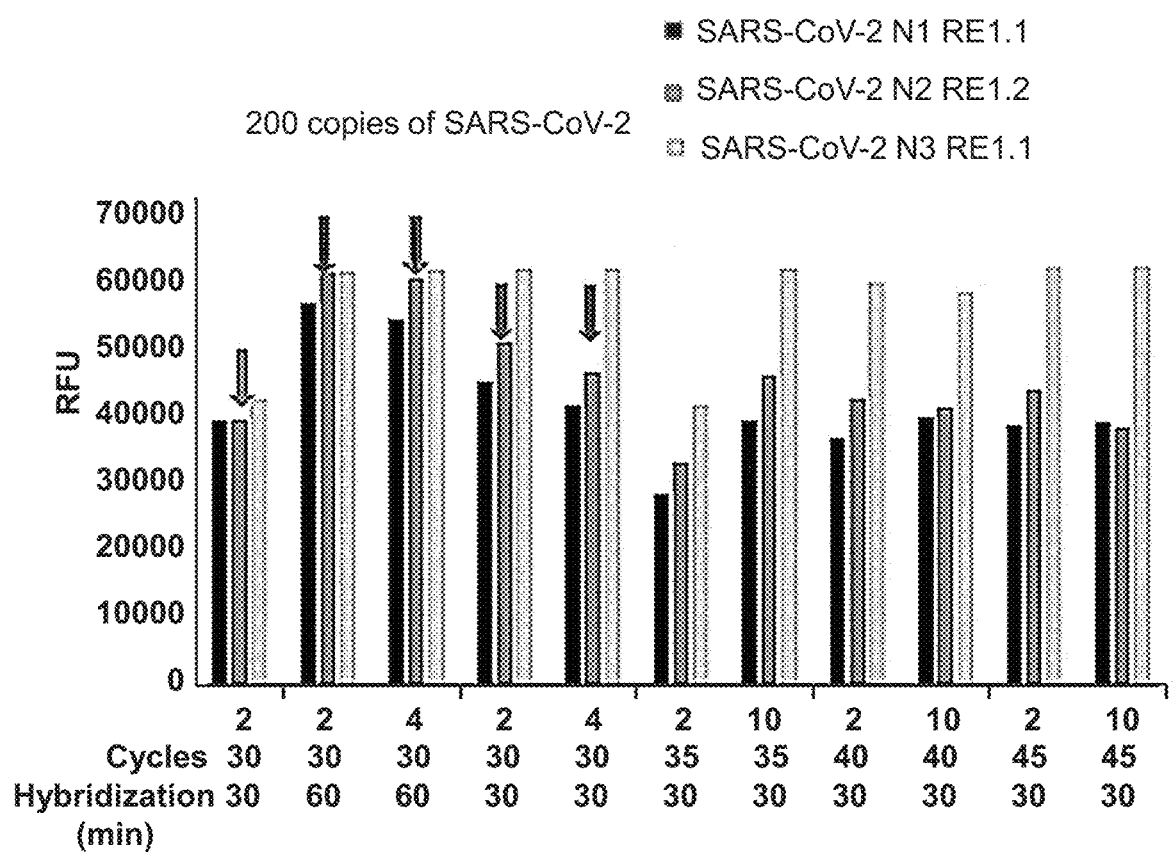

Methods to improve signal strength and overall performance were analyzed for 96-well plates (FIGS. 17A-17D) and led to the following basic principles for 96-well plates, which were similarly deployed in the analysis of 384-well plates.

a) Plates must be cross-linked prior to mounting of the 96-well (or 384-well) polycarbonate top.

b) A modest increase in signal strength is obtained by mixing and/or an extension of hybridization time from 30 min to 60 min (FIG. 17E). Mixing alone improves signal strength and may be facilitated with a plate shaker. Optimization data for the hybridization in 96-well format are summarized in FIG. 17F.

c) Image quality is improved by introducing a 1 min plate centrifugation. This step is performed prior to loading the plates onto the Sensovation Imager.

Asymmetric One-Step RT-PCR Optimization

Validation of Asymmetric One-Step RT-PCR Using Purified SARS-CoV2 RNA

Materials:
1. 12-well glass slides—99030002 print series.
2. DETECTX-RV kit.
3. Purified SARS-CoV2 RNA (ATCC, NR-52285)
4. Labeling primers Optimization 1

To determine if the Tandem 2-step (RT-PCR+Labelling PCR) reaction can be combined to a single step (Asymmetric One-Step RT-PCR) to reduce assay times, first, different primer ratios (labeled:unlabeled) were used in the PCR reaction to establish optimal cycle number to achieve sensitivities similar to the 2-step reaction (LoD ~2 copies/reaction, 125 copies/mL)

Four different primer concentrations and ratios (labeled: unlabeled 4:1, 4:1, double concentration, 8:1, 2:1) were used. Three different cycling conditions were used over a dilution (500 copies/reaction=62,500 copies/mL to 2 copies/reaction=125 copies/mL) of purified SARS-CoV2 RNA. The purified SARS-CoV2 RNA was diluted in sterile water from 500, 250, 100, 50, 25, 10, 5 and 2 copies/reaction. NTC (No Template Control) and External extraction controls were also used. The PCR parameters were as follows:

Cycling conditions: 35, 40, 45
RT-PCR Program: 45° C., 45 min
PCR Program:

| Initial denature | 95° C. 2 min |
|---|---|
| Cycling | 95° C.-30 sec; 55° C.-30 sec; 68°C.-30 sec |
| Final extension | 68° C.-5 min |

Figure 18A:
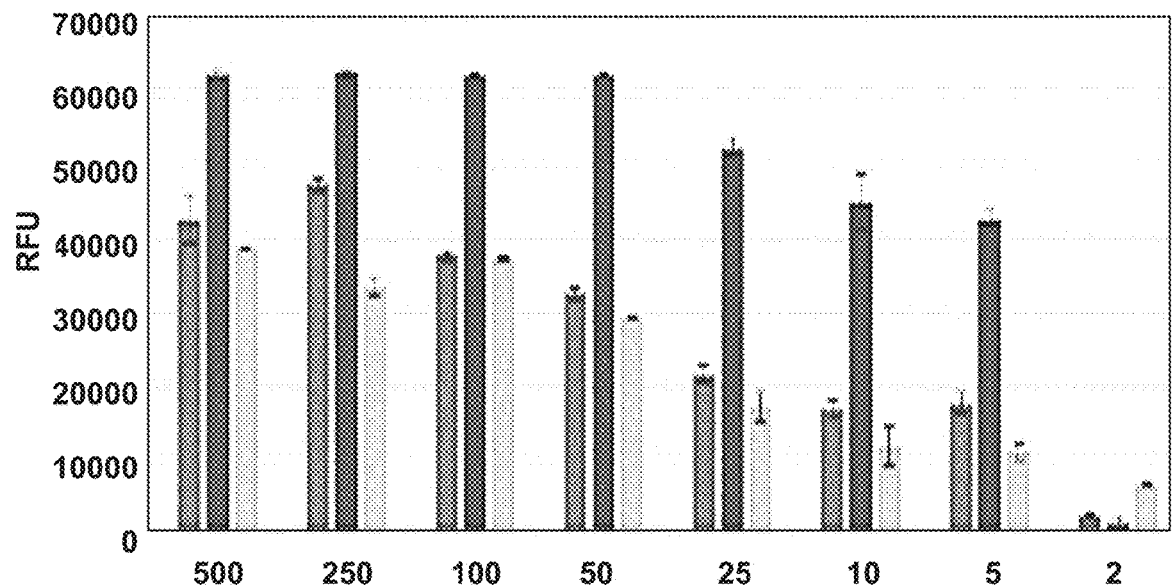
FIGS. 18A-18B shows optimization data for Asymmetric One-Step RT-PCR reaction.
Figure 18B:
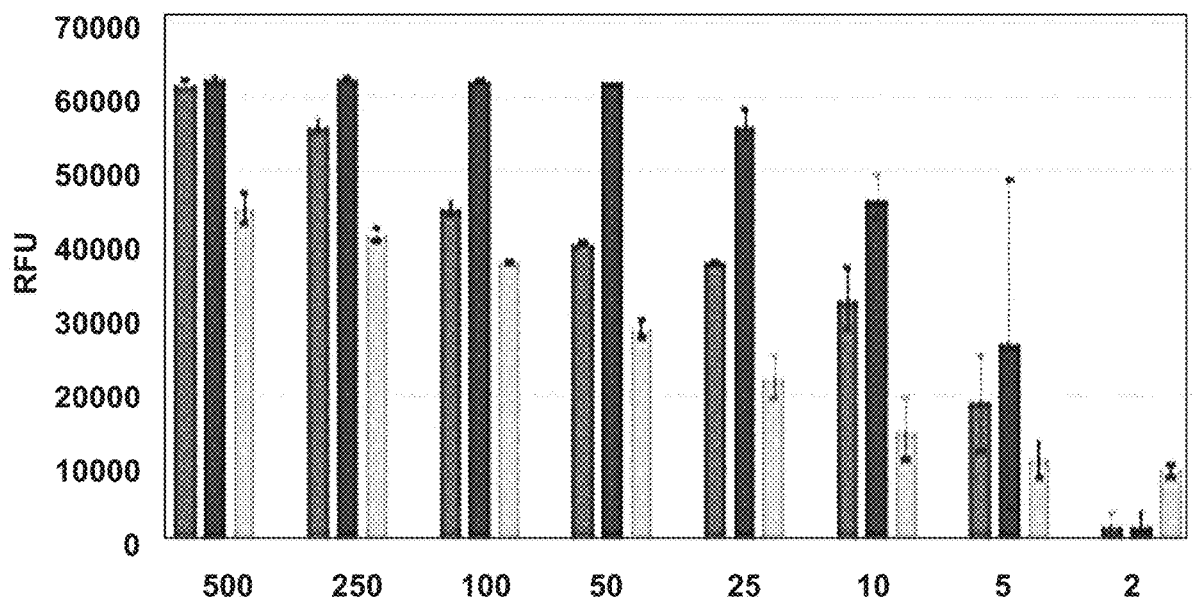

FIGS. 18A and 18B show the results of this optimization for the Asymmetric One-Step RT-PCR reaction applied to SARS-CoV-2 in 12-well microarrays for 40 PCR cycles and primer ratios of 4.1 and 8:1 respectively. Both ratios displayed a dropout at 35 and 45 cycles but performed consistently and robustly at 40 cycles. Based on these results it is concluded that an 4:1 primer ratio at 40 cycles provides the strongest signal over the range of concentrations tested. The LLoD is between 5 copies/reaction and 10 copies/reaction.

In conclusion. Asymmetric One-Step RT-PCR provides a slightly higher LLoD compared with the 2-step tandem RT-PCR (Asymmetric One-Step RT-PCR 5-10 copies/reaction=1250-625 copies/mL versus tandem RT-PCR 2 copies/reaction=125 copies/mL).

Optimization 2
Materials:
1. LLoD samples: Negative nasopharyngeal swab/VTM (Boca Biolistics) spiked with 25 copies/reaction (62.5 copies/ml) of purified SARS-CoV2 RNA (ATCC, NR-52285).
2. Clinical samples Positive and negative nasopharyngeal swab samples (Boca Biolistics).
3. DETECTX-RV kit.
4. 12-well glass slides—99030002 print series.
5. Labeling primer Using the same sample as used for the analysis shown in Example 11 and Table 13, a formal LLoD was obtained for the Asymmetric One-Step RT-PCR (Tables 15 and 16), which was determined to be relatively superior to that discussed in the previous section (Example 12, 'Optimization 1'). The data in Tables 15 and 16 are identical within experimental accuracy to that observed using the 2-Step (RT-PCR+PCR) reaction.

Furthermore, data obtained for clinical sensitivity and specificity analysis using 30 Positive and 30 negative nasopharyngeal swab samples (Table 17) showed unaltered specificity and negative predictive value (NPV), but a preliminary reduction in sensitivity from 100% to 79% due to a general reduction in hybridization signal strength.

The reduction in signal strength was remedied by the following modifications:
 i) increasing concentration of input RNA template;
 ii) increasing primer concentration;
 iii) employing RNA samples analyzed within 48 hours of extraction Optimization 3
Materials:
1. Clinical samples—Positive nasopharyngeal swab samples (Boca Biolistics).
2. DETECTX-RV kit.
3. 384-well test print—9980001001
4. Labeling primers Performance of the 384-well DETECTX-RV microarray was performed against a set of 30 positive nasopharyngeal swab samples. This analysis differed from the previous example (Example 12, 'Optimization 2') in that. RNA was freshly extracted and used immediately without freeze/thawing or storage, the primer concentration is increased 2-fold to 400 nM. Samples were evaluated based on average and standard deviation signal intensity, sensitivity, specificity, positive predictive value (PPV) and negative predictive value (NPV).

Results:
An improved performance was observed with clinical isolates (Table 18) over the previous optimization described above ('Optimization 2'). An improvement in clinical sensitivity was observed for all probes (range of clinical sensitivity, 88%-100%). The overall AUGURY readouts however report a specificity of 100% since AUGURY aggregates hybridization data from all three independent loci tests.

TABLE 15

Lowest limit of detection anaysis for Asymmetric One-Step RT-PCR

| Probe Description | Average | Standard Deviation | (a) True Positives | (b) False Positives | (c) False Negatives | (d) True Negatives | LoB | LoD (copies/ reactioin) | Sensitivity | Specificity | PPV | NPV |
|---|---|---|---|---|---|---|---|---|---|---|---|---|
| 62-Negcont-B | 2155 | 370 | 30 | N/A | 0 | N/A | N/A | 25 | 100 | N/A | N/A | N/A |
| SARS.COV2-N1-pub | 32556 | 9721 | 30 | N/A | 0 | N/A | N/A | 25 | 100 | N/A | N/A | N/A |
| SARS.COV2-N2-pub | 48152 | 119443 | 30 | N/A | 1 | N/A | N/A | 25 | 97 | N/A | N/A | N/A |
| SARS.COV2-N3-pub | 30106 | 8777 | 30 | N/A | 0 | N/A | N/A | 25 | 100 | N/A | N/A | N/A |
| SARS.COV2-N1-RE1.1 | 14887 | 7673 | 30 | N/A | 0 | N/A | N/A | 25 | 100 | N/A | N/A | N/A |
| SARS.COV2-N2-RE1.3 | 38222 | 12691 | 30 | N/A | 1 | N/A | N/A | 25 | 97 | N/A | N/A | N/A |
| SARS.COV2-N2-RE1.4 | 52709 | 11996 | 30 | N/A | 0 | N/A | N/A | 25 | 100 | N/A | N/A | N/A |
| SARS.COV2-N1-RE1.1 | 14290 | 7419 | 30 | N/A | 1 | N/A | N/A | 25 | 97 | N/A | N/A | N/A |
| RNAse.P.Probe-pub1.1 | 6224 | 6480 | 30 | N/A | 0 | N/A | N/A | 25 | 100 | N/A | N/A | N/A |

TABLE 16

Lowest limit of detection analysis for Asymmetric One-Step RT-PCR

| Probe Description | Average | Standard Deviation | (a) True Positives | (b) False Positives | (c) False Negatives | (d) True Negatives | LoB | LoD (copies/ reaction) | Sensitivity | Specificity | PPV | NPV |
|---|---|---|---|---|---|---|---|---|---|---|---|---|
| 62-Negcont-B | 2040 | 243 | 30 | N/A | 0 | N/A | N/A | 25 | 100 | N/A | N/A | N/A |
| SARS.COV2-N1-pub | 42768 | 8284 | 30 | N/A | 0 | N/A | N/A | 25 | 100 | N/A | N/A | N/A |
| SARS.COV2-N2-pub | 38869 | 10563 | 30 | N/A | 1 | N/A | N/A | 25 | 97 | N/A | N/A | N/A |
| SARS.COV2-N3-pub | 38788 | 6433 | 30 | N/A | 0 | N/A | N/A | 25 | 100 | N/A | N/A | N/A |
| SARS.COV2-N1-RE1.1 | 27733 | 10172 | 30 | N/A | 1 | N/A | N/A | 25 | 97 | N/A | N/A | N/A |
| SARS.COV2-N2-RE1.3 | 30135 | 12727 | 30 | N/A | 1 | N/A | N/A | 25 | 97 | N/A | N/A | N/A |
| SARS.COV2-N2-RE1.4 | 46156 | 11074 | 30 | N/A | 1 | N/A | N/A | 25 | 97 | N/A | N/A | N/A |
| SARS.COV2-N1-RE1.1 | 14349 | 4334 | 30 | N/A | 1 | N/A | N/A | 25 | 97 | N/A | N/A | N/A |
| RNAse.P.Probe-pub1.1 | 3684 | 3395 | 30 | N/A | 0 | N/A | N/A | 25 | 100 | N/A | N/A | N/A |

TABLE 17

Clinical sensitivity and specificity analysis for Asymmetric One-Step RT-PCR

|  | Limit of blank (LoB) | Limit of detection (LoD) | Sensitivity | Specificity | PPV | NPV |
| --- | --- | --- | --- | --- | --- | --- |
| 62-Negcont-B | 2455 | N/A | 100 | 100 | 100 | 100 |
| SARS.COV2-N1-pub | 2372 | N/A | 79 | 100 | 100 | 79 |
| SARS.COV2-N2-pub | 2835 | N/A | 79 | 100 | 100 | 79 |
| SARS.COV2-N3-pub | 2293 | N/A | 79 | 100 | 100 | 79 |
| SARS.COV2-N1-RE1.1 | 2184 | N/A | 79 | 100 | 100 | 79 |
| SARS.COV2-N2-RE1.3 | 2102 | N/A | 79 | 97 | 97 | 79 |
| SARS.COV2-N2-RE1.4 | 4941 | N/A | 79 | 100 | 100 | 79 |
| SARS.COV2-N3-RE1.1 | 605 | N/A | 79 | 100 | 100 | 79 |
| RNAse.P.Probe-pub1.1 | 40038 | N/A | 100 | 100 | 100 | 100 |

TABLE 18

Analysis of clinical nasopharyngeal swab sampes on a DETECTX-RV microarray using Asymmetric One-Step RT-PCR

| Probe Name | Position on R&D array | * 384 array (current) | * 384 array (next) | 1 CoV2 IDT plasmid | 2 SARS IDT plasmid | 3 MERS IDT plasmid | 4 CoV2 gRNA (D) | 5 (D)614gene fragment | 6 (D)614gene fragment | 7 influenza A gene fragment | 8 influenza B gene fragment | 9 influenza A gRNA | 10 influenza B gRNA | No template control |
|---|---|---|---|---|---|---|---|---|---|---|---|---|---|---|
| Negative Control probe | 1 | | | 1421 | 1254 | 921 | 886 | 1726 | 2312 | 1259 | 1009 | 1325 | 1206 | 2360 |
| SARS.COV2-N1-RE1.1 | 2 | * | * | 36815 | 1231 | 95 | 54332 | 225 | 644 | 169 | 60 | 295 | 413 | 758 |
| SARS.COV2-N2-RE1.3 | 3 | * | * | 38270 | 1198 | 1448 | 47713 | 939 | 1517 | 907 | 955 | 1139 | 1410 | 1729 |
| SARS.COV2-N2-RE1.4 | 4 | * | * | 62149 | 2410 | 2017 | 61697 | 1875 | 2013 | 2580 | 2423 | 2276 | 1904 | 3571 |
| SARS.COV2-N3-RE1.1 | 5 | * | * | 60538 | 48906 | 3721 | 61693 | 3523 | 3867 | 3254 | 3661 | 4126 | 3819 | 1814 |
| RNAse.P.Probe | 6 | * | * | 2080 | 3282 | 2407 | 2139 | 1452 | 2023 | 2185 | 2803 | 1409 | 2434 | 1432 |
| InfA.7.univ-pubRev | 7 | | * | −62 | −5 | 138 | 5 | −70 | 670 | 47983 | 362 | 36700 | 772 | −170 |
| InfB.8.univ-pub | 8 | | * | −286 | 5 | −11 | −333 | −191 | 25 | 543 | 62289 | 745 | 57508 | −194 |
| Universal D + G sense probe (1.1) | 13 | * | | 779 | 647 | 377 | 41182 | 61839 | 62125 | 575 | 629 | 561 | 456 | 1288 |
| 614D sense probe (1.4) | 16 | * | | 1841 | 636 | 853 | 36175 | 61651 | 10531 | 680 | 622 | 430 | 728 | 1188 |
| 614D sense probe (1.1) | 11 | | | 552 | 176 | 195 | 13969 | 45654 | 1378 | 613 | 518 | 1155 | 2019 | 849 |
| 614D sense probe (1.2) | 14 | | | 1298 | 342 | 285 | 6149 | 37398 | 2280 | 245 | −2 | −296 | −36 | 695 |
| 614D sense probe (1.3) | 15 | | | 840 | 630 | 712 | 4435 | 32101 | 1380 | 804 | 679 | 1264 | 516 | 1186 |
| 614G sense probe (1.4) | 19 | | * | 789 | 736 | 822 | 1346 | 1452 | 59019 | 916 | 1048 | 587 | 1466 | 1317 |
| 614G sense probe (1.1) | 17 | | | 1351 | 903 | 955 | 1736 | 7397 | 47967 | 968 | 1257 | 1447 | 984 | 1171 |
| 614G sense probe (1.2) | 12 | | | 1002 | 117 | 139 | 240 | 3048 | 36606 | 661 | 538 | 2008 | 480 | 393 |
| 614G sense probe (1.3) | 18 | | | 1631 | 1500 | 1487 | 2268 | 4681 | 17963 | 1745 | 1856 | 1142 | 1350 | 2036 |
| Universal D + G antisense probe (1.1) | 36 | | | 246 | 1538 | 1338 | 2529 | 1886 | 2072 | 323 | 302 | 1237 | 869 | 186 |
| 614D antisense probe (1.4) | 20 | * | | 506 | 241 | 477 | 1367 | 274 | 585 | 355 | 682 | 479 | 2132 | 977 |
| 614D antisense probe (1.1) | 9 | * | | 752 | 541 | 496 | 696 | 280 | 278 | 743 | 529 | 746 | 1828 | 913 |
| 614D antisense probe (1.2) | 37 | | | 706 | 726 | 964 | 633 | 932 | 1156 | 916 | 299 | 221 | 326 | 1254 |
| 614D antisense probe (1.3) | 38 | | | 1370 | 1257 | 1177 | 1241 | 1367 | 2066 | 1274 | 1053 | 659 | 750 | 2263 |
| 614G antisense probe (1.4) | 21 | | * | 1169 | 1131 | 821 | 691 | 635 | 976 | 1051 | 606 | 1230 | 345 | 1235 |
| 614G antisense probe (1.1) | 10 | * | | 1264 | 1514 | 1472 | 1256 | 911 | 1359 | 1288 | 954 | 1429 | 1025 | 1527 |
| 614G antisense probe (1.2) | 39 | | | 1330 | 1162 | 1387 | 1425 | 1231 | 1738 | 1353 | 1043 | 889 | 826 | 2180 |
| 614G antisense probe (1.3) | 40 | | | 2309 | 2843 | 3013 | 2680 | 2615 | 2804 | 3015 | 2427 | 9517 | 4717 | 5021 |
| SARS.CoV2-N2-RE1.5 | | | | 39160 | 548 | 1996 | 48636 | 89 | 432 | 1006 | 865 | 2369 | 2645 | 1039 |
| SARS.CoV2-N2-RE1.6 | | | | 62149 | 2156 | 4407 | 61697 | 2610 | 3024 | 2530 | 2862 | 2456 | 2631 | 2057 |
| SARS.CoV1-N2-RE1.5 | | | | 433 | 45995 | 161 | 782 | −56 | 121 | 386 | 372 | 2592 | 706 | 116 |
| SARS.CoV1-N2-RE1.6 | | | | 114 | 48560 | 95 | 79 | 805 | 2108 | 479 | −170 | 338 | 266 | 751 |
| hCoV19/PANG1-N2-RE1.2 | | | | 9921 | 379 | 628 | 13736 | 360 | 872 | 402 | 162 | 5 | 164 | 1236 |
| hCoV19/PANG1-N2-RE1.4 | | | | 689 | 795 | 687 | 1268 | 1104 | 479 | 677 | 450 | 771 | 391 | 1242 |
| hCoV19/PANG2-N2-RE1.2 | | | | 2729 | 869 | 934 | 3829 | 918 | 1525 | 985 | 890 | 467 | 685 | 1928 |
| hCoV19/PANG2-N2-RE1.4 | | | | 2167 | 16061 | 2824 | 4880 | 2485 | 4792 | 2232 | 9856 | 2885 | 2613 | 3893 |
| BAT2.CoV-N2-RE1.2 | | | | 4368 | 1955 | 2137 | 7769 | 1697 | 2115 | 2164 | 1938 | 2779 | 2343 | 2614 |
| BAT2.CoV-N2-RE1.4 | | | | 704 | 825 | 570 | 994 | 238 | 730 | 129 | 323 | 274 | 803 | 864 |
| SARS-rel.CoV-N2-RE1.2 | | | | 695 | 463 | 703 | 414 | 644 | 762 | 818 | 504 | 604 | 1121 | 1011 |
| SARS-relCoV-N2-RE1.4 | | | | 1271 | 386 | 640 | 2313 | 406 | 538 | 794 | 589 | 878 | 1588 | 623 |
| hCoV19/BAITYUN-N2-RE1.2 | | | | 2243 | 1161 | 1729 | 3706 | 1131 | 1202 | 1353 | 1294 | 1973 | 1564 | 1447 |
| hCoV19/BAITYUN-N2-RE1.5 | | | | 1697 | 946 | 1407 | 1540 | 718 | 1069 | 847 | 669 | 1643 | 1255 | 1131 |
| RNAse.P.Probe-pub1.3 | | | | 62149 | 61822 | 61921 | 61697 | 61839 | 62125 | 62099 | 62388 | 61165 | 61732 | 62625 |
| RNAse.P.Probe-RE1.4 | | | | 62070 | 61822 | 61921 | 61578 | 61837 | 62125 | 62011 | 62361 | 61120 | 61602 | 62656 |
| RNAse.P.Probe-pub2.1 | | | | 1204 | 2380 | 3812 | 1626 | 1394 | 1551 | 1304 | 1726 | 5618 | 6899 | 903 |

TABLE 18-continued

Analysis of clinical nasopharyngeal swab sampes on a DETECTX-RV microarray using Asymmetric One-Step RT-PCR

| Probe Name | Position on R&D array | *384 array (current) | *384 array (next) | 1 CoV2 IDT plasmid | 2 SARS IDT plasmid | 3 MERS IDT plasmid | 4 CoV2 gRNA (D) | 5 (D)614gene fragment | 6 (D)614gene fragment | 7 influenza A gene fragment | 8 influenza B gene fragment | 9 influenza A gRNA | 10 influenza B gRNA | No template control |
|---|---|---|---|---|---|---|---|---|---|---|---|---|---|---|
| RNAse.P.Probe-RE2.2 | | | | −261 | −620 | −614 | −676 | 337 | −164 | −703 | −161 | −1094 | −530 | −41 |
| RdRP_Ber_P2_CoV2 | | | | −123 | −287 | −131 | −68 | −48 | −106 | −212 | −227 | −811 | −101 | −42 |
| RdRP_P2_CoV2_RE1.1 | | | | −1134 | −1223 | −1059 | −1130 | −1183 | −1077 | −1126 | −964 | −1842 | −1067 | −1008 |
| RdRP_P2_PAN_RE1.1 | | | | 1151 | 729 | 1259 | 1334 | 876 | 1145 | 1259 | 971 | 686 | 1446 | 862 |
| E_Sarb_Pan_RE1.2 | | | | 2817 | 5010 | 3941 | 3161 | 3546 | 3840 | 3165 | 2743 | 7209 | 3221 | 4507 |
| B2M_RE1.1 | | | | 746 | 758 | 1017 | 946 | 714 | 1707 | 1080 | 1442 | 776 | 1159 | 974 |
| B2M_RE2.1 | | | | 302 | −144 | −27 | −5 | −84 | −13 | 112 | 480 | −135 | 175 | 162 |

Optimization 4
Materials:
1. LLoD samples: Freshly collected positive and negative nasopharyngeal swab samples (TriCore) spiked with 25 copies/400 µl reaction (62.5 copies/ml) of purified SARS-CoV2 RNA.
2. Clinical samples: Freshly collected positive and negative nasopharyngeal swab samples (TriCore).
3. DETECTX-RV kit.
4. 96-well glass microarray print series—9903003 plates
5. Labeling primer Thirty positive and 30 negative samples were used for LLoD analysis. Freshly prepared and negative NP-VTM samples from TriCore (New Mexico) samples doped with purified. SARS-CoV-2 RNA standard were used. All 60 NP-VTM samples were analyzed using the 4:1 asymmetric PCR primer ratio (at 2× higher concentration). Each hybridization probe was analyzed individually to yield average and standard deviation of signal intensity (RFU), sensitivity, specificity, PPV and NPV. Tables 18 and 19 summarizes the results of the LLoD and the Clinical Sensitivity/Specificity analysis respectively.

The LLoD analysis (Tables 19 and 20) was found to be identical within experimental accuracy to the Asymmetric One-Step RT-PCR optimization obtain earlier (('Optimization 3') as well as the 2-step RT-PCR reaction discussed above. Thus, these data confirm what was previously seen in 12 well slides, namely that the LLoD obtained with the Asymmetric One-Step RT-PCR protocol is identical, within experimental accuracy to that obtained via the Asymmetric, Tandem 2-Step RT-PCR reaction profile and is not affected by transition from 12 well to 96-well processing.

Analysis of the full set of 30+ and 30− TriCore samples, each previously analyzed via an industry standard Roche predicate q-rt-PCR assay (Tables 21 and 22) yielded clinical sensitivity of 100% for both the Asymmetric One-Step RT-PCR and Asymmetric Two Step RT-PCR methods, for the full set of 30 positive and 30 negative samples.

Clinical specificity at the local probe level on the other hand were not 100%, being about 94% for the Asymmetric One-Step RT-PCR method and 100% for the 2-Step RT-PCR method. Thus, the 2-Step method detected 3 false positives and the Asymmetric One-Step RT-PCR detected 2 false positives in the same set of 30 TriCore Negatives. This discordance was resolved by third party sequencing and it was shown that the positives detected by microarray analysis did in fact contain SARS-CoV-2, which had not been detected by the predicate Q-RTPCR assay.

TABLE 19

Analysis of clinical nasopharyngeal swab samples on a DETECTX-RV microarray using Asymmetric-Step One RT-PCR

| Clinical Samples | PS2 | PS5 | gRNA | Neg1 | Neg4 | NTC | PS2 (infA,B) | PS5 (infA,B) | CoV2 gRNA (infA, B) | Neg1 (infA, B) | Neg4 (infA, B) | NTC (infA, B) | Average signals from clinical sample |
|---|---|---|---|---|---|---|---|---|---|---|---|---|---|
| 62-Negcont-B | 1601 | 962 | 1028 | 2101 | 1603 | 1110 | 1825 | 1853 | 938 | 1458 | 1058 | 1245 | 1640 |
| SARS.COV2-N1-RE1.1 | 31578 | 29980 | 61449 | −5 | −259 | 1407 | 12105 | 14927 | 61362 | −11 | −50 | 170 | 32850 |
| SARS.COV2-N2-RE1.3 | 17229 | 16374 | 49596 | 960 | 661 | 2050 | 12280 | 11392 | 50163 | 628 | 871 | 1994 | 38570 |
| SARS.COV2-N2-RE1.4 | 47605 | 46614 | 61603 | 1922 | 2346 | 2893 | 38540 | 39854 | 61479 | 1574 | 2286 | 3895 | 43670 |
| SARS.COV2-N3-RE1.1 | 60036 | 49602 | 61602 | 4327 | 4941 | 2141 | 43957 | 42055 | 61498 | 3921 | 3351 | 4090 | 59723 |
| RNAse.P.Probe-pub1.1 | 3307 | 3890 | 1702 | 4561 | 4585 | 2454 | 2565 | 2643 | 2451 | 2985 | 3082 | 3162 | |
| InfA.7.univ-pubRev | 422 | 1257 | 369 | 443 | 2033 | 552 | 39579 | 40285 | 20903 | 38128 | 22691 | 42846 | |
| InfB.8.univ-pub | 102 | 953 | 112 | 34 | 1437 | 414 | 45076 | 39136 | 38437 | 39559 | 35394 | 40884 | |
| 614U-SE-S1-RE1.1 * | 14908 | 13172 | 41545 | 335 | 425 | 461 | 6546 | 6309 | 38526 | 316 | 229 | 321 | |
| 614D-SE-S1-RE1.4 ¶ | 833 | 785 | 37215 | 336 | 489 | 410 | 833 | 547 | 34632 | 361 | 922 | 1103 | |
| 614G-SE-S1-RE1.4 § | 5728 | 4792 | 1762 | 920 | 803 | 559 | 2815 | 3218 | 1584 | 493 | 1104 | 835 | |
| SARS.CoV2-N2-RE1.5 | 20132 | 17893 | 54453 | 370 | 797 | 637 | 13826 | 14895 | 53076 | 429 | 2129 | 1494 | |
| SARS.CoV2-N2-RE1.6 | 44125 | 44266 | 61603 | 1466 | 2298 | 3423 | 38153 | 39052 | 61498 | 1748 | 2830 | 2944 | |
| SARS.CoV1-N2-RE1.5 | 656 | 888 | 820 | 1026 | 1634 | 564 | 1224 | 7027 | 936 | 1730 | 2996 | 1261 | |
| SARS.CoV1-N2-RE1.6 | 821 | 1239 | 35 | 948 | 1678 | 655 | 1106 | 1400 | −151 | 1120 | 1936 | 469 | |

* Spike = D + G,
¶ D Variant = Wuhan like,
§ G Variant = European like

TABLE 20

Limit of detection analysis for Asymmetric One-Step RT-PCR using 12-well array format and a 4:1 primer mix.

| Proper Description | Average | Standard Deviation | (a) True Positives | (b) False Positives | (c) False Negatives | (d) True Negatives | LoB | LoD copies/ reaction | Sensitivity | Specificity | PPV | NPV |
|---|---|---|---|---|---|---|---|---|---|---|---|---|
| 62-Negcont-B | 2155 | 370 | 30 | N/A | 0 | N/A | N/A | 25 | 100.0 | N/A | N/A | N/A |
| SARS.COV2-N1-pub | 32556 | 9721 | 30 | N/A | 0 | N/A | N/A | 25 | 100.0 | N/A | N/A | N/A |
| SARS.COV2-N2-pub | 48152 | 11944 | 30 | N/A | 1 | N/A | N/A | 25 | 96.8 | N/A | N/A | N/A |
| SARS.COV2-N3-pub | 30106 | 8777 | 30 | N/A | 0 | N/A | N/A | 25 | 100.0 | N/A | N/A | N/A |

TABLE 20-continued

Limit of detection analysis for Asymmetric One-Step
RT-PCR using 12-well array format and a 4:1 primer mix.

| Proper Description | Average | Standard Deviation | (a) True Positives | (b) False Positives | (c) False Negatives | (d) True Negatives | LoB | LoD copies/ reaction | Sensitivity | Specificity | PPV | NPV |
|---|---|---|---|---|---|---|---|---|---|---|---|---|
| SARS.COV2-N1-RE1.1 | 14887 | 7673 | 30 | N/A | 0 | N/A | N/A | 25 | 100.0 | N/A | N/A | N/A |
| SARS.COV2-N2-RE1.3 | 38222 | 12691 | 30 | N/A | 1 | N/A | N/A | 25 | 96.8 | N/A | N/A | N/A |
| SARS.COV2-N2-RE1.4 | 52709 | 11996 | 30 | N/A | 0 | N/A | N/A | 25 | 100.0 | N/A | N/A | N/A |
| SARS.COV2-N1-RE1.1 | 14290 | 7419 | 30 | N/A | 1 | N/A | N/A | 25 | 96.8 | N/A | N/A | N/A |
| RNAse.P.Probe-pub1.1 | 6224 | 6480 | 30 | N/A | 0 | N/A | N/A | 25 | 100.0 | N/A | N/A | N/A |

TABLE 21

Clinical Sensitivity and Specificity Analysis for Asymmetric One-Step RT-PCR

| Probe Description | Average Positives | Standard Deviation Positives | Average Negatives | Standard Deviation Negatives | (a) True Positive | (b) False Positives | (c) False Negative | (d) True Negative | LoB | LoD | Sensitivity | Specificity | PPV | NPV |
|---|---|---|---|---|---|---|---|---|---|---|---|---|---|---|
| 62-NegCont-B | 1581 | 1477 | 1195 | 620 | 30 | 0 | 0 | 30 | N/A | N/A | 100 | 100 | 100 | 100 |
| SARS.COV2-N1-RE1.1 | 49470 | 15630 | 2111 | 5626 | 30 | 2 | 1 | 30 | N/A | N/A | 97 | 94 | 94 | 97 |
| SARS.COV2-N2-RE1.3 | 50383 | 16691 | 2306 | 4298 | 30 | 2 | 2 | 30 | N/A | N/A | 94 | 94 | 94 | 94 |
| SARS.COV2-N2-RE1.4 | 55425 | 11305 | 18258 | 9984 | 30 | 0 | 0 | 30 | N/A | N/A | 100 | 100 | 100 | 100 |
| SARS.COV2-N3-RE1.1 | 53144 | 14343 | 4403 | 8808 | 30 | 2 | 0 | 30 | N/A | N/A | 100 | 94 | 94 | 100 |
| RNAse.P.Probe-pub1.1 | 6009 | 7451 | 18237 | 13677 | 30 | 0 | 0 | 30 | N/A | N/A | 100 | 100 | 100 | 100 |
| Overall Results | N/A | N/A | N/A | N/A | 30 | 2 | 0 | 30 | N/A | N/A | 100 | 94 | 94 | 100 |

TABLE 22

Clinical Sensitivity and Specificity Analysis for Standard DETECTX-RV (RT-PCR + Labeling PCR)

| Probe Description | Average Positives | Standard Deviation Positives | Average Negatives | Standard Deviation Negatives | (a) True Positive | (b) False Positives | (c) False Negative | (d) True Negative | LoB | LoD | Sensitivity | Specificity | PPV | NPV |
|---|---|---|---|---|---|---|---|---|---|---|---|---|---|---|
| 62-Negcont-B | 1626 | 426 | 2196 | 1928 | 30 | 0 | 0 | 30 | N/A | N/A | 100 | 100 | 100 | 100 |
| SARS.COV2-N1-RE1.1 | 57318 | 5808 | 4316 | 15424 | 30 | 3 | 0 | 30 | N/A | N/A | 100 | 91 | 91 | 100 |
| SARS.COV2-N2-RE1.3 | 58079 | 3173 | 7929 | 15774 | 30 | 4 | 0 | 30 | N/A | N/A | 100 | 88 | 88 | 100 |
| SARS.COV2-N2-RE1.4 | 59119 | 469 | 10853 | 20248 | 30 | 5 | 0 | 30 | N/A | N/A | 100 | 86 | 86 | 100 |
| SARS.COV2-N3-RE1.1 | 59354 | 473 | 12372 | 23104 | 30 | 6 | 0 | 30 | N/A | N/A | 100 | 83 | 83 | 100 |
| RNAse.P.Probe-pub1.1 | 59103 | 461 | 60174 | 698 | 30 | 0 | 0 | 30 | N/A | N/A | 100 | 100 | 100 | 100 |
| Overall Results | N/A | N/A | N/A | N/A | 30 | 4 | 0 | 30 | N/A | N/A | 100 | 88 | 88 | 100 |

A detailed analysis of individual probe Clinical Sensitivity revealed that 2 probes ([N1, 1.1], [N2, 1.3]) have generated 1 and 2 false negatives respectively. These 3 rare events did not affect the Overall AUGURY sensitivity, which remained at 100% because of its use of multiple probes to make a call.

Conclusions

Asymmetric One-Step RT-PCR performance with Clinical Isolates in the 96-well format has improved significantly over prior optimizations due to use of RNA extracted from fresh samples and 2× increase of Primer Concentration 2×. Sensitivity among all probes tested has yielded an increase in Average N1, N2 and N3 probe Clinical Sensitivity to about 97% (range=94%-100%). However, the aggregated AUGURY readouts obtained provide a 100% Sensitivity, since Augury aggregates hybridization data from all (3) independent loci tests.

Optimization 5
Optimized Clinical Validation of Mini-RV Panel
Materials and Methods:
1. The 12-well Mini-RV Array (R&D Format) was deployed.
2. Testing was performed on fresh clinical isolates (Boca Biolistics) via the Asymmetric One-Step RT-PCR reaction for the entire set of targets (S, N1, N2, N3, P, PanA, PanB) but with a more efficient set of PCR primers for RNAse P
3. Influenza A and Influenza B was tested by use of purified Influenza A or Influenza B gRNA (ATCC reference standards) added to positive or negative clinical isolates for detection using "PanA" and "PanB" probes on the array.
4. Optimized Asymmetric, One-Step RT-PCR was deployed and standard Hybridization/Wash Conditions.

5. Results: Using a small number of clinical isolates (2 positives, 2 negatives) the full panel of probes described in Table 12 (S, N1, N2, N3, PanA, PanB) were used to analyze the product of the Asymmetric, One-Step RT-PCR reaction. To offset low RNase P signals seen in the previous optimization (Tables 18-22), an alternative, higher efficiency RNAse P primer pair was used (SEQ ID: 43 and SEQ ID: 44). Additionally, the RNase-P primer concentration was increased 2× Table 23 shows a summary of the data for the 12-well format.

Asymmetric One-Step RT-PCR Performance Optimization

Freshly collected NP/VTM samples (TriCore) matched with a complete set of Roche Cobas 6800 Q-RT-PCR Ct thresholds were used. Analysis was performed on 384-well plates using 30 positive and 30 negative clinical isolates in an RNAse P modified multiplex PCR reaction. The data obtained (Table 23) was in good agreement with that obtained for the 96-well format using previous RNAse P primers (Tables 18-22) and further provided a better RNAse P signal than previously observed (Tables 18-22).

Gel Analysis and Sequencing

Figure 19A:
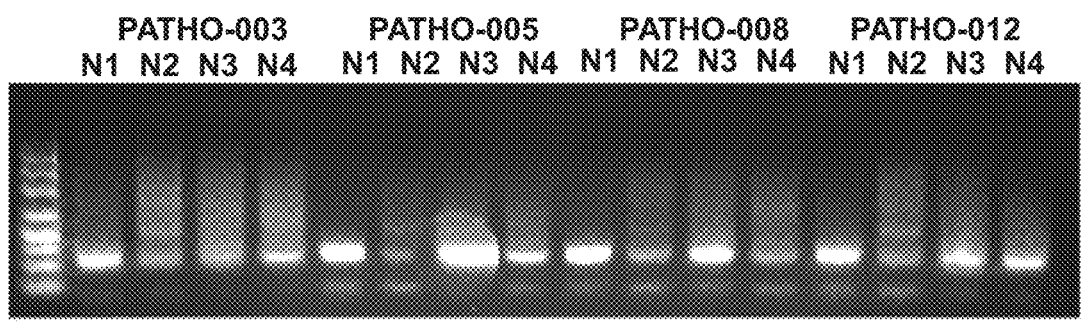
FIGS. 19A-19B show gel analysis for discordant TriCore clinical samples.
Figure 19B:
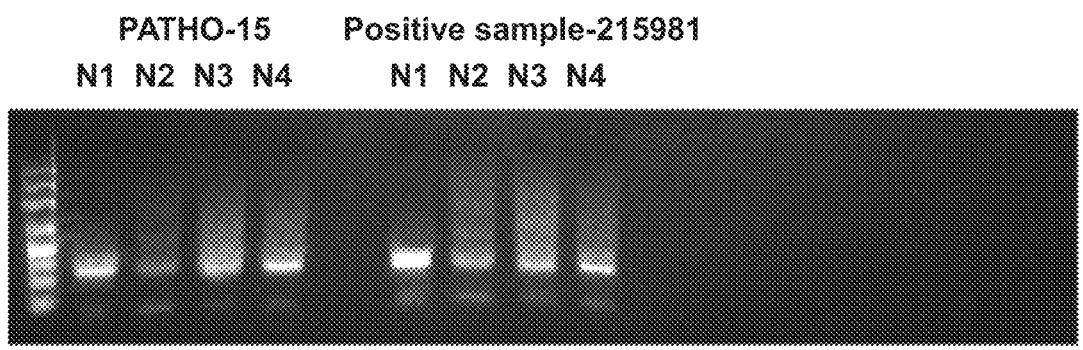

Four sequencing primers with M13 tags were created and the amplicons generated using the Asymmetric One-Step RT-PCR method (Asymmetric One-Step RT-PCR) were analyzed by gel electrophoresis. FIGS. 19A and 19B show that discordant samples each produce an amplicon fragment of the correct size associated with the expected SARS-CoV2 amplification. N1, N2, N3 refer to microarray probes specific the N1, N2, and N3 sites in SARS-CoV-2 and P refers to probe specific for human RNAse P, which are used as an internal positive control.

Sequence Analysis of Discordant Clinical Samples.

Figure 20:
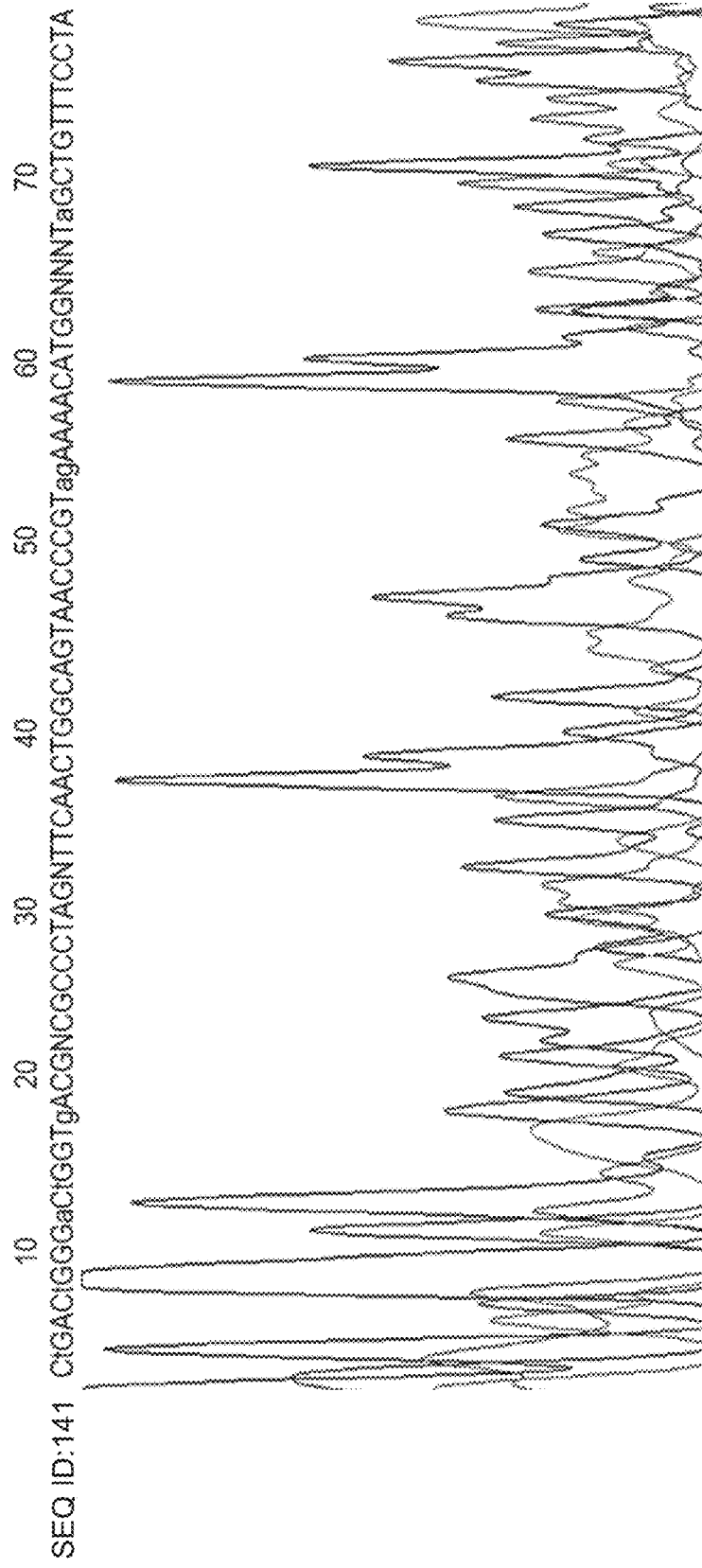
FIG. 20 shows a representative sequencing chromatograph for N1-M13F sample.

TriCore samples identified as "Negative" by Cobas but identified as "Positive" on multiple repeats of the DETECTX-RV assay were sequenced (third party sequencing, University of Arizona). The sequencing data shown in FIG. 20 for a representative PATHO-003 sample (N1-M13F) was found to agree with the gel data. This confirmed that the discordant samples each contain measurable SARs-CoV2 infection (loci N1 & N2).

Improved Sequence Analysis of Discordant Clinical Samples.

Clinical samples (30 positive/30 negative NP/VTM, TriCore) tested using the Cobas 6800 platform were used as clinical reference samples to evaluate sensitivity and specificity of the DETECTX-RV assay using Two-Step Tandem and Asymmetric One-Step RT-PCR reaction methods. To confirm accuracy of the DETECTX-RV "Positive" readouts, Sanger sequencing was performed within the N Region, on all 6 discordant samples and one of the many 'Positive' samples, which had been identified as "Positive" by both COBAS and DETECTX-RV. The results shown in Table 24 are in agreement with DETECTX-RV—all 6 discordant samples were identified by Sanger sequencing as containing measurable SARS-CoV-2 RNA. Sequence heterogeneity (N) in several of the negative samples was also observed.

TABLE 23

Asymmetric One-Step RT-PCR of Full Mini-RV Array (S, N1, N2, N3, P, PanA, PanB) for Clinical Isolates on 12-well slides using higher effency RNAse P primers (SEQ ID: 43 and SEQ ID: 44) as internal control.

|  | PS-1 | PS-2 | PS-1 (InfA) | PS-1 (InfB) | CoV2 gRNA | Neg-1 | Neg-2 | Neg-1 (InfA) | Neg-1 (InfB) | NTC |
|---|---|---|---|---|---|---|---|---|---|---|
| 62-Negcont-B | 895 | 1332 | 826 | 1241 | 777 | 1658 | 1763 | 1441 | 1231 | 1368 |
| SARS.COV2-N1-RE1.1 | 61824 | 48746 | 51658 | 61633 | 36639 | 751 | 1164 | 224 | 166 | 3336 |
| SARS.COV2-N2-RE1.3 | 50873 | 38694 | 39954 | 48652 | 17141 | 598 | 1102 | 566 | 873 | 589 |
| SARS.COV2-N2-RE1.4 | 61857 | 62211 | 62104 | 61720 | 37147 | 883 | 738 | 879 | 1068 | 1012 |
| SARS.COV2-N3-RE1.1 | 61807 | 56525 | 61989 | 61689 | 54650 | 2668 | 1979 | 2941 | 3422 | 2596 |
| RNAse.P.Probe-pub1.1 | 53845 | 39257 | 38696 | 44316 | 2148 | 52419 | 40222 | 44258 | 50423 | 1471 |
| infA.7.univ-pubRev | 132 | −176 | 34385 | 32 | −38 | 481 | 64 | 49966 | 997 | 1 |
| infB.8.univ-pub | −171 | −184 | 2231 | −290 | −403 | −78 | −312 | 209 | 13251 | −42 |
| 614U-SE-S1-RE1.1 | 61838 | 43200 | 48452 | 58826 | 13240 | 729 | 582 | 335 | 350 | 714 |
| 614D-SE-S1-RE1.4 | 13956 | 4858 | 7082 | 12120 | 9885 | 33 | 79 | 809 | 306 | 209 |
| 614G-SE-S1-RE1.4 | 49820 | 35581 | 39167 | 44014 | 1467 | 734 | 653 | 752 | 549 | 568 |

TABLE 24

SARS-CoV-2 Sequencing of "Discordant" Clinical NP/VTM Samples

| Sample | SEQ ID Number | Primer Alignment | Discordant and SARS-CoV-2 Sequences Aligned | Percent Alignment | One Step | Two Step |
|---|---|---|---|---|---|---|
| Discordant-1 | SEQ ID: 98 | TTCCNNCGGNAGGCCNGCCATTGGG[C]<br>\|\|\|* \|\|\| \|*\|*\| **\|\|\|\| \|\|\|<br>TTCTT CGGAATGTCGCGCATT GGC | Discordant-1 SARS-CoV-2 | 62% | + | + |
|  | SEQ ID: 99 | -AAACNTGGACNNNNGCGTGNTTTCC<br>\|\|\|\| \|\|\|*\| \|\| \|\| \|\|\|\|\|<br>-AAACATGGTCATA GC TG TTTCCT | Discordant-1 SARS-CoV-2 |  |  |  |
| Discordant-2 | SEQ ID: 100 | TTCTTCGGGAGGGCGNGCATTGGGC[N]<br>\|\|\|\|\|\|\|\|*\|*\|*\|\| \|\|\|\| \|\|\|<br>TTCTTCGGAATGTCGCGCATT GGCA | Discordant-2 SARS-CoV-2 | 84% | − | + |

TABLE 24-continued

SARS-CoV-2 Sequencing of "Discordant" Clinical NP/VTM Samples

| Sample | SEQ ID Number | Primer Alignment | Discordant and SARS-CoV-2 Sequences Aligned | Percent Alignment | One Step | Two Step |
|---|---|---|---|---|---|---|
| | SEQ ID: 99 | -AACATGGGTCATAGCTGTTTCCT<br>\|\|\|\|\|\|\| \|\|\|\|\|\|\|\|\|\|\|\|\|\|\|\|<br>-AACATG GTCATAGCTGTTTCCT | Discordant-2<br>SARS-CoV-2 | | | |
| Discordant-3 | SEQ ID: 101 | TTCTTCGGGAANGTCGCGGCATNGG$^C$<br>\|\|\|\|\|\|\|\| \|\| \|\|\|\|\|\| \|\|\| \|\|\|<br>TTCTTCGG AATGTCGCG CATTGGC | Discordant-3<br>SARS-CoV-2 | 84% | - | + |
| | SEQ ID: 99 | -AAACATGGGGTCATAGGCTGNTTTCCT<br>\|\|\|\|\|\|\|\| \|\|\|\|\|\|\| \|\|\| \|\|\|\|\|\|<br>-AAACATG GTCATAG CTG TTTCCT | Discordant-3<br>SARS-CoV-2 | | | |
| Discordant-4 | SEQ ID: 102 | TTCTTCGGGAAGGTCGNGGCATTGG$^C$<br>\|\|\|\|\|\|\|\| \|\| \|\|\| \| \|\|\|\|\|\|\|<br>TTCTTCGG AATGTCGCG CATTGGC | Discordant-4<br>SARS-CoV-2 | 76% | - | + |
| | SEQ ID: 99 | -AAACATGGGNTCATAGGCNTGATTTCCT<br>\|\|\|\|\|\|\|\| \|\|\|\|\|\| \| \| \|\|\|\|\|\|<br>-AAACATG GTCATAG CTG TTTCCT | Discordant-4<br>SARS-CoV-2 | | | |
| Discordant-5 | SEQ ID: 103 | TTCTTCGGGAANGTCGCGCATNGGC$^A$<br>\|\|\|\|\|\|\|\| \|\| \|\|\|\|\|\|\|\|\| \|\|\|\|<br>TTCTTCGG AATGTCGCGCATTGGCA | Discordant-5<br>SARS-CoV-2 | 75% | + | + |
| | SEQ ID: 99 | -AACANGGTCATAGCTGGTTTCCT<br>\|\|\|\|\| \|\|\|\|\|\|\|\|\|\|\|\| \|\|\|\|\|\|<br>-AACATGGTCATAGCTG TTTCCT | Discordant-5<br>SARS-CoV-2 | | | |
| Discordant-6 | SEQ ID: 104 | TTCTTCGGGAAGGTCGCGGCATTGG$^C$<br>\|\|\|\|\|\|\|\| \|\| \|\|\|\|\| \|\|\|\|\|\|\|\|<br>TTCTTCGG AATGTCGC GCATTGGC | Discordant-6<br>SARS-CoV-2 | 97% | - | Return |
| | SEQ ID: 99 | -AAACATGGATCATAGTNTGNTTTCCT<br>\|\|\|\|\|\|\|\|\| \|\|\|\|\|\| \|\| \|\|\|\|\|\|<br>-AAACATGG TCATAG CTG TTTCCT | Discordant-6<br>SARS-CoV-2 | | | |
| SARS-CoV-2 Positive Control | SEQ ID: 105 | TTCTTCGGAATGTCGCGCATTGGCA$^A$<br>\|\|\|\|\|\|\|\|\|\|\|\|\|\|\|\|\|\|\|\|\|\|\|\|<br>TTCTTCGGAATGTCGCGCATTGGCAA | Positive Control SARS-CoV-2 | 99% | + | + |
| | SEQ ID: 99 | -ACATGGTCATAGCNTGTTTCCT<br>\|\|\|\|\|\|\|\|\|\|\|\|\|\| \|\|\|\|\|\|\|\|<br>-ACATGGTCATAGC TGTTTCCT | Positive Control SARS-CoV-2 | | | |

99002-M13R (N2-Reverse) Reverse Complement

Example 13

Incorporation of Influenza Probes into the Array

Influenza A & B probes and primers were added to the 12-well array during analysis using the 2-step method. The hybridization data (Table 25) show that the influenza probes and primers may be used as such with no further refinement.

Example 14

Raw Sample Feasibility Testing
Materials:
1. Mouthwash from patients diagnosed with SARS-CoV2
2. Asymmetric One-Step RT-PCR and labelling primers
3. Two-step RT-PCR
4. DETECTX-RV kit
5. Tris-HCl pH 9 with MgCl$_2$ at pH 3, 4, 5, 6, 8 and 10 mM Reducing the time taken from obtaining the sample to performing the microarray analysis is expected to significantly increase the number of sample that may be processed per day, a factor that is critical during a pandemic. To establish the feasibility of bypassing the RNA isolation step in the method, experiments were performed using clinical mouthwash samples (QuikSal) from patients diagnosed with SARS-CoV2. The data in Table 26 shows the results of analysis in samples where the RNA extraction step was omitted. It was observed that raising the pH to the ordinary PCR range of pH 9.0 and adding Mg$^2$ to coordinate EDTA and citrate in the QuikSal, mouthwash enabled microarray analysis in crude samples with no further RNA purification.

Example 15

Automation and Analysis: 96-Well and 384-Well Plates

RNA Extraction using Zymo Magnetic Beads and RNA loading onto PCR plates for RT-PCR was established using Tecan. Hybridization and Washing Automation for Asymmetric One-Step RT-PCR in 96-well format was completed for the Tecan and a first 96-well plate. It was run through with 20 positive Clinical Isolates (TriCor)+76 negative (water-only) samples. The corresponding 384 well software was also tested with clinical samples using a Tecan code modified for 384-well plate operation, capable of 384-well function with a 96-pipette head.

TABLE 25

Incorporation of influenza Lead primers and probes in the Two-step PCR and hybridization analysis Influenza A primer set 1
RT-PCR
Forward Primer SEQ ID: 17    TTTATGGCTAAAGACAAGACCRATCCTG
Reverse Primer SEQ ID: 18    TTTTTAAGGGCATTYTGGACAAAKCGTC
Label-PCR
Forward Primer SEQ ID: 39    TTTCAAGACCRATCCTGTCACCTCTGAC
Reverse Primer SEQ ID: 40    /5CY3/TTTAAGGGCATTYTGGACAAAKCGTCTA Influenza A primer set 2
RT-PCR
Forward Primer SEQ ID: 17    TTTATGGCTAAAGACAAGACCRATCCTG
Reverse Primer SEQ ID: 40    TTTAAGGGCATTYTGGACAAAKCGTCTA
Label-PCR
Forward Primer SEQ ID: 39    TTTCAAGACCRATCCTGTCACCTCTGAC
Reverse Primer SEQ ID: 81    /5CY3/TTTGGGCATTYTGGACAAAKCGTCTACG Influenza B primer set 1
RT-PCR
Forward Primer SEQ ID: 19    TTTGGATGAAGATGGCCATCGGATC
Reverse Primer SEQ ID: 20    TTTTCTAATTGTCTCCCCTTCTGGTGA
Label-PCR
Forward Primer SEQ ID: 82    TTTGGATCCTCAACTCACTCTTCGAGCG
Reverse Primer SEQ ID: 42    /5CY3/TTTTAATCGGTGCTCTTGACCAAATTGG Influenza B primer set 2
RT-PCR
Forward Primer SEQ ID: 82    TTTGGATCCTCAACTCACTCTTCGAGCG
Reverse Primer SEQ ID: 106   TTTTCCCTTCTGGTGATAATCGGTGC
Label-PCR
Forward Primer SEQ ID: 41    TTTGCGTTCAATGAAGGACATTCAAAG
Reverse Primer SEQ ID: 42    /5CY3/TTTTAATCGGTGCTCTTGACCAAATTGG

| | Probe Name (specificity) | Influenza A primer set 1 infA Target Well 1 | Influenza A primer set 2 Well 2 | Influenza A primer set 1 No template Well 5 | Influenza A primer set 2 primer control Well 6 | Influenza B primer set 1 infB Target Well 9 | Influenza A primer set 2 Well 10 | Influenza B primer set 1 No template Well 11 | Influenza A primer set 2 Well 12 |
|---|---|---|---|---|---|---|---|---|---|
| 1 | 62-Negcont-B | 1807 | 1714 | 1727 | 1429 | 1679 | 1359 | 1406 | 1211 |
| 2 | SARS.COV2-N1-pub | 636 | 693 | 889 | 455 | 534 | 530 | 588 | 493 |
| 3 | SARS.COV2-N1-RE1.1 | 730 | 750 | 633 | 630 | 859 | 657 | 641 | 640 |
| 4 | SARS.COV2-N1-RE1.2 | 305 | 185 | 168 | 29 | 160 | 93 | 128 | 103 |
| 5 | SARS.COV2-N1-RE1.3 | 161 | 290 | 355 | -6 | 146 | 60 | 179 | 135 |

TABLE 25-continued

| | | | | | | | | | |
|---|---|---|---|---|---|---|---|---|---|
| 6 | SARS.COV2-N2-pub | 894 | 968 | 976 | 732 | 630 | 399 | 707 | 650 |
| 7 | SARS.COV2-N2-RE1.1 | 1112 | 1300 | 1150 | 987 | 1006 | 1017 | 1264 | 1018 |
| 8 | SARS.COV2-N2-RE1.2 | 724 | 755 | 567 | 482 | 661 | 610 | 590 | 558 |
| 9 | SARS.COV2-N2-RE1.3 | 1532 | 1796 | 1449 | 1086 | 1493 | 1205 | 1245 | 1255 |
| 10 | SARS.COV2-N2-pbVAR | 660 | 979 | 1008 | 640 | 1118 | 803 | 598 | 551 |
| 11 | SARS.CoV1-N2-RE1.1 | 580 | 521 | 1157 | 477 | 468 | 560 | 759 | 571 |
| 12 | SARS.CoV1-N2-RE1.2 | 744 | 588 | 1278 | 749 | 939 | 885 | 869 | 719 |
| 13 | SARS.CoV1-N2-RE1.3 | 1045 | 915 | 967 | 1005 | 1298 | 856 | 1157 | 1001 |
| 14 | SARS.COV2-N3-pub | 335 | 168 | 246 | 164 | 248 | 50 | -35 | 89 |
| 15 | SARS.COV2-N3-RE1.1 | 344 | 313 | 365 | 283 | 374 | 234 | 224 | 269 |
| 16 | SARS.COV2-N3-RE1.2 | -12 | 15 | -26 | -56 | -70 | -13 | -98 | -22 |
| 17 | SARS.COV2-N3-RE1.3 | 204 | 297 | 123 | 207 | 238 | 260 | 284 | 231 |
| 18 | RNAse.P.Probe-pub1.1 | 1128 | 892 | 853 | 714 | 768 | 652 | 814 | 807 |
| 19 | RNAse.P.Probe-pub1.2 | 1013 | 854 | 981 | 891 | 940 | 773 | 863 | 981 |
| 20 | InfA.7.univ-Fwd.RE1.1 | 573 | 593 | 553 | 382 | 541 | 220 | 465 | 541 |
| 21 | InfA.7.univ-pubRev | 22662 | 21290 | 289 | 284 | 355 | 157 | 292 | 247 |
| 22 | InfA.7.univ-RE1.1 | 38326 | 35727 | 331 | 305 | 178 | 378 | 292 | 160 |
| 23 | InfA.7.univ-RE1.3 | 28211 | 29917 | 40 | -9 | 82 | 184 | 55 | -34 |
| 24 | InfB.8.univ-pub | 70 | -26 | 1097 | 80 | 59985 | 60694 | -2 | 30 |
| 25 | InfB.8.univ-RE1.1 | 193 | 197 | 214 | 179 | 58811 | 53771 | 216 | 285 |
| 26 | InfB.8.univ-RE1.3 | 455 | 434 | 422 | 469 | 22626 | 16671 | 494 | 390 |
| 27 | H1N1.4.Sel-RE1.1 | -39 | -56 | -29 | 50 | 142 | -29 | 8 | 5 |
| 28 | H1N1.4.Sel-RE1.3 | -45 | -18 | -39 | 10 | -15 | -103 | 2 | -13 |
| 29 | upE.Lu-RE1.1 | 713 | 578 | 674 | 819 | 703 | 831 | 754 | 566 |
| 30 | upE.Lu-RE1.2 | 475 | 410 | 305 | 262 | 250 | 252 | 294 | 227 |
| 31 | MERS.N2.RE-1.1 | 297 | 75 | 141 | 174 | 235 | 125 | 355 | 313 |
| 32 | MERS.N2.RE-1.2 | 1092 | 1067 | 989 | 1097 | 928 | 604 | 909 | 831 |

TABLE 25-continued

| | | | | | | | | | |
|---|---|---|---|---|---|---|---|---|---|
| 33 | MERS.N3.pub-1.1 | 262 | 397 | 289 | 217 | 189 | 361 | 247 | 220 |
| 34 | MERS.N3.RE-1.1 | 1182 | 1110 | 1266 | 801 | 832 | 853 | 972 | 710 |
| 35 | 62-KEL578t-1.2-A | 1038 | 1105 | 1056 | 1064 | 729 | 788 | 820 | 791 |
| 36 | 62-Duf-67T-SE-6.1b | 870 | 1140 | 1749 | 929 | 881 | 1223 | 967 | 981 |
| 37 | SARS.CoV1-N2B-RE1.1 | 355 | 390 | 650 | 432 | 483 | 536 | 964 | 404 |
| 38 | SARS.CoV2-lab-pub | -155 | -153 | -121 | -95 | -30 | -158 | -141 | -111 |
| 39 | SARS.CoV2-lab-RE1.1 | 598 | 615 | 536 | 362 | 657 | 580 | 538 | 480 |
| 40 | SARS.CoV2-lab-RE1.3 | 41 | 140 | 83 | 61 | 156 | 144 | 111 | 8 |
| 41 | HCoV.229E.M-RE1.1 | 809 | 806 | 896 | 786 | 972 | 832 | 997 | 751 |
| 42 | HCoV.229E.M-RE1.2 | 649 | 545 | 511 | 816 | 675 | 286 | 526 | 300 |
| 43 | HCoV.HKU1.N-RE1.1 | 1024 | 1213 | 1382 | 1008 | 977 | 792 | 1003 | 726 |
| 44 | HCoV.HKU1.N-RE1.2 | -557 | -599 | -376 | -589 | -628 | -563 | -529 | -526 |
| 45 | HCoV.NL63.N-RE1.1 | -641 | -623 | -593 | -590 | -504 | -472 | -548 | -553 |
| 46 | HCoV.NL63.N-RE1.2 | -551 | -618 | -531 | -590 | -602 | -527 | -569 | -559 |
| 47 | HCoV.OC43.M-RE1.1 | -582 | -589 | -536 | -608 | -522 | -497 | -527 | 575 |
| 48 | HCoV.OC43.M-RE1.2 | -643 | -614 | -576 | -611 | -590 | -513 | -553 | -553 |
| 49 | SARS.CoV1-N1-RE1.2 | 368 | 358 | 333 | 352 | 225 | 222 | 373 | 284 |
| 50 | SARS.CoV1-N1-RE1.3 | 371 | 370 | 411 | 528 | 515 | 415 | 473 | 552 |

TABLE 26

Asymmetric One-Step RT-PCR and Two-step
RT-PCR analysis in total RNA samples

| Slide Number/Type | 9903 Series | |
|---|---|---|
| Extraction Kit/Primer Set | One-Step | Two-Step |
| Mouthwash Samples | | Sample 6 |
| Probe Description | 8 mM MgCl2 | 8 mM MgCl2 |
| 62-Negcont-B | 3932 | 1748 |
| SARS.COV2-N1-pub | 15307 | 5763 |
| SARS.COV2-N1-RE1.1 | 8982 | 1514 |
| SARS.COV2-N1-RE1.2 | 1574 | 424 |
| SARS.COV2-N1-RE1.4 | 125 | 16 |
| SARS.COV2-N2-pub | 7935 | 34384 |
| SARS.COV2-N2-RE1.1 | 3843 | 5488 |
| SARS.COV2-N2-RE1.2 | 3334 | 4791 |
| SARS.COV2-N2-RE1.3 | 6777 | 11085 |
| SARS.CoV1-N2-pbVAR | 1607 | 1225 |
| SARS.CoV1-N2-RE1.4 | 1816 | 1067 |
| SARS.CoV1-N2-RE1.2 | 1912 | 1138 |
| SARS.CoV1-N2-RE1.3 | 2956 | 1109 |
| SARS.COV2-N3-pub | 22759 | 25631 |
| SARS.COV2-N3-RE1.1 | 11702 | 20475 |
| SARS.COV2-N3-RE1.2 | 5522 | 15413 |
| SARS.COV2-N3-RE1.3 | 5365 | 8871 |
| RNAse.P.Probe-pub1.1 | 3847 | 52902 |
| RNAse.P.Probe-pub1.2 | 1506 | 63217 |
| SARS.COV2-N2-RE1.4 | 11577 | 39409 |

Results

Figure 21:
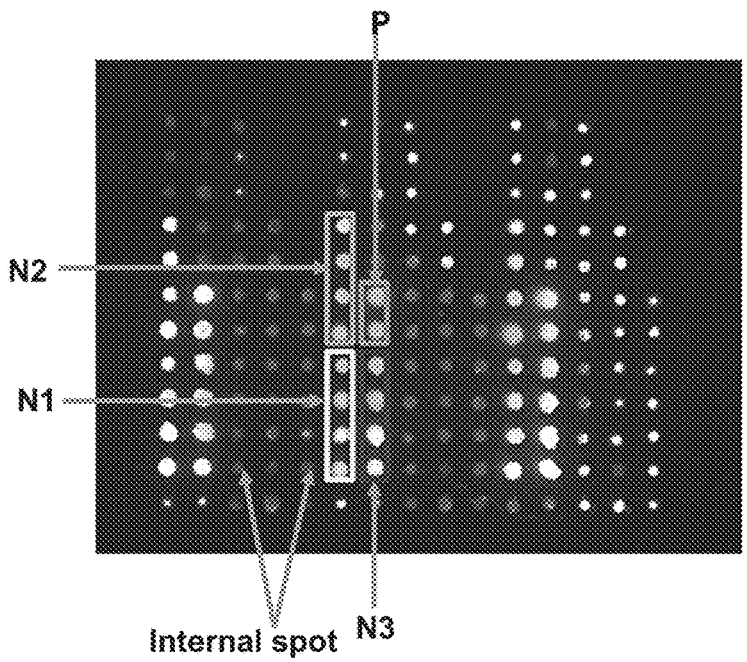
FIG. 21 shows a representative fully automated hybridization and wash in 96-well format.

FIG. 21 shows one well (C3) from the slide (Tricor, COVID-19 Positive sample), which is statistical identical to all 20 of the COVID-19 wells. Nineteen of the twenty positives were correctly identified AUGURY as COVID positive.

Automation End-to-End Mini-RV 96-Well Format.

Time and Resources Required to Execute the Automation Script:

Approximate time elapsed to process 1×96 well slide
  i. RNA extraction—4 h 10 min (including 90 min dry time)
  ii. PCR plate preparation—12.5 min
  iii. PCR amplification (Asymmetric One-Step RT-PCR)—2 h 40 min
  iv. Hybridization script—1 h 45 min
  v. Slide imaging—15 min
Total time ~9 h Tip boxes required to process 1×96 well slide
  i. RNA extraction—4×200 µl+6.5×1000 µl
  ii. PCR plate preparation—1×50 µl
  iii. Hybridization script—0.5×1000 µl+2.5×200 µl+1×50 µl
Total tip boxes: 1 ml-7 boxes, 200 µl-6.5 boxes, 50 µl-2 boxes Two full runs were performed with the Tecan EVO using the 96-well format;

Run 1. Comparison of automation versus manual: A series of contrived samples were created using irradiated SARS-CoV2 lysate in VTM. A checkered board pattern was created to evaluate the robotics and the potential for cross-contamination.

Figure 22A:
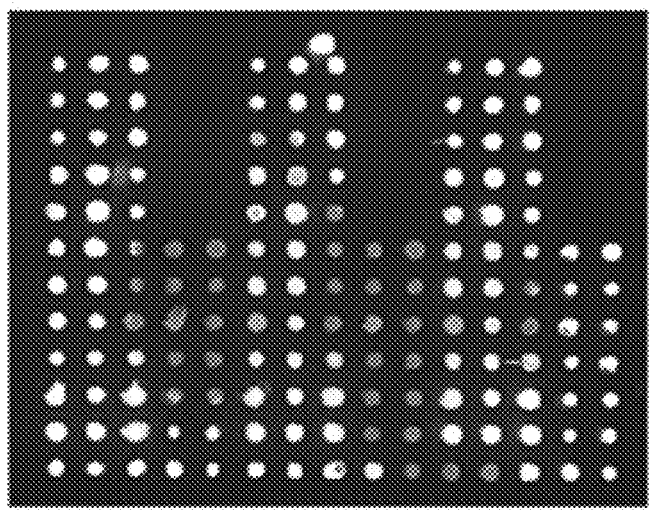
FIGS. 22A and 22B show a comparison of automated and manual hybridization analysis in 96-well format.
Figure 22B:
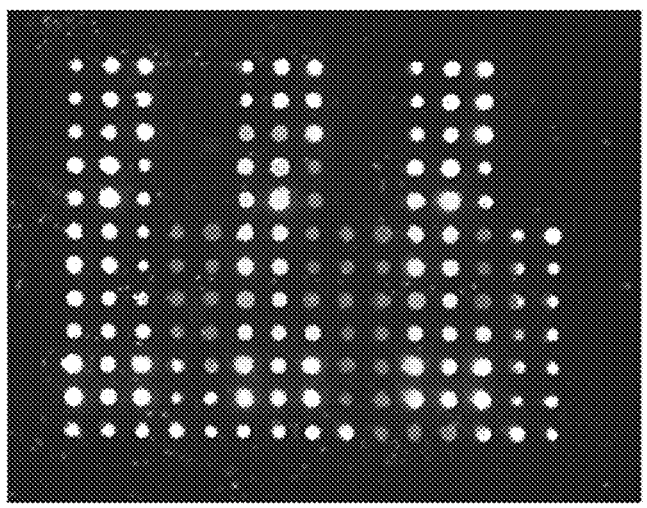

Results: The hybridization signals obtained (FIGS. 22A and 22B) were found to be stronger than that observed in FIG. 21. Data obtained using automation (FIG. 22A, well A1, slide 9903003012) was in excellent agreement with the manual method (FIG. 22B, well G1, slide 9903003012).

Run 2. Clinical sample evaluation: Known positive (25 samples) and negative (22 samples) COVID samples from TriCore were employed, including 49 water blanks. A checkered board pattern was created as above to evaluate the robotics and the potential for cross-contamination.

Results: The hybridization signals obtained were found to be stronger than that observed in FIG. 21. Data obtained using automation was in excellent agreement with the manual method. AUGURY correctly identified all 25 COVID positive samples and 21 of the COVID negative samples Example 16

In Silico Analysis of Human Respiratory Syncytial Virus (HRSV) Feasibility

Adding a RSV test to the previously discussed content (SARS-CoV2, Clade Variant and Influenza A, B) was considered be valuable in this analysis. To test this, a fast-track analysis for implementing a HRSV test with the SARS-CoV2 content was performed. Assay Design. An established Q-RT-PCR assays for HRSV (Table 27) was modified using PDx design principles (Table 28) into a PDx format comprising a single RT-PCR reaction and 3 probes (Pan HRSV probe, Subfamily A probe, Subfamily B Probe).

Incusivity analysis Table 29 shows an inclusivity analysis of the primers and probes for the Hu et al and the PDx assays using the following sequences—HRSV (taxid:11250), HRSV-A (taxid:208893) and HRSV-B (taxid:208895). The analysis revealed that PDx probes have adequate Inclusivity and well suited to distinguish HRSV A subtype from HRSV B subtypes.

TABLE 27

A well-referenced RT-PCR assay to detect HRSV subtypes A and B

```
NC_038235.1.HRSV.A              A-FP                    A-Probe
(SEQ ID: 107)         ------------------------>
                      GATGGCTCTTAGCAAAGTCAAGTTGAATGATACACTCAACAAAGATCAACTTCTGTCATC 1198

NC-001781.1.HRSV.B              B-FP                    B-Probe
(SEQ ID: 108)         -------------------->
                      GATGGCTCTTAGCAAAGTCAAGTTAAATGATACATTAAATAAGGATCAGCTGCTGTCATC 1198
                      ************************ *************** *  *** *** ********

NC_038235.1.HRSV.A    CAGCAAATACACCATCCAACGGAGCACAGGAGATAGTATTGATACTCCTAATTATGATGT 1258
(SEQ ID: 109)               <-----------------
                                   A-RP
```

TABLE 27-continued

| A well-referened RT-PCR assay to detect HRSV subtypes A and B | | |
|---|---|---|
| NC_001781.1.HRSV.B (SEQ ID: 110) | CAGCAAATACACTATTCAACGTAGTACAGGAGATAATATTGACACTCCCAATTATGATGT<br>************ *** ********** ********* **** ********** ******<br><----------------------------<br>B-RP | 1258 |

Hu, A., Colella, M., Tam, J.S., Rappaport, R., Cheng, S., 2003, Journal of Clinical Microbiology 41, 149-154.

TABLE 28

| PDX redesign with common PCR primers for HRSV subtypes A and B and probes centered over the mismatches | | |
|---|---|---|
| NC_038235.1.HRSV.A (SEQ ID: 107) | A + B-Forward Primer (PDX) A-Probe<br>------------------------><br>GATGGCTCTTAGCAAAGTCAAGTTGAATGATACACTCAACAAAGATCAACTTCTGTCATC | 1198 |
| NC-001781.1.HRSV.B (SEQ ID: 108) | B-Probe<br>GATGGCTCTTAGCAAAGTCAAGTTAAATGATACATTAAATAAGGATCAGCTGCTGTCATC<br>*********************** *************** * *** *** ******** | 1198 |
| NC_038235.1.HRSV.A (SEQ ID: 109) | <-------<br>A + B-Reverse Primer (PDX)<br>CAGCAAATACACCATCCAACGGAGCACAGGAGATAGTATTGATACTCCTAATTATGATGT | 1258 |
| NC_001781.1.HRSV.B (SEQ ID: 110) | CAGCAAATACACTATTCAACGTAGTACAGGAGATAATATTGACACTCCCAATTATGATGT<br>************ *** ********** ********* **** ********** ****** | 1258 |

TABLE 29

Inclusivity analysis of Hu et al. vs PDx Probes

| Assay | Primer/ Probe | SEQ ID NO | Sequence (5' to 3') | Number of sequences with 100% complementarity HRSV | HRSV-A | HRSV-B |
|---|---|---|---|---|---|---|
| Hu et al, (2003) | A-FP | SEQ ID: 111 | GCTCTTAGCAAAGTCAAGTTGAATGA | 1971 (2258)[1] | 331 (530)[1] | 196 |
| A (N gene) | A-RP | SEQ ID: 112 | TGCTCCGTTGGATGGTGTATT | 536 (1403)[2] | 262 (543)[2] | NSC |
| | A-probe | SEQ ID: 113 | ACACTCAACAAAGATCAACTTCTGTCATCCAGC | 449 (1408)[3] | 247 (531)[3] | NSC |
| Hu et al. (2003) | B-FP | SEQ ID: 114 | GATGGCTCTTAGCAAAGTCAAGTTAA | 102 (1106)[4] | 1 | 25 (234)[4] |
| B (N gene) | B-RP | SEQ ID: 115 | TGTCAATATTATCTCCTGTACTACGTTGAA | 1075 | NSC | 265 |
| | B-probe | SEQ ID: 116 | TGATACATTAAATAAGGATCAGCTGCTGTCATCCA | 904 | NSC | 226 |
| PathogenDx proposed | A + B FP | SEQ ID: 117 | AAARATGGCTCTTAGCAAAGTCAAG | 2429 | 530 | 233 |
| A + B (N gene) | A + B RP | SEQ ID: 118 | CGTTGRATRGTRTATTTGCTGGATG | 2439 | 536 | 266 |
| | A-probe | SEQ ID: 119 | ACACTCAACAAAGATCAACTTCT | 1406 | 536 | NSC |
| | B-probe | SEQ ID: 120 | ACATTAAATAAGGATCAGCTGCT | 910 | NSC | 229 |

NSC-No sgnfficant complementarity

[1]Hits increase when removing 3'TGA

[2]Hits increase changing 3' TGTATT to TRTATT

[3]Hits increase when 1 mismatch allowed

[4]Hits increase when 3'-TTAA removed

Exclusivity. Table 30 shows that for both the Hu et al and the PDx assays using the following sequences—*Homo sapiens* (taxid:9606), HCoV229E (taxid:11137), HCoV-OC43 (taxid:31631), HCoV-HKU1 (taxid:290028), HCoV-NL63 (taxid:277944), MERS-CoV (taxid:1335626). Human metapneumovirus (taxid:162145), Human adenovirus sp. (taxid:1907210), HPIV-1 (taxid:12730), HPIV-2 (taxid: 1979160), HPIV4 (taxid:1979161), Influenza A virus (taxid:

11320), Influenza B virus (taxid:11520), Enterovirus (taxid: 12059), Human parainfluenza virus 4b (taxid:11226), *Streptococcus pneumoniae* (taxid:1313), HRSV (taxid: 11250), Rhinovirus (taxid:12059), *Chlamydia pneumoniae* (taxid:83558), *Haemophilus* virus HP2 (taxid:157239), *Legionella pneumophila* (taxid:446). *Mycobacterium tuberculosis* (taxid:1773), *Streptococcus pyogenes* (taxid:1314), *Bordetella pertussis* (taxid:520), *Mycoplasma pneumoniae* (taxid:2104). *Pneumocystis jirovecii* (taxid:42068), *Candida albicans* (taxid:5476), *Pseudomonas aeruginosa* (taxid: 287), *Staphylococcus epidermidis* (taxid:1282), *Streptococcus salivarius* (taxid:1304), HPIV-3 (taxid:11216); and exclude: HCoV-SARS (taxid:694009), SARS-CoV2 (taxid: 2697049).

As seen from Table 30, there is negligible experimental cross reaction with human DNA/RNA or any of the standard panel of respiratory pathogens required for analysis of Exclusivity in SARS-CoV-2 testing.

Feasibility. The calculations obtained suggests feasibility of implementing the HRSV assay capacity to the present 12 probe Mini-RV assay.

Example 17

Automation of 96-Well and 384-Well Plates

A hybridization script on the Tecan was upgraded to reduce reagent waste. A new hybridization script was tested and found to provide results equivalent to non-automated two-step RT-PCR (with labeling) as shown in Table 31. The script was edited for compatibility with plate processing ancillary equipment and the protocol used to run the Zymo kits.

Example 18

Asymmetric One-Step RT-PCR QC Test Development & Validation

A QC/QA test protocol was developed (for [S, N1, N2, N3, P, PanA, PanB). Multiple Tricore samples were pooled to generate a stock solution of purified clinically derived RNA for QC/QA. Table 32 summarizes the results from this analysis.

TABLE 30

Exclusivity analysis of Primers &P robes for Hu et al. vs PDx[1]

| Assay | Primer/Probe | | seq 5' to 3 | Homo sapiens | Non-human |
|---|---|---|---|---|---|
| Hu et al. (2003) A (N gene) | A-FP | SEQ ID: 111 | GCTCTTAGCAAAGTCAAGTTGAATGA | 69% | *Streptococcus* |
| | A-RP | SEQ ID: 112 | TGCTCCGTTGGATGGTGTATT | 90% | *Pseudomonas* |
| | A-probe | SEQ ID: 113 | ACACTCAACAAAGATCAACTTCTGTCATCCAGC | — | |
| Hu et al. (2003) B (N gene) | B-FP | SEQ ID: 114 | GATGGCTCTTAGCAAAGTCAAGTTAA | 69% | *Streptococcus* |
| | B-RP | SEQ ID: 115 | TGTCAATATTATCTCCTGTACTACGTTGAA | 57% | *Legionella* |
| | B-probe | SEQ ID: 116 | TGATACATTAAATAAGGATCAGCTGCTGTCATCCA | — | *pneumophila* 60% |
| PathogenDx proposed A + B (N gene) | A + B FP | SEQ ID: 117 | AAARATGGCTCTTAGCAAAGTCAAG | 68% | *Streptococcus salivarius* 64% |
| | A + B RP | SEQ ID: 118 | CGTTGRATRGTRTATTTGCTGGATG | 64% | *Streptococcus pneumoniae* 52% |
| | A-probe | SEQ ID: 119 | ACACTCAACAAAGATCAACTTCT | N/A[2] | |
| | B-probe | SEQ ID: 120 | ACATTAAATAAGGATCAGCTGCT | N/A[2] | |

[1] Exclusivity respiratory panel % complementarity (organism with closest match). Generally, <80% total complementarity requires no deeper analysis
[2] Surface Bound non-PCR oligos are not subjected to sequences other than amplimers generated from the PCR primers

TABLE 31

Summary of the 96-well automated hybridization test*

| | Average Positives | Standard Deviation Positives | Average Negatives | Standard Deviation Negatives | (a) True Positive | (b) False Positives | (c) False Negative | (d) True Negative | LoB | LoD | Sensitivity | Specificity | PPV | NPV |
|---|---|---|---|---|---|---|---|---|---|---|---|---|---|---|
| 62-Negcont-B | 2084 | 729 | 2005 | 1197 | 30 | 0 | 0 | 30 | N/A | N/A | 100 | 100 | 100 | 100 |
| RNAse.P.Probe-pub1.1 | 56092 | 1324 | 59532 | 1281 | 30 | 0 | 0 | 30 | N/A | N/A | 100 | 100 | 100 | 100 |
| SARS.COV2-N1-RE1.1 | 55102 | 3898 | 5625 | 15613 | 30 | 3 | 0 | 30 | N/A | N/A | 100 | 90.91 | 91 | 100 |
| SARS.COV2-N1-RE1.1 | 55190 | 3091 | 6328 | 15471 | 30 | 3 | 0 | 30 | N/A | N/A | 100 | 90.91 | 91 | 100 |
| SARS.COV2-N2-RE1.3 | 52644 | 4131 | 7791 | 15341 | 30 | 5 | 0 | 30 | N/A | N/A | 100 | 85.71 | 86 | 100 |
| SARS.COV2-N2-RE1.3 | 53041 | 4202 | 8336 | 14677 | 30 | 5 | 0 | 30 | N/A | N/A | 100 | 85.71 | 86 | 100 |
| SARS.COV2-N2-RE1.4 | 56120 | 1324 | 9323 | 19459 | 30 | 5 | 0 | 30 | N/A | N/A | 100 | 85.71 | 86 | 100 |
| SARS.COV2-N3-RE1.1 | 56120 | 1324 | 12704 | 22979 | 30 | 7 | 0 | 30 | N/A | N/A | 100 | 81.08 | 81 | 100 |
| SARS.COV2-N3-RE1.1 | 56119 | 1321 | 12635 | 23308 | 30 | 7 | 0 | 30 | N/A | N/A | 100 | 81.08 | 81 | 100 |
| TOTAL | N/A | N/A | N/A | N/A | 30 | 4 | 0 | 30 | N/A | N/A | 100 | 88.24 | 88 | 100 |

*Tecan Automated Hybridization Protocol-Two-Step RT-PCR and Labeling Reaction with TriCore NP Samples

TABLE 32

Optimizing complete [S.N1, N2, N3.P, PanA, PanB] using pooled positive and pooled negative samples

| Sample | Positive pooled | Positive pooled (infA) | Positive pooled (infB) | Positive pooled (infA, B) | Negative pooled | Negative pooled (infA) | Negative pooled (infB) | Negative pooled (infA, B) |
|---|---|---|---|---|---|---|---|---|
| 62-Negcont-B | 2502 | 1703 | 2947 | 1012 | 1950 | 2380 | 1870 | 1728 |
| SARS.COV2-N1-RE1.1 | 62053 | 60858 | 58695 | 55988 | 2330 | 2227 | 2067 | 1417 |
| SARS.COV2-N2-RE1.3 | 53469 | 50035 | 48069 | 48001 | 696 | 860 | 751 | 223 |
| SARS.COV2-N2-RE1.4 | 62125 | 61966 | 62838 | 60932 | 1445 | 1229 | 1274 | 946 |
| SARS.COV2-N3-RE1.1 | 62378 | 62148 | 63048 | 61164 | 6858 | 4820 | 5932 | 4001 |
| RNAse.P.Probe-pub1.1 | 47022 | 39703 | 39083 | 37667 | 62564 | 61029 | 62077 | 55084 |
| InfA.7.univ-pubRev | 257 | 2913 | 450 | 2852 | 329 | 37312 | −44 | 36881 |
| InfB.8 univ-pub | 24 | −134 | 8691 | 5335 | −161 | −68 | 17062 | 16098 |
| 614D-AS-S1-RE1.1 | 905 | 721 | 1573 | −52 | 596 | 643 | 584 | 13 |
| 614G-AS-S1-RE1.1 | 1466 | 1486 | 3129 | 437 | 1176 | 1121 | 1070 | 775 |
| 614D-SE-S1-RE1.1 | 2680 | 1429 | 9252 | 100 | 745 | 680 | 818 | 238 |
| 614G-SE-S1-RE1.2 | 30306 | 14561 | 14828 | 12906 | 840 | 617 | 1104 | 710 |

Example 19

96-Well and 384-Well Test Optimization

Clinical sensitivity and specificity analysis performed on the Mini-RV content in 9985 array format using Asymmetric One-Step RT-PCR revealed a 100% sensitivity and 94% specificity for each of the 96-well and 384-well samples. Tables 33 and 34 shows an improvement in specificity for the SARS.COV2-N1-RE1.1 probe. Signal strength for the RNase-P control is also improved.

Example 20

Influenza Testing on Clinical Samples (NP/VTM) Using Mini-RV, Asymmetric One-Step RT-PCR Influenza Positive TriCore Clinical Samples (NP/VTM) were used for clinical evaluation of Influenza A and B primer and probes in two positive Influenza A, validated on a respiratory panel (RESPAN, TriCore) and two positive Influenza B, validated on an Influenza A/B and RSV panel (FLURSV, TriCore), analyzed on Mini-RV slide format. Table 35 shows that Influenza A and B were detected in confirmed clinical samples via standard Asymmetric One-Step RT-PCR (Zymo), with a clear discrimination between Influenza A vs Influenza B.

Example 21

Analysis of Mouthwash Samples Using Mini-RV Asymmetric One-Step RT-PCR.

Mouthwash/saliva samples were separated and evaluated by itself (MW-1), spiked with SARS-CoV2 viral lysate from ATCC (MW-2), or with SARS-CoV2 purified viral RNA from ATCC (MW-3). The mouthwash sample was taken through Zymo's RNA purification and amplified using the Asymmetric One-Step RT-PCR method. Amplicons were analyzed on Mini-RV format (12-well slides). Table 36-shows that SARS-CoV2 was detected in contrived mouthwash samples.

TABLE 33

Clinical Sensitivity and Specificity in 96-well format

| | Average Positives | Standard Deviation Positives | Average Negatives | Standard Deviation Negatives | (a) True Positive | (b) False Positives | (c) False Negative | (d) True Negative | LoB | LoD | Sensitivity | Specificity | PPV | NPV |
|---|---|---|---|---|---|---|---|---|---|---|---|---|---|---|
| 62-Negcont-B | 1576 | 978 | 1255 | 561 | 30 | 0 | 0 | 30 | N/A | N/A | 100 | 100 | 100 | 100 |
| RNAse.P.Probe-pub1.1 | 53737 | 13600 | 48392 | 23841 | 30 | 0 | 0 | 30 | N/A | N/A | 100 | 100 | 100 | 100 |
| SARS.COV2-N1-RE1.1 | 49089 | 17417 | 7544 | 4311 | 30 | 2 | 0 | 30 | N/A | N/A | 100 | 94 | 94 | 100 |
| SARS.COV2-N2-RE1.3 | 40485 | 21135 | 2567 | 4861 | 30 | 2 | 0 | 30 | N/A | N/A | 100 | 94 | 94 | 100 |
| SARS.COV2-N2-RE1.4 | 50842 | 17848 | 1702 | 734 | 30 | 2 | 0 | 30 | N/A | N/A | 100 | 94 | 94 | 100 |
| SARS.COV2-N3-RE1.1 | 51720 | 16137 | 8152 | 4697 | 30 | 2 | 0 | 30 | N/A | N/A | 100 | 94 | 94 | 100 |
| Overall | N/A | N/A | N/A | N/A | 30 | 2 | 0 | 30 | N/A | N/A | 100 | 94 | 94 | 100 |

TABLE 34

Clinical Sensitivity and Specificity format in 384-well

| | Average Positives | Standard Deviation Positives | Average Negatives | Standard Deviation Negatives | (a) True Positive | (b) False Positives | (c) False Negative | (d) True Negative | LoB | LoD | Sensitivity | Specificity | PPV | NPV |
|---|---|---|---|---|---|---|---|---|---|---|---|---|---|---|
| 62-Negcont-B | 2286 | 793 | 2696 | 1177 | 30 | 0 | 0 | 30 | N/A | 62.5 | 100 | 100 | 100 | 100 |
| RNAse.P.Probe-pub1.1 | 49278 | 15639 | 48208 | 21205 | 30 | 0 | 0 | 30 | N/A | 62.5 | 100 | 100 | 100 | 100 |
| SARS.COV2-N1-RE1.1 | 41364 | 18774 | 5041 | 1377 | 30 | 2 | 3 | 30 | N/A | 62.5 | 91 | 94 | 94 | 91 |
| SARS.COV2-N2-RE1.3 | 35109 | 18663 | 1200 | 716 | 30 | 2 | 3 | 30 | N/A | 62.5 | 91 | 94 | 94 | 91 |
| SARS.COV2-N2-RE1.4 | 47691 | 17794 | 1465 | 648 | 30 | 2 | 3 | 30 | N/A | 62.5 | 91 | 94 | 94 | 91 |
| SARS.COV2-N3-RE1.1 | 48073 | 16722 | 5004 | 2292 | 30 | 2 | 3 | 30 | N/A | 62.5 | 91 | 94 | 94 | 91 |
| Overall | N/A | N/A | N/A | N/A | 30 | 0 | 3 | 30 | N/A | 62.5 | 91 | 100 | 100 | 91 |

TABLE 35

DETECTX-RV (Mini-RV) Influenza evaluation

| 9985 Probes | No Template Control (NTC) | Influenza A/B (Positive Control) Influenza A/B (10,000 copies/reaction) | Influenza A (Clinical Sample) #179502 | Influenza A (Clinical Sample) #179504 | Influenza B (Clinical Sample) #170231 | Influenza B (Clinical Sample) #170232 |
|---|---|---|---|---|---|---|
| 62-Negcont-B | 3869 | 2584 | 2392 | 2934 | 2339 | 4421 |
| SARS.COV2-N1- | 5155 | 293 | 584 | 291 | 3342 | 1125 |
| SARS.COV2-N2- | 825 | −21 | −19 | −34 | 42 | 361 |
| SARS.COV2-N2- | 991 | 921 | 1055 | 1068 | 1460 | 1434 |
| SARS.COV2-N3- | 7727 | 1415 | 4105 | 6139 | 7031 | 4604 |
| RNAse.P.Probe- | 2498 | 1465 | 54868 | 61894 | 59917 | 54383 |
| InfA.7.univ-pubRev | −185 | 11670 | 54328 | 50269 | 658 | 555 |
| InfB.8.univ-pub | 397 | 61813 | 255 | 366 | 10304 | 30340 |
| 614D-AS-S1-RE1.1 | 321 | 549 | 135 | 219 | 311 | 110 |
| 614G-AS-S1-RE1.1X | 1056 | 845 | 654 | 925 | 905 | 1171 |
| 614D-SE-S1-RE1.1 | 421 | 416 | 189 | 515 | 176 | 569 |
| 614G-SE-S1-RE1.2 | 228 | 454 | 208 | 422 | 327 | 666 |

Example 22

Design of a Pan-Cold Coronavirus Probe Assay

The assay is based on RdRp and has an inclusivity of (NL63+OC43+229E+HKU1). Primers and Probes used for the assay are shown in Tables 37 and 38. In Silico analysis demonstrates that the primers and probes are specific for their targets and do not demonstrate off target interactions—less than 80% homology to any off-target sequence. Table 39 shows the exclusivity analysis using the following sequences—*Homo sapiens* (taxid:9606), HCoV-229E (taxid:11137), HCoV-OC43 (taxid:31631), HCoV-HKU1 (taxid:290028), HCoV-NL63 (taxid:277944), MERS-CoV (taxid:1335626), Human metapneumovirus (taxid:162145), Human adenovirus sp. (taxid:1907210), HPIV-1 (taxid: 12730), HPIV-2 (taxid:1979160), HPIV4 (taxid:1979161), Influenza A virus (taxid:11320), Influenza B virus (taxid: 11520), Enterovirus (taxid:12059), Human parainfluenza virus 4b (taxid:11226), *Streptococcus pneumoniae* (taxid: 1313), HRSV (taxid:11250), Rhinovirus (taxid:12059), *Chlamydia pneumoniae* (taxid:83558), *Haemophilus* virus HP2 (taxid:157239), *Legionella pneumophila* (taxid:446), *Mycobacterium tuberculosis* (taxid:1773), *Streptococcus pyogenes* (taxid:1314), *Bordetella pertussis* (taxid:520), *Mycoplasma pneumoniae* (taxid:2104), *Pneumocystis jirovecii* (taxid:42068), *Candida albicans* (taxid:5476), *Pseudomonas aeruginosa* (taxid:287), *Staphylococcus epidermidis* (taxid:1282), *Streptococcus salivarius* (taxid: 1304), HPIV-3 (taxid:11216); and exclude: HCoV-SARS (taxid:694009), SARS-CoV2 (taxid:2697049). No complementarity (<80%) was observed compared to the full standard exclusivity panel. Inclusivity analysis (Table 40) using the sequences HCoV-NL63 (taxid:277944) HCoV-C43 (taxid:31631), HCoV-229E (taxid:11137), HCoV-HKU1 (taxid:290028) MERS-CoV (taxid:1335626) showed >98% compared to GenBank (NL63+OC43+229E+HKU1) plus several other animal Coronavirus.

TABLE 36

DETECTX-RV (Mini-RV) SARS-CoV-2 evaluation in contrived mouthwash samples

| 9985 Probes | NTC | SARS-CoV-2 (Positive Control Plasmid) SARS-CoV-2 1000 copies/reaction | Pooled Sample (Positive Control) SARS-CoV-2 (Clinical Positive, NP/VTM) | Contrived Mouthwash Samples MW-1* | MW-2¶ | MW-3§ |
|---|---|---|---|---|---|---|
| 62-Negcont-B | 3869 | 2719 | 3196 | 3486 | 2342 | 1955 |
| SARS.COV2-N1-RE1.1 | 5155 | 37071 | 61691 | 3379 | 48808 | 35396 |
| SARS.COV2-N2-RE1.3 | 825 | 21979 | 42964 | 551 | 40579 | 11916 |
| SARS.COV2-N2-RE1.4 | 991 | 51528 | 61773 | 2273 | 61671 | 40734 |
| SARS.COV2-N3-RE1.1 | 7727 | 52631 | 61944 | 4932 | 61745 | 44499 |
| RNAse.P.Probe-pub1.1 | 2498 | 2482 | 46178 | 39598 | 13423 | 36278 |
| InfA.7.univ-pubRev | −185 | −36 | 47 | 128 | 27 | 162 |
| InfB.8.univ-pub | 397 | 485 | 50 | −115 | 112 | −17 |
| 614D-AS-S1-RE1.1 | 321 | 1031 | 716 | 833 | 1420 | 727 |
| 614G-AS-S1-RE1.1X | 1056 | 1834 | 1615 | 1201 | 1608 | 979 |
| 614D-SE-S1-RE1.1 | 421 | 1336 | 3467 | 637 | 18936 | 1133 |
| 614G-SE-S1-RE1.2 | 228 | 1207 | 36769 | 964 | 1444 | 552 |

*MW - 1 - Mouthwash collected, not spiked with SARS-CoV-2
¶MW - 2 - Mouthwash, spiked with SARS-CoV-2 Viral Lysate, 1 × 10⁸ PFU (BEI, Wuhan)
§MW - 3 - Mouthwash, spiked with SARS-CoV-2 purified RNA at 1000 copies total for input to RNA extraction (BEI, Wuhan)

TABLE 37

Primer sequences for Pan-cold Coronavirus probe assay

| SEQ ID NO. | Target | Gene | Primer Sequence (5' to 3') |
|---|---|---|---|
| SEQ ID: 23 | SARS-CoV-2 Nucleocapsid | N1 | TTTTAATGGACCCCAAAATCAGCGAAAT |
| SEQ ID: 24 | SARS-CoV-2 Nucleocapsid | N1 | (FL) TTTTTCTGGTTACTGCCAGTTGAATCTG |
| SEQ ID: 25 | CoV Nucleocapsid | N2 | TTTACTGATTACAAACATTGGCCGCAAA |
| SEQ ID: 74 | CoV Nucleocapsid | N2 | (FL) TTTTGCCAATGCGCGACATTCCGAAGAA |
| SEQ ID: 27 | CoV Nucleocapsid | N3 | TTTAGGGAGCCTTGAATACACCAAAAGA |
| SEQ ID: 28 | CoV Nucleocapsid | N3 | (FL) TTTAAGTTGTAGCACGATTGCAGCATTG |
| SEQ ID: 75 | SARS-CoV-2 Spike Gene | S | TTTAGTGTTATAACACCAGGAACAAATA |
| SEQ ID: 76 | SARS-CoV-2 Spike Gene | S | (FL) TTTTGCATGAATAGCAACAGGGACTTCT |
| SEQ ID: 77 | Pan-CoV RdRp | RdRp | TTTTTTAATAAGTATTTTAAGCAYTGGAGT |
| SEQ ID: 78 | Pan-CoV RdRp | RdRp | (FL) TTTAAGAGTGTGTTAAAATTTGAACAATG |
| SEQ ID: 79 | Pan-CoV RdRp | RdRp | TTTTGTTTAAGAAGTATTTTAARTATTGGG |
| SEQ ID: 80 | Pan-CoV RdRp | RdRp | (FL) TTTAATAGTGTATTRAAATTAGCACAATG |
| SEQ ID: 39 | Influenza A | M | TTTCAAGACCRATCCTGTCACCTCTGAC |
| SEQ ID: 81 | Influenza B | M | TTTGGATCCTCAACTCACTCTTCGAGCG |
| SEQ ID: 82 | Influenza A | NS1 | (FL) TTTGGGCATTYTGGACAAAKCGTCTACG |
| SEQ ID: 42 | Influenza B | NS1 | (FL) TTTTAATCGGTGCTCTTGACCAAATTGG |
| SEQ ID: 83 | HRSV | N | TTTAAARATGGCTCTTAGCAAAGTCAAG |

TABLE 37-continued

Primer sequences for Pan-cold Coronavirus probe assay

| SEQ ID NO. | Target | Gene | Primer Sequence (5' to 3') |
|---|---|---|---|
| SEQ ID: 84 | HRSV | N | (FL)TTTCGTTGRATRGTRTATTTGCTGGATG |
| SEQ ID: 43 | Human RNAse P control | RNAse P | TTTGTTTGCAGATTTGGACCTGCGAGO |
| SEQ ID: 44 | Human RNAse P control | RNAse P | (FL)TTTAAGGTGAGCGGCTGTCTCCACAAGT |

(FL) = fluorescent label.

TABLE 38

Nucleic acid probe sequences used for hybridization in Pan-cold Coronavirus probe assay

| SEQ ID NO. | Target | Detects | Probe Sequence |
|---|---|---|---|
| SEQ ID: 45 | SARS-CoV-2 | SARS-CoV-2 614G, SARS-CoV-2 614D | TTTTTTTCCGCATTACGTTTGGTGTTTTT |
| SEQ ID: 48 | SARS-CoV-2 | SARS-CoV-2 614G, SARS-CoV-2 614D | TTTTTTACAATTTGCCCCCAGCGTCTTTT |
| SEQ ID: 49 | SARS | SARS | TTTTTTTTTGCTCCRAGTGCCTCTTTTTT |
| SEQ ID: 85 | CoV Bat precursor | Bat SARS-like CoV | TTTTTTGTTTGCACCTAGTGCTTCCTTTTT |
| SEQ ID: 86 | CoV Pangolin precursor | Pangolin CoV S. China | TTTTTTTTGCTCCTAGCGCTTCTTTTTT |
| SEQ ID: 53 | CoV Bat precursor-Yunnan 2013 | Bat precursor (Yunnan 2013) | TTTTTGTTTGCACCCAGTGCTTCTGCTCTTTT |
| SEQ ID: 54 | CoV Bat precursor-Yunnan 2019 | New bat CoVs (Yunnan 2019) | TTTTTTACAATTCGCTCCCAGCGTCTTTT |
| SEQ ID: 55 | CoV Nucleocapsid | SARS-CoV-2 614G, SARS-CoV-2 614D, SARS, Bat-SARS-like CoV, Pangolin CoV, S. China, Bat precursor (Yunnan 2013), New Bat CoVs (Yunnan 2019) | TTTTTCTGGCACCCGCAATCCTGTCTTTTT |
| SEQ ID: 87 | SARS-CoV-2 614 All | SARS-CoV-2 614G, SARS-CoV-2 614D | TTTTTCTCTTTATCAGGRTGTTAACTGCTTTTTT |
| SEQ ID: 88 | SARS-CoV-2 614 "G" | SARS-CoV-2 614G | TTTTTTCCTATCAGGGTGTTAACTTTTTT |
| SEQ ID: 89 | SARS-CoV-2 614 "D" | SARS-CoV-2 614D | TTTTTCTTATCAGGATGTTAACTTTTTTT |
| SEQ ID: 90 | HCoV-OC43 | HCoV-OC43 | TTTTTATATCATCCTAACACTGTTGATTGTTTTT |
| SEQ ID: 91 | NHCoV-NL63 | HCoV-NL63 | TTTTTTTATCATCCTAATTGTAGTGACTGTTTTT |
| SEQ ID: 92 | NHCoV-HKU1 | HCoV-HKU1 | TTTTTGTATCATCCTAATACTGTGGATTGTTTTT |
| SEQ ID: 93 | HCoV-229E | HCoV-229E | TTTTTTTATCATCCTGATTGTGTTGATTGCTTTTT |
| SEQ ID: 94 | MERS | MERS-CoV | TTTTTAATTGCGTTAATTGTACTGATGACCTTTTT |
| SEQ ID: 67 | Influenza A | Influenza A | TTTTTTTCGTGCCCAGTGAGCGAGTTTTT |

TABLE 38-continued

Nucleic acid probe sequences used for hybridization in Pan-cold Coronavirus probe assay

| SEQ ID NO. | Target | Detects | Probe Sequence |
|---|---|---|---|
| SEQ ID: 95 | Influenza B | Influenza B | TTTTCCAATTCGAGCAGCT GAAACTGCGGTGTTTTT |
| SEQ ID: 96 | HRSV-A | HRSV-A | TTTTTCACACTCAACAAAG ATCAACTTCTTCTTCTT |
| SEQ ID: 97 | HRSV-B | HRSV-B | TTTTTCGATACATTAAATAA GGATCAGCTTTTTTT |
| SEQ ID: 71 | RNAse P control | Human RNAse P | TTTTTTTTCTGACCTGAAG GCTCTGCGCGTTTTT |
| SEQ ID: 73 | Negative Control | Human RNAse P | TTTTTTCTACTACCTATGCT GATTCACTCTTTTT |

Example 23

Analysis of Contrived Samples

Emory Test Samples. Emory contrived a sample with heat inactivated CoV2 virus (BEI standards) in VTM, covering a dilution series from $10^6$ to 0 virus/ml. The sample was then shipped to PDx in double-blinded form. PDx performed the full manual process in the 96-well format (that is, Zymo RNA purification+One-Step PCR+Hybridization/Wash+Imaging+AUGURY). The results obtained were then reported to Emory, which was tasked with reporting concordance with the number of virus particles/ml originally added.

TABLE 39

Pan CoV - Exclusivity respiratory panel % complementarity[1] (Organism with closest match)

| | | SEQ ID NO | Sequence | Homo sapiens | Non-human |
|---|---|---|---|---|---|
| Forward Primer seq (5' to 3') | | | | | |
| PathogenDx | NL63/ OC43 | SEQ ID: 121 | TTTAATAAGTATTTTAAGCAYTGGAGT | 66% | Streptococcus pyogenes 59% |
| Proposed Pan-CoV (RdRP gene) | 229E HKU1 MERS | SEQ ID: 122 | TGTTTAAGAAGTATTTTAARTATTGGG | 70% | Staphylococcus epidermis 60% |
| Reverse Primer seq (5' to 3') | | | | | |
| | 299E | SEQ ID: 123 | AAGAGTGTGTTAAAATTTGAACAATG | 73% | Streptococcus pneumoniae 73% |
| | NL63 OC43 HKU1 MERS | SEQ ID: 124 | AATAGTGTATTRAAATTAGOACAATG | 79% | Staphylococcus epidermis 61% |
| Probe sequence (seq 5' to 3') | | | | | |
| | NL63 | SEQ ID: 125 | TTATCATCCTAATTGTAGTGACTGT | N/A[2] | N/A[2] |
| | 229E | SEQ ID: 126 | TTATCATCCTGATTGTGTTGATTGC | N/A[2] | N/A[2] |
| | OC43 | SEQ ID: 127 | ATATCATCCTAACACTGTTGATTGT | N/A[2] | N/A[2] |
| | HKU1 | SEQ ID: 128 | GTATCATCCTAATACTGTGGATTGT | N/A[2] | N/A[2] |
| | MERS* | SEQ ID: 129 | AATTGCGTTAATTGTACTGATGACC | N/A[2] | N/A[2] |

*shifted to avoid palindromic seq
[1]Generally, <80% total complementarity requires no deeper analysis
[2]Surface Bound non-PCR oligos are not subjected to sequences other than amplimers generated from the PCR primers

TABLE 40

Pan CoV-Inclusivity Analysis (Genbank). Number of sequences with 100% complementarity (unless noted)

| | | SEQ ID NO. | Sequence used for comparison | HCoV-NL63 | HCoV-OC43 | HCoV-229E | HCoV-HKU1 | MERS-CoV |
|---|---|---|---|---|---|---|---|---|
| *Forward Primer seq (5' to 3')* | | | | | | | | |
| PathogenDx Proposed Pan-CoV (RdRP gene) | NL63 OC43 | SEQ ID: 130 | TTYAATAAGTAYTTTAAGCAYTGGAGT | 89/89 100% | 245/247 99.2% | N/A | N/A | N/A |
| | 229E HKU1 MERS | SEQ ID: 131 | TSTTTRABAAGTAYTTTAARTATTGGG | N/A | N/A | 51/51 100% | 47/47 100% | 578/581 99.5% |
| *Reverse Primer seq (5' to 3')* | | | | | | | | |
| | 299E | SEQ ID: 132 | AAGAGTGTGTTAAAATTTGAACAATG | N/A | N/A | 51/51 100% | N/A | N/A |
| | NL63 OC43 HKU1 MERS | SEQ ID: 133 | AAHARTRYRTTRAAATTAGCACAATG | 89/89 100% | 245/247 99.2% | N/A | 53/53 100% | 580/581 99.8% |
| *Probe sequence (seq 5' to 3')* | | | | | | | | |
| | NL63 | SEQ ID: 134 | TTATCATCCTAATTGTAGTGACTGT | 88/89 99% | N/A | N/A | N/A | N/A |
| | 229E | SEQ ID: 135 | TTATCATCCTGATTGTGTTGATTGC | N/A | N/A | 51/51 100% | N/A | N/A |
| | OC43 | SEQ ID: 136 | ATATCATCCTAACACKGTTGATTGT | N/A | 244/247 98.7% | N/A | N/A | N/A |
| | HKU1 | SEQ ID: 137 | GTATCATCCTAATACTGTGGATTGT | N/A | N/A | N/A | 47/47 100% | N/A |
| | MERS* | SEQ ID: 138 | ATTGCGTTAATTGTACTGATGACC | N/A | N/A | N/A | N/A | 577/580 99.5% |

*shifted to avoid palindromic seq

TABLE 41

Emory testing of samples provided by PathogenDx*

| | Heat inactivated | | | | Irradiated cell lysate | | | | KP mouthwash | KP swab | Positive control | Negative control | 116 X |
|---|---|---|---|---|---|---|---|---|---|---|---|---|---|
| | 10 1 | 1 2 | 0.1 3 | 0.01 4 | 10 5 | 1 6 | 0.1 7 | 0.01 8 | 9 | 10 | | | |
| RNAse.P.Probe-pub1.1 | + | + | + | + | + | + | + | + | + | + | + | − | + |
| SARS.COV2-N3-RE1.1 | + | + | + | +/− | +/− | + | + | + | − | − | + | − | + |
| SARS.COV2-N2-RE1.4 | + | +/− | − | − | + | + | +/− | − | − | − | + | − | + |
| SARS.COV2-N2-RE1.3 | +/− | − | − | − | + | − | − | − | − | − | − | − | + |
| SARS.COV2-N1-RE1.1 | + | +/− | − | − | + | + | +/− | − | − | − | + | − | + |
| 62-Negcont-B | − | − | − | − | − | − | − | − | − | − | − | − | − |
| Overall call | POS | POS | RERUN | NEG | POS | POS | POS | RERUN | NEG | NEG | POS | NEG | POS |

*units are in copies/ml input into the RNA extraction

TABLE 42

PathogenDx run testing*

| | Heat inactivated | | | | Irradiated cell lysate | | | | KP mouthwash | KP swab | Positive control | Negative control | 116 X |
|---|---|---|---|---|---|---|---|---|---|---|---|---|---|
| | 10 1 | 1 2 | 0.1 3 | 0.01 4 | 10 5 | 1 6 | 0.1 7 | 0.01 8 | 9 | 10 | | | |
| RNAse.P.Probe-pub1.1 | + | + | + | + | + | + | + | + | + | + | + | − | + |
| SARS.COV2-N3-RE1.1 | + | + | + | +/− | + | + | + | + | − | − | + | − | + |

TABLE 42-continued

| | PathogenDx run testing* | | | | | | | | | | | | |
|---|---|---|---|---|---|---|---|---|---|---|---|---|---|
| | Heat inactivated | | | | Irradiated cell lysate | | | | KP | KP | | | |
| | 10 | 1 | 0.1 | 0.01 | 10 | 1 | 0.1 | 0.01 | mouthwash | swab | Positive control | Negative control | 116 |
| | 1 | 2 | 3 | 4 | 5 | 6 | 7 | 8 | 9 | 10 | | | X |
| SARS.COV2-N2-RE1.4 | + | +/− | − | − | + | + | +/− | − | − | − | + | − | + |
| SARS.COV2-N2-RE1.3 | +/− | − | − | − | + | − | − | − | − | − | − | − | + |
| SARS.COV2-N1-RE1.1 | + | +/− | − | − | + | + | +/− | − | − | − | + | − | + |
| 62-Negcont-B | − | − | − | − | − | − | − | − | − | − | − | − | − |
| Overall call | POS | POS | RERUN | NEG | POS | POS | POS | RERUN | NEG | NEG | POS | NEG | POS |

*units are in copies/ml input into the RNA extraction

Training Samples. PDx completed validation and shipped to Emory, a full suite of stepwise training materials, "Imaging Test"; "Hybridization/Wash+Imaging Test"; "PCR+Hybridization/Wash+Imaging Test". Two sets of blinded contrived samples were made from both γ-inactivated and heat inactivated reference standards (BEI) in pooled nasal fluid, diluted from $10^4$ copies/ml to 10 copies/ml (Tables 41 and 42).

Results:

Emory testing of blinded contrived samples from PDx: Emory's data for the test samples provided by PDx, which required the full processing workflow (RT-PCR+Hybridization/Wash+Imaging+AUGURY) had readouts of the blinded PDx-contrived samples that were identical within experimental accuracy to that obtained independently at PDx.

TABLE 43

Summary of PDx Validation Data on Blinded Emory Samples*

| Cov-2 virus particles/ml VTM (prepared by Emory) | PDx Positive calls | Comments |
|---|---|---|
| $10^6$ | 2 of 2 | |
| $10^5$ | 2 of 2 | |
| $10^4$ | 2 of 2 | |
| $10^3$ | 1 of 3 | +1 "re-run" |
| $10^2$ | 0 of 3 | +1 "re-runs" |
| 10 | 0 of 3 | +2 "re-runs" |
| 0 | 0 of 3 | No false positives detected at 0 CoV-2 virus/ml |
| 0 (OC43) | 0 of 4 | OC43 was not detected at both 100 and 1000 OC43 virus/ml |

*PDx Scoring Criteria: "Positive calls" = (≥2) N probes; "re-run" = (1) N probe; "Negative calls" = (0) N probes PDx Testing of Double-Blinded Contrived Samples from Emory:

PDx's data readout on the double blinded samples provided by Emory (Tables 43 and 44) indicated a LoD of ~1000 viral copies/ml for the contrived heat inactivated CoV-2 samples. It is interesting to note that the apparent LoD obtained by PDx is identical within experimental accuracy to that obtained by Emory and PDx (1000 copies/ml, Table 45).

It should be noted that if the PDx standard were relaxed to that used in most Q-RT-PCR assays, that is, ≥1 probe detected comprising a positive readout, the LoD thus obtained by PDx analysis on the Emory samples would be in the 10-100 copies/ml range, because reruns would have been identified as "positives" using the less stringent analytical standard (Tables 43).

TABLE 44

PDx Analysis of Contrived Samples Prepared by Emory

| Sample # | Blinded Sample ID | Overall Call | gRNA/ml | Cov-2 virus/ml (prepared by Emory) | PDx Positive calls | Comment |
|---|---|---|---|---|---|---|
| 1 | 8819 | NEG | OC43, 1000 | $10^6$ | 2 of 2 | |
| 2 | 8833 | POS | $10^5$ | $10^5$ | 2 of 2 | |
| 3 | 8814 | NEG | 0 | $10^4$ | 2 of 2 | |
| 4 | 8826 | NEG | OC43, 1000 | $10^3$ | 1 of 3 | 1 "re-run" |
| 5 | 8812 | NEG | 10 | $10^2$ | 0 of 3 | 1 "re-run" |
| 6 | 8809 | POS | $10^5$ | 10 | 0 of 3 | 2 "re-runs" |
| 7 | 8806 | RERUN | $10^2$ | 0 | 0 of 3 | |
| 8 | 8813 | NEG | OC43, 100 | 0 (OC43) | 0 of 4 | |
| 9 | 8821 | POS | $10^4$ | | | |
| 10 | 8832 | NEG | $10^2$ | | | |
| 11 | 8808 | RERUN | $10^3$ | | | |
| 12 | 8804 | NEG | OC43, 100 | | | |
| 13 | 8817 | NEG | $10^2$ | | | |
| 14 | 8820 | RERUN | 10 | | | |
| 15 | 8815 | RERUN | 10 | | | |
| 16 | 8811 | NEG | 0 | | | |

TABLE 44-continued

PDx Analysis of Contrived Samples Prepared by Emory

| Sample # | Blinded Sample ID | Overall Call | gRNA/ml | Cov-2 virus/ml (prepared by Emory) | PDx Positive calls | Comment |
|---|---|---|---|---|---|---|
| 17 | 8825 | POS | $10^5$ | | | |
| 18 | 8822 | NEG | 0 | | | |
| 19 | 8818 | POS | $10^3$ | | | |
| 20 | 8823 | POS | $10^5$ | | | |
| 21 | 8805 | POS | $10^4$ | | | |
| 22 | 8827 | NEG | $10^3$ | | | |
| 23 | PDx External Extraction Control | POS | | | | |
| 24 | PDx NEG Control | NEG | | | | |

PDx Analysis criteria:

"Positive" = >2 positive N probe signals

"Re-run" = 1 positive N probe signals

"Negative" = 0 positive N probe signals

TABLE 45

Summary of Emory Training Data on Blinded PDx Samples

| Analysts | LoD obtained on PDx samples (copies/ml) | Contrived sample type |
|---|---|---|
| Both Emory and PDx | 100< to >1000 | γ-Irradiated CoV-2 |
| Both Emory and PDx | 1000 | Heat Inactivated CoV-2 |

It is also interesting to note that for the contrived samples prepared by PDx and measured by Emory (Table 42) and the contrived samples prepared by Emory and measured by PDx (Table 40) all samples lacking CoV-2 gave 100% negative results per PDx analysis (Tables 41, 42 and 44) indicative of desired specificity even when the samples were contrived to contain significant amounts of another coronavirus (OC43) as in the Emory contrived samples (Tables 44).

Example 24

Optimization of the Mini-RV Assay in the 96-Well Format: Approaching 2-Step on Slides Improvements made in Hybridization/Washing of the Mini-RV array were implemented manually, but via pipetting that can map over directly to the Tecan.

Method—96-Well Plates

1. Samples were extracted using standard manual protocol (Zymo).
2. Clinical samples used had previously been tested on the Roche COBAS 8800 platform (TriCore). Positive Clinical samples (13<Cq<35) as measured by Roche Cobas. were subdivided into high, med and low Cq levels
3. Contrived samples were prepared from TriCore/Cobas Negatives at 25 gRNA copies/400 μL=62.5 copies/ml
4. RT-PCR was performed using the following conditions:

| | Asymmetric One-Step RT-PCR conditions | |
|---|---|---|
| i. | Access Quick Master mix (2x) | 25 μl |
| ii. | RT-PCR primer | 2 μl |
| iii. | AMV reverse transcriptase | 1 μl |
| iv. | Water | 17 μl |
| v. | Sample | 5 μl |

Access Quick RT-PCR

Step i. 45° C., 45 min. 1 cycle

Step ii. 94° C. 2 min. 1 cycle

Step iii. 94° C. 30 sec. 40 cycles

Step iv. 55° C., 30 sec, 40 cycles

Step v. 68° C., 30 sec, 40 cycles

Step vi. 68° C. 7 min. 1 cycle

Step vii. 4° C.,

5. Manual hybridization and washing of RT-PCR product was performed on the 96-well plates.

Results—96-Well Plates:

Contrived negative samples TriCore Negative NP at 62.5 copies/ml.

Clinical LoD for Asymmetric One-Step RT-PCR in 96-Well Mini-RV approached matched 2-step PCR with slides (≤62.5 copies/mL) (Tables 46 and 47). The LoB appeared to approach slides with manual operation.

TABLE 46

Negative Clinical Samples for LoB (Cq > 35)

| | DetectX RV Call | | | | | | | | | |
|---|---|---|---|---|---|---|---|---|---|---|
| | – | – | – | – | – | – | – | – | – | – |
| | Roche Cq | | | | | | | | | |
| Well description | 35-38 PATHO-001 | 35-38 PATHO-002 | 35-38 PATHO-003 | 35-38 PATHO-004 | 35-38 PATHO-005 | 35-38 PATHO-006 | 35-38 PATHO-007 | 35-38 PATHO-008 | 35-38 PATHO-009 | 35-38 PATHO-010 |
| Threshold: 6K; 4K; 10K | Well 33 | Well 34 | Well 35 | Well 36 | Well 37 | Well 38 | Well 39 | Well 40 | Well 41 | Well 42 |
| 614D-SE-S1-RE1.4 | 1569 | 1739 | 2443 | 941 | 2494 | 796 | 667 | 1391 | 948 | 605 |
| 614G-SE-S1-RE1.4 | 1612 | 2030 | 2198 | 1715 | 2098 | 1355 | 882 | 1639 | 1060 | 743 |
| 614U-SE-S1-RE1.1 | 1041 | 1780 | 2285 | 1432 | 2725 | 1060 | 839 | 1533 | 1448 | 1545 |
| 62-Negcont-B | 190 | 205 | 2040 | 1600 | 2624 | 963 | 1742 | 2710 | 220 | 203 |
| InfA | 261 | 398 | 226 | −7 | −70 | 26 | 477 | 1518 | −65 | −7 |
| InfB | 40 | 41 | 477 | 200 | 1264 | 164 | −80 | −32 | 82 | 236 |
| RNAse.P.Probe-pub1.1 | 64285 | 64356 | 63611 | 62691 | 63406 | 62341 | 61277 | 62185 | 64297 | 64283 |
| SARS.COV2-N1-pub | 5141 | 5626 | 8989 | 6180 | 10508 | 6720 | 6390 | 8833 | 5856 | 8904 |
| SARS.COV2-N1-RE1.1 | 1001 | 1421 | 4129 | 2343 | 2972 | 1623 | 2177 | 3855 | 1408 | 2965 |
| SARS.COV2-N2-RE1.3 | 623 | 773 | 1945 | 979 | 2509 | 1321 | 1536 | 1205 | 866 | 434 |
| SARS.COV2-N2-RE1.4 | 667 | 826 | 2133 | 1538 | 2572 | 2536 | 1126 | 2320 | 533 | 617 |
| SARS.COV2-N3-RE1.1 | 3914 | 4892 | 7773 | 7221 | 3844 | 2518 | 7985 | 5725 | 2888 | 2671 |

| | DetectX RV Call | | | | | | | | | |
|---|---|---|---|---|---|---|---|---|---|---|
| | – | RERUN | – | – | – | – | – | – | – | – |
| | Roche Cq | | | | | | | | | |
| Well description | 35-38 PATHO-011 | 35-38 PATHO-012 | 35-38 PATHO-013 | 35-38 PATHO-014 | 35-38 PATHO-015 | 35-38 PATHO-016 | 35-38 PATHO-017 | 35-38 PATHO-018 | 35-38 PATHO-019 | 35-38 PATHO-020 |
| Threshold: 6K; 4K; 10K | Well 43 | Well 44 | Well 45 | Well 46 | Well 47 | Well 48 | Well 49 | Well 50 | Well 51 | Well 52 |
| 614D-SE-S1-RE1.4 | 1832 | 1227 | 2043 | 829 | 1640 | 1093 | 1317 | 1577 | 2254 | 1666 |
| 614G-SE-S1-RE1.4 | 2022 | 1462 | 1352 | 644 | 1926 | 2411 | 1804 | 1816 | 2135 | 1623 |
| 614U-SE-S1-RE1.1 | 1629 | 1272 | 1911 | 1069 | 2048 | 2077 | 1449 | 1101 | 2227 | 1296 |
| 62-Negcont-B | 1216 | 877 | 2236 | 1336 | 3313 | 776 | −33 | 94 | 1845 | 1139 |
| InfA | 1509 | 71 | 285 | 733 | −83 | 56 | 295 | 71 | 243 | 473 |
| InfB | 10 | 189 | 551 | −3 | 487 | 24 | 92 | 4 | 374 | −14 |
| RNAse.P.Probe-pub1.1 | 64134 | 62543 | 63437 | 62572 | 62492 | 62954 | 64236 | 64248 | 36197 | 62468 |
| SARS.COV2-N1-pub | 5137 | 5810 | 6049 | 6931 | 10119 | 10668 | 3815 | 5094 | 2547 | 4992 |
| SARS.COV2-N1-RE1.1 | 2550 | 2272 | 2627 | 2283 | 3367 | 2808 | 833 | 616 | 1754 | 1357 |
| SARS.COV2-N2-RE1.3 | 2887 | 1427 | 1618 | 1343 | 1896 | 3665 | 339 | 210 | 1119 | 1316 |
| SARS.COV2-N2-RE1.4 | 3226 | 1625 | 2066 | 832 | 2308 | 2195 | 636 | 291 | 1453 | 1201 |
| SARS.COV2-N3-RE1.1 | 7911 | 10842 | 4860 | 5189 | 8967 | 8296 | 2476 | 5302 | 2325 | 5931 |

| | DetectX RV Call | | | | | | | | | |
|---|---|---|---|---|---|---|---|---|---|---|
| | – | – | – | RERUN | – | – | RERUN | – | RERUN | – |
| | Roche Cq | | | | | | | | | |
| Well description | 35-38 PATHO-021 | 35-38 PATHO-022 | 35-38 PATHO-023 | 35-38 PATHO-024 | 35-38 PATHO-025 | 35-38 PATHO-026 | 35-38 PATHO-027 | 35-38 PATHO-028 | 35-38 PATHO-029 | 35-38 PATHO-030 |
| Threshold: 6K; 4K;1 0K | Well 53 | Well 54 | Well 55 | Well 56 | Well 57 | Well 58 | Well 59 | Well 60 | Well 61 | Well 62 |
| 614D-SE-S1-RE1.4 | 2209 | 1557 | 1528 | 1917 | 1496 | 1546 | 1512 | 1343 | 2429 | 1993 |
| 614G-SE-S1-RE1.4 | 1908 | 1751 | 2100 | 6149 | 1872 | 1574 | 1127 | 1448 | 2875 | 1367 |
| 614U-SE-S1-RE1.1 | 2539 | 1673 | 2186 | 1831 | 981 | 1300 | 1167 | 1500 | 2672 | 2048 |
| 62-Negcont-B | 3050 | 1662 | 1365 | 2221 | 39 | 39 | 1331 | 909 | 1299 | 1813 |
| InfA | −36 | −15 | 426 | 1138 | 240 | 85 | 121 | 132 | 750 | −16 |
| InfB | 1320 | 642 | 530 | 113 | 87 | 215 | 20 | 178 | −58 | 1192 |
| RNAse.P.Probe-pub1.1 | 62897 | 62942 | 61442 | 62268 | 64177 | 63884 | 62980 | 62404 | 63589 | 63575 |
| SARS.COV2-N1-pub | 7549 | 5376 | 6517 | 8961 | 10142 | 6738 | 7125 | 8100 | 9074 | 8946 |
| SARS.COV2-N1-RE1.1 | 3326 | 2497 | 1688 | 2222 | 1925 | 1840 | 3237 | 2777 | 2373 | 3262 |
| SARS.COV2-N2-RE1.3 | 3254 | 1772 | 1884 | 1791 | 887 | 1148 | 1984 | 2587 | 2259 | 3146 |
| SARS.COV2-N2-RE1.4 | 3584 | 1620 | 2119 | 2114 | 1194 | 1183 | 2023 | 986 | 2432 | 2223 |
| SARS.COV2-N3-RE1.1 | 7887 | 6507 | 5352 | 11168 | 1388 | 1935 | 11533 | 9546 | 11583 | 8293 |

TABLE 47

Contrived Samples for LOD (at 62.5 copies/ml)

DETECTX RV Call

| | + | + | + | + | + | + | + | + | + | + | + | + |
|---|---|---|---|---|---|---|---|---|---|---|---|---|
| | | | | | | Roche Cq | | | | | | |
| Well description | na LoD | na LoD | na LoD | na LoD | na LoD | na LoD | na LoD | na LoD | na LoD | na LoD | na LoD | na LoD |
| Threshold: 6K; 4K; 10K | Well 65 | Well 66 | Well 67 | Well 68 | Well 69 | Well 70 | Well 71 | Well 72 | Well 73 | Well 74 | Well 75 | Well 76 |
| 614D-SE-S1-RE1.4 | 3484 | 3245 | 3556 | 3327 | 2871 | 2955 | 3215 | 4688 | 2376 | 3106 | 3127 | 3608 |
| 614G-SE-S1-RE1.4 | 1642 | 1542 | 1745 | 1886 | 2449 | 1759 | 1776 | 2333 | 1610 | 1892 | 1186 | 2330 |
| 614U-SE-S1-RE1.1 | 6504 | 8639 | 5886 | 6293 | 7253 | 5724 | 6247 | 9771 | 5196 | 4319 | 5278 | 5000 |
| 62-Negcont-B | 174 | 236 | 1220 | 1935 | 1646 | 1417 | 1720 | 1462 | −11 | 10 | 457 | 1441 |
| InfA.7.univ-pubRev | 304 | 756 | 516 | −250 | 397 | 578 | −58 | 1252 | 796 | 447 | 698 | −8 |
| InfB.8.univ-pub | −19 | 8 | −35 | 285 | 137 | −128 | 489 | −186 | 86 | 72 | −61 | 106 |
| RNAse.P.Probe-pnb1.1 | 64140 | 63980 | 63208 | 62801 | 62778 | 62654 | 62379 | 62257 | 64023 | 64035 | 62275 | 62997 |
| SARS.COV2-N1-pub | 47158 | 50266 | 47720 | 49275 | 48853 | 46530 | 47431 | 50286 | 51818 | 50304 | 46915 | 47317 |
| SARS.COV2-N1-RE1.1 | 30375 | 38749 | 38833 | 39965 | 40642 | 38697 | 39535 | 38895 | 39039 | 35832 | 37634 | 37856 |
| SARS.COV2-N2-RE1.3 | 12315 | 11772 | 16989 | 18934 | 22002 | 18178 | 20475 | 29839 | 17666 | 10185 | 21361 | 15242 |
| SARS.COV2-N2-RE1.4 | 41784 | 43045 | 45998 | 48386 | 50500 | 45570 | 48290 | 52478 | 41701 | 40695 | 49169 | 46306 |
| SARS.COV2-N3-RE1.1 | 42343 | 44361 | 47653 | 47233 | 50989 | 45577 | 51288 | 55057 | 44002 | 43018 | 47688 | 48303 |

DetectX RV Call

| | + | + | + | + | + | + | + | + | + | + | + | + |
|---|---|---|---|---|---|---|---|---|---|---|---|---|
| | | | | | | Roche Cq | | | | | | |
| Well description | na LoD | na LoD | na LoD | na LoD | na LoD | na LoD | na LoD | na LoD | na LoD | na LoD | na LoD | na LoD |
| Threshold: 6K; 4K; 10K | Well 77 | Well 78 | Well 79 | Well 80 | Well 81 | Well 82 | Well 83 | Well 84 | Well 85 | Well 86 | Well 87 | Well 88 |
| 614D-SE-S1-RE1.4 | 2706 | 2104 | 2870 | 3725 | 4289 | 4027 | 3342 | 3156 | 3265 | 2343 | 3175 | 4059 |
| 614G-SE-S1-RE1.4 | 1711 | 1502 | 1344 | 2229 | 1739 | 1900 | 1758 | 1791 | 1595 | 1154 | 2043 | 2621 |
| 614U-SE-S1-RE1.1 | 4927 | 4992 | 3914 | 5663 | 7510 | 7646 | 5182 | 4995 | 5502 | 4124 | 6109 | 8547 |
| 62-Negcont-B | 869 | 1174 | 3551 | 2318 | 3 | 298 | 1737 | 1479 | 1561 | 1242 | 1181 | 3322 |
| InfA.7.univ-pubRev | −97 | −55 | 1234 | 827 | 675 | 600 | 728 | 447 | 399 | 61 | 1440 | 342 |
| InfB.8.univ-pub | 171 | 74 | 258 | 573 | 90 | 59 | 196 | −290 | 94 | 184 | 31 | 472 |
| RNAse.P.Probe-pub1.1 | 62233 | 62560 | 61052 | 62383 | 64039 | 63991 | 62844 | 62609 | 62597 | 63192 | 61990 | 62505 |
| SARS.COV2-N1-pub | 44165 | 47728 | 50017 | 48117 | 59064 | 55916 | 49944 | 50132 | 47374 | 48650 | 46566 | 53293 |
| SARS.COV2-N1-RE1.1 | 34365 | 39082 | 35650 | 39708 | 41211 | 39946 | 40245 | 39444 | 38059 | 40858 | 38973 | 40578 |
| SARS.COV2-N2-RE1.3 | 14193 | 17099 | 17656 | 17698 | 20779 | 20034 | 22299 | 20606 | 20893 | 20264 | 23322 | 29091 |
| SARS.COV2-N2-RE1.4 | 45517 | 45484 | 47099 | 48945 | 46318 | 46005 | 47927 | 49480 | 47143 | 47961 | 49109 | 52795 |
| SARS.COV2-N3-RE1.1 | 49069 | 46998 | 49050 | 50124 | 50115 | 47555 | 47408 | 46946 | 46820 | 46577 | 49863 | 54869 |

TABLE 48

96-Well Mini-RV analysis of positive clinical isolates for optimized manual hybridization-wash

| DetectX RV Call | Cycle number | Well description | Threshold: 6K; 4K; 10K | 614D-SE-S1-RE1.4 | 614G-SE-S1-RE1.4 | 614U-SE-S1-RE1.1 | 62-Negcont-B | InfA.7.univ-pubRev | InfB.8.univ-pub | RNAse.P.Probe-pub1.1 | SARS.COV2-N1-pub | SARS.COV2-N1-RE1.1 | SARS.COV2-N2-RE1.3 | SARS.COV2-N2-RE1.4 | SARS.COV2-N3-RE1.1 |
|---|---|---|---|---|---|---|---|---|---|---|---|---|---|---|---|
| + | 14.46 | 217215 | Well 1 | 10035 | 61638 | 62910 | 66 | 274 | 478 | 63613 | 63199 | 63343 | 62085 | 63263 | 63477 |
| + | 14.06 | 217372 | Well 2 | 8625 | 61438 | 63436 | 1 | 112 | 538 | 64162 | 63751 | 63894 | 55180 | 63719 | 63939 |
| + | 13.75 | 214495 | Well 3 | 8788 | 56914 | 61021 | 862 | 78 | 6 | 61649 | 61309 | 61533 | 61277 | 61269 | 61502 |
| + | 14.43 | 217142 | Well 4 | 11462 | 60770 | 62023 | 1203 | −140 | 215 | 62686 | 62416 | 62557 | 62247 | 62278 | 62474 |
| + | 14.93 | 215025 | Well 5 | 9763 | 56460 | 61720 | 1261 | 67 | 576 | 62411 | 62047 | 62251 | 62019 | 62101 | 62303 |
| + | 15.97 | 217179 | Well 6 | 6412 | 51400 | 61943 | 780 | 581 | 75 | 62684 | 62266 | 62478 | 62202 | 62244 | 62471 |
| + | 16 | 216036 | Well 7 | 7039 | 47960 | 60133 | 325 | 864 | −388 | 60847 | 60465 | 60691 | 60479 | 60617 | 60719 |
| + | 15.72 | 216106 | Well 8 | 7966 | 54076 | 61563 | 2049 | 725 | −220 | 62314 | 61917 | 62146 | 61836 | 61828 | 62130 |
| + | 15.85 | 216019 | Well 9 | 6044 | 43578 | 61276 | 273 | 73 | 610 | 52569 | 63846 | 63859 | 60277 | 63700 | 63833 |
| + | 15.07 | 216052 | Well 10 | 9204 | 59996 | 63589 | −2 | 458 | 761 | 46378 | 63902 | 63996 | 51748 | 63771 | 63995 |
| + | 27.5 | 217370 | Well 11 | 1137 | 11291 | 38534 | 1553 | 595 | −15 | 62525 | 61794 | 46992 | 36999 | 62044 | 62190 |
| + | 27.03 | 217358 | Well 12 | 1798 | 4990 | 19265 | 1521 | 1130 | −56 | 62947 | 50482 | 40029 | 16939 | 54703 | 47822 |
| + | 27.04 | 217213 | Well 13 | 760 | 1314 | 1750 | 1460 | 1636 | −4 | 62057 | 35143 | 18255 | 4099 | 20504 | 22385 |
| + | 24.09 | 217235 | Well 14 | 3098 | 24720 | 49041 | 1445 | 1605 | −29 | 63607 | 63324 | 61686 | 40548 | 63209 | 63376 |
| + | 20.27 | 217347 | Well 15 | 3358 | 39157 | 61303 | 1795 | 1593 | −137 | 62010 | 61660 | 61858 | 54570 | 61591 | 61736 |
| + | 22.07 | 217348 | Well 16 | 3648 | 37331 | 61276 | 2420 | 947 | −126 | 50836 | 61634 | 61836 | 54769 | 61566 | 61766 |
| + | 20.48 | 217354 | Well 17 | 8164 | 23487 | 40566 | 1113 | 909 | −26 | 63983 | 63320 | 41200 | 23301 | 53807 | 54707 |
| + | 19.25 | 217353 | Well 18 | 5120 | 14394 | 35556 | 597 | 970 | −22 | 63914 | 56749 | 41288 | 18293 | 47393 | 53551 |
| + | 15.63 | 217355 | Well 19 | 18839 | 47553 | 62866 | 1317 | 637 | −60 | 63679 | 63303 | 63441 | 44179 | 63217 | 63376 |
| + | 28.48 | 217351 | Well 20 | 1242 | 1800 | 1873 | 4748 | 253 | −73 | 63108 | 10421 | 7902 | 4135 | 7594 | 12818 |
| + | 31.03 | 217345 | Well 21 | 795 | 693 | 1101 | 1171 | 360 | −2 | 62688 | 3861 | 1476 | 1809 | 2671 | 6874 |
| − | 32.34 | 217217 | Well 22 | 1515 | 1739 | 1601 | 5128 | 737 | −99 | 63040 | 5924 | 8463 | 6573 | 3962 | 9896 |
| + | 30.53 | 217212 | Well 23 | 1974 | 2027 | 2018 | 5598 | 1254 | −118 | 62350 | 4926 | 15918 | 8517 | 5099 | 14687 |
| + | 31.74 | 217210 | Well 24 | 1570 | 2371 | 1764 | 5923 | 596 | −72 | 62685 | 7121 | 9032 | 4278 | 2747 | 10886 |
| + | 30.48 | 217344 | Well 25 | 1161 | 1962 | 2068 | −2 | 391 | 39 | 61127 | 14979 | 3692 | 4607 | 10158 | 15234 |
| − | 32.6 | 217357 | Well 26 | 1314 | 1597 | 1148 | 269 | 513 | −34 | 64223 | 6064 | 1614 | 739 | 681 | 4211 |
| RERUN | 31.92 | 217360 | Well 27 | 1343 | 1577 | 1594 | 1022 | 1649 | −63 | 62233 | 3443 | 543 | 1984 | 2478 | 12966 |
| − | 34.35 | 217356 | Well 28 | 1202 | 1693 | 1303 | 1150 | 777 | −22 | 62705 | 4624 | 1553 | 1222 | 1475 | 7812 |
| + | 30.68 | 216048 | Well 29 | 1813 | 2761 | 5045 | 2341 | −28 | 1070 | 62700 | 40330 | 27405 | 9906 | 38716 | 41757 |
| + | 32.13 | 216133 | Well 30 | 1303 | 1478 | 1206 | 1034 | 179 | 148 | 62487 | 13099 | 5329 | 2873 | 4488 | 14454 |
| RERUN |  | NTC | Well 31 | 2631 | 2882 | 2009 | 2602 | 2150 | −186 | 9239 | 8657 | 3174 | 4261 | 3911 | 4639 |
| RERUN |  | NTC | Well 32 | 2434 | 2264 | 2378 | 3401 | 173 | 1250 | 10046 | 12014 | 5307 | 1872 | 2373 | 14001 |
| − |  | PATHO-001 | Well 33 | 1569 | 1612 | 1041 | 190 | 261 | 40 | 64285 | 5141 | 1001 | 623 | 667 | 3914 |
|  | 35-38 | PATHO-001 | Well 34 | 1739 | 2030 | 1780 | 205 | 398 | 41 | 64356 | 5626 | 1421 | 773 | 826 | 4892 |
|  | 35-38 | PATHO-002 | Well 35 | 2443 | 2198 | 2285 | 2040 | 226 | 477 | 63611 | 8989 | 4129 | 1945 | 2133 | 7773 |
|  | 35-38 | PATHO-003 | Well 36 | 941 | 1715 | 1432 | 1600 | −7 | 200 | 62691 | 6180 | 2343 | 979 | 1538 | 7221 |
|  | 35-38 | PATHO-004 | Well 37 | 2494 | 2098 | 2725 | 2624 | −70 | 1264 | 63406 | 10508 | 2972 | 2509 | 2572 | 3844 |
|  | 35-38 | PATHO-005 | Well 38 | 796 | 1355 | 1060 | 963 | 26 | 164 | 62341 | 6720 | 1623 | 1321 | 2536 | 2518 |
|  | 35-38 | PATHO-006 |  |  |  |  |  |  |  |  |  |  |  |  |  |

TABLE 48-continued

96-Well Mini-RV analysis of positive clinical isolates for optimized manual hybridization-wash

| DetectX RV Call | Cycle number | Well description | Threshold: 6K; 4K; 10K | 614D-SE-S1-RE1.4 | 614G-SE-S1-RE1.4 | 614U-SE-S1-RE1.1 | 62-Negcont-B | InfA.7.univ-pubRev | InfB.8.univ-pub | RNAse.P.Probe-pub1.1 | SARS.COV2-N1-pub | SARS.COV2-N1-RE1.1 | SARS.COV2-N2-RE1.3 | SARS.COV2-N2-RE1.4 | SARS.COV2-N3-RE1.1 |
|---|---|---|---|---|---|---|---|---|---|---|---|---|---|---|---|
| — | 35-38 | PATHO-007 | Well 39 | 667 | 882 | 839 | 1742 | 477 | -80 | 61277 | 6390 | 2177 | 1536 | 1126 | 7985 |
| — | 35-38 | PATHO-008 | Well 40 | 1391 | 1639 | 1533 | 2710 | 1518 | -32 | 62185 | 8833 | 3855 | 1205 | 2320 | 5725 |
| — | 35-38 | PATHO-009 | Well 41 | 948 | 1060 | 1448 | 220 | -65 | 82 | 64297 | 5856 | 1408 | 866 | 533 | 2888 |
| — | 35-38 | PATHO-010 | Well 42 | 605 | 743 | 1545 | 203 | -7 | 236 | 64283 | 8904 | 2965 | 434 | 617 | 2671 |
| — | 35-38 | PATHO-011 | Well 43 | 1832 | 2022 | 1629 | 1216 | 1509 | 10 | 64134 | 5137 | 2550 | 2887 | 3226 | 7911 |
| RERUN | 35-38 | PATHO-012 | Well 44 | 1227 | 1462 | 1272 | 877 | 71 | 189 | 62543 | 5810 | 2272 | 1427 | 1625 | 10842 |
| — | 35-38 | PATHO-013 | Well 45 | 2043 | 1352 | 1911 | 2236 | 285 | 551 | 63437 | 6049 | 2627 | 1618 | 2066 | 4860 |
| — | 35-38 | PATHO-014 | Well 46 | 829 | 644 | 1069 | 1336 | 733 | -3 | 62572 | 6931 | 2283 | 1343 | 832 | 5189 |
| — | 35-38 | PATHO-015 | Well 47 | 1640 | 1926 | 2048 | 3313 | -83 | 487 | 62492 | 10119 | 3367 | 1896 | 2308 | 8967 |
| — | 35-38 | PATHO-016 | Well 48 | 1093 | 2411 | 2077 | 776 | 56 | 24 | 62954 | 10668 | 2808 | 3665 | 2195 | 8296 |
| — | 35-38 | PATHO-017 | Well 49 | 1317 | 1804 | 1449 | -33 | 295 | 92 | 64236 | 3815 | 833 | 339 | 636 | 2476 |
| — | 35-38 | PATHO-018 | Well 50 | 1577 | 1816 | 1101 | 94 | 71 | 4 | 64248 | 5094 | 616 | 210 | 291 | 5302 |
| — | 35-38 | PATHO-019 | Well 51 | 2254 | 2135 | 2227 | 1845 | 243 | 374 | 36197 | 2547 | 1754 | 1119 | 1453 | 2325 |
| — | 35-38 | PATHO-020 | Well 52 | 1666 | 1623 | 1296 | 1139 | 473 | -14 | 62468 | 4992 | 1357 | 1316 | 1201 | 5931 |
| — | 35-38 | PATHO-021 | Well 53 | 2209 | 1908 | 2539 | 3050 | -36 | 1320 | 62897 | 7549 | 3326 | 3254 | 3584 | 7887 |
| — | 35-38 | PATHO-022 | Well 54 | 1557 | 1751 | 1673 | 1662 | -15 | 642 | 62942 | 5376 | 2497 | 1772 | 1620 | 6507 |
| — | 35-38 | PATHO-023 | Well 55 | 1528 | 2100 | 2186 | 1365 | 426 | 530 | 61442 | 6517 | 1688 | 1884 | 2119 | 5352 |
| RERUN | 35-38 | PATHO-024 | Well 56 | 1917 | 6149 | 1831 | 2221 | 1138 | 113 | 62268 | 8961 | 2222 | 1791 | 2114 | 11168 |
| — | 35-38 | PATHO-025 | Well 57 | 1496 | 1872 | 981 | 39 | 240 | 87 | 64177 | 10142 | 1925 | 887 | 1194 | 1388 |
| — | 35-38 | PATHO-026 | Well 58 | 1546 | 1574 | 1300 | 39 | 85 | 215 | 63884 | 6738 | 1840 | 1148 | 1183 | 1935 |
| RERUN | 35-38 | PATHO-027 | Well 59 | 1512 | 1127 | 1167 | 1331 | 121 | 20 | 62980 | 7125 | 3237 | 1984 | 2023 | 11533 |
| — | 35-38 | PATHO-028 | Well 60 | 1343 | 1448 | 1500 | 909 | 132 | 178 | 62404 | 8100 | 2777 | 2587 | 986 | 9546 |

TABLE 48-continued

96-Well Mini-RV analysis of positive clinical isolates for optimized manual hybridization-wash

| DetectX RV Call | Cycle number | Well description | Threshold: 6K; 4K; 10K | 614D-SE-S1-RE1.4 | 614G-SE-S1-RE1.4 | 614U-SE-S1-RE1.1 | 62-Negcont-B | InfA.7.univ-pubRev | InfB.8.univ-pub | RNAse.P.Probe-pub1.1 | SARS.COV2-N1-pub | SARS.COV2-N1-RE1.1 | SARS.COV2-N2-RE1.3 | SARS.COV2-N2-RE1.4 | SARS.COV2-N3-RE1.1 |
|---|---|---|---|---|---|---|---|---|---|---|---|---|---|---|---|
| RERUN | 35-38 | PATHO-029 | Well 61 | 2429 | 2875 | 2672 | 1299 | 750 | -58 | 63589 | 9074 | 2373 | 2259 | 2432 | 11583 |
| - | 35-38 | PATHO-030 | Well 62 | 1993 | 1367 | 2048 | 1813 | -16 | 1192 | 63575 | 8946 | 3262 | 3146 | 2223 | 8293 |
| RERUN | | NTC | Well 63 | 1742 | 1938 | 1771 | 917 | 1021 | 468 | 6875 | 12850 | 5624 | 1504 | 1747 | 11872 |
| RERUN | | NTC | Well 64 | 2740 | 2525 | 2529 | 1907 | 1542 | -41 | 7237 | 15457 | 4113 | 2688 | 3144 | 19038 |
| + | | LoD | Well 65 | 3484 | 1642 | 6504 | 174 | 304 | -19 | 64140 | 47158 | 30375 | 12315 | 41784 | 42343 |
| + | | LoD | Well 66 | 3245 | 1542 | 8639 | 236 | 756 | 8 | 63980 | 50266 | 38749 | 11772 | 43045 | 44361 |
| + | | LoD | Well 67 | 3556 | 1745 | 5886 | 1229 | 516 | -35 | 63208 | 47720 | 38833 | 16989 | 45998 | 47653 |
| + | | LoD | Well 68 | 3327 | 1886 | 6293 | 1935 | -250 | 285 | 62801 | 49275 | 39965 | 18934 | 48386 | 47233 |
| + | | LoD | Well 69 | 2871 | 2449 | 7253 | 1646 | 397 | 137 | 62778 | 48853 | 40642 | 22002 | 50500 | 50989 |
| + | | LoD | Well 70 | 2955 | 1759 | 5724 | 1417 | 578 | -128 | 62654 | 46530 | 38697 | 18178 | 45570 | 45577 |
| + | | LoD | Well 71 | 3215 | 1776 | 6247 | 1720 | -58 | 489 | 62379 | 47431 | 39535 | 20475 | 48290 | 51288 |
| + | | LoD | Well 72 | 4688 | 2333 | 9771 | 1462 | 1252 | -186 | 62257 | 50286 | 38895 | 29839 | 52478 | 55057 |
| + | | LoD | Well 73 | 2376 | 1610 | 5196 | -11 | 796 | 86 | 64023 | 51818 | 39039 | 17666 | 41701 | 44002 |
| + | | LoD | Well 74 | 3106 | 1892 | 4319 | 10 | 447 | 72 | 64035 | 50304 | 35832 | 10185 | 40695 | 43018 |
| + | | LoD | Well 75 | 3127 | 1186 | 5278 | 457 | 698 | -61 | 62275 | 46915 | 37634 | 21361 | 49169 | 47688 |
| + | | LoD | Well 76 | 3608 | 2330 | 5000 | 1441 | -8 | 106 | 62997 | 47317 | 37858 | 15242 | 46306 | 48393 |
| + | | LoD | Well 77 | 2706 | 1711 | 4927 | 869 | -97 | 171 | 62233 | 44165 | 34365 | 14193 | 45517 | 49069 |
| + | | LoD | Well 78 | 2104 | 1502 | 4992 | 1174 | -55 | 74 | 62560 | 47728 | 39082 | 17099 | 45484 | 46998 |
| + | | LoD | Well 79 | 2870 | 1344 | 3914 | 3551 | 1234 | 258 | 61052 | 50017 | 35650 | 17656 | 47099 | 49050 |
| + | | LoD | Well 80 | 3725 | 2229 | 5663 | 2318 | 827 | 573 | 62383 | 48117 | 39708 | 17698 | 48945 | 50124 |
| + | | LoD | Well 81 | 4289 | 1739 | 7510 | 3 | 675 | 90 | 64039 | 59064 | 41211 | 20779 | 46318 | 50115 |
| + | | LoD | Well 82 | 4027 | 1900 | 7646 | 298 | 600 | 59 | 63991 | 55916 | 39946 | 20034 | 46005 | 47555 |
| + | | LoD | Well 33 | 3342 | 1758 | 5182 | 1737 | 728 | 196 | 62844 | 49944 | 40245 | 22299 | 47927 | 47408 |
| + | | LoD | Well 84 | 3156 | 1791 | 4995 | 1479 | 447 | -290 | 62609 | 50132 | 39444 | 20606 | 49480 | 46946 |
| + | | LoD | Well 85 | 3265 | 1595 | 5502 | 1561 | 399 | 94 | 62597 | 47374 | 38059 | 20893 | 47143 | 46820 |
| + | | LoD | Well 86 | 2343 | 1154 | 4124 | 1242 | 61 | 184 | 63192 | 48650 | 40858 | 20264 | 47961 | 46577 |
| + | | LoD | Well 87 | 3175 | 2043 | 6109 | 1181 | 1440 | 31 | 61990 | 46566 | 38973 | 23322 | 49109 | 49863 |
| + | | LoD | Well 88 | 4059 | 2621 | 8547 | 3322 | 342 | 472 | 62505 | 53293 | 40578 | 29091 | 52795 | 54869 |
| + | | Empty | Well 89 | 1039 | 549 | 1173 | 461 | -6 | 679 | 5670 | 9646 | 1322 | 864 | 1030 | 873 |
| RERUN | | | Well 90 | 1768 | 2246 | 2237 | -11 | 709 | 233 | 8598 | 16006 | 4014 | 973 | 1306 | 9239 |
| - | | | Well 91 | 1499 | 696 | 1323 | 1346 | -113 | 275 | 11659 | 15042 | 3282 | 3908 | 2298 | 11617 |
| - | | | Well 92 | 1206 | 1493 | 1182 | 837 | 84 | 5 | 4996 | 10852 | 4432 | 1429 | 1082 | 3273 |
| - | | | Well 93 | 2039 | 1451 | 2308 | 2237 | 45 | 961 | 6829 | 11735 | 3323 | 2362 | 1734 | 2942 |
| - | | | Well 94 | 1394 | 1811 | 1402 | 1262 | 202 | 228 | 6505 | 9046 | 2507 | 1511 | 1043 | 3843 |
| + | | | Well 95 | 1397 | 1315 | 1064 | 1532 | 128 | 339 | 6512 | 12167 | 4989 | 6348 | 2609 | 19776 |
| - | | | Well 96 | 877 | 1388 | 1448 | 1569 | 948 | -143 | 3207 | 5496 | 1436 | 2221 | 4107 | 3768 |

Clinical Isolates. TriCore NP Positive and Negative. Analysis of clinical samples showed 91% specificity and 100% selectivity (N1, N2, N3, P) (Tables 48 and 49). Three false Negatives were found to coincide with clinical samples with Cq>30.

TABLE 49

Analysis of clinical isolates

| Probe name | Average positives | Standard deviation positives | Average negatives | Standard deviation negatives | (a) True positive | (b) False positive | (c) False negative | (d) True negative | LoB | LoD | Sensitivity | Specificity | PPV | NPV |
|---|---|---|---|---|---|---|---|---|---|---|---|---|---|---|
| RNase P | 61474 | 4084 | 62272 | 5002 | 30 | 0 | 0 | 30 | 70501 | 14045 | 100 | 100 | 100 | 100 |
| N1 | 38209 | 26123 | 2317 | 871 | 30 | 0 | 3 | 30 | 3749 | 46351 | 91 | 100 | 100 | 91 |
| N21.3 | 31303 | 25588 | 1624 | 882 | 30 | 0 | 3 | 30 | 3075 | 44666 | 91 | 100 | 100 | 91 |
| N21.4 | 39763 | 27126 | 1672 | 827 | 30 | 0 | 3 | 30 | 3033 | 46831 | 91 | 100 | 100 | 91 |
| N3 | 42311 | 24102 | 6224 | 3041 | 30 | 0 | 3 | 30 | 11226 | 47045 | 91 | 100 | 100 | 91 |
| Overall Call | N/A | N/A | N/A | N/A | 30 | 0 | 3 | 30 | N/A | N/A | 91 | 100 | 100 | 91 |

Example 25

Well-to-Well Cross Contamination in Mini-RV Workflow

To test the potential of cross contamination of the negative sample wells with the positive samples various checkerboard patterns were tested in the Min-RV 96-well workflow. The goals of these experiments were:

1. Measure the rate of well-to-well transfer of high copy number positive samples into negatives.
2. Quantitate the baseline cross contamination rate due to well-well transfer during processing.
3. Perform a full workflow (Zymo→Asymmetric One-Step RT-PCR→Hybridization/Wash→Sensovation 96-well imaging) in 96-well format.
4. Testing of positive and negative samples were performed in a checkerboard pattern.
5. Measure rate of well-to-well transfer during manual and automated (Tecan) workflows.

Four different checkerboard patterns were tested in duplicate (8×96 data points) for pooled positive Boca NP swab samples (in VTM) extracted on the Tecan robot. Table 50 shows the four checkerboard patterns used with the positive wells shown in bold numerals. Tables 51 and 52 show the full representative data sets for Checkerboard patterns 2 and 3. These data revealed no well-to-well cross contamination across all 8 sets of experiments (602 negatives) and are summarized in Table 53.

TABLE 50

Checkerboard pattern for testing well-to-well cross contamination in Mini-RV workflow

| Checkerboard 1 | | | | | | | | | | | | 24 Positive Samples | |
|---|---|---|---|---|---|---|---|---|---|---|---|---|---|
| | 1 | 2 | 3 | 4 | 5 | 6 | 7 | 8 | 9 | 10 | 11 | 12 | One Step PCR |
| A | 1 | 9 | 17 | 25 | 33 | 41 | 49 | 57 | 65 | 73 | 81 | 89 Reagent | 1X 100X |
| B | 2 | 10 | 18 | 26 | 34 | 42 | 50 | 58 | 66 | 74 | 82 | 90 Master Mix | 25 μL 2500 μL |
| C | 3 | 11 | 19 | 27 | 35 | 43 | 51 | 59 | 67 | 75 | 83 | 91 Primer | 2 μL 200 μL |
| D | 4 | 12 | 20 | 28 | 36 | 44 | 52 | 60 | 68 | 76 | 84 | 92 AMV | 1 μL 100 μL |
| E | 5 | 13 | 21 | 29 | 37 | 45 | 53 | 61 | 69 | 77 | 85 | 93 H2O | 17 μL 1700 μL |
| F | 6 | 14 | 22 | 30 | 38 | 46 | 54 | 62 | 70 | 78 | 86 | 94 | |
| G | 7 | 15 | 23 | 31 | 39 | 47 | 55 | 63 | 71 | 79 | 87 | 95 | |
| H | 8 | 16 | 24 | 32 | 40 | 48 | 56 | 64 | 72 | 80 | 88 | 96 | |
| Checkerboard 2 | | | | | | | | | | | | 16 Positive Samples | |
| | 1 | 2 | 3 | 4 | 5 | 6 | 7 | 8 | 9 | 10 | 11 | 12 | One Step PCR |
| A | 1 | 9 | 17 | 25 | 33 | 41 | 49 | 57 | 65 | 73 | 81 | 89 Reagent | 1X 100X |
| B | 2 | 10 | 18 | 26 | 34 | 42 | 50 | 58 | 66 | 74 | 82 | 90 Master Mix | 25 μL 2500 μL |
| C | 3 | 11 | 19 | 27 | 35 | 43 | 51 | 59 | 67 | 75 | 83 | 91 Primer | 2 μL 200 μL |
| D | 4 | 12 | 20 | 28 | 36 | 44 | 52 | 60 | 68 | 76 | 84 | 92 AMV | 1 μL 100 μL |
| F | 5 | 13 | 21 | 29 | 37 | 45 | 53 | 61 | 69 | 77 | 85 | 93 H2O | 17 μL 1700 μL |
| H | 6 | 14 | 22 | 30 | 38 | 46 | 54 | 62 | 70 | 78 | 86 | 94 | |
| G | 7 | 15 | 23 | 31 | 39 | 47 | 55 | 63 | 71 | 79 | 87 | 95 | |
| H | 8 | 16 | 24 | 32 | 40 | 48 | 56 | 64 | 72 | 80 | 88 | 96 | |
| Checkerboard 3 | | | | | | | | | | | | 25 Positive Samples | |
| | 1 | 2 | 3 | 4 | 5 | 6 | 7 | 8 | 9 | 10 | 11 | 12 | One Step PCR |
| A | 1 | 9 | 17 | 25 | 33 | 41 | 49 | 57 | 65 | 73 | 81 | 89 Reagent | 1X 100X |
| B | 2 | 10 | 18 | 26 | 34 | 42 | 50 | 58 | 66 | 74 | 82 | 90 Master Mix | 25 μL 2500 μL |
| C | 3 | 11 | 19 | 27 | 35 | 43 | 51 | 59 | 67 | 75 | 83 | 91 Primer | 2 μL 200 μL |

TABLE 50-continued

Checkerboard pattern for testing well-to-well cross contamination in Mini-RV workflow

| | 1 | 2 | 3 | 4 | 5 | 6 | 7 | 8 | 9 | 10 | 11 | 12 | | | |
|---|---|---|---|---|---|---|---|---|---|---|---|---|---|---|---|
| D | 4 | 12 | 20 | 28 | 36 | 44 | 52 | 60 | 68 | 76 | 84 | 92 | AMV | 1 μL | 100 μL |
| E | 5 | 13 | 21 | 29 | 37 | 45 | 53 | 61 | 69 | 77 | 85 | 93 | H2O | 17 μL | 1700 μL |
| F | 6 | 14 | 22 | 30 | 38 | 46 | 54 | 62 | 70 | 78 | 86 | 94 | | | |
| G | 7 | 15 | 23 | 31 | 39 | 47 | 55 | 63 | 71 | 79 | 87 | 95 | | | |
| H | 8 | 16 | 24 | 32 | 40 | 48 | 56 | 64 | 72 | 80 | 88 | 96 | | | |

| Checkerboard 4 | | | | | | | | | | | | | 18 Positive Samples | | |
|---|---|---|---|---|---|---|---|---|---|---|---|---|---|---|---|
| | 1 | 2 | 3 | 4 | 5 | 6 | 7 | 8 | 9 | 10 | 11 | 12 | One Step PCR | | |
| A | 1 | 9 | 17 | 25 | 33 | 41 | 49 | 57 | 65 | 73 | 81 | 89 | Reagent | 1X | 100X |
| B | 2 | 10 | 18 | 26 | 34 | 42 | 50 | 58 | 66 | 74 | 82 | 90 | Master Mix | 25 μL | 2500 μL |
| C | 3 | 11 | 19 | 27 | 35 | 43 | 51 | 59 | 67 | 75 | 83 | 91 | Primer | 2 μL | 200 μL |
| D | 4 | 12 | 20 | 28 | 36 | 44 | 52 | 60 | 68 | 76 | 84 | 92 | AMV | 1 μL | 100 μL |
| L | 5 | 13 | 21 | 29 | 37 | 45 | 53 | 61 | 69 | 77 | 85 | 93 | H2O | 17 μL | 1700 μL |
| F | 6 | 14 | 22 | 30 | 38 | 46 | 54 | 62 | 70 | 78 | 86 | 94 | | | |
| G | 7 | 15 | 23 | 31 | 39 | 47 | 55 | 63 | 71 | 79 | 87 | 95 | | | |
| H | 8 | 16 | 24 | 32 | 40 | 48 | 56 | 64 | 72 | 80 | 88 | 96 | | | |

TABLE 51

Representative data set for Checkerboard pattern# 2

| Sample | Well # | InfA.7.univ-pubRev | No Print | RNAse.P.Probe-pub1.1 | No Print | SARS.COV2-N3-RE1.1 | 614G-SE-S1-RE1.4 | SARS.COV2-N2-RE1.4 | 614D-SE-S1-RE1.4 | SARS.COV2-N2-RE1.3 | 614U-SE-S1-RE1.1 | SARS.COV2-N1-RE1.1 | SARS.COV2-N1-pub | 62-Negcont-B | InfB.8.univ-pub |
|---|---|---|---|---|---|---|---|---|---|---|---|---|---|---|---|
| NEG | 1 | 118 | −1907 | 4432 | −1859 | 12122 | 1340 | 913 | 1859 | 1134 | 1494 | 3369 | 9755 | 214 | −60.5 |
| NEG | 2 | 23 | −1350 | 5391 | −1408 | 7426 | 2019 | 1119 | 2185 | 1397 | 1896 | 3678 | 10620 | 1090 | 58.75 |
| NEG | 3 | 571 | −1824 | 4933 | −1917 | 2562 | 1124 | 1081 | 910 | 1049 | 1209 | 1361 | 11603 | 511 | −53.25 |
| NEG | 4 | −3 | −1362 | 3733 | −1439 | 3123 | 1721 | 1887 | 1830 | 3201 | 1523 | 4720 | 13574 | 1016 | 14.25 |
| NEG | 5 | 366 | −4043 | 2532 | −4034 | 9973 | 382 | 68 | 626 | 1503 | 201 | 2485 | 6281 | 346 | 453.75 |
| NEG | 6 | 1573 | −2715 | 4594 | −2703 | 10370 | 1677 | 436 | 1924 | 921 | 1401 | 4064 | 12580 | 534 | 214 |
| NEG | 7 | −86 | −2370 | 4989 | −2334 | 9584 | 2481 | 1855 | 2236 | 2724 | 1781 | 4468 | 12617 | 2261 | 793 |
| NEG | 8 | −43 | −2237 | 4110 | −2678 | 1691 | 2455 | 895 | 2188 | 1482 | 1906 | 4293 | 12503 | 2121 | 358 |
| NEG | 9 | −22 | −1295 | 3486 | −1315 | 10057 | 2141 | 1130 | 4581 | 1609 | 2337 | 5131 | 15599 | 921 | 394 |
| NEG | 10 | 5 | −1458 | 36946 | −1510 | 20840 | 1621 | 18838 | 1565 | 7516 | 1389 | 20043 | 34141 | 753 | 262 |
| NEG | 11 | −15 | −1951 | 3076 | −1888 | 3325 | 1711 | 1667 | 1729 | 1688 | 1309 | 1797 | 7597 | 680 | 85 |
| + | 12 | 287 | −2069 | 29118 | −2017 | 15066 | 1903 | 14995 | 1650 | 4842 | 1464 | 31436 | 31436 | 493 | −70 |
| NEG | 13 | 7 | −3019 | 5728 | −3004 | 3425 | 1044 | 3326 | 1628 | 2192 | 984 | 2308 | 12208 | 199 | 100 |
| + | 14 | −260 | −2710 | 26602 | −2687 | 19669 | 1493 | 18300 | 1964 | 6869 | 1767 | 10794 | 24673 | 2078 | 840 |
| NEG | 15 | 204 | −3033 | 5242 | −3027 | 141 | 1668 | 548 | 1650 | 1500 | 1154 | 2847 | 12344 | 291 | 149 |
| + | 16 | 26 | −2918 | 17040 | −2969 | 20502 | 1801 | 16373 | 1488 | 5982 | 1319 | 7165 | 19803 | 1945 | 127 |
| NEG | 17 | −15 | −1188 | 3356 | −1184 | 2912 | 1587 | 704 | 1746 | 1117 | 1677 | 2913 | 12075 | 695 | 252 |
| NEG | 18 | −39 | −1541 | 2954 | −1494 | 575 | 1200 | 567 | 1039 | 792 | 963 | 2978 | 4303 | 481 | 113 |
| NEG | 19 | 94 | −1541 | 4230 | −1524 | 3397 | 2298 | 1087 | 2451 | 1292 | 2099 | 4463 | 13335 | 1007 | 212 |
| NEG | 20 | −94 | −1351 | 3758 | −1393 | 5250 | 1549 | 917 | 1413 | 1127 | 1319 | 2996 | 11174 | 518 | 127 |
| NEG | 21 | 914 | −2729 | 4694 | −2723 | 3664 | 1398 | 2122 | 1471 | 2993 | 1058 | 3944 | 14906 | 626 | 9 |
| NEG | 22 | −125 | −2539 | 3382 | −2440 | 835 | 1291 | 2838 | 1572 | 4581 | 1023 | 2253 | 8777 | 748 | 173 |
| NEG | 23 | −349 | −2850 | 2377 | −2791 | 7492 | 1064 | 743 | 1094 | 3007 | 779 | 3002 | 13335 | 345 | 200 |
| NEG | 24 | −49 | −2710 | 5214 | −2712 | 8411 | 806 | 690 | 970 | 3096 | 698 | 2242 | 10423 | 461 | 335 |
| NEG | 25 | 166 | −2030 | 1783 | −2001 | 5722 | 656 | 1793 | 2145 | 1732 | 1196 | 4159 | 12296 | 490 | 27 |
| NEG | 26 | −93 | −1227 | 2955 | −1226 | 545 | 1705 | 500 | 1693 | 533 | 1386 | 2010 | 8115 | 369 | 599 |
| NEG | 27 | −11 | −1759 | 2986 | −1780 | 9535 | 1390 | 921 | 1589 | 2893 | 1289 | 4595 | 10959 | 221 | 151 |
| NEG | 28 | −11 | −1450 | 4041 | −1408 | 7221 | 1651 | 396 | 1746 | 1028 | 1307 | 2177 | 8574 | 241 | 213 |
| NEG | 29 | 319 | −3344 | 4139 | −3389 | 315 | 1394 | 218 | 1981 | 1852 | 948 | 3068 | 12062 | 1042 | 537 |
| NEG | 30 | 67 | −3059 | 4797 | −3050 | 6836 | 1224 | 303 | 1696 | 784 | 1045 | 3080 | 12023 | 392 | 651 |
| + | 31 | 60 | −3720 | 5904 | −3643 | 106 | 1203 | 1238 | 1456 | 3556 | 702 | 2760 | 14284 | 771 | 73 |
| NEG | 32 | −18 | −2875 | 2786 | −2788 | 757 | 1219 | 2148 | 1199 | 5673 | 754 | 3668 | 16084 | 483 | 338 |
| NEG | 33 | −3 | −1123 | 22244 | −1072 | 13071 | 1586 | 12327 | 1455 | 5153 | 1472 | 10072 | 22841 | 683 | 173 |
| NEG | 34 | −25 | −1253 | 4395 | −1299 | 6322 | 1350 | 2043 | 1327 | 4391 | 1286 | 3653 | 10387 | 654 | 72 |
| + | 35 | 22 | −1336 | 21314 | −1359 | 14531 | 1633 | 16323 | 1647 | 5435 | 1151 | 9588 | 20000 | 575 | 54 |
| NEG | 36 | 449 | −1624 | 3231 | −1676 | 1318 | 2056 | 1780 | 2170 | 4173 | 1784 | 2999 | 8572 | 478 | 9 |
| + | 37 | −251 | −1984 | 22828 | −1941 | 14254 | 2536 | 11441 | 2600 | 4341 | 2318 | 7794 | 18638 | 1215 | 857 |
| NEG | 38 | −39 | −2819 | 4467 | −2798 | 171 | 962 | 2205 | 1516 | 1519 | 1061 | 2693 | 10641 | 2270 | 235 |
| + | 39 | −178 | −2456 | 37117 | −2498 | 24316 | 2106 | 13960 | 1802 | 4836 | 1589 | 12824 | 32203 | 849 | 692 |
| NEG | 40 | −51 | −2019 | 3888 | −2086 | 4616 | 2362 | 1295 | 2547 | 1929 | 1783 | 3219 | 10379 | 2937 | 1208 |
| NEG | 41 | −59 | −1251 | 2833 | −1255 | 757 | 1522 | 586 | 1499 | 2320 | 1458 | 2348 | 9343 | 518 | 119 |
| NEG | 42 | −21 | −1314 | 3870 | −1355 | 5794 | 1478 | 2373 | 1313 | 2868 | 1329 | 4271 | 10641 | 728 | 277 |
| NEG | 43 | −12 | −1438 | 4139 | −1378 | 2315 | 1253 | 373 | 1270 | 630 | 943 | 3449 | 10383 | 244 | 293 |
| NEG | 44 | −34 | −1433 | 3208 | −1362 | 5800 | 1440 | 4640 | 1458 | 934 | 1436 | 1976 | 7530 | 527 | 652 |
| NEG | 45 | 62 | −2446 | 3407 | −2448 | 4137 | 1401 | 3987 | 1350 | 5072 | 990 | 2032 | 8129 | 567 | 133 |

TABLE 51-continued

Representative data set for Checkerboard pattern# 2

| Sample | Well # | InfA.7.iniv-pubRev | No Print | RNAse.P.Probe-pub1.1 | No Print | SARS.COV2-N3-RE1.1 | 614G-SE-S1-RE1.4 | SARS.COV2-N2-RE1.4 | 614D-SE-S1-RE1.4 | SARS.COV2-N2-RE1.3 | 614U-SE-S1-RE1.1 | SARS.COV2-N1-RE1.1 | SARS.COV2-N1-pub | 62-Negcont-B | InfB.8.univ-pub |
|---|---|---|---|---|---|---|---|---|---|---|---|---|---|---|---|
| NEG | 46 | -174 | -2355 | 9551 | -2386 | 5179 | 1872 | 1875 | 2308 | 2945 | 1471 | 3349 | 9783 | 1453 | 827 |
| NEG | 47 | 675 | -2771 | 2271 | -2834 | 6312 | 719 | 274 | 595 | 1203 | 784 | 3382 | 9207 | 534 | 220 |
| NEG | 48 | 85 | -2636 | 2591 | -2679 | -36 | 1164 | 1009 | 1048 | 1374 | 904 | 2275 | 9122 | 789 | 225 |
| NEG | 49 | -154 | -1511 | 3073 | -1370 | 3192 | 1384 | 896 | 1288 | 1821 | 1371 | 3681 | 9941 | 258 | 313 |
| NEG | 50 | -7 | -1119 | 3379 | -1209 | 2876 | 1720 | 1435 | 1560 | 1417 | 1496 | 2272 | 10181 | 653 | 318 |
| NEG | 51 | 156 | -2002 | 3021 | -2001 | 2784 | 1209 | 6834 | 1208 | 5231 | 1037 | 3602 | 10629 | 262 | -36 |
| NEG | 52 | 2 | -1603 | 3891 | -1578 | 5283 | 1285 | 288 | 910 | 473 | 1345 | 2754 | 8469 | 170 | 166 |
| + | 53 | 1212 | -3493 | 2878 | -3543 | 12708 | 1065 | 1314 | 169 | 1678 | 491 | 526 | 6014 | 1980 | 1366 |
| NEG | 54 | 90 | -2658 | 2792 | -2738 | 4064 | 1372 | 203 | 1654 | 823 | 841 | 4521 | 11224 | 141 | 707 |
| NEG | 55 | -91 | -3323 | 9352 | -3391 | 1560 | 1926 | 1638 | 1901 | 1983 | 1071 | 3306 | 14560 | 1585 | 149 |
| NEG | 56 | -30 | -2234 | 3919 | -2976 | 12009 | 1393 | 225 | 1136 | 769 | 896 | 3732 | 10164 | 1164 | 138 |
| NEG | 57 | -16 | -1545 | 3351 | -1453 | 12146 | 1646 | 1159 | 1191 | 859 | 1361 | 3959 | 12784 | 357 | 23 |
| NEG | 58 | -4 | -1596 | 21193 | -1547 | 16615 | 1258 | 10103 | 1161 | 3517 | 1449 | 12028 | 26975 | 363 | 52 |
| + | 59 | 123 | -1337 | 3298 | -1375 | 10052 | 1315 | 636 | 1349 | 865 | 1580 | 4346 | 10190 | 558 | -71 |
| NEG | 60 | -13 | -1451 | 18003 | -1185 | 8505 | 1591 | 8500 | 1550 | 3338 | 1212 | 7833 | 20392 | 471 | 140 |
| NEG | 61 | 279 | -2906 | 5274 | -2948 | 4098 | 1100 | 592 | 1335 | 1356 | 1292 | 1826 | 9222 | 429 | 159 |
| NEG | 62 | 215 | -3052 | 19537 | -3092 | 11803 | 1487 | 7647 | 1524 | 3250 | 902 | 4874 | 15940 | 1263 | 422 |
| NEG | 63 | -68 | -2820 | 7514 | -2866 | 5668 | 2126 | 4590 | 2470 | 1868 | 1188 | 3032 | 9546 | 949 | 220 |
| + | 64 | 157 | -2904 | 14972 | -2926 | 23291 | 1518 | 11144 | 1757 | 5401 | 1117 | 11756 | 29368 | 2146 | -67 |
| NEG | 65 | 54 | -1218 | 2857 | -1184 | 448 | 1168 | 174 | 1197 | 406 | 1091 | 3082 | 9216 | 458 | 8 |
| NEG | 66 | -16 | -1285 | 3554 | -1298 | 829 | 931 | 1802 | 835 | 1395 | 1134 | 5479 | 12094 | 516 | 327 |
| NEG | 67 | -105 | -1581 | 3410 | -1600 | 8279 | 1723 | 897 | 1592 | 750 | 1463 | 3181 | 9593 | 639 | 365 |
| NEG | 68 | -39 | -1137 | 2967 | -461 | 760 | 1467 | 1125 | 1587 | 1507 | 1319 | 1325 | 3297 | 709 | 657 |
| NEG | 69 | 892 | -1735 | 4661 | -1721 | 3944 | 2460 | 1529 | 2356 | 2076 | 1941 | 2461 | 11216 | 1083 | -20 |
| NEG | 70 | -172 | -1878 | 5274 | -1893 | 4091 | 2309 | 2572 | 2110 | 2314 | 1801 | 3204 | 6008 | 1748 | 943 |
| NEG | 71 | -192 | -2011 | 4205 | -2041 | 12119 | 1790 | 1757 | 2222 | 2987 | 1073 | 4453 | 11224 | 1461 | 648 |
| NEG | 72 | 87 | -2408 | 3670 | -2521 | 6645 | 2042 | 2569 | 975 | 2255 | 1762 | 3967 | 10082 | 638 | 51 |
| NEG | 73 | 319 | -1746 | 2435 | -1751 | 1437 | 812 | 2047 | 1029 | 4517 | 537 | 2657 | 7523 | 74 | 53 |
| NEG | 74 | 167 | -1339 | 3599 | -1316 | 7396 | 777 | 1262 | 1424 | 1638 | 961 | 3325 | 10597 | 160 | 23 |
| NEG | 75 | 397 | -1919 | 2771 | -1942 | 1807 | 1660 | 400 | 1343 | 537 | 1282 | 2824 | 9477 | -39 | 84 |
| + | 76 | -65 | -1086 | 3632 | -1071 | 7432 | 1319 | 546 | 1592 | 632 | 1062 | 3287 | 9538 | 997 | 643 |
| NEG | 77 | 316 | -3781 | 4935 | -3797 | 3671 | 2555 | 1382 | 2699 | 1995 | 2184 | 2140 | 9579 | 714 | 818 |
| NEG | 78 | 84 | -2608 | 5274 | -2713 | 2848 | 388 | 1823 | 772 | 3108 | 963 | 2804 | 11688 | 647 | 279 |
| NEG | 79 | 1001 | -2924 | 5373 | -3082 | 4091 | 1963 | 2572 | 2032 | 2917 | 1213 | 2297 | 12577 | 911 | -87 |
| + | 80 | -98 | -2394 | 6070 | -2403 | 2303 | 1790 | 2039 | 1422 | 2987 | 1073 | 2066 | 6489 | 1212 | 354 |
| NEG | 81 | 545 | -1241 | 2761 | -3089 | 3315 | 1918 | 665 | 2058 | 1220 | 1146 | 11442 | 25290 | 528 | -29 |
| NEG | 82 | 19 | -1278 | 24720 | -2324 | 17022 | 1472 | 11744 | 1459 | 4644 | 1219 | 4609 | 12546 | 455 | 208 |
| NEG | 83 | -62 | -1242 | 3589 | -1241 | 2778 | 1612 | 275 | 1188 | 578 | 1246 | 15913 | 30687 | 470 | 62 |
| NEG | 84 | -20 | -1119 | 29074 | -1348 | 120212 | 2033 | 14068 | 2166 | 5615 | 2468 | 2737 | 11813 | 726 | 420 |
| + | 85 | 560 | -2495 | 4985 | -1262 | 5181 | 1569 | 460 | 1786 | 1228 | 1605 | 17519 | 35422 | 75 | 524 |
| NEG | 86 | 81 | -3062 | 36659 | -1131 | 28652 | 1583 | 26129 | 2239 | 8269 | 1398 | 1725 | 11119 | 1286 | 138 |
| + | 87 | -326 | -2297 | 5006 | -2403 | 3827 | 1265 | 66 | 1616 | 759 | 1117 | 19936 | 36119 | 960 | 367 |
| NEG | 88 | 64 | -2818 | 33766 | -3089 | 27195 | 1945 | 22834 | 1847 | 11494 | 1412 | 3106 | 15116 | 2282 | -15 |
| NEG | 89 | 355 | -1388 | 5515 | -2627 | 3917 | 1707 | 907 | 1556 | 2269 | 1284 | 2622 | 11517 | 500 | -51 |
| NEG | 90 | -54 | -1246 | 5759 | -1362 | 649 | 1433 | 402 | 1298 | 879 | 1282 | 3350 | 11644 | 385 | 492 |
| NEG | 91 | 21 | -934 | 3419 | -1287 | 4018 | 1343 | 1634 | 1297 | 2191 | 991 | 2604 | 6778 | 554 | 27 |
| NEG | 92 | 195 | -1361 | 4460 | -1260 | 4451 | 706 | 842 | 909 | 1186 | 1381 | 3600 | 8615 | 493 | 154 |

TABLE 51-continued

Representative data set for Checkerboard pattern# 2

| Sample | Well # | InfA.7.iniv-pubRev | No Print | RNAse.P.Probe-pub1.1 | No Print | SARS.COV2-N3-RE1.1 | 614G-SE-S1-RE1.4 | SARS.COV2-N2-RE1.4 | 614D-SE-S1-RE1.4 | SARS.COV2-N2-RE1.3 | 614U-SE-S1-RE1.1 | SARS.COV2-N1-RE1.1 | SARS.COV2-N1-pub | 62-Negcont-B | InfB.8.univ-pub |
|---|---|---|---|---|---|---|---|---|---|---|---|---|---|---|---|
| NEG | 93 | −39 | −2069 | 3075 | −1989 | 12896 | 1105 | 1856 | 1832 | 4240 | 1700 | 4397 | 10498 | 788 | 623 |
| NEG | 94 | −189 | −2084 | 4572 | −2169 | 1273 | 1184 | 886 | 1290 | 1293 | 942 | 4445 | 12232 | 746 | 297 |
| NEG | 95 | −43 | −1962 | 2353 | −1971 | 6754 | 1755 | 1027 | 1807 | 1802 | 1490 | 2793 | 10460 | 1168 | 305 |
| NEG | 96 | 211 | −2411 | 3321 | −2449 | 633 | 1257 | 1940 | 1411 | 4380 | 1362 | 4077 | 11616 | 584 | 45 |

TABLE 52

Representative data set for Checkerboard pattern# 3

| Sample | Well # | InfA.7.univ-pubRev | No Print | RNAse.P.Probe-pub1.1 | No Print | SARS.COV2-N3-RE1.1 | 614G-SE-S1-RE1.4 | SARS.COV2-N2-RE1.4 | 614D-SE-S1-RE1.4 | SARS.COV2-N2-RE1.3 | 614U-SE-S1-RE1.1 | SARS.COV2-N1-RE1.1 | SARS.COV2-N1-pub | 62-Negcont-B | InfB.8.univ-pub |
|---|---|---|---|---|---|---|---|---|---|---|---|---|---|---|---|
| + | 1 | −145 | −1347 | 13513 | −1273 | 11552 | 1560 | 12396 | 2134 | 4859 | 1561 | 9479 | 22501 | 1008 | 309 |
| NEG | 2 | 2766 | −882 | 3165 | −852 | 3560 | 1628 | 751 | 1594 | 902 | 1235 | 2750 | 12791 | 157 | −12 |
| NEG | 3 | 9 | −1774 | 4377 | −1733 | 667 | 1913 | 548 | 2041 | 1175 | 1460 | 4903 | 12923 | 715 | 81 |
| + | 4 | 11 | −1288 | 18587 | −1368 | 6454 | 1372 | 9753 | 1613 | 4169 | 1613 | 9425 | 18071 | 311 | 113 |
| NEG | 5 | 41 | −2969 | 3941 | −2868 | 45 | 1835 | 632 | 1572 | 2223 | 1508 | 3099 | 13406 | 1425 | 85 |
| NEG | 6 | −6 | −2250 | 3571 | −2271 | 12648 | 1369 | 1189 | 1698 | 3266 | 1121 | 5306 | 15088 | 832 | 46 |
| NEG | 7 | −203 | −2909 | 3938 | −2789 | 846 | 2835 | 1939 | 2641 | 3441 | 2066 | 4737 | 14011 | 2974 | 625 |
| + | 8 | −96 | −2252 | 25352 | −2267 | 12305 | 1449 | 12305 | 1947 | 7464 | 1758 | 13782 | 25693 | 1596 | 546 |
| NEG | 9 | 16 | −1396 | 3938 | −2789 | 11733 | 1820 | 1681 | 1689 | 3315 | 1305 | 3511 | 12867 | 822 | 181 |
| NEG | 10 | 21 | −1003 | 25979 | −1049 | 14030 | 1823 | 12938 | 2368 | 4919 | 2312 | 10684 | 22896 | 731 | 71 |
| + | 11 | 16 | −1525 | 2710 | −1536 | 6160 | 1330 | 773 | 1540 | 1438 | 1269 | 2732 | 9330 | 843 | 215 |
| NEG | 12 | −35 | −1715 | 2541 | −1667 | 1076 | 1911 | 847 | 1831 | 1242 | 1748 | 3936 | 9460 | 1797 | 63 |
| NEG | 13 | 407 | −2261 | 3216 | −2258 | 1248 | 2013 | 1088 | 1817 | 2047 | 1260 | 5101 | 15333 | 634 | 51 |
| NEG | 14 | 25 | −2492 | 4125 | −2524 | 2217 | 1151 | 173 | 1701 | 1368 | 1414 | 3699 | 9857 | 1890 | 286 |
| + | 15 | 126 | −2361 | 38860 | −2304 | 32693 | 1758 | 34169 | 2216 | 13289 | 1722 | 28227 | 40198 | 647 | 85 |
| NEG | 16 | 938 | −2019 | 3917 | −2001 | 1111 | 1408 | −83 | 2009 | 2624 | 1924 | 3857 | 11013 | 2076 | 640 |
| NEG | 17 | 5 | −1278 | 3845 | −1308 | 1361 | 1195 | 337 | 1401 | 1437 | 1445 | 4135 | 11629 | 680 | 47 |
| NEG | 18 | 32 | −1393 | 3169 | −1409 | 2383 | 1167 | 1352 | 1315 | 2067 | 1240 | 4458 | 11356 | 463 | 153 |
| + | 19 | 32 | −1492 | 25184 | −1402 | 13261 | 1198 | 13348 | 1395 | 4601 | 1440 | 9350 | 23518 | 677 | 14 |
| NEG | 20 | −22 | −1314 | 3346 | −1336 | 1862 | 1341 | 989 | 1098 | 1944 | 1255 | 3932 | 10956 | 737 | 441 |
| NEG | 21 | −245 | −1707 | 2937 | −1700 | 1224 | 1820 | 2415 | 1639 | 3156 | 1780 | 2874 | 10312 | 1119 | 335 |
| + | 22 | −128 | −2271 | 25983 | −2171 | 16445 | 1741 | 18779 | 1628 | 7542 | 1925 | 11633 | 26389 | 1945 | 296 |
| NEG | 23 | 11 | −2297 | 4221 | −2277 | 2769 | 1321 | 142 | 1212 | 1656 | 1109 | 3992 | 9252 | 944 | 747 |
| NEG | 24 | 80 | −2388 | 4253 | −2353 | 3295 | 1292 | 87 | 797 | 1726 | 1237 | 4851 | 12835 | 1302 | 603 |
| NEG | 25 | −15 | −1961 | 3215 | −1960 | 248 | 761 | 1357 | 1127 | 4518 | 669 | 4749 | 11845 | 95 | 489 |
| NEG | 26 | 167 | −1332 | 3245 | −1480 | 705 | 1375 | 194 | 1535 | 270 | 1132 | 1854 | 9174 | 56 | −6 |
| NEG | 27 | 45 | −1738 | 3201 | −1716 | 2231 | 1240 | 493 | 1414 | 2531 | 1320 | 4036 | 15147 | 250 | 10 |
| NEG | 28 | −9 | −1339 | 13102 | −1379 | 5357 | 1416 | 5263 | 1515 | 2952 | 1349 | 5422 | 14555 | 420 | 205 |
| + | 29 | −7 | −3055 | 5616 | −3061 | 8413 | 1820 | 1801 | 2010 | 3168 | 1808 | 3138 | 11740 | 2868 | 782 |
| NEG | 30 | 44 | −2729 | 4512 | −2673 | 4608 | 2409 | 200 | 1678 | 1982 | 1174 | 4201 | 11540 | 499 | 39 |
| + | 31 | 172 | −3557 | 4239 | −3131 | 3112 | 1632 | −5 | 2259 | 1827 | 1529 | 3834 | 11775 | 2611 | 250 |
| NEG | 32 | 28 | −2707 | 31840 | −2635 | 13702 | 2352 | 19138 | 1450 | 8440 | 898 | 16093 | 32257 | 604 | 155 |
| NEG | 33 | −38 | −1223 | 3240 | −1268 | 4222 | 1874 | 455 | 1182 | 432 | 987 | 2577 | 7125 | 420 | 528 |
| NEG | 34 | 33 | −1412 | 3563 | −1490 | 1066 | 1057 | 96 | 1067 | 373 | 907 | 3877 | 9215 | 203 | 129 |
| NEG | 35 | −26 | −1441 | 3076 | −1485 | 2518 | 1108 | 503 | 1432 | 935 | 1112 | 2903 | 10539 | 666 | 86 |
| NEG | 36 | −26 | −1489 | 2841 | −1474 | 2981 | 1598 | 817 | 1392 | 1396 | 1591 | 2977 | 9879 | 555 | 310 |
| + | 37 | −42 | −2611 | 14747 | −2496 | 18927 | 1452 | 7935 | 1371 | 3939 | 1343 | 8192 | 18537 | 274 | 155 |
| NEG | 38 | 10 | −2615 | 4039 | −2734 | 1142 | 1470 | 73 | 1218 | 1810 | 984 | 2956 | 8002 | 1112 | 160 |
| + | 39 | 84 | −2543 | 2745 | −2541 | 272 | 783 | 227 | 2267 | 2080 | 1103 | 2592 | 14261 | 665 | 434 |
| NEG | 40 | −32 | −2639 | 3798 | −2675 | 718 | 1939 | 873 | 2099 | 4887 | 1305 | 3930 | 11612 | 1690 | 533 |
| NEG | 41 | 10 | −1177 | 2797 | −1151 | 2445 | 1332 | 754 | 1224 | 904 | 1196 | 2186 | 6180 | 544 | −54 |
| NEG | 42 | 42 | −1096 | 2637 | −1143 | 751 | 1385 | 560 | 1192 | 767 | 1307 | 2987 | 7288 | 633 | 436 |
| + | 43 | 747 | −1520 | 19273 | −1469 | 9631 | 1544 | 10717 | 1549 | 4542 | 1739 | 8797 | 17595 | 959 | 56 |
| NEG | 44 | −117 | −1717 | 2698 | −1623 | 1254 | 1044 | 367 | 1277 | 1017 | 1086 | 1519 | 5525 | 628 | 416 |
| NEG | 45 | 495 | −1727 | 2935 | −1766 | 2195 | 1999 | 1773 | 1752 | 3412 | 1607 | 3647 | 8520 | 806 | 169 |

TABLE 52-continued

Representative data set for Checkerboard pattern# 3

| Sample | Well # | InfA.7.univ-pubRev | No Print | RNAse.P.Probe-pub1.1 | No Print | SARS.COV2-N3-RE1.1 | 614G-SE-S1-RE1.4 | SARS.COV2-N2-RE1.4 | 614D-SE-S1-RE1.4 | SARS.COV2-N2-RE1.3 | 614U-SE-S1-RE1.1 | SARS.COV2-N1-RE1.1 | SARS.COV2-N1-pub | 62-Negcont-B | InfB.8.univ-pub |
|---|---|---|---|---|---|---|---|---|---|---|---|---|---|---|---|
| + | 46 | -348 | -1791 | 24816 | -1770 | 14867 | 2509 | 15026 | 2130 | 5967 | 2176 | 9030 | 19347 | 1584 | 614 |
| NEG | 47 | -113 | -2044 | 4076 | -1789 | 3977 | 3511 | 2553 | 3199 | 3015 | 2668 | 3722 | 8044 | 2173 | 913 |
| NEG | 48 | 65 | -2745 | 2638 | -2994 | 8603 | 818 | 689 | 840 | 4999 | 459 | 3683 | 8515 | 688 | 72 |
| NEG | 49 | 9 | -1374 | 2610 | -1434 | 3297 | 747 | 371 | 1250 | 1475 | 1154 | 2079 | 6407 | 543 | 198 |
| + | 50 | 87 | -1488 | 21434 | -1588 | 11066 | 1175 | 10325 | 565 | 5222 | 1412 | 12167 | 26093 | 85 | 56 |
| NEG | 51 | 133 | -1734 | 2250 | -1809 | 1037 | 1034 | 22 | 1119 | 546 | 853 | 2677 | 7378 | 345 | 28 |
| NEG | 52 | -124 | -1525 | 2035 | -1531 | 1662 | 1560 | 652 | 1666 | 3295 | 1304 | 2536 | 6944 | 488 | 238 |
| NEG | 53 | -65 | -3628 | 2709 | -3661 | 2327 | 902 | 730 | 1034 | 1161 | 798 | 1696 | 6693 | 173 | 185 |
| NEG | 54 | -170 | -2115 | 3168 | -2085 | 1475 | 2465 | 2174 | 3223 | 2197 | 2875 | 3130 | 9902 | 1847 | 1018 |
| NEG | 55 | -55 | -2428 | 18535 | -2501 | 5147 | 2273 | 7791 | 2450 | 4658 | 1888 | 5871 | 13814 | 1827 | 973 |
| + | 56 | 834 | -2289 | 2946 | -2293 | 2633 | 2110 | -454 | 2466 | 1452 | 1207 | 4380 | 11465 | 1176 | 785 |
| NEG | 57 | 165 | -1263 | 12569 | -1301 | 13662 | 1140 | 9272 | 1002 | 4419 | 1257 | 9722 | 18937 | 376 | -61 |
| NEG | 58 | 205 | -1246 | 2901 | -1251 | 2153 | 1191 | 505 | 1076 | 3265 | 984 | 1804 | 6497 | 394 | 45 |
| NEG | 59 | 10 | -1354 | 3013 | -1366 | 1729 | 1192 | 3107 | 1498 | 1368 | 1073 | 2443 | 5677 | 325 | 125 |
| + | 60 | -101 | -1068 | 8987 | -1165 | 4430 | 1932 | 6573 | 1612 | 3908 | 1895 | 7573 | 14010 | 851 | 885 |
| NEG | 61 | -126 | -1901 | 2632 | -1946 | 517 | 1323 | 159 | 1475 | 1657 | 1310 | 2365 | 7134 | 477 | 333 |
| NEG | 62 | 664 | -2451 | 2219 | -2472 | 1783 | 1614 | 334 | 1549 | 3134 | 1730 | 3060 | 8111 | 1173 | 386 |
| NEG | 63 | -19 | -2174 | 3240 | -2137 | 700 | 2672 | 543 | 1789 | 2708 | 1550 | 3599 | 8336 | 824 | 1155 |
| + | 64 | 14 | -2512 | 16859 | -2438 | 4932 | 2028 | 10263 | 1962 | 6662 | 998 | 15475 | 29930 | 1799 | 323 |
| NEG | 65 | 50 | -1545 | 3136 | -1126 | 1829 | 1120 | 376 | 1209 | 1077 | 1192 | 3484 | 7877 | 414 | 40 |
| NEG | 66 | -8 | -1238 | 2665 | -1210 | 1673 | 1161 | 404 | 929 | 642 | 1118 | 2097 | 5971 | 247 | 289 |
| + | 67 | 321 | -1214 | 14727 | -1217 | 5624 | 1390 | 7049 | 1639 | 3302 | 1567 | 8403 | 18913 | 658 | -31 |
| NEG | 68 | 55 | -1161 | 2521 | -1194 | 2944 | 1630 | 569 | 1227 | 678 | 1111 | 2998 | 6709 | 234 | 156 |
| NEG | 69 | 374 | -1941 | 2697 | -1992 | 1095 | 1366 | -67 | 1472 | 1244 | 1185 | 2579 | 13838 | 576 | 82 |
| NEG | 70 | 37 | -2400 | 3026 | -2448 | 1389 | 1287 | 867 | 852 | 3758 | 1430 | 2911 | 9277 | 561 | 291 |
| NEG | 71 | -138 | -2553 | 20514 | -2593 | 6508 | 1335 | 12211 | 1052 | 5686 | 883 | 15055 | 31208 | 397 | 161 |
| + | 72 | 216 | -1808 | 31837 | -1772 | 15165 | 2148 | 15265 | 2648 | 5991 | 3746 | 14104 | 28376 | 1740 | 710 |
| NEG | 73 | -61 | -1767 | 2893 | -1892 | 2702 | 2355 | 413 | 2411 | 2861 | 1465 | 3160 | 7311 | 1575 | 5 |
| NEG | 74 | 190 | -1849 | 2025 | -1891 | 830 | 1391 | 979 | 1395 | 1883 | 1285 | 3178 | 6344 | 889 | 691 |
| NEG | 75 | 153 | -1320 | 3112 | -1397 | 3628 | 1132 | 517 | 1219 | 675 | 990 | 2943 | 7512 | 330 | 528 |
| + | 76 | 534 | -1736 | 3660 | -1418 | 4359 | 1407 | 1674 | 1466 | 1386 | 1173 | 2486 | 8965 | 328 | 94 |
| NEG | 77 | 22 | -1268 | 3033 | -1263 | 1347 | 1322 | 189 | 1301 | 673 | 1096 | 2929 | 6760 | 199 | 139 |
| NEG | 78 | -41 | -2503 | 2987 | -2625 | 1892 | 1632 | 472 | 1711 | 2117 | 1449 | 2199 | 5421 | 202 | 553 |
| NEG | 79 | -224 | -1808 | 31837 | -1772 | 15165 | 2148 | 15265 | 2648 | 5991 | 3746 | 14104 | 28376 | 1441 | 270 |
| + | 80 | -111 | -1767 | 2893 | -1892 | 2702 | 2355 | 413 | 2411 | 2861 | 1465 | 3160 | 5170 | 1575 | 545 |
| NEG | 81 | -83 | -1849 | 2025 | -1891 | 830 | 1391 | 979 | 1395 | 1883 | 1285 | 3178 | 6344 | 970 | 691 |
| NEG | 82 | 107 | -1320 | 3112 | -1397 | 3628 | 1132 | 517 | 1219 | 675 | 990 | 2943 | 7512 | 889 | 528 |
| NEG | 83 | 617 | -1386 | 3660 | -1418 | 4359 | 1407 | 1674 | 1466 | 1386 | 1173 | 2486 | 8965 | 485 | 94 |
| NEG | 84 | -184 | -1309 | 3033 | -1263 | 1347 | 1322 | 189 | 1301 | 673 | 1096 | 2929 | 6760 | 361 | 139 |
| + | 85 | 1034 | -1158 | 2819 | -1157 | 1921 | 1103 | 953 | 1274 | 2668 | 1508 | 2107 | 5202 | 427 | 15 |
| NEG | 86 | -61 | -2012 | 27788 | -1967 | 17653 | 1170 | 17719 | 1586 | 7198 | 2980 | 14960 | 29760 | 561 | 219 |
| NEG | 87 | 1218 | -2373 | 4368 | -2280 | 510 | 1083 | 2564 | 1558 | 5268 | 2567 | 2567 | 8793 | 157 | 66 |
| NEG | 88 | 302 | -1949 | 2976 | -1868 | 834 | 3039 | 183 | 3533 | 2648 | 2412 | 4472 | 8238 | 1312 | 8 |
| + | 89 | -383 | -1983 | 36246 | -1988 | 14961 | 2030 | 19467 | 2355 | 10461 | 2474 | 23545 | 36200 | 932 | 694 |
| NEG | 30 | 14 | -1011 | 2460 | -778 | 3793 | 1095 | 342 | 1089 | 1237 | 1477 | 2768 | 7072 | 2543 | 626 |
| NEG | 91 | 164 | -782 | 3460 | -813 | 2387 | 1568 | 714 | 1138 | 1251 | 1010 | 2520 | 5202 | 490 | 67 |
| NEG | 92 | 113 | -1221 | 2598 | -1134 | 2683 | 1365 | 982 | 1267 | 3620 | 1479 | 3474 | 7996 | 426 | -84 |
| + | | 72 | -858 | 18886 | -869 | 8671 | 1180 | 9678 | 885 | 5339 | 1339 | 11890 | 26105 | 486 | 17 |
| | | | | | | | | | | | | | | 422 | 25 |

TABLE 52-continued

Representative data set for Checkerboard pattern# 3

| Sample | Well # | InfA.7.univ-pubRev | No Print | RNAse.P.Probe-pub1.1 | No Print | SARS.COV2-N3-RE1.1 | 614G-SE-S1-RE1.4 | SARS.COV2-N2-RE1.4 | 614D-SE-S1-RE1.4 | SARS.COV2-N2-RE1.3 | 614U-SE-S1-RE1.1 | SARS.COV2-N1-RE1.1 | SARS.COV2-N1-pub | 62-Negcont-B | InfB.8.univ-pub |
|---|---|---|---|---|---|---|---|---|---|---|---|---|---|---|---|
| NEG | 93 | −91 | −1607 | 2637 | −1504 | 542 | 1063 | 1226 | 1584 | 3335 | 1207 | 3071 | 7377 | 929 | 179 |
| NEG | 94 | 27 | −1525 | 3170 | −1571 | 1585 | 837 | 244 | 1388 | 1048 | 1085 | 2830 | 6893 | 671 | 466 |
| + | 95 | 13 | −1313 | 14643 | −1451 | 3177 | 1266 | 6639 | 1455 | 5249 | 1489 | 5288 | 8768 | 1138 | 168 |
| NEG | 96 | 79 | −1573 | 3658 | −1590 | 2961 | 1076 | 306 | 1467 | 1412 | 1374 | 3785 | 6930 | 1911 | 156 |

TABLE 53

Summary of checkerboard analysis for well-to-well cross contamination

| Checkerboard | # Positive Samples Added | # Negative Samples Added | # Positive Samples Detected | # Negative Samples Detected | Overall Call (POS/NEG) |
|---|---|---|---|---|---|
| 1.1 | 24 | 72 | 24 | 72 | 100%/100% |
| 1.2 | 24 | 72 | 24 | 72 | 100%/100% |
| 2.1 | 16 | 16 | 16 | 16 | 100%/100% |
| 2.2 | 16 | 16 | 16 | 16 | 100%/100% |
| 3.1 | 25 | 25 | 25 | 25 | 100%/100% |
| 3.2 | 25 | 25 | 25 | 25 | 100%/100% |
| 4.1 | 18 | 18 | 18 | 18 | 100%/100% |
| 4.2 | 18 | 18 | 18 | 18 | 100%/100% |

Increase Efficiency of Asymmetric One-Step RT-PCR Obtained at 39 PCR Cycles/Reaction To reduce time needed to perform the assay, temperature and time parameters in the Asymmetric One-Step RT-PCR were varied. The general change in the method steps were as follows:

1. Hold the total number of PCR cycles to <40, to minimize the perceived risk of false positives, which might occur during >40 cycles of endpoint PCR.
2. Test the increase of Taq Polymerase 2× and 3× in the current Mini-RV Asymmetric One-Step RT-PCR master mix, to reduce product mediated polymerase inhibition at high cycle number.
3. Test the effect of a 30% reduction of heat denaturation time in the PCR cycle (30 sec→20 sec) to reduce the thermal footprint accumulated by Taq over <40 cycles.
4. Determine using the present Mini-RV Asymmetric One-Step RT-PCR Reaction, the effect of a 2× and 3× increase in [Taq] on analytical LoD and clinical sensitivity, as assessed by hybridization in the 96-Well format
5. Determine using the present Mini-RV Asymmetric One-Step RT-PCR Reaction, the effect of a reduction of heat denaturation time from 30 sec to 20 sec on analytical LoD and clinical sensitivity, as assessed by hybridization in the 96-Well format.

Figure 23A:
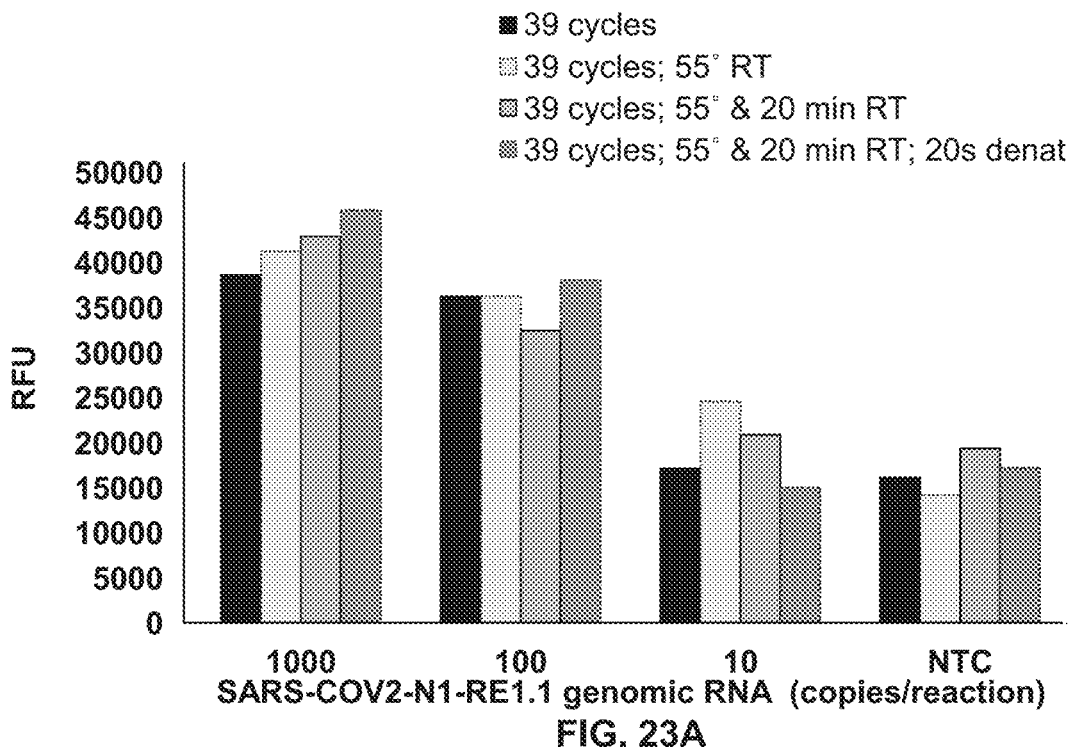
FIGS. 23A-23C show the results of altering RT-PCR parameters on hybridization analysis.
Figure 23B:
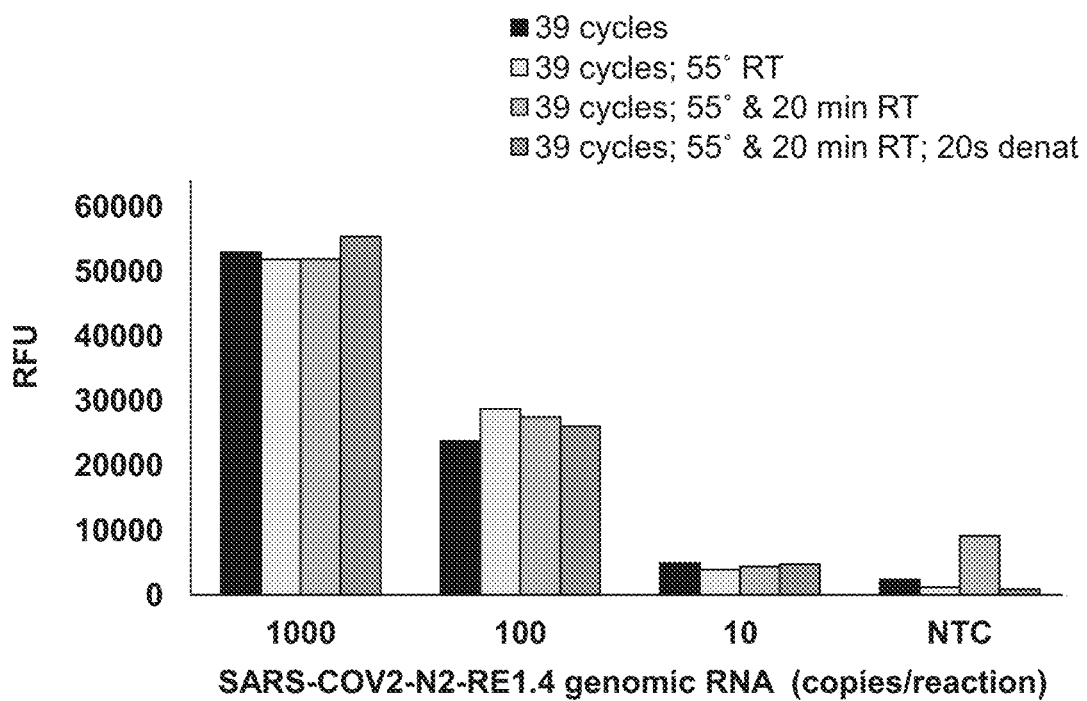
Figure 23C:
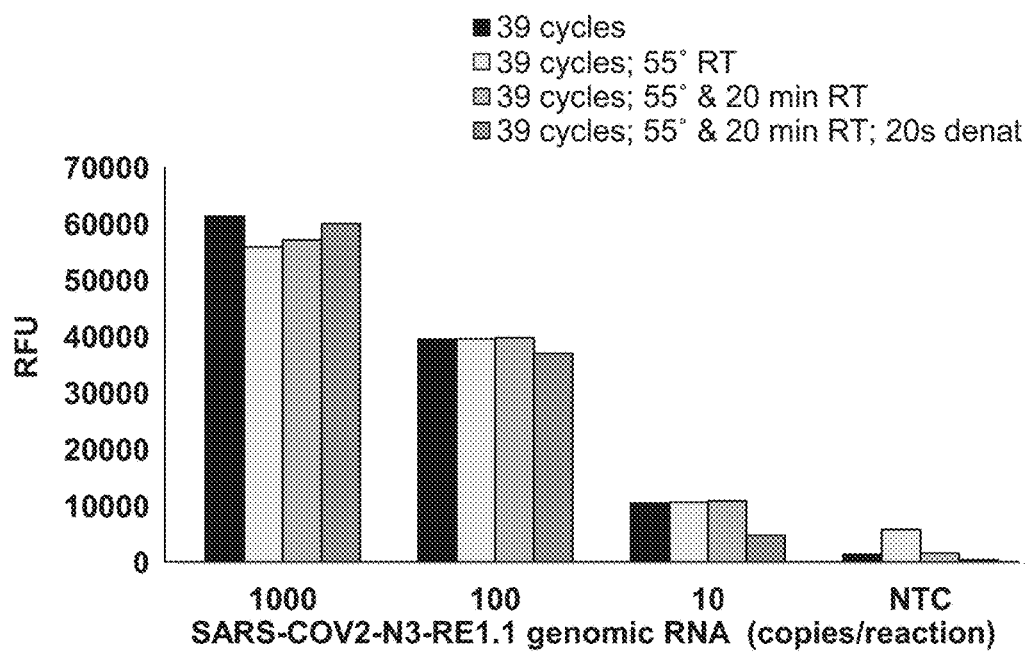

A summary of 4 different RT-PCR reaction protocols is shown in Table 54. Results from these studies summarized in FIGS. 23A-23C show that the Asymmetric One-Step PCR reaction can accommodate an increase in temperature from 37° C. to 55° C. in the reverse transcription phase of the reaction, without significantly altering efficiency of the Asymmetric One-Step PCR, as assessed by hybridization analysis in the 96 well Mini-RV format. It was also established that at 55° C. reverse transcription time could be reduced from 45 min to 20 min and additionally, heat denaturation time (protocol D, step 3 Table 54) could be reduced from 30 sec to 20 sec with no loss of RT-PCR efficiency. Importantly, by deploying protocol D (Table 54) the total duration for completing of the Asymmetric One-Step RT-PCR is reduced to 2 hours (Reverse transcription time at 30 min+PCR time at 1.5 hours).

This modification to the protocol also has additional advantages. Increasing the reverse transcription temperature to 55° C. makes the protocol compatible with a concurrent Uracil-DNA Glycosylase enzyme (UNG, Cod UNG from ArticZymes Technologies) reaction (see below). Further, reducing the time for heat denaturation from 30 sec to 20 sec reduces the Taq Thermal footprint during the RT-PCR reaction.

TABLE 54

RT-PCR reaction protocols used to test potential reduction in assay time

| | Protocol A AccessQuick RT-PCR | | | | Protocol B AccessQuick RT-PCR | | |
|---|---|---|---|---|---|---|---|
| Steps | Temperature | Time | Cycles | Steps | Temperature | Time | Cycles |
| 1 | 45° C. | 45 min | 1 | 1 | 55° C. | 45 min | 1 |
| 2 | 94° C. | 2 min | 1 | 2 | 94° C. | 2 min | 1 |
| 3 | 94° C. | 30 sec | 39 | 3 | 94° C. | 30 sec | 39 |
| 4 | 55° C. | 30 sec | | 4 | 55° C. | 30 sec | |
| 5 | 68° C. | 30 sec | | 5 | 68° C. | 30 sec | |
| 6 | 68° C. | 7 min | 1 | 6 | 68° C. | 7 min | 1 |
| 7 | 4° C. | ∞ | | 7 | 4° C. | ∞ | |

| | Protocol C AccessQuick RT-PCR | | | | Protocol D AccessQuick RT-PCR | | |
|---|---|---|---|---|---|---|---|
| Steps | Temperature | Time | Cycles | Steps | Temperature | Time | Cycles |
| 1 | 55° C. | 20 min | 1 | 1 | 55° C. | 20 min | 1 |
| 2 | 94° C. | 2 min | 1 | 2 | 94° C. | 2 min | 1 |
| 3 | 94° C. | 30 sec | 39 | 3 | 94° C. | 20 sec | 39 |
| 4 | 55° C. | 30 sec | | 4 | 55° C. | 30 sec | |
| 5 | 68° C. | 30 sec | | 5 | 68° C. | 30 sec | |
| 6 | 68° C. | 7 min | 1 | 6 | 68° C. | 7 min | 1 |
| 7 | 4° C. | ∞ | | 7 | 4° C. | ∞ | |

Mitigate Potential Assay Contamination Due to Low Copy Number RNA Sample Contamination by Ambient High Copy Number Amplicon Products from Previous Assays Amplicon contamination has the undesired consequence of generating false positive results in the assay. This problem may be offset by the introduction of Uracil-DNA Glycosylase into the reverse transcription phase of the Asymmetric One-Step RT-PCR reaction. One of the requirements for using UNG is a reaction temperature of 55° C. As discussed above increasing the temperature from 37° C. to 55° C. during reverse transcription does not alter efficiency of the Asymmetric One-Step PCR (Table 54, FIGS. 23A-23C) thereby supporting a modified protocol where UNG and dUTP are introduced into the master mix. Cod UNG from ArticZymes Technologies is used for this purpose. The utility of UNG is established by testing the effect of 50% substitution of dTTP with dUTP and verifying no not significant alteration in analytical LoD occurs in the present Mini-RV workflow (Zymo)→Asymmetric One-Step RT-PCR→Hybridization/Wash→Sensovation (96-well imaging)

Validation of Higher Temperature Reverse Transcription for UNG Deployment

Further validation for employing a higher temperature for the reverse transcription was obtained using multiple clinical isolates (NP-VTM from TriCore) and contrived samples (in nasal fluid) titrated with gamma irradiated CoV-2 virion (BEI, 5,000 virion/ml to 500/ml).

Protocol:
  Sample 1—Eight (8) Positive clinical samples.
    NP/VTM (TriCore)→Ceres→RT-PCR→Hybridization (96-well)
  Sample 2—Eight (8) Negative clinical samples.
    NP/VTM (TriCore)→Ceres→RT-PCR→Hybridization (96-well)
  Sample 3—Four (4) gamma irradiated virus (BEI). 5000, 1000, 500, 0 copies/mL
    VTM+10% Nasal Fluid (Lee Bio)→Ceres→RT-PCR→Hybridization (96-well)

Three different RT-PCR conditions were tested with each of the above sample sets as shown in Table 55.

TABLE 55

RT-PCR conditions for testing UNG deployment

| Condition 1 Standard reverse transcription 45° C., 45 min AccessQuick RT-PCR parameters | | | | Condition 2 High temperature reverse transcription 55° C., 45 min AccessQuick RT-PCR parameters | | | | Condition 3 High temperature reverse transcription 55° C., 20 min AccessQuick RT-PCR parameters | | | |
|---|---|---|---|---|---|---|---|---|---|---|---|
| Steps | T (° C.) | Time | Cycles | Steps | T (° C.) | Time | Cycles | Steps | T (° C.) | Time | Cycles |
| 1 | 45 | 45 min | 1 | 1 | 45 | 45 min | 1 | 1 | 45 | 45 min | 1 |
| 2 | 94 | 2 min | 1 | 2 | 94 | 2 min | 1 | 2 | 94 | 2 min | 1 |
| 3 | 94 | 30 sec | 40 | 3 | 94 | 30 sec | 40 | 3 | 94 | 30 sec | |
| 4 | 55 | 30 sec | | 4 | 55 | 30 sec | | 4 | 55 | 30 sec | 40 |
| 5 | 68 | 30 sec | | 5 | 68 | 30 sec | | 5 | 68 | 30 sec | |
| 6 | 68 | 7 min | 1 | 6 | 68 | 7 min | 1 | 6 | 68 | 7 min | 1 |
| 7 | 4 | ∞ | | 7 | 4 | ∞ | | 7 | 4 | ∞ | |

The data shown in Tables 56 and 57 confirms no change in N1 and N2 signals for these samples. Interestingly, the combination of 55° C. and a reduced, 20 min reverse transcription incubation step was statistically identical to 45° C. and 45 min, confirming that that the combined RT-PCR reaction can be performed about 25 min faster than the standard protocol.

Fine Tuning of Hybridization/Wash in 96-Well Format Using a Vibratory Plate Shaker Using an on-board plate shaker permits fluid phase mixing and laminar flow over the array surface during ambient temperature hybridization and washing, which helps reduce by at least 30%, the number of hybridization/wash steps in 96-well format. Two experiments were performed to test this.

TABLE 56

Validation of higher temperature reverse transcription in TriCore samples

| SARS-COV2 probe | Sample | Cq | Condition 1 | | Condition 2 | | Condition 3 | | One-way ANOVA p-value |
|---|---|---|---|---|---|---|---|---|---|
| | | | Average RFU | Standard deviation | Average RFU | Standard deviation | Average RFU | Standard deviation | |
| N1 | TriCore Clinical Positive | 13.75-31.65 | 31475 | 20498 | 30956 | 19613 | 29372 | 20289 | 0.97 |
| | TriCore Clinical Positive | >35 | 2312 | 2027 | 1469 | 795 | 698 | 659 | 0.07 |
| N2 | TriCore Clinical Positive | 13.75-31.65 | 41015 | 21583 | 41172 | 20199 | 39517 | 22069 | 0.99 |
| | TriCore Clinical Positive | >35 | 1638 | 559 | 7333 | 14980 | 790 | 373 | 0.28 |

TABLE 57

Validation of higher temperature reverse transcription in γ-irradiated virion samples

| SARS-COV2 probe | Gamma-Irradiated virions copies/mL | Condition 1 | | Condition 2 | | Condition 3 | | One-way ANOVA p-value |
|---|---|---|---|---|---|---|---|---|
| | | Average RFU | Standard deviation | Average RFU | Standard deviation | Average RFU | Standard deviation | |
| N1 | 5000 | 15776 | 7935 | 15411 | 9934 | 16783 | 9466 | 0.97 |
| | 1000 | 5642 | 2357 | 2821 | 1215 | 4255 | 1341 | 0.12 |
| | 500 | 3193 | 1132 | 3507 | 1633 | 2012 | 1728 | 0.38 |
| | 0 | 2969 | 682 | 2466 | 1093 | 1043 | 444 | O.QI |
| N2 | 5000 | 29720 | 11369 | 26923 | 13706 | 29065 | 11935 | 0.95 |
| | 1000 | 7411 | 3740 | 3739 | 783 | 5349 | 1946 | 0.17 |
| | 500 | 3603 | 966 | 3461 | 2418 | 2713 | 2961 | 0.84 |
| | 0 | 1053 | 452 | 1483 | 474 | 594 | 596 | 0.1 |

Experiment 1: To test the effect of shaking on signals, 24 pooled positive samples were prepared (Boca) and tested under 3 separate hybridization conditions as follows:
X1—Plate remains static for 30 min hybridization incubation period.
X2—Plate is shaken at 1000 RPM for 30 min hybridization incubation period.
X3—Hybridization cocktail is mixed by pipetting up and down during hybridization period.

Results: Table 58 showed that condition X2 gave the highest average RFU across 8 wells on the appropriate probes, along with a lower standard deviation and lower background. These data reveal that shaking during hybridization improves signal strength when compared with the static hybridization method (X1) and the pipetting method (X3).

TABLE 58

Comparison of static, shaking and pipetting hybridization method

| | X1 Static Hybridization | | X2 Shake at 1000 RPM | | X3 Pipette to mix | |
|---|---|---|---|---|---|---|
| | Average across 8 wells | Std Dev | Average across 8 wells | Std Dev | Average across 8 wells | Std. Dev |
| SARS.COV2-N2-RE1.3 | 45967 | 2155 | 58539 | 2053 | 34560 | 1229 |
| SARS.COV2-N2-RE1.3 | 52055 | 3942 | 60242 | 337 | 36302 | 829 |
| SARS.COV2-N2-RE1.2 | 40439 | 1415 | 45335 | 4543 | 21923 | 2807 |
| SARS.COV2-N2-RE1.1 | 42262 | 3507 | 53268 | 6185 | 20897 | 7331 |
| RNAse. P. Probe-pub 1.2 | 61403 | 467 | 60418 | 357 | 59383 | 431 |
| RNAse. P. Probe-pub 1.1 | 61421 | 452 | 60426 | 364 | 58997 | 514 |
| SARS.COV2-N3-RE1.3 | 57433 | 5118 | 59976 | 581 | 44605 | 1535 |
| SARS.COV2-N1-RE1.2 | 33539 | 6896 | 46886 | 10031 | 27384 | 9464 |
| SARS.COV2-N3-RE1.2 | 55612 | 5070 | 60166 | 431 | 40722 | 6945 |
| SARS.COV2-N1-RE1.2 | 33665 | 5370 | 45564 | 7351 | 13312 | 11187 |
| SARS.COV2-N1-RE1.1 | 61432 | 424 | 60437 | 360 | 58662 | 1715 |
| SARS.COV2-N3-RE1.1 | 61293 | 423 | 60435 | 362 | 55161 | 3482 |
| SARS.COV2-N1-RE1.1 | 61277 | 382 | 60297 | 407 | 58487 | 1519 |
| 62-Negcont-B | 2266 | 818 | 4031 | 3155 | 2126 | 601 |
| SARS.COV2-N3-RE1.1 | 60725 | 1117 | 60428 | 361 | 55329 | 4479 |

Experiment 2: RNA extracted (Zymo kit) from contrived samples (gamma irradiated cell lysates+nasal fluid in RNA Shield™ reagent (Zymo research) was used as the first sample at 0.4-40 copies per reaction. SARS-COV2 RNA was used as a second sample at 1-100 copies per reaction. RT-PCR parameters described in Protocol C (Table 54) was used.

Figure 24A:
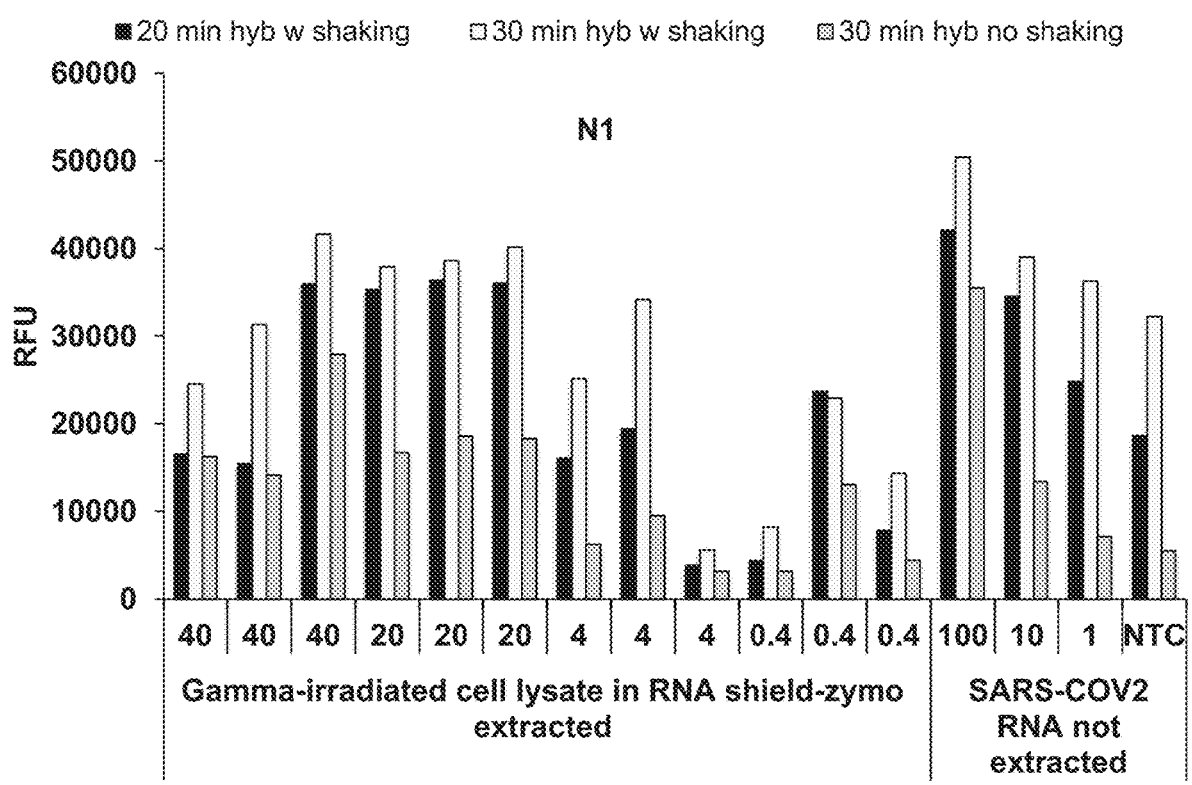
FIGS. 24A-24C compares the effect of hybridization conditions on the analysis.
Figure 24B:
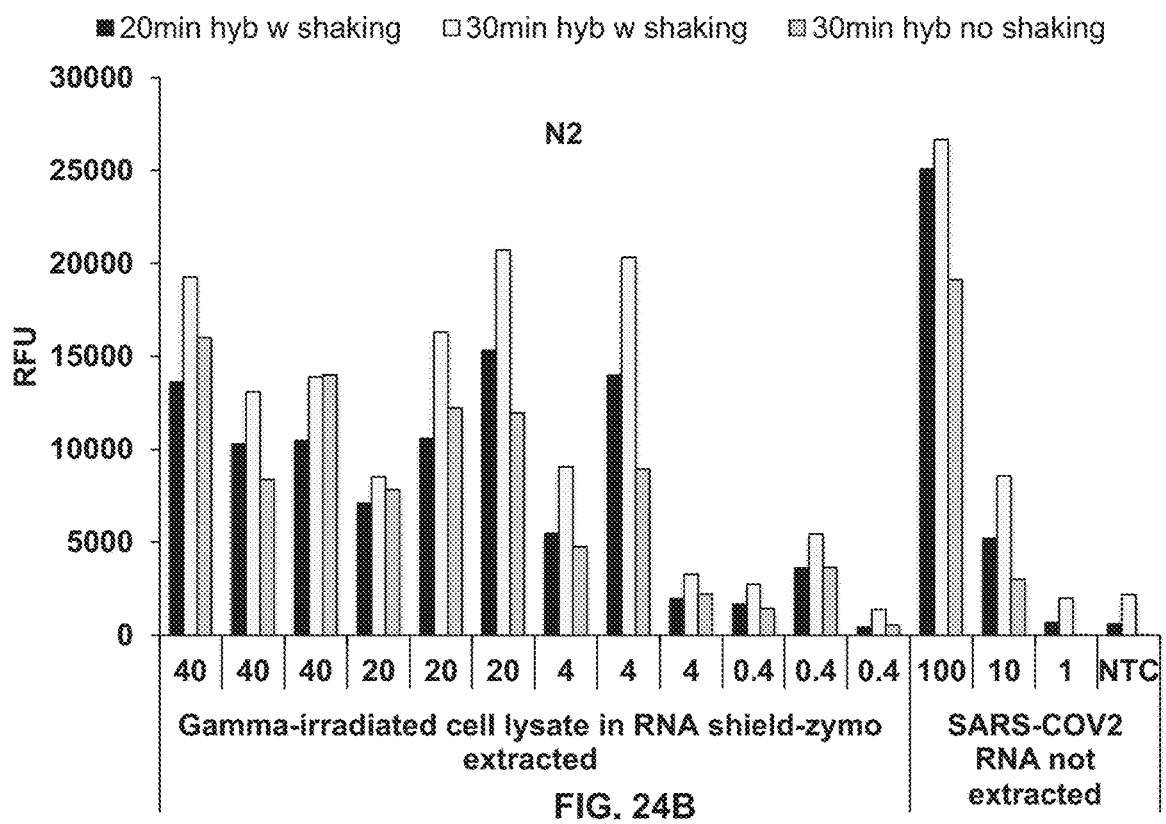
Figure 24C:
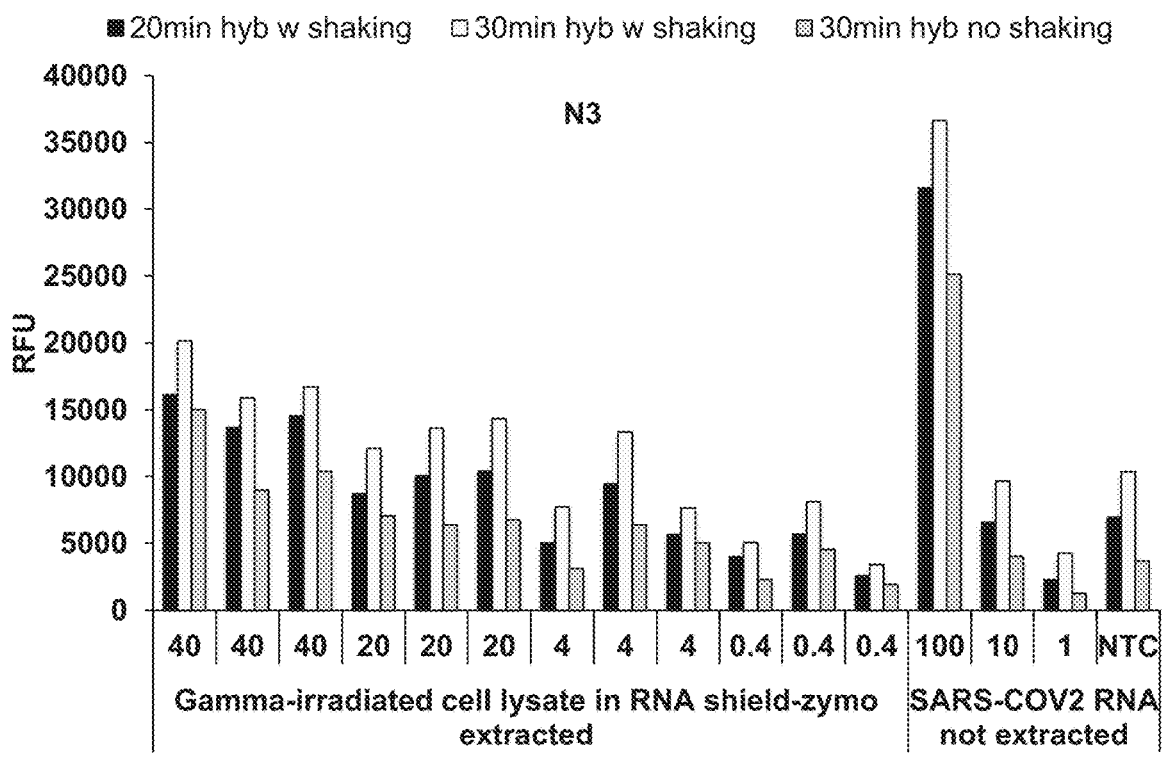

Results. The data in FIGS. 24A-24C clearly show that mixing during the 30 min hybridization increases hybridization signal strength about 2-fold among all probes tested.

Evaluate Simplified Alternatives to Standard Magnetic Bead CoV-2 Purification from NP/VTM and Mouthwash A CERES NANOTRAP (Ceres Nanosciences, Inc.) technology for RNA extraction was evaluated for reducing time and costs of raw sample processing over the Zymo Quick-DNA/RNA Viral technology.

Alternate methods for reducing assay time and costs during raw sample processing were tested including the CERES NANOTRAP (Ceres Nanosciences Inc.) and Chitosan Coated Magnetic Beads (Creative Diagnostics Inc). Specifically, compared to Zymo's Quick-DNA/RNA Viral method the CERES NANOTRAP method is 1.5 hours faster requiring $\frac{1}{3}^{rd}$ of total manipulations, consumes 75% less consumables and may be automated for 96-well format.

Contrived NP/VTM Samples

Figure 25:
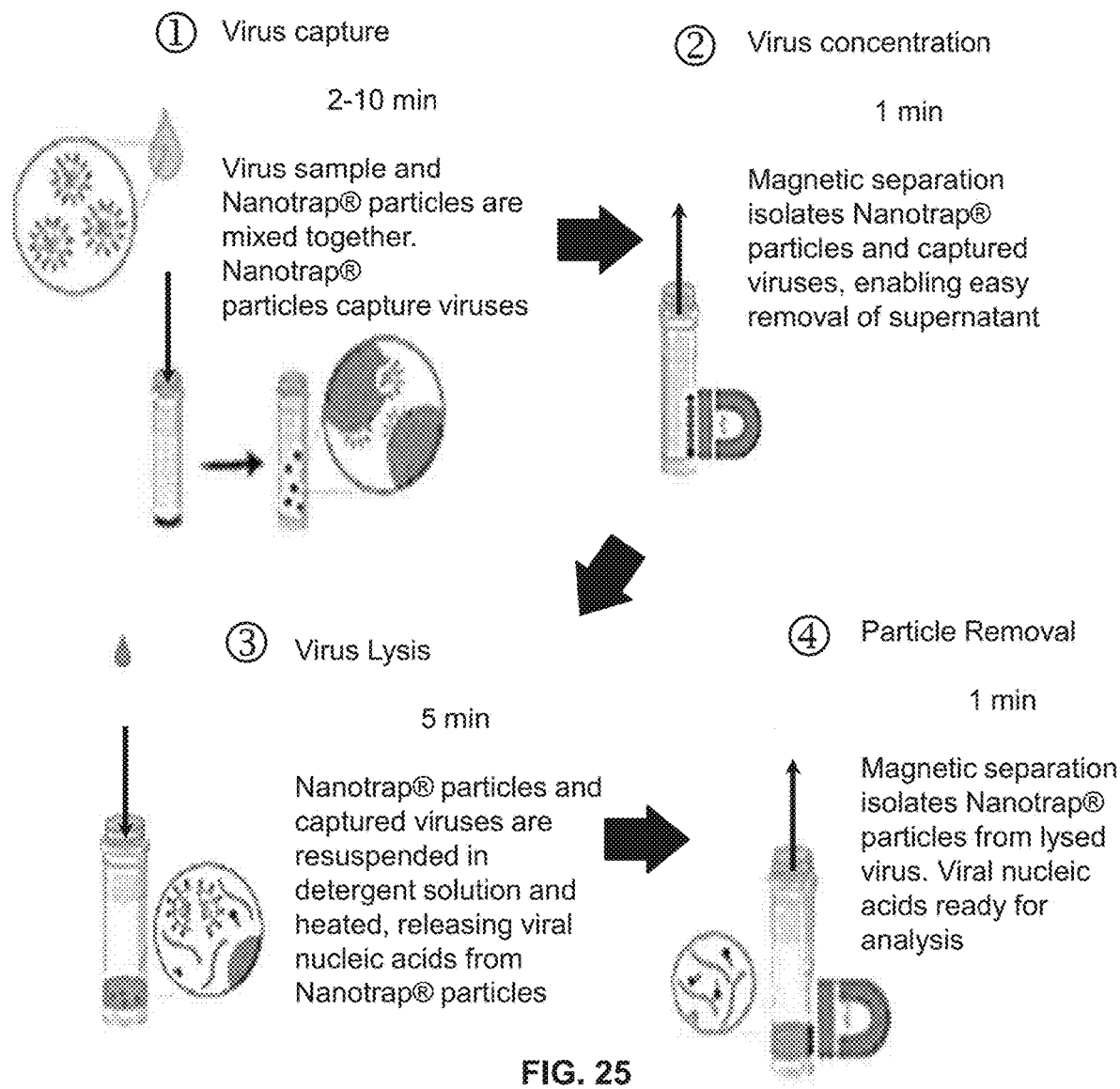
FIG. 25 shows an illustration of the CERES NANOTRAP method.
Figure 26:
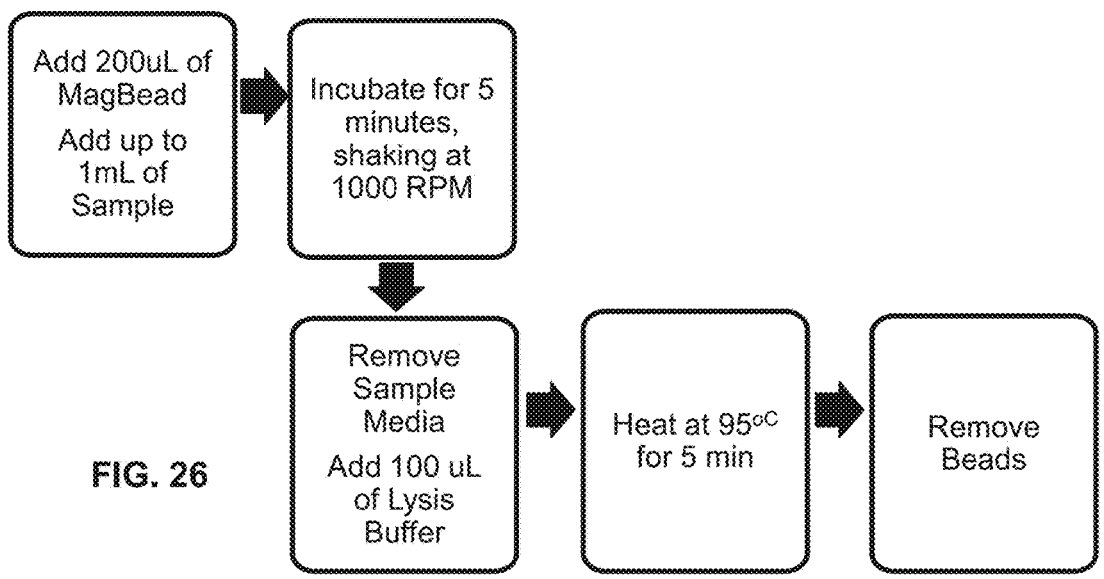
FIG. 26 shows a flowchart for the CERES NANOTRAP method.
Figures 27A, 27B, 27C, 27D:
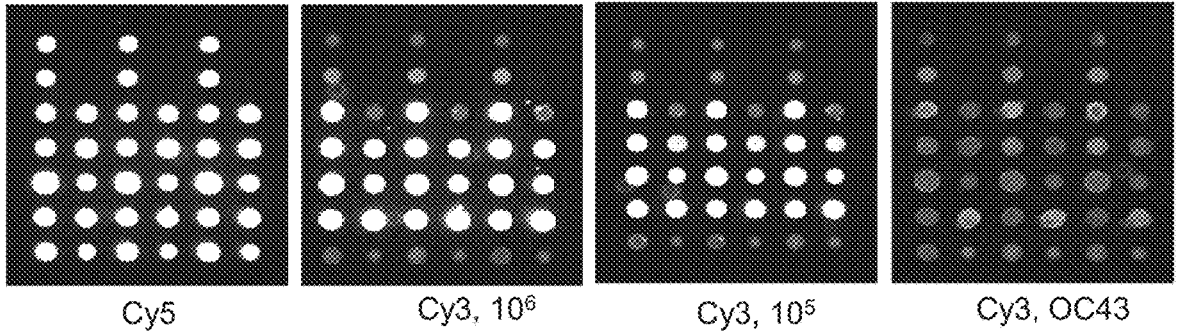
FIGS. 27A-27D shows microarray images from samples processed using the CERES NANOTRAP method.
Figure 28:
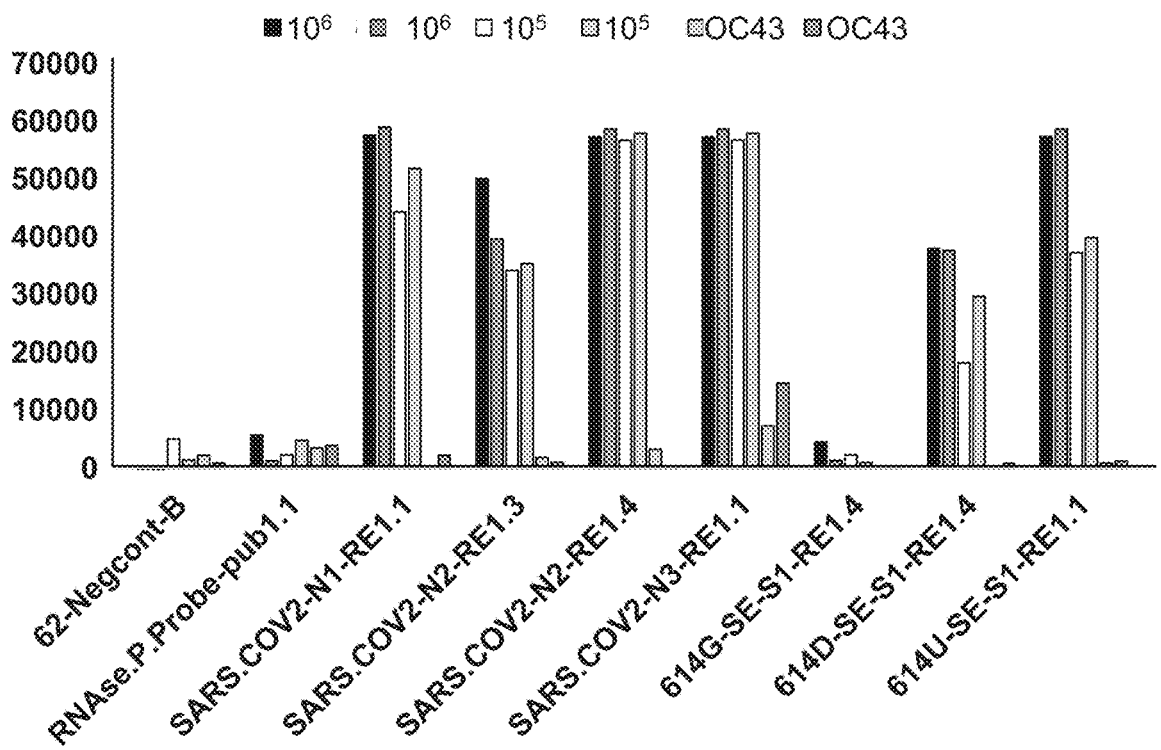
FIG. 28 is a graphical representation of hybridization analysis for samples processed using the CERES NANOTRAP method.

A comparison between the Zymo method described earlier with the CERES NANOTRAP method was performed for contrived NP/VTM samples prepared by Emory (heat-killed Cov-2 virus from BEI, in VTM). The CERES NANOTRAP method (FIGS. 25-26) was deployed on the raw samples to yield a pellet that was heat lysed in 1% Triton-X-100 in Molecular Grade Water before direct use in Asymmetric One-Pot RT-PCR, followed by Mini-RV analysis in the 96-well format. The results of these experiments are shown in FIGS. 27A-27D, 28 and 29 and Tables 59-61.

Among all 3 SARS-CoV-2 probes tested, the sensitivity of the Mini-RV assay subsequent to CERES NANOTRAP is identical or superior to that obtained using Quick-DNA/RNA Viral method for sample processing.

TABLE 59

Figure 29:
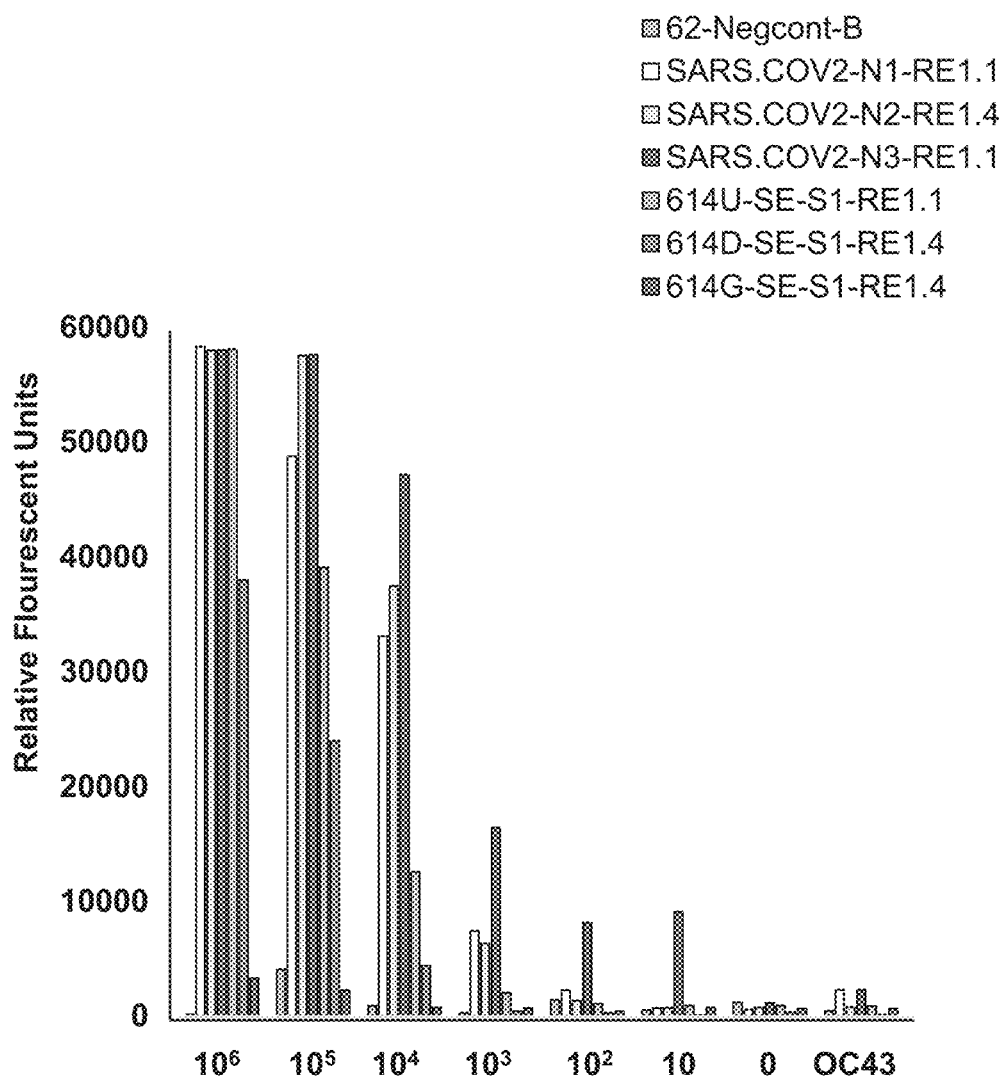
FIG. 29 is a graphical representation of hybridization analysis for samples processed using the CERES NANOTRAP method.
Figure 30A:
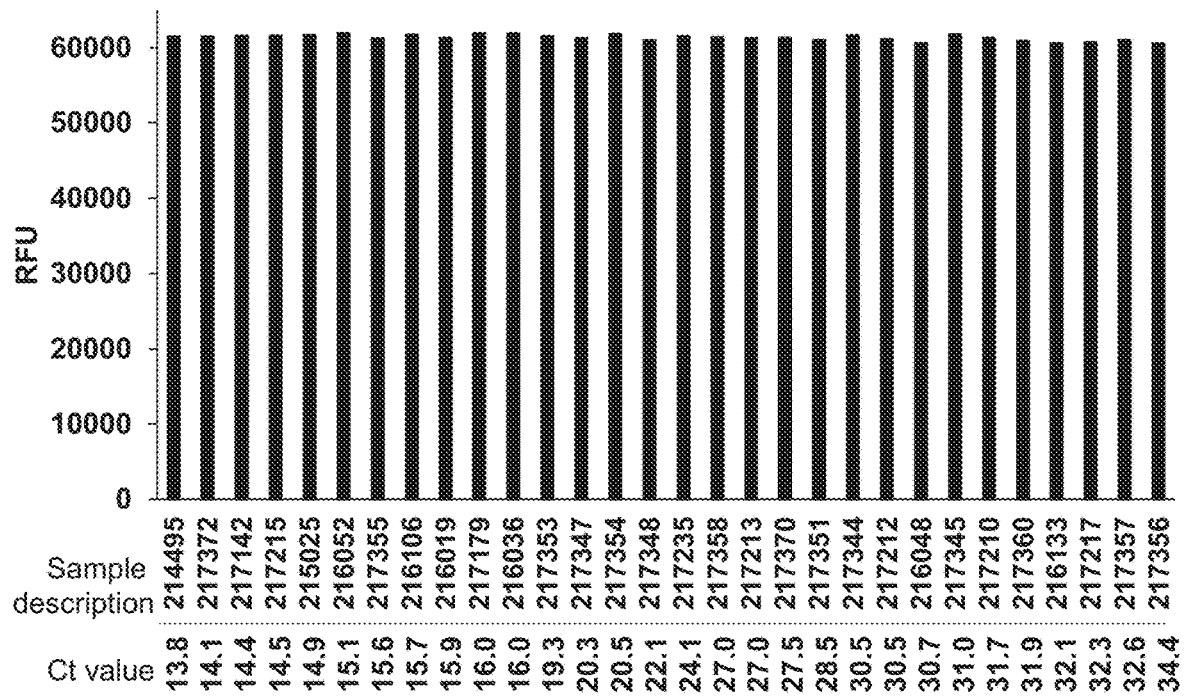
FIGS. 30A-30D show clinical sensitivity and specificity of the CERES NANOTRAP Mini-RV technology using the Cobas-Positive TriCore samples.
Figure 30B:
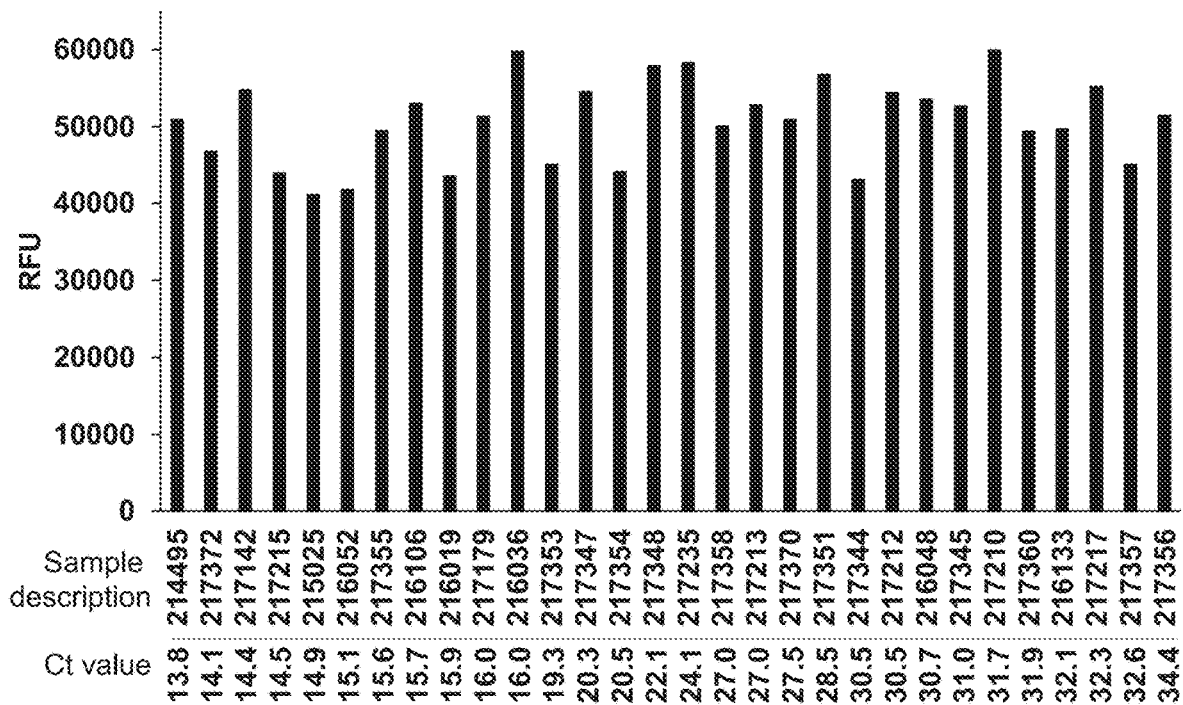
Figure 30C:
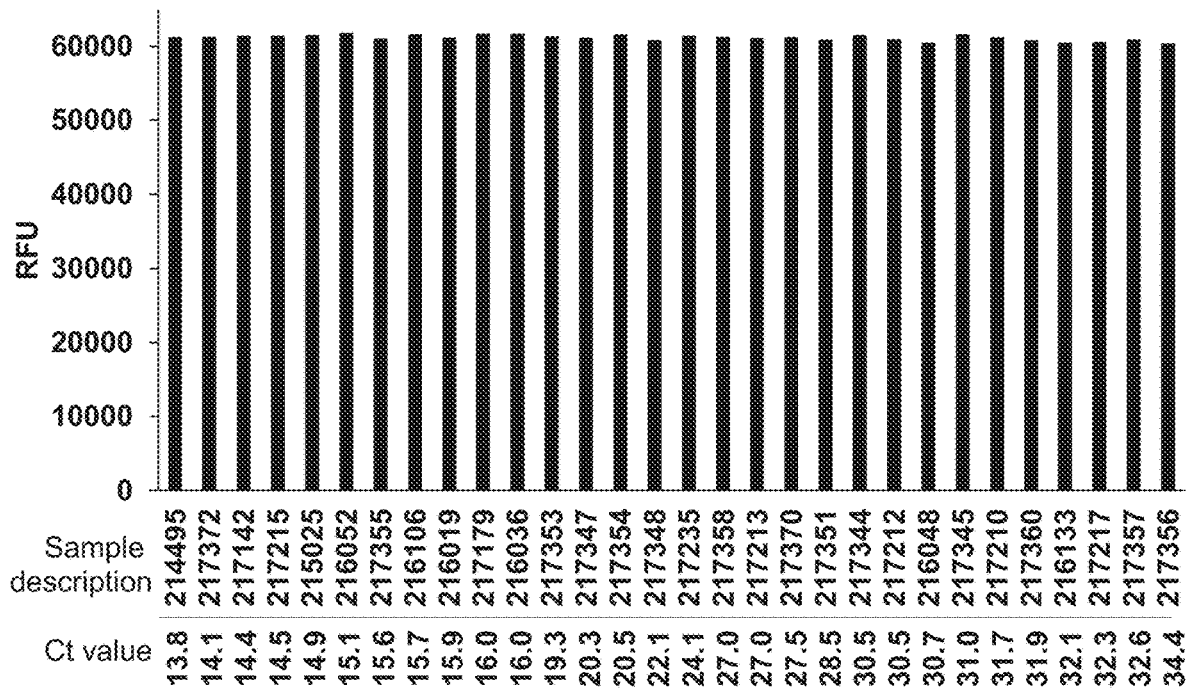
Figure 30D:
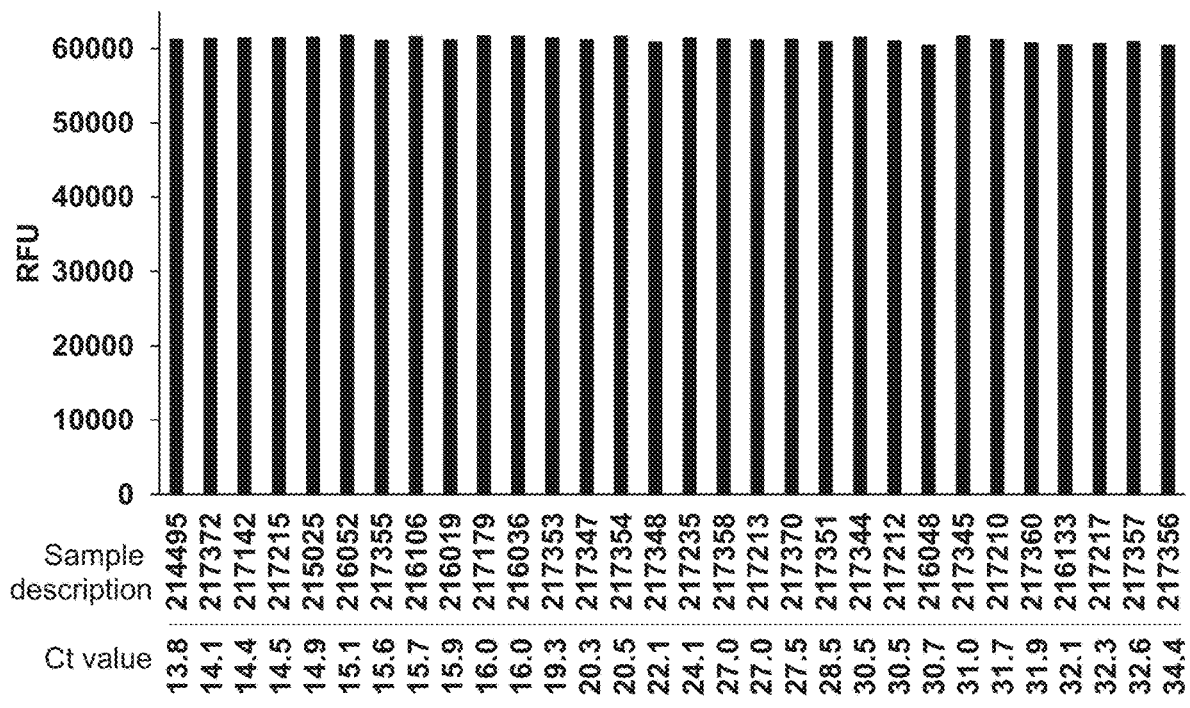

Average RFU from data shown in FIG. 29

|  | 62-Negcont-B | SARS.COV2-N1-RE1.1 | SARS.COV2-N2-RE1.4 | SARS.COV2-N3-RE1.1 | 614U-SE-S1-RE1.1 | 614D-SE-S1-RE1.4 | 614G-SE-S1-RE1.4 |
|---|---|---|---|---|---|---|---|
| $10^6$ | 131 | 58313 | 57988 | 57999 | 58088 | 37984 | 3296 |
| $10^5$ | 4071 | 48742 | 57533 | 57611 | 39089 | 23960 | 2242 |
| $10^4$ | 887 | 33078 | 37461 | 47154 | 12553 | 4366 | 734 |
| $10^3$ | 272 | 7420 | 6335 | 16416 | 2026 | 398 | 694 |
| $10^2$ | 1410 | 2253 | 1335 | 8144 | 1066 | 263 | 408 |
| 10 | 525 | 684 | 727 | 9090 | 923 | 73 | 743 |
| 0 | 1179 | 551 | 739 | 1140 | 918 | 335 | 643 |
| OC43 1000 | 437 | 2266 | 773 | 2266 | 869 | 105 | 641 |
| OC43 100 | 1413 | 1289 | 1863 | 1026 | 1026 | 489 | 246 |

TABLE 60

Comparison of the Zymo and Ceres sample preparation methods

|  | 62-Negcont-B | SARS.COV2-N1-RE1.1 | SARS.COV2-N2-RE1.4 | SARS.COV2-N3-RE1.1 | 614U-SE-S1-RE1.1 | 614D-SE-S1-RE1.4 | 614G-SE-S1-RE1.4 |
|---|---|---|---|---|---|---|---|
| Zymo Quick-DNA/RNA Viral method | | | | | | | |
| $10^6$ | 896 | 47139 | 55897 | 62143 | 29221 | 13325 | 2665 |
| $10^6$ | 1808 | 55909 | 53708 | 62344 | 37797 | 25071 | 3751 |
| $10^5$ | 1718 | 38649 | 40395 | 54649 | 10208 | 4424 | 1842 |
| $10^5$ | 933 | 37272 | 31301 | 48548 | 10566 | 4974 | 2484 |
| $10^4$ | 422 | 18915 | 17861 | 35288 | 3085 | 2238 | 1859 |
| $10^4$ | 2252 | 16966 | 27864 | 37627 | 3640 | 3046 | 2473 |
| $10^3$ | 1368 | 8840 | 11798 | 18995 | 2271 | 2212 | 2342 |
| $10^3$ | 2011 | 8059 | 7444 | 18287 | 2686 | 2669 | 2196 |
| $10^3$ | 1200 | 3244 | 5002 | 31634 | 3081 | 3001 | 2956 |
| $10^2$ | 1103 | 3987 | 2694 | 3050 | 3334 | 1906 | 2574 |
| $10^2$ | 17 | 3771 | 1605 | 4689 | 2369 | 3048 | 2785 |
| $10^2$ | 3107 | 2520 | 682 | 15590 | 2718 | 1956 | 2204 |
| 10 | 740 | 1264 | 2803 | 3325 | 2386 | 2560 | 2530 |
| 10 | 4141 | 4491 | 2980 | 15011 | 4070 | 2541 | 3374 |
| 10 | 3089 | 4057 | 2924 | 12836 | 3333 | 3167 | 3355 |
| 0 | 2456 | 3339 | 1624 | 4413 | 2635 | 2940 | 3001 |
| 0 | 914 | 3445 | 1187 | 1317 | 1918 | 2325 | 2137 |
| 0 | 1920 | 1901 | 2111 | 6152 | 2761 | 2728 | 2670 |
| OC43 | 744 | 6579 | 2470 | 1897 | 2473 | 2319 | 2376 |
| OC43 | 2584 | 1558 | 2255 | 2164 | 2635 | 2484 | 2735 |
| OC43 | 2295 | 2754 | 1833 | 3665 | 2947 | 2237 | 2721 |
| OC43 | 2547 | 3974 | 1783 | 1925 | 3200 | 2980 | 3131 |
| CERES NANOTRAP method | | | | | | | |
| $10^6$ | 250 | 57479 | 57171 | 57220 | 57289 | 38216 | 4936 |
| $10^6$ | 11 | 59147 | 58805 | 58778 | 58886 | 37751 | 1656 |
| $10^5$ | 6569 | 44814 | 57138 | 57290 | 37991 | 18235 | 2982 |
| $10^5$ | 1573 | 52670 | 57929 | 57933 | 40187 | 29685 | 1501 |
| $10^4$ | −394 | 34067 | 37511 | 47610 | 12552 | 4869 | 1357 |
| $10^4$ | 2167 | 32089 | 37411 | 46697 | 12553 | 3863 | 111 |
| $10^3$ | 271 | 8264 | 5231 | 17420 | 2401 | 834 | 609 |
| $10^3$ | 454 | 2721 | 3397 | 11240 | 1035 | −169 | 839 |
| $10^3$ | 91 | 11275 | 10378 | 20588 | 2643 | 529 | 633 |
| $10^2$ | 1724 | 251 | 411 | 7294 | 739 | 236 | 189 |
| $10^2$ | 1375 | 4602 | 852 | 7084 | 1664 | 513 | 747 |
| $10^2$ | 1133 | 1907 | 2743 | 10052 | 794 | 39 | 289 |
| 10 | 591 | 1047 | 1535 | 7319 | 939 | 5 | 785 |
| 10 | 243 | 855 | 164 | 7037 | 788 | 66 | 716 |
| 10 | 741 | 148 | 480 | 12913 | 1042 | 149 | 729 |
| 0 | 588 | 260 | 296 | 2093 | 577 | 160 | 801 |
| 0 | 1248 | 982 | 679 | 241 | 1013 | 363 | 487 |
| 0 | 1702 | 410 | 1243 | 1087 | 1165 | 482 | 643 |
| OC43 1000 | 176 | 3011 | 888 | 3011 | 830 | 140 | 707 |
| OC43 1000 | 698 | 1522 | 658 | 1522 | 909 | 70 | 575 |
| OC43 100 | 2307 | 399 | 3585 | 967 | 967 | 44 | 86 |
| OC43 100 | 520 | 2179 | 141 | 1086 | 1086 | 935 | 405 |

TABLE 61

Comparison of the CERES NANOTRAP method for various sample inputs

| | Well number | 62-Negcont-B | SARS.COV2-N1-RE1.1 | SARS.COV2-N2-RE1.4 | SARS.COV2-N3-RE1.1 | 614U-SE-S1-RE1.1 | 614D-SE-S1-RE1.4 | 614G-SE-S1-RE1.4 |
|---|---|---|---|---|---|---|---|---|
| | | | 5 µL Input | | | | | |
| $10^4$ | Well 1 | −394 | 34067 | 37511 | 47610 | 12552 | 4869 | 1357 |
| $10^4$ | Well 2 | 2167 | 32089 | 37411 | 46697 | 12553 | 3863 | 111 |
| $10^3$ | Well 3 | 271 | 8264 | 5231 | 17420 | 2401 | 834 | 609 |
| $10^3$ | Well 4 | 454 | 2721 | 3397 | 11240 | 1035 | −169 | 839 |
| $10^2$ | Well 5 | 91 | 11275 | 10378 | 20588 | 2643 | 529 | 633 |
| $10^2$ | Well 6 | 1724 | 251 | 411 | 7294 | 739 | 236 | 189 |
| $10^2$ | Well 7 | 1375 | 4602 | 852 | 7084 | 1664 | 513 | 747 |
| $10^3$ | Well 8 | 1133 | 1907 | 2743 | 10052 | 794 | 39 | 289 |
| 10 | Well 9 | 591 | 1047 | 1535 | 7319 | 939 | 5 | 785 |
| 10 | Well 10 | 243 | 855 | 164 | 7037 | 788 | 66 | 716 |
| 10 | Well 11 | 741 | 148 | 480 | 12913 | 1042 | 149 | 729 |
| 0 | Well 12 | 588 | 260 | 296 | 2093 | 577 | 160 | 801 |
| 0 | Well 13 | 1248 | 982 | 679 | 241 | 1013 | 363 | 487 |
| 0 | Well 14 | 1702 | 410 | 1243 | 1087 | 1165 | 482 | 643 |
| OC43 | Well 15 | 176 | 3011 | 888 | 3011 | 830 | 140 | 707 |
| OC43 | Well 16 | 698 | 1522 | 658 | 1522 | 909 | 70 | 575 |
| | | | 10 µL Input | | | | | |
| $10^4$ | Well 25 | 508 | 31130 | 35936 | 36363 | 9159 | 1571 | 1 |
| $10^4$ | Well 26 | 96 | 28367 | 37529 | 37733 | 9360 | 2261 | 400 |
| $10^3$ | Well 27 | 801 | 11549 | 16029 | 23418 | 2364 | 234 | 579 |
| $10^3$ | Well 28 | 2517 | 6724 | 5685 | 11865 | 2251 | 751 | 915 |
| $10^2$ | Well 29 | 1399 | 9409 | 14780 | 27387 | 2622 | 1280 | 235 |
| $10^2$ | Well 30 | 91 | 660 | 1407 | 3042 | 472 | 279 | 491 |
| $10^2$ | Well 31 | 751 | 2155 | 1513 | 6435 | 696 | 346 | 221 |
| $10^3$ | Well 32 | 189 | 1490 | 1170 | 3681 | 1322 | 45 | 980 |
| 10 | Well 33 | 1218 | 54 | 1215 | 4366 | 287 | 220 | 487 |
| 10 | Well 34 | 1536 | 668 | 716 | 1044 | 904 | 30 | 509 |
| 10 | Well 35 | 1325 | 1563 | 2139 | 7748 | 671 | 134 | 277 |
| 0 | Well 36 | 1054 | 284 | 636 | 5169 | 624 | 207 | 339 |
| 0 | Well 37 | 36 | 1423 | 1026 | 9562 | 1188 | 936 | 689 |
| 0 | Well 38 | 1135 | 747 | 1148 | 1345 | 994 | 303 | 407 |
| OC43 | Well 39 | 1053 | 1498 | 2731 | 932 | 692 | 342 | 373 |
| OC43 | Well 40 | 949 | 990 | 640 | 4995 | 712 | 303 | 200 |
| | | | 15 µL Input | | | | | |
| $10^4$ | Well 41 | 713 | 31449 | 39029 | 44974 | 18520 | 4425 | 180 |
| $10^4$ | Well 42 | 624 | 33111 | 37242 | 40909 | 14729 | 3098 | −22 |
| $10^3$ | Well 43 | 1110 | 14349 | 18064 | 28520 | 3414 | 106 | −86 |
| $10^3$ | Well 44 | 1917 | 4070 | 7575 | 11626 | 2144 | −53 | 668 |
| $10^3$ | Well 45 | 849 | 15887 | 18735 | 32519 | 3206 | 283 | −50 |
| $10^2$ | Well 46 | 322 | 2366 | 1268 | 8336 | 952 | 75 | 514 |
| $10^2$ | Well 47 | 968 | 2696 | 3649 | 3395 | 1270 | 64 | 466 |
| $10^2$ | Well 48 | 1454 | 3282 | 3230 | 3102 | 1311 | 134 | 507 |
| 10 | Well 49 | 1523 | −93 | 2046 | 2658 | 725 | 745 | 1167 |
| 10 | Well 50 | 1245 | 863 | 86 | 3717 | 1027 | 181 | 880 |
| 10 | Well 51 | 805 | 1726 | 1070 | 10586 | 1637 | 459 | 265 |
| 0 | Well 52 | 981 | 189 | 1559 | 12322 | 622 | 856 | 781 |
| 0 | Well 53 | 561 | 1033 | 1240 | 2424 | 577 | 713 | 74 |
| 0 | Well 54 | 1942 | 81 | 29 | 2846 | 1613 | 1201 | 593 |
| OC43 | Well 55 | 217 | 1466 | 1025 | 3771 | 815 | 3 | 241 |
| OC43 | Well 56 | 918 | −111 | 972 | 2819 | 1692 | 705 | 576 |

Clinical NP/VTM Samples

Clinical samples (positive and negative NP/VTM samples) previously characterized at TriCore via the Roche, Cobas 6800 SARS-CoV-2 platform, were analyzed to generate a 0-RT-PCR based Cq values for each clinical isolate. All samples were subjected to viral capture and enrichment using CERES NANOTRAP, followed by direct heat lysis of the resulting viral pellet in 1% Triton-X-100 as described above. The lysate (5 µL) from each of the 61 samples was used as input without additional purification, in the Asymmetric One-Step RT-PCR, followed by Mini-RV hybridization analysis. Two types of analysis were performed on the hybridization data.

Analysis 1. Hybridization signals (RFU) from all Mini-RV probes in the positive and negative TriCore samples was used to generate mean and standard deviation for the LOB, which was then used to determine the RFU threshold to be deployed in analysis of the samples. The Clinical and Laboratory Standards Institute (CLSI) standard was applied in threshold determination. To account for user differences, LoB was modified using the equation:

LoB=(3*Standard Deviation)+Average

Using this threshold value (Table 62), clinical sensitivity, and specificity, PPV and NPV were calculated for each probe in the Mini-RV test, and in turn for the overall call generated by AUGURY from those multiplex probe data (Table 62).

Analysis 2. To facilitate analysis of the relationship between Q-RT-PCR signal strength (Cq) and the Ceres+ Mini-RV signal strength (RFU), the data from TriCore, NPN™ clinical positives was rank-ordered based on their Cobas Cq value—lowest Cq (highest viral load) at the top and highest Cq (lowest viral load) at the bottom (Table 63). Cq values from Roche Cobas 6800 for the negative samples is shown in Table 64.

Results

The data show 100% clinical sensitivity and clinical specificity (Table 62, bottom row). Highest affinity Mini-RV probes (SARS.COV2-N2-RE1.3 and SARS.COV2-N3-RE1.1) remained positive even in the highest Cq (lowest viral load) positive samples, producing clearly defined calls, throughout (Table 62, columns 7,9). Additionally, the relationship between Q-RT-PCR (Cq) values and RFU signals (Table 63) manifest in the comparison of high affinity versus medium affinity Mini-RV probes enables microarray-based quantitation of Cov-2 RNA load.

TABLE 62

One-Pot Bias Labeling RT-PCR-CERES NANOTRAP

| | Threshold |
|---|---|
| 62-Negcont-B | 2309 |
| RNAse.P.Probe-pub1.1 | N/A |
| SARS.COV2-N1-RE1.1 | 2263 |
| SARS.COV2-N2-RE1.3 | 2145 |
| SARS.COV2-N2-RE1.4 | 2128 |
| SARS.COV2-N3-RE1.1 | 5662 |
| 614U-SE-S1-RE1.1 | 1466 |
| 614D-SE-S1-RE1.4 | N/A |
| 614G-SE-S1-RE1.4 | N/A |

| | Average Positives | Standard Deviation | Average Negatives | Standard Deviation | (a) True Positive | (b) False Positive | (c) False Negatives | (d) True Negatives | LoB | Sensitivity | Specificity | PPV | NPV |
|---|---|---|---|---|---|---|---|---|---|---|---|---|---|
| 62-Negcont-B | 543 | 361 | 853 | 485 | 30 | 0 | 0 | 31 | 1652 | 100 | 100 | 100 | 100 |
| RNAse.P.Probe-pub1.1 | 54843 | 12349 | 35575 | 13431 | 30 | 0 | 0 | 31 | N/A | 100 | 100 | 100 | 100 |
| SARS.COV2-N1-RE1.1 | 22384 | 23833 | 973 | 430 | 30 | 0 | 11 | 31 | 1680 | 74 | 100 | 100 | 74 |
| SARS.COV2-N2-RE1.3 | 16605 | 18344 | 1268 | 292 | 30 | 0 | 1 | 31 | 1749 | 97 | 100 | 100 | 97 |
| SARS.COV2-N2-RE1.4 | 25298 | 25435 | 615 | 504 | 30 | 0 | 11 | 31 | 1445 | 74 | 100 | 100 | 74 |
| SARS.COV2-N3-RE1.1 | 36436 | 16105 | 2271 | 1131 | 30 | 0 | 0 | 31 | 4130 | 100 | 100 | 100 | 100 |
| 614U-SE-S1-RE1.1 | 16317 | 22839 | 569 | 299 | 30 | 0 | 15 | 31 | 1061 | 68 | 100 | 100 | 67 |
| 614D-SE-S1-RE1.4 | 877 | 701 | 428 | 344 | 30 | 0 | N/A | 31 | 993 | N/A | 100 | 100 | N/A |
| 614G-SE-S1-RE1.4 | 8695 | 14376 | 474 | 324 | 30 | 0 | N/A | 31 | 1007 | N/A | 100 | 100 | N/A |
| Overall Call | N/A | N/A | N/A | N/A | 30 | 0 | 0 | 31 | N/A | 100 | 100 | 100 | 100 |

TABLE 63

Analysis of clinical positive samples using CERES NANOTRAP + Mini-RV

| Patient ID | Ct Value | PDx Overall Call | 62-Negcont-B | RNAse.P.Probe-pub1.1 | SARS.COV2-N1-RE1.1 | SARS.COV2-N2-RE1.3 | SARS.COV2-N2-RE1.4 | SARS.COV2-N3-RE1.1 | 614U-SE-S1-RE1.1 | 614D-SE-S1-RE1.4 | 614G-SE-S1-RE1.4 |
|---|---|---|---|---|---|---|---|---|---|---|---|
| 216708 | 16.3 | + | 1025 | 60184 | 60031 | 42974 | 59873 | 59842 | 57442 | 1564 | 34799 |
| 216005 | 17 | + | 532 | 61079 | 39962 | 14688 | 40212 | 39328 | 33600 | 412 | 7758 |
| 216002 | 17.6 | + | 382 | 60937 | 15357 | 2951 | 9051 | 15378 | 740 | 66 | 302 |
| 215989 | 18.8 | + | 1214 | 60636 | 60733 | 59869 | 60499 | 60580 | 60441 | 2790 | 43307 |
| 216565 | 19.4 | + | 791 | 61053 | 42644 | 35231 | 60325 | 47596 | 16915 | 466 | 4334 |
| 215997 | 19.5 | + | 791 | 60641 | 61080 | 57518 | 60766 | 60899 | 60772 | 2658 | 42760 |
| 215988 | 19.6 | + | 171 | 61208 | 13544 | 3714 | 15728 | 15301 | 1001 | 786 | 1069 |
| 215999 | 19.8 | + | 671 | 61032 | 60921 | 41919 | 60692 | 60753 | 55691 | 1458 | 35558 |
| 215992 | 20.5 | + | 335 | 60833 | 55607 | 38292 | 60412 | 60202 | 34336 | 1168 | 8008 |
| 215982 | 21.4 | + | 320 | 60990 | 34856 | 22652 | 42393 | 37004 | 7092 | 406 | 1875 |
| 215993 | 21.4 | + | 399 | 60757 | 26397 | 9905 | 36512 | 33408 | 3419 | 555 | 1149 |
| 215995 | 23.2 | + | 435 | 61025 | 9130 | 4462 | 8029 | 32541 | 314 | 563 | 837 |
| 216001 | 23.9 | + | 232 | 61511 | 469 | 1842 | 20 | 14758 | 98 | 361 | 512 |
| 215983 | 24.1 | + | 271 | 61561 | 40190 | 26371 | 50555 | 47049 | 39053 | 750 | 12218 |
| 216003 | 24.2 | + | 1372 | 52363 | 60745 | 49426 | 60579 | 60625 | 60468 | 2503 | 39610 |
| 215996 | 24.8 | + | 262 | 58165 | 11307 | 7098 | 22354 | 36237 | 4127 | 34 | 1227 |
| 215998 | 25.2 | + | 861 | 61126 | 60506 | 46522 | 60843 | 60913 | 60715 | 1435 | 37778 |
| 216701 | 25.9 | + | −116 | 60209 | 41064 | 27185 | 49944 | 54044 | 37956 | 856 | 12876 |
| 216564 | 26.1 | + | 137 | 39263 | 21521 | 12341 | 36847 | 38661 | 7944 | 257 | 1981 |
| 216566 | 26.3 | + | 52 | 44491 | 29418 | 16484 | 36751 | 39826 | 11800 | 252 | 3070 |
| 216700 | 26.5 | + | 142 | 60946 | 31126 | 19117 | 41213 | 35461 | 10845 | 35 | 2391 |
| 215987 | 27 | + | 801 | 61899 | −14 | 3017 | 584 | 15086 | 526 | 1259 | 1253 |
| 215994 | 29.2 | + | 741 | 39522 | 363 | 2949 | 862 | 35620 | 487 | 1253 | 970 |
| 216007 | 29.9 | + | 234 | 61208 | 138 | 2243 | 1357 | 16169 | 189 | 789 | 395 |
| 215991 | 30.7 | + | 828 | 43373 | 396 | 2761 | 638 | 34696 | 275 | 754 | 381 |
| 215986 | 30.9 | + | 759 | 60999 | 360 | 3427 | 1772 | 29400 | 567 | 953 | 2165 |

TABLE 63-continued

Analysis of clinical positive samples using CERES NANOTRAP + Mini-RV

| Patient ID | Ct Value | PDx Overall Call | 62-Negcont-B | RNAse.P.Probe-pub1.1 | SARS.COV2-N1-RE1.1 | SARS.COV2-N2-RE1.3 | SARS.COV2-N2-RE1.4 | SARS.COV2-N3-RE1.1 | 614U-SE-S1-RE1.1 | 614D-SE-S1-RE1.4 | 614G-SE-S1-RE1.4 |
|---|---|---|---|---|---|---|---|---|---|---|---|
| 215984 | 32.1 | + | 560 | 16179 | 533 | 2968 | 752 | 37023 | 738 | 441 | 631 |
| 215990 | 33.4 | + | 662 | 38405 | −36 | 5394 | 911 | 27314 | 711 | 1061 | 822 |
| 215981 | 34.3 | + | 1188 | 62578 | −72 | 4987 | 1020 | 18036 | 972 | 1622 | 729 |
| 215985 | 34.5 | + | 552 | 14973 | 450 | 2849 | 34 | 41135 | 596 | 812 | 1066 |

TABLE 64

Analysis of clinical negative samples using CERES NANOTRAP + Mini-RV

| Patient ID | Ct Value from Roche Cobas 6800 | PDx Overall Call | 62-Negcont-B | RNAse.P.Probe-pub1.1 | SARS.COV2-N1-RE1.1 |
|---|---|---|---|---|---|
| PATHO-001 | T1 > 35; T2 > 38 | − | 1443 | 25554 | 1071 |
| PATHO-002 | T1 > 35; T2 > 38 | − | 528 | 23470 | 847 |
| PATHO-003 | T1 > 35; T2 > 38 | − | 728 | 41852 | 817 |
| PATHO-004 | T1 > 35; T2 > 38 | − | 303 | 43625 | 462 |
| PATHO-005 | T1 > 35; T2 > 38 | − | 725 | 54472 | 1205 |
| PATHO-006 | T1 > 35; T2 > 38 | − | 251 | 36887 | 683 |
| PATHO-007 | T1 > 35; T2 > 38 | − | 1307 | 60550 | 1313 |
| PATHO-009 | T1 > 35; T2 > 38 | − | 1291 | 24409 | 966 |
| PATHO-010 | T1 > 35; T2 > 38 | − | 718 | 36868 | 554 |
| PATHO-011 | T1 > 35; T2 > 38 | − | 862 | 37259 | 506 |
| PATHO-012 | T1 > 35; T2 > 38 | − | 152 | 14057 | 62 |
| PATHO-013 | T1 > 35; T2 > 38 | − | 1207 | 54393 | 884 |
| PATHO-014 | T1 > 35; T2 > 38 | − | 428 | 18317 | 852 |
| PATHO-015 | T1 > 35; T2 > 38 | − | 856 | 16642 | 983 |
| PATHO-016 | T1 > 35; T2 > 38 | − | 292 | 51315 | 962 |
| PATHO-017 | T1 > 35; T2 > 38 | − | 694 | 42375 | 453 |
| PATHO-018 | T1 > 35; T2 > 38 | − | 241 | 14001 | 265 |
| PATHO-019 | T1 > 35; T2 > 38 | − | 602 | 10226 | 905 |
| PATHO-020 | T1 > 35; T2 > 38 | − | 791 | 37377 | 817 |
| PATHO-021 | T1 > 35; T2 > 38 | − | 1352 | 55209 | 684 |
| PATHO-022 | T1 > 35; T2 > 38 | − | 1760 | 47587 | 1313 |
| PATHO-023 | T1 > 35; T2 > 38 | − | 1506 | 35160 | 1517 |
| PATHO-024 | T1 > 35; T2 > 38 | − | 529 | 21418 | 1064 |
| PATHO-025 | T1 > 35; T2 > 38 | − | 751 | 41096 | 2052 |
| PATHO-026 | T1 > 35; T2 > 38 | − | 647 | 35665 | 886 |
| PATHO-027 | T1 > 35; T2 > 38 | − | 718 | 40323 | 1532 |
| PATHO-028 | T1 > 35; T2 > 38 | − | 181 | 32818 | 849 |
| PATHO-029 | T1 > 35; T2 > 38 | − | 2028 | 39589 | 1361 |
| PATHO-030 | T1 > 35; T2 > 38 | − | 1135 | 25638 | 1223 |
| LoB Threshold | N/A | N/A | 2309 | N/A | 2263 |

| Patient ID | SARS.COV2-N2-RE1.3 | SARS.COV2-N2-RE1.4 | SARS.COV2-N3-RE1.1 | 614U-SE-S1-RE1.1 | 614D-SE-S1-RE1.4 | 614G-SE-S1-RE1.4 |
|---|---|---|---|---|---|---|
| PATHO-001 | 1250 | 405 | 953 | 255 | 131 | 148 |
| PATHO-002 | 759 | −32 | 2755 | 450 | 215 | 191 |
| PATHO-003 | 1111 | 417 | 3177 | 466 | 175 | 626 |
| PATHO-004 | 1239 | 181 | 2498 | 181 | 197 | 338 |
| PATHO-005 | 1220 | 1468 | 2247 | 503 | 603 | 479 |
| PATHO-006 | 1167 | 457 | 1302 | 322 | 254 | 302 |
| PATHO-007 | 546 | 668 | 3975 | 527 | 314 | −10 |
| PATHO-009 | 1323 | 24 | 1402 | 631 | 426 | 178 |
| PATHO-010 | 1347 | 447 | 1961 | 282 | 409 | 348 |
| PATHO-011 | 1640 | 661 | 2102 | 389 | −13 | 163 |
| PATHO-012 | 1036 | 167 | 857 | 512 | 221 | 165 |
| PATHO-013 | 1303 | 379 | 2087 | 593 | 242 | 98 |
| PATHO-014 | 1106 | 846 | 2416 | 425 | 475 | 65 |
| PATHO-015 | 961 | 153 | 1857 | 257 | 38 | 220 |
| PATHO-016 | 1639 | 963 | 4367 | 356 | −24 | 473 |
| PATHO-017 | 1182 | 8 | 1705 | 359 | 40 | 213 |
| PATHO-018 | 938 | 197 | 125 | 436 | 23 | 267 |
| PATHO-019 | 985 | −4 | 614 | 707 | 116 | 275 |
| PATHO-020 | 1113 | 291 | 2603 | 249 | 223 | 557 |
| PATHO-021 | 1705 | 920 | 2657 | 1194 | 797 | 1051 |
| PATHO-022 | 1772 | 2134 | 3656 | 1235 | 1011 | 863 |
| PATHO-023 | 1726 | 742 | 3535 | 1095 | 782 | 780 |
| PATHO-024 | 1268 | 1017 | 1666 | 447 | 338 | 459 |
| PATHO-025 | 1171 | 408 | 819 | 575 | 889 | 1057 |

TABLE 64-continued

Analysis of clinical negative samples using CERES NANOTRAP + Mini-RV

| | | | | | | |
|---|---|---|---|---|---|---|
| PATHO-026 | 1543 | 677 | 4850 | 573 | 839 | 742 |
| PATHO-027 | 1440 | 941 | 2718 | 703 | 521 | 503 |
| PATHO-028 | 1178 | 543 | 2412 | 403 | 436 | 579 |
| PATHO-029 | 1248 | 1401 | 3490 | 524 | 1017 | 1135 |
| PATHO-030 | 1634 | 781 | 1714 | 1206 | 1253 | 946 |
| LoB Threshold | 2145 | 2128 | 5662 | 1466 | N/A | N/A |

Example 26

Clinical Sensitivity and Specificity Using the CERES NANOTRAP Mini-RV Technology The protocol used 200 µL of beads and elution in 100 µL of extraction buffer (0.5% TritonX-100 in water) and additionally, a wash step after the first pelleting step. Clinical sensitivity and specificity analysis of the CERES NANOTRAP Mini-RV technology using 30 Tricore (Cobas-Pos) and 30 (Cobas-Neg) NP-VTM samples were 100% relative to the Cobas predicate. Probe threshold was calculated from LoB data obtained from the matched clinical negative samples using the formula:

Threshold=3×(STV)+Mean where Mean is the Mean value of RFU signal and STV is one standard deviation about that mean.

FIGS. 30A-30D show the 30 "Cobas-Positive" TriCore samples arranged such that the apparent viral load decreases from left to right (lowest Cq value→highest Cq value). Thus, using the modified Ceres bead protocol, a signal/threshold ratio greater than 10 was obtained for all COVID-19 probes (N1, N2 and N3) in all of the 30 samples even at the Limit of Detection for the Cobas Assay (Cq values ~35). The RFU signals obtained in these experiments provide support for using the CERES NANOTRAP Mini-RV technology even at the Cobas Limit of Detection (~35) when pooled testing is desired.

LoD Analysis Using the CERES NANOTRAP Mini-RV Technology

Figure 31A:
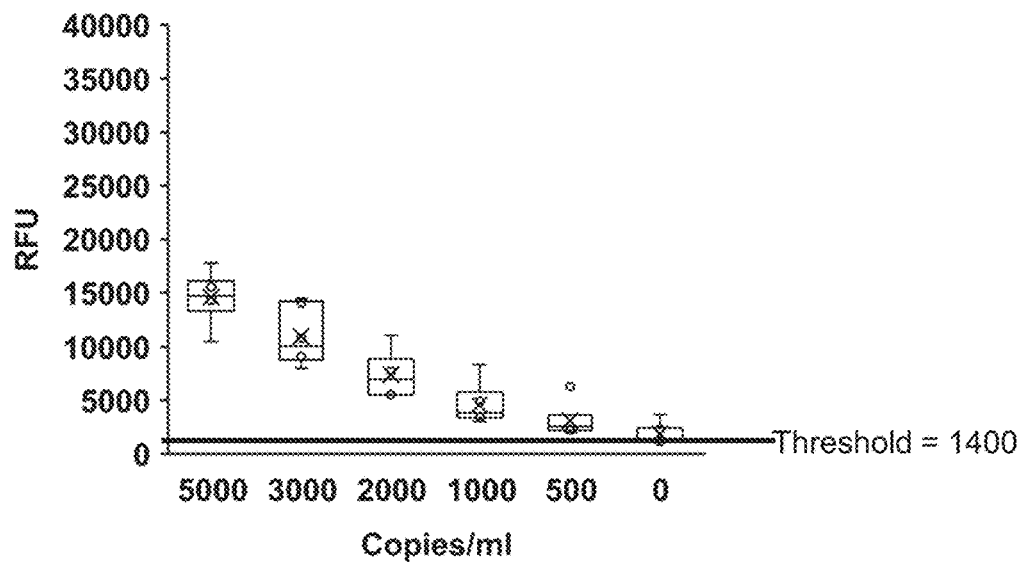
FIGS. 31A-31C show LoD analysis of the samples using CERES NANOTRAP Mini-RV technology.
Figure 31B:
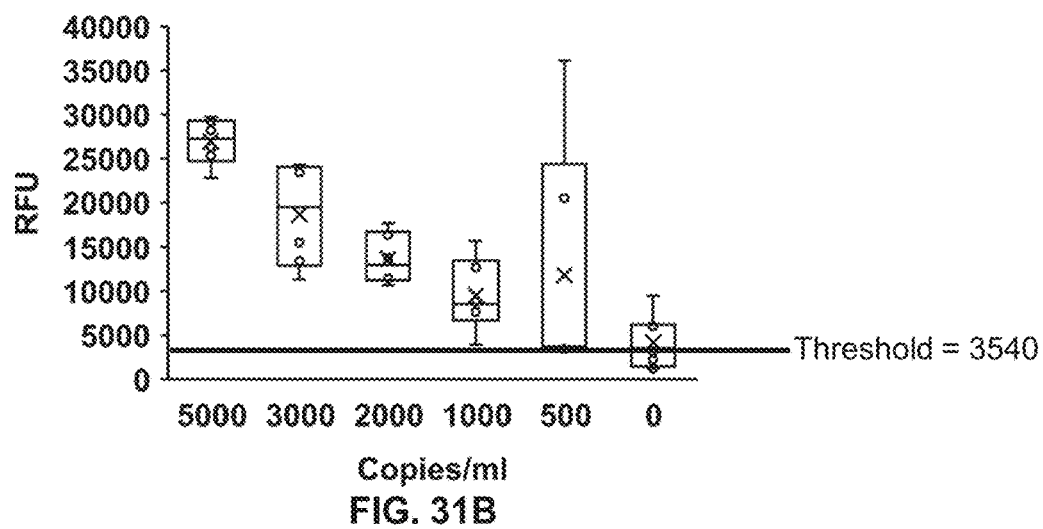
Figure 31C:
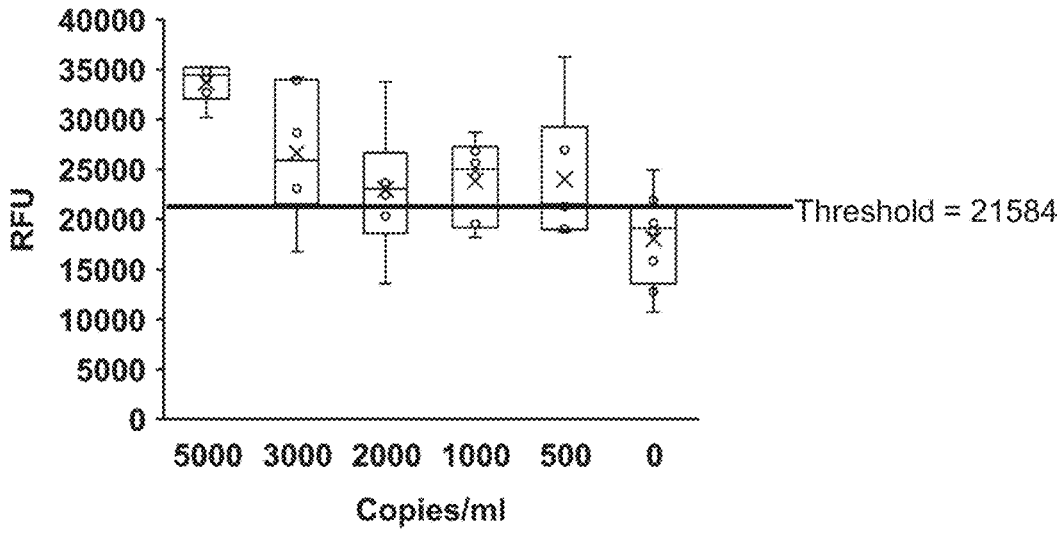
Figure 32A:
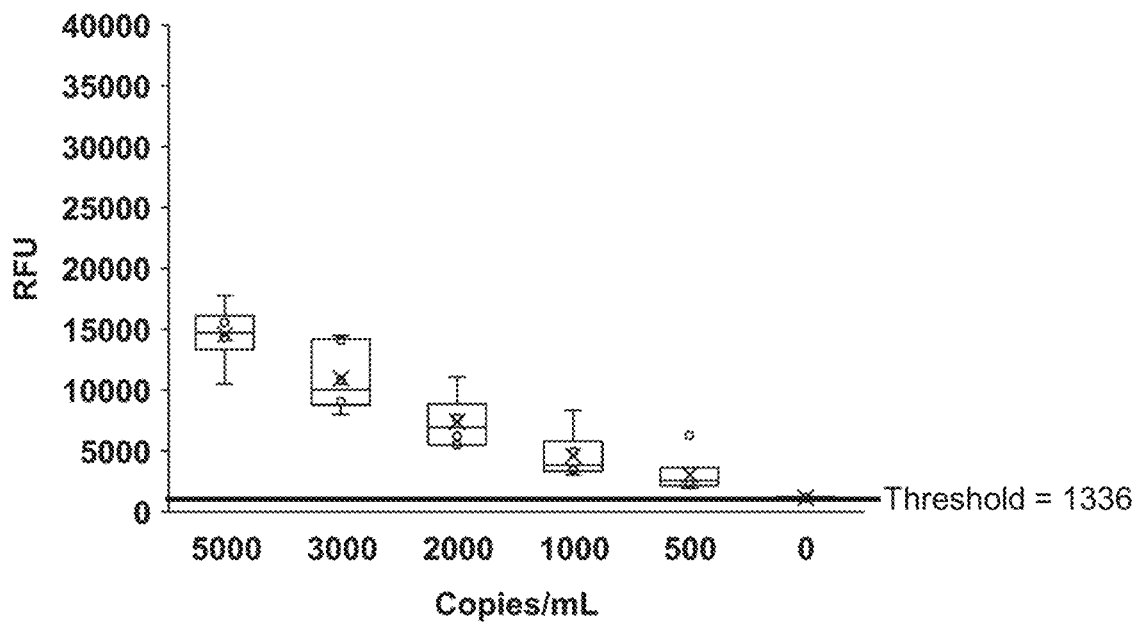
FIGS. 32A-32E shows the LoD analysis for contrived samples in VTM.
Figure 32B:
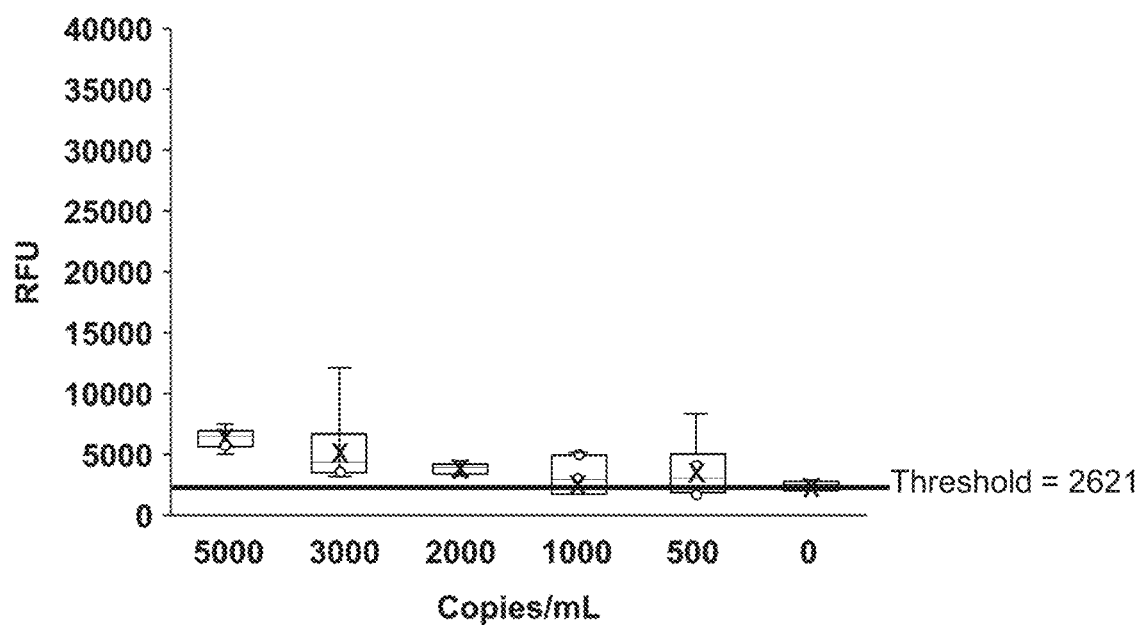
Figure 32C:
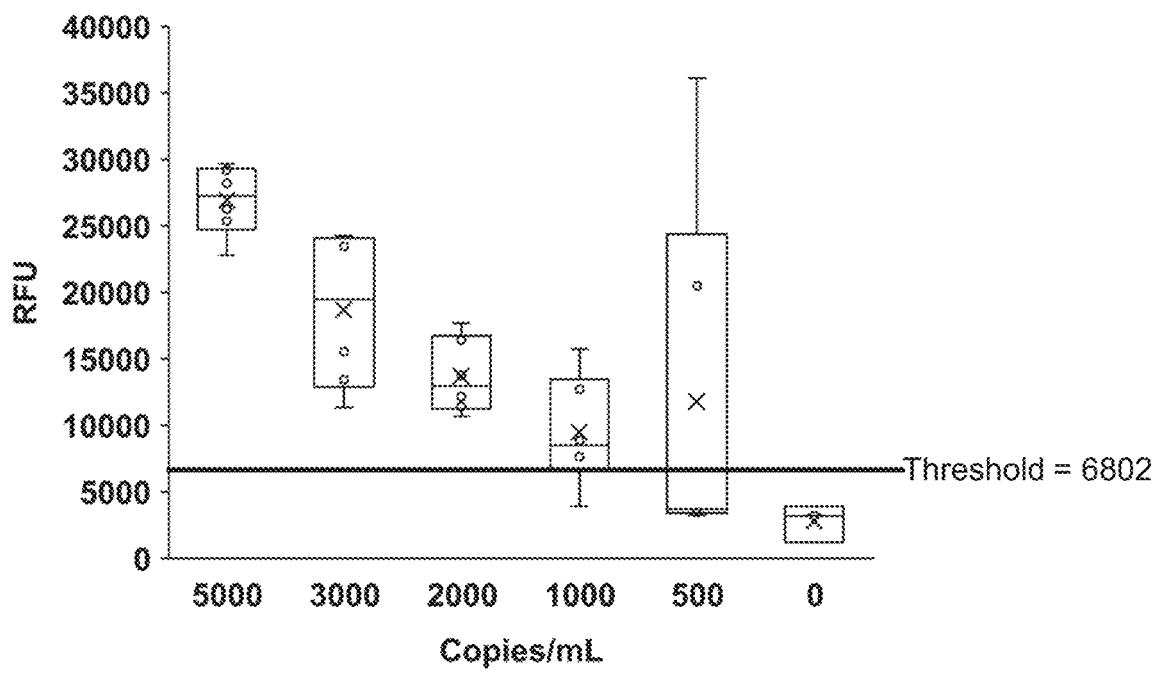
Figure 32D:
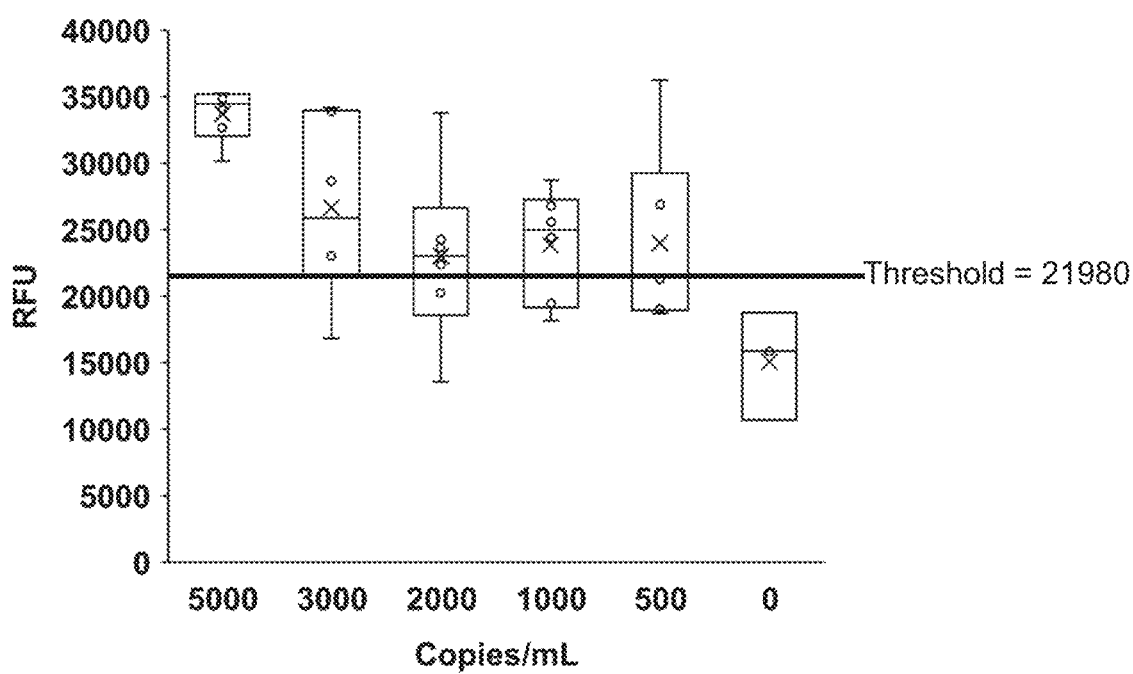
Figure 32E:
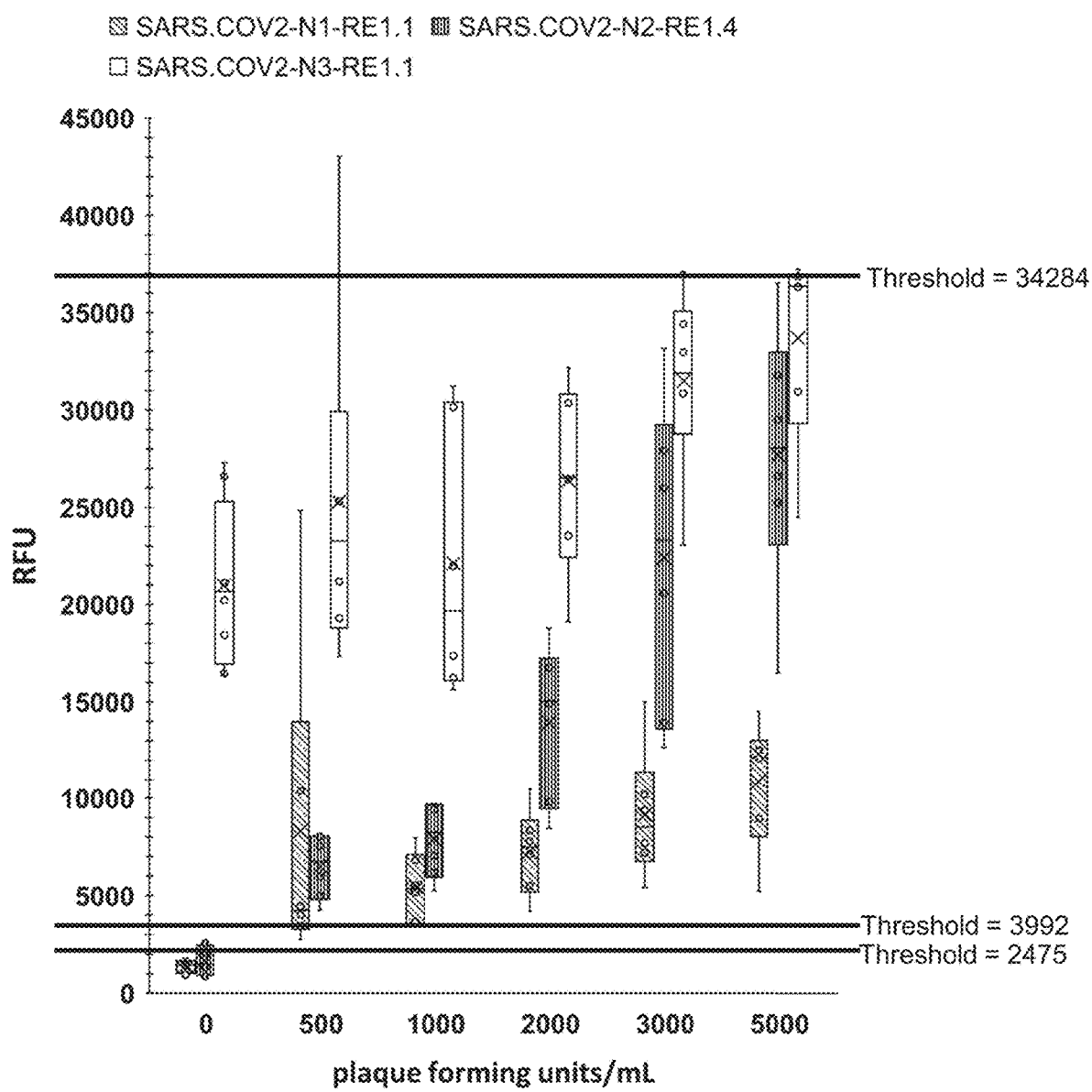

In addition to clinical sensitivity and specificity analysis, determination of LoD in units of virions/ml, were performed using virus that were subjected to heat, radiative or chemical denaturation. On contrived samples distributed as PT standards (FDA's SARS-CoV-2 Reference Panel Comparative Data) the Roche Cobas Q-RT PCR assay delivered a LoD of 1,800 copies/mL Thus, all 30 positive clinical samples studied here (TriCore, with Cobas Predicate) are expected to contain >1,800 copies/mL As shown in FIGS. 31A-31C, using the same procedural improvements deployed with the TriCore clinical samples the Signal/Threshold values and the resulting LoD values obtained in the contrived samples were somewhat lower than would be expected from the clinical isolates. The improvements made to the CERES NANOTRAP Mini-RV protocol suggest a LoD in the 500 copies/mL range. To further refine the LoD to harmonize with the clinical results (Roche Cobas LoD 1800 copies/mL), modifications were done to the protocol as follows:

Experiment 1

A finer dilution of the heat inactivated SARS-CoV-2 in VTM was tested at 5000, 3000, 2000, 1000 and 500 copies/mL (N=6 for each concentration). The samples were prepared in 500 µL of VTM and processed using the Ceres protocol with a final elution/lysis volume of 100 µL. The results showed 100% detection capability down to 500 copies/mL for N1 and N2, whereas a high background and variability for the N3 probe (FIGS. 32A-32E).

Experiment 2

Figure 33A:
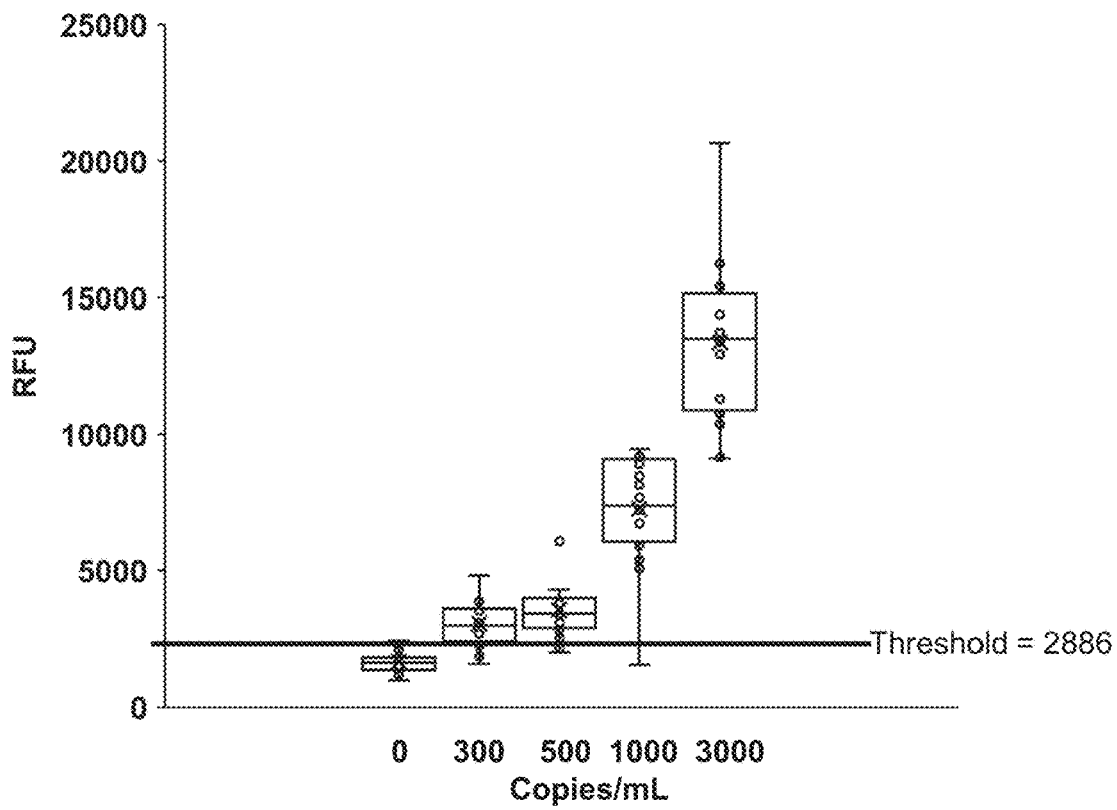
FIGS. 33A-33B shows LoD analysis for contrived samples in VTM.
Figure 33B:
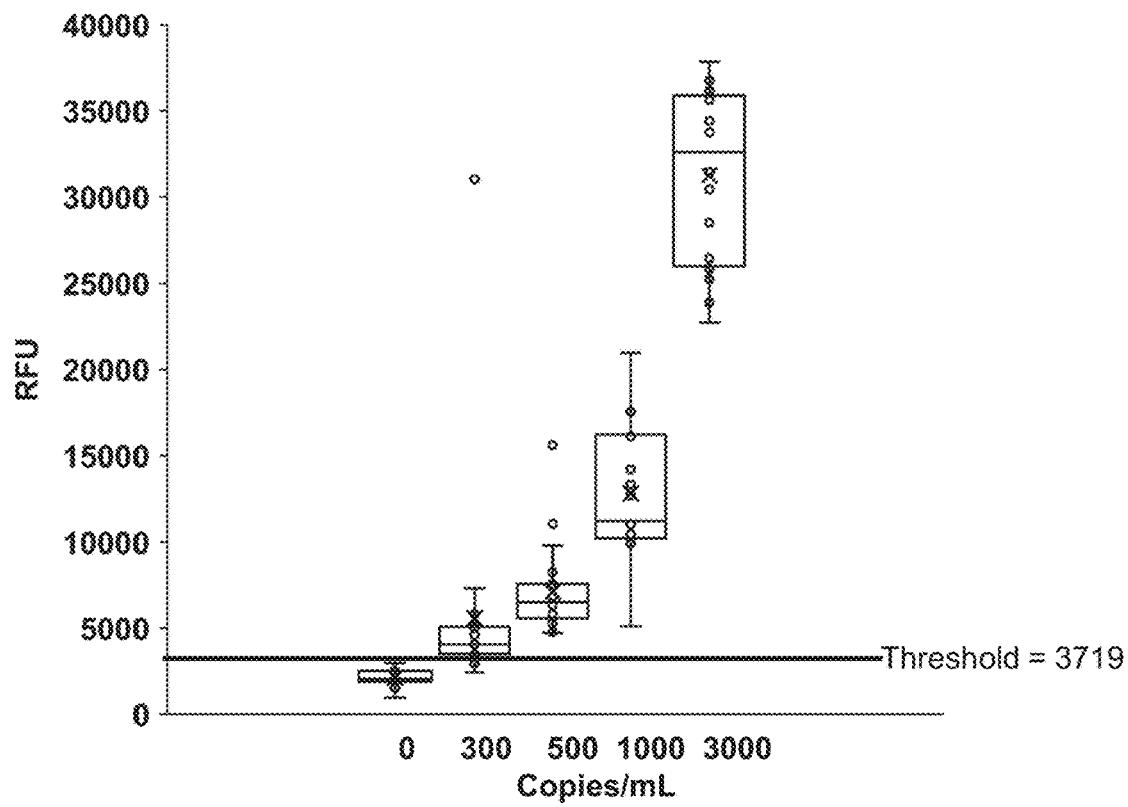

Based on the result from Experiment 1 above, additional LoD experiments were performed with increased sample number towards obtaining 95% positive results at 500 copies/mL. For this purpose, three sets of LoD samples were created at 3000, 1000, 500, 300, and 0 cp/mL (N=20 each) in VTM. Additionally, fresh vial of SARS-CoV-2 heat inactivated virus was used and prepared in VTM containing 10% glycerol prior to diluting to the concentrations tested. The results in FIGS. 33A-33B, demonstrate the ability of this method to yield an LoD at or just below 500 cp/mL. At 3000 cp/mL, the RFU values are closer to that observed with clinical samples. It is clear from this experiment that improper storage and/or degradation of the virus through multiple freeze thaws is a key contributor to LoD values obtained.

Experiment 3

Figures 34, 35:
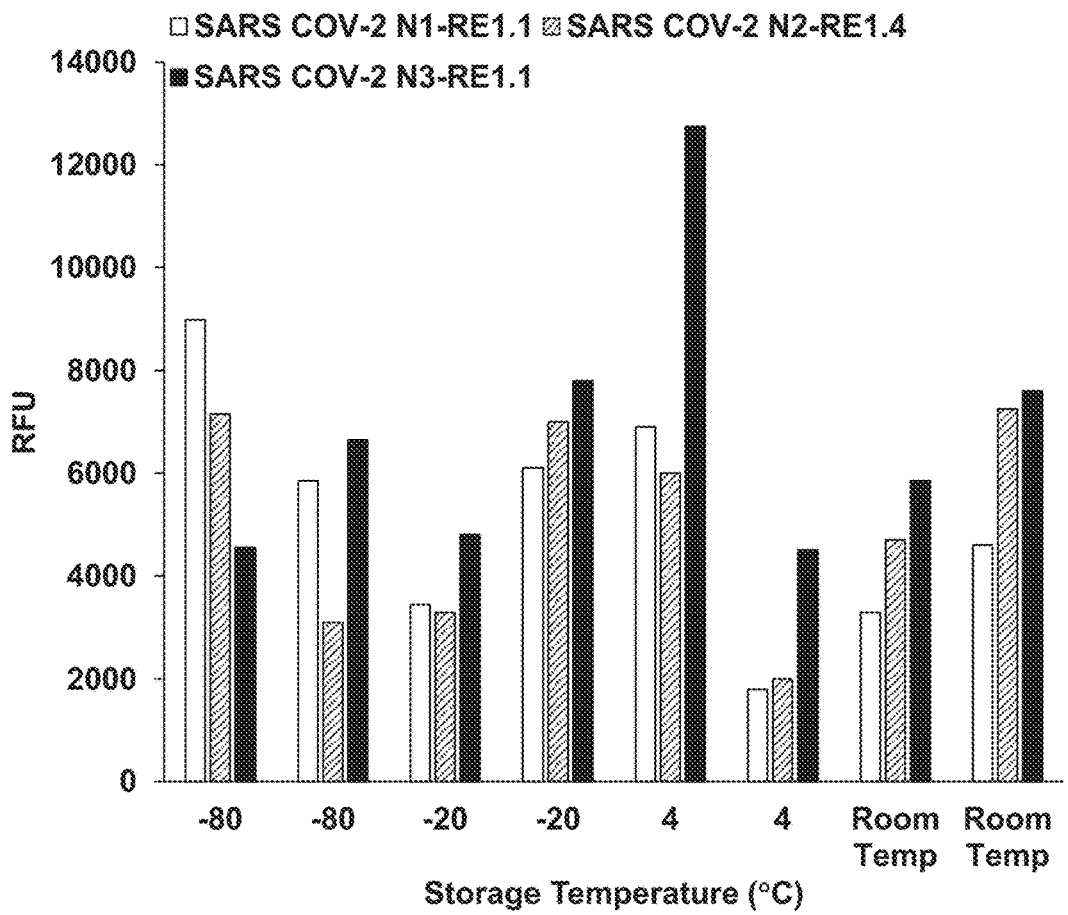
FIG. 34 shows the results of stability testing for probes SARS-COV-2 N1-RE1.1, SARS-COV-2 N2-RE1.4 and SARS-COV-2 N3-RE1.1.
FIG. 35 shows a checkerboard pattern to evaluate the Ceres run on the Tecan EVO150.

In the last experiment the hypothesis that freeze thaws might impact the background signal was tested. A large, pooled sample was created in which heat inactivated SARS-CoV-2 virus was diluted into VTM at 5000 cp/mL. The samples were aliquoted and stored at −80, −20, 4, and room temperature for 72 hours. The samples were then thawed or removed from the refrigerator and prepared using the CERES NANOTRAP beads followed by the DETECTX-RV protocol. No differences in background or signal strength were observed due to the different storage conditions or freeze thaws (FIG. 34).

Example 27

LoD Analysis of the CERES NANOTRAP Mini-RV Technology Pairing with Heat-Denatured CoV-2 (BEI) in VTM.

The clinical and LoD results presented in the previous example demonstrated excellent sensitivity and specificity and an LoD at or below 500 copies/mL. In addition, it was noted that there was variability in the baseline signal for the N3 probe. To further refine the protocol, pooling studies were undertaken and additionally, the platform was evaluated for multiplexed detection of Influenza A and B.

Experiment 1: A fully automated Ceres run was performed on the Tecan EVO150. In order to evaluate the run a checkerboard pattern (FIG. 35) was created and in the asterisked wells was added, clinical negative sample spiked with 25000 or 5000 copies/mL of irradiated SARS-CoV-2. This analysis revealed that 97% of the wells were called correctly, with two negative samples called as positive, and one positive sample called as negative.

Experiment 2: Three different lots of SARS-CoV-2 viral material (heat inactivated and gamma irradiated) were tested under different storage conditions (Table 65). A dilution from 30,000 to 1.000 copies/mL was used for each source material. The results shown in Table 65 demonstrate that absence of 10% glycerol displayed the lowest overall RFU and poor LoD followed by the heat inactivated virus stored in 10% glycerol. The best performing material was gamma irradiated lysates, which exhibited strong RFU signals down to 1000 copies/mL.

TABLE 65

Comparison of cell lysates under different storage conditions

| | Heat inactivated cell lysate | | | | Heat inactivated cell lysate 10% glycerol | | | | Gamma-irradiated cell lysate | | |
| --- | --- | --- | --- | --- | --- | --- | --- | --- | --- | --- | --- |
| copies/ mL | RNAase P Probe pub1.1 | SARS COV-2 N1 RE1.1* | SARS COV-2 N2 RE1.4¶ | copies/ mL | RNAase P Probe pub1.1 | SARS COV-2 N1 RE1.1* | SARS COV-2 N2 RE1.4¶ | copies/ mL | RNAase P Probe pub1.1 | SARS COV-2 N1 RE1.1* | SARS COV-2 N2 RE1.4¶ |
| | 47318 | 12381 | 27959 | | 57261 | 26168 | 39634 | | 54384 | 33810 | 46348 |
| 30K | 48826 | 8368 | 41434 | 30K | 56497 | 25473 | 41102 | 30K | 54294 | 29690 | 48684 |
| | 55016 | 11608 | 26506 | | 55182 | 23042 | 50369 | | 57171 | 33843 | 47384 |
| | 56838 | 1374 | 1548 | | 59248 | 7759 | 12921 | | 58174 | 11137 | 25297 |
| 3K | 51094 | 3531 | 2543 | 3K | 53062 | 6307 | 8648 | 3K | 58564 | 15688 | 28588 |
| | 58134 | 3110 | 5744 | | 50181 | 6059 | 7683 | | 57006 | 12938 | 26804 |
| | 56519 | 1058 | 7254 | | 58584 | 2940 | 3386 | | 48008 | 11141 | 20910 |
| 1K | 52534 | 2503 | 764 | 1K | 53593 | 7365 | 3611 | 1K | 57634 | 9339 | 13513 |
| | 56423 | 1449 | 1229 | | 53792 | 4577 | 4903 | | 51369 | 10479 | 13458 |

*Threshold = 2190;
¶threshold = 3292;
RFU > LoD

Experiment 3: To evaluate the ability to pool using the CERES NANOTRAP beads a series of positive samples with Ct values ranging from ~15 to ~35 by 5 Ct values was evaluated in relation to pooling 4 and/or 8 samples. To create the pooled samples, 100 μL of each sample was combined into a single tube such that, for example, a pool of 4 samples has a final volume of 400 μL. To each of the pooled samples was added 200 μL of CERES NANOTRAP beads and the pooled sample eluted into 100 μL of lysis buffer.

The results from this analysis demonstrate that with a pooling size of 4 or 8 samples with a Ct value of ~30 is detectable (Table 66). The RFU values for that sample demonstrate linearity from the sample alone (~10.000 RFU), 4:1 (~5,000 RFU), and 8:1 (~2500 RFU) starting at a Ct value of ~25.

TABLE 66

Pooling studies using CERES NANOTRAP Mini-RV technology

| Roche Cobas reported Ct value (Tg1/Tg2) | Positive sample ID and pooling dilution | RNAse P | SARS COV-2 N1-RE1.1* | SARS COV-2 N2-RE1.4¶ |
| --- | --- | --- | --- | --- |
| 34.32/34.17 | 432-Alone | 60203 | 3836 | 890 |
| | 432-4:1 | 59900 | 2873 | 673 |
| | 432-8:1 | 60406 | 2162 | 782 |
| 28.71/29.6 | 415-alone | 56995 | 9245 | 10540 |
| | 415-4:1 | 60307 | 4530 | 5339 |
| | 415-8:1 | 60175 | 3349 | 2238 |

TABLE 66-continued

Pooling studies using CERES NANOTRAP Mini-RV technology

| Roche Cobas reported Ct value (Tg1/Tg2) | Positive sample ID and pooling dilution | RNAse P | SARS COV-2 N1-RE1.1* | SARS COV-2 N2-RE1.4¶ |
| --- | --- | --- | --- | --- |
| 25.76/26.7 | 412-alone | 54171 | 14150 | 34450 |
| | 412-4:1 | 59797 | 20210 | 30751 |
| | 412-8:1 | 60698 | 8566 | 9658 |

TABLE 66-continued

Pooling studies using CERES NANOTRAP Mini-RV technology

| Roche Cobas reported Ct value (Tg1/Tg2) | Positive sample ID and pooling dilution | RNAse P | SARS COV-2 N1-RE1.1* | SARS COV-2 N2-RE1.4¶ |
| --- | --- | --- | --- | --- |
| 19.19/19.8 | 418-Alone | 59683 | 50496 | 59140 |
| | 418-4:1 | 59425 | 51793 | 58919 |
| | 418-8:1 | 60371 | 46331 | 59888 |
| 17.27/17.42 | 425-Alone | 42238 | 52803 | 58829 |
| | 425-4:1 | 44192 | 40680 | 59106 |
| | 425-8:1 | 52430 | 38046 | 59696 |

*Threshold = 2190;
¶Threshold = 3292

Experiment 4: To evaluate the ability of including Influenza A and B in the multiplexed array, the PCR conditions were modified to accommodate the incorporation of UNG. A comparison of the current room temperature (RT) condition at 45° to the 55°—conditions needed for UNG denaturation is shown in Table 67. The data shows that the change from 45° to 55° increases the RFU signals at the lower concentration without any adversely impacting signal strength. An LoD of 100 copies/mL was obtained using gRNA on the Zymo platform.

Experiment 5: Next, to test specificity of the platform for Influenza A and B, a series of samples were extracted using both Zymo and Ceres protocols. The samples were acquired through TriCore and were tested using the Respiratory Virus Panel by Real Time PCR (BioFire Diagnostics) with an LoD ~300 copies/mL for Influenza A (RESPAN). The results of this analysis shown in Table 68 demonstrate specificity within the assay. Table 69 shows that the CERES NANOTRAP beads capture/lysis/analysis protocol described above for CoV-2 (0.5 ml VTM+0.2 ml Ceres, magnetic bead isolation, elution & lysis in 0.1 ml) may also be adopted for detecting InfB signals on clinical positives that were greater than 8× the threshold obtained from matched clinical negatives.

TABLE 67

Effect of reverse transcription temperature on sensitivity and specificity

| Slide 9985 | Influenza A, B 1000 copies/reaction | Influenza A, B 500 copies/reaction | Influenza A, B 100 copies/reaction | Clinical infA-3b* | Clinical infA-4b* | CoV gRNA¶ 500 | NTC§ |
|---|---|---|---|---|---|---|---|
| 45° C., 45 min reverse transcription | | | | | | | |
| 62-Negcont-B | 613 | 533 | 978 | 2637 | 1617 | 1882 | 894 |
| 614D-SE-S1-RE1.4 | 554 | 454 | 245 | 1891 | 1345 | 22838 | 1033 |
| 614G-SE-S1-RE1.4 | −10 | 694 | 265 | 1653 | 1285 | 1755 | 1043 |
| 614U-SE-S1-RE1.4 | 509 | 462 | 885 | 1482 | 1309 | 36490 | 1092 |
| InfA 7 univ-pubRev | 44122 | 24795 | 7297 | 62387 | 1104 | 64 | 225 |
| InfB 8 univ-pub | 40626 | 39582 | 33881 | −110 | −55 | 341 | 48 |
| RNAase P Probe pub1.1 | 3321 | 4166 | 4439 | 62073 | 61697 | 5298 | 5635 |
| SARS COV-2 N1 pub | 6505 | 9633 | 557 | 6352 | 6829 | 61851 | 13421 |
| SARS COV-2 N1 RE1.1 | 1481 | 4342 | 6254 | 4504 | 3610 | 53173 | 5376 |
| SARS COV-2 N2 RE1.3 | 2704 | 1561 | 1553 | 2671 | 2975 | 35840 | 1697 |
| SARS COV-2 N2 RE1.4 | 2577 | 724 | 201 | 2180 | 2353 | 61274 | 1053 |
| SARS COV-2 N3 RE1.1 | 4765 | 4570 | 4981 | 8193 | 7288 | 61356 | 15052 |
| 55° C., 45 min reverse transcription | | | | | | | |
| 62-Negcont-B | 579 | 1776 | 724 | 2108 | 1395 | 3633 | 1514 |
| 614D-SE-S1-RE1.4 | 220 | 211 | 292 | 1851 | 845 | 19490 | 631 |
| 614G-SE-S1-RE1.4 | 15 | 303 | 329 | 1542 | 458 | 2052 | 865 |
| 614U-SE-S1-RE1.4 | 658 | 708 | 985 | 1832 | 945 | 31619 | 1267 |
| InfA 7 univ-pubRev | 43972 | 41491 | 20854 | 59646 | 9286 | 9 | 135 |
| InfB 8 univ-pub | 44453 | 41012 | 36009 | −180 | 40 | 633 | 323 |
| RNAase P Probe pub1.1 | 3410 | 3336 | 5745 | 62270 | 60936 | 5770 | 2321 |
| SARS COV-2 N1 pub | 21951 | 12594 | 16458 | 6847 | 5066 | 62714 | 10895 |
| SARS COV-2 N1 RE1.1 | 5450 | 8669 | 7638 | 5278 | 3115 | 58984 | 7296 |
| SARS COV-2 N2 RE1.3 | 1184 | 2624 | 1899 | 3336 | 2358 | 37323 | 5356 |
| SARS COV-2 N2 RE1.4 | 854 | 1955 | 1028 | 2480 | 2591 | 61442 | 2524 |
| SARS COV-2 N3 RE1.1 | 5053 | 5609 | 11129 | 4300 | 9510 | 62109 | 13624 |

*confirmed clinical samples extracted using Zymo;
¶SARS CoV-2 RNA;
§no template control

TABLE 68

Specificity of the platform for Influenza A for samples extracted by Zymo and Ceres methods

| Slide- 9982 | Extraction - Zymo InfA | | | | | | | | |
|---|---|---|---|---|---|---|---|---|---|
| Sample | infA-1 | infA-2 | infA-3 | infA-4 | infA-5 | infA-6 | infA-7 | infA-8 | NTC§ |
| 62-Negcont-B | 4178 | 3748 | 2392 | 2296 | 2934 | 1393 | 2108 | 1395 | 3$69 |
| RNAase P Probe pub1.1 | 62228 | 61848 | 54868 | 3069 | 61894 | 60'7S6 | 622'70 | 61i936 | 2498 |
| SAPS COV-2 N1 RE1.1 | 3843 | 2145 | 584 | 6524 | 291 | 1685 | 527$ | 3115 | 5155 |
| SARS COV-2 N2 RE1.4 | 1791 | 1734 | 1055 | 957 | 1068 | 313 | 2480 | 2591 | 991 |
| SARS COV-2 N3 RE1.1 | 6005 | $635 | ~IOS | 2633 | 6139 | 3593 | 4300 | 9510 | 7727 |
| InfA 7 univ-pubRev | 4389 | 2106 | 54328 | 236 | 50269 | 61072 | 59646 | 92$6 | −185 |
| InfB 8 univ-pub | −15 | 398 | 255 | 118 | 366 | 787 | −180 | 40 | 397 |

| Slide 9987 | Extraction -Ceres InfA | | | | | | | |
|---|---|---|---|---|---|---|---|---|
| Sample | Cr-infA-1 | Cr-infA-2 | Cr-infA-3 | Cr-infA-4 | Cr-infA-5 | Cr-infA-6 | NTC§ | NTC§ |
| 62-Negcont-B | 514 | 536 | 623 | 605 | 622 | 459 | 592 | 630 |
| RNAase P Probe pub1.1 | 40667 | 30593 | 42960 | 41415 | 42819 | 43331 | 280 | 464 |
| SARS COV-2 N1 RE1.1 | 1435 | 742 | 1020 | 677 | 887 | 1003 | 1609 | 1516 |
| SARS COV-2 N2 RE1.4 | 1919 | 1993 | 1207 | 1614 | 1936 | 1520 | 1056 | 1326 |
| SARS COV-2 N3 RE1.1 | 2852 | 2671 | 4168 | 3650 | 3114 | 3232 | 2122 | 3885 |
| InfA 7 univ-pubRev | 21474 | 4.3408 | 13709 | −73 | 85 | 38326 | −132 | −308 |
| InfA 7 univ-RE1.1 | 17678 | 43457 | 20880 | 604 | 519 | 39903 | −85 | 158 |
| InfA SE-PR99524 | 17321 | 45435 | 19193 | 592 | 1267 | 41711 | 778 | 295 |
| InfA SE-PR99525 | 11668 | 38574 | 10048 | 141 | 1141 | 35424 | 551 | 252 |
| InfB 8 univ-pub | −188 | −212 | −71 | −346 | −5 | −290 | 60 | −292 |

§no template control

TABLE 69

Specificity of the platform for Influenza B for samples extracted by Zymo and Ceres methods

| Slide- 9982 | Extraction - Zymo InfA | | | | | | | | |
|---|---|---|---|---|---|---|---|---|---|
| Sample | infB-1 | infB-2 | infB-3 | infB-4 | infB-5 | infB-6 | infB-7 | infB-8 | NTC[§] |
| 62-Negcont-B | 4268 | 3341 | 2339 | 4421 | 3565 | 5347 | 2409 | 1589 | 3869 |
| RNAase P Probe pub1.1 | 1273 | 8010 | 59917 | 54383 | 61210 | 41002 | 60997 | 39722 | 2498 |
| SARS COV-2 N1 RE1.1 | 1972 | 6733 | 3342 | 1125 | 469 | 8875 | 6118 | 10978 | 5155 |
| SARS COV-2 N2 RE1.4 | 1147 | 1727 | 1460 | 1434 | 2191 | 5331 | 1452 | 3346 | 991 |
| SARS COV-2 N3 RE1.1 | 1686 | 2440 | 7031 | 4604 | 6266 | 10289 | 6596 | 8030 | 7727 |
| InfA 7 univ-pubRev | −16 | −94 | 658 | 555 | 340 | 32 | 8100 | 11431 | −185 |
| InfB 8 univ-pub | 37775 | 763 | 10304 | 30340 | 36467 | 12787 | 13859 | 10563 | 397 |

| Slide 9987 | Extraction -Ceres InfB | | | | | | | |
|---|---|---|---|---|---|---|---|---|
| Sample | Cr-infB-1 | Cr-infB-2 | Cr-infB-3 | Cr-infB-4 | Cr-infB-5 | Cr-infB-6 | NTC[§] | NTC[§] |
| 62-Negcont-B | 213 | 234 | 344 | 723 | 545 | 410 | 592 | 630 |
| RNAase P Probe pub1.1 | 681 | 35042 | 46145 | 40655 | 22259 | 40078 | 280 | 464 |
| SARS COV-2 N1 RE1.1 | 1125 | 864 | 942 | 624 | 866 | 827 | 1609 | 1516 |
| SARS COV-2 N2 RE1.4 | 1474 | 1039 | 1268 | 455 | 1504 | 1421 | 1056 | 1326 |
| SARS COV-2 N3 RE1.1 | 2275 | 1895 | 3001 | 2639 | 3131 | 2982 | 2722 | 3885 |
| InfA 7 univ-pubRev | −263 | −117 | −165 | −88 | 37 | −19 | −132 | −308 |
| Infb 8 univ-PUB | 209 | 12948 | 28137 | 23356 | 18372 | 12004 | 60 | −292 |
| InfB SE-PR99519 | 1532 | 14837 | 28237 | 25538 | 16526 | 16402 | 875 | 401 |
| InfB SE-PR99520 | 1447 | 11975 | 17636 | 15775 | 14112 | 12413 | 916 | 485 |

[§]no template control

Example 28

Threshold Determination for the Ceres-DETECTX-RV Combination.

Repeat measurements (n=72) from a single pooled clinical negative sample (50 mls, TriCore NP-VTM) using the Ceres processing protocol and DETECTX-RV analysis were performed as 72 independent 0.5 ml Ceres extractions. The experiments were performed on multiple days over 2 weeks, followed by Ceres processing, RT-PCR and analysis in a 96-well format for N1 and N2 CoV-2 markers.

Clinical Matrix Samples for Threshold Analysis protocol:
1. Clinical matrix=TriCore negative clinical samples (NP-VTM, Cobas 6800)
2. 200 μL Ceres beads were added to 500 μL of Contrived Clinical Matrix (N=10)
3. Samples were shaken for 10 mins.
4. Quick spin was performed before adding samples to a magnetic plate and removing supernatant.
5. 100 μL of 0.5% TritonX-100 was added to the samples.
6. Samples were shaken for 2 mins followed by heating at 95° C. for 10 mins.
7. Samples were centrifuged briefly before adding to magnetic plate.
8. Eluate was transferred to a PCR plate for storage.
8. Samples were run using standard RT-PCR cycling parameters.
9. Hybridization and Washing steps were performed in 96-well format.
10. Steps 1-9 were repeated for multiple days.
11. The threshold was calculated using the formula; Threshold=3×STD+RFU (blank)

Figure 36:
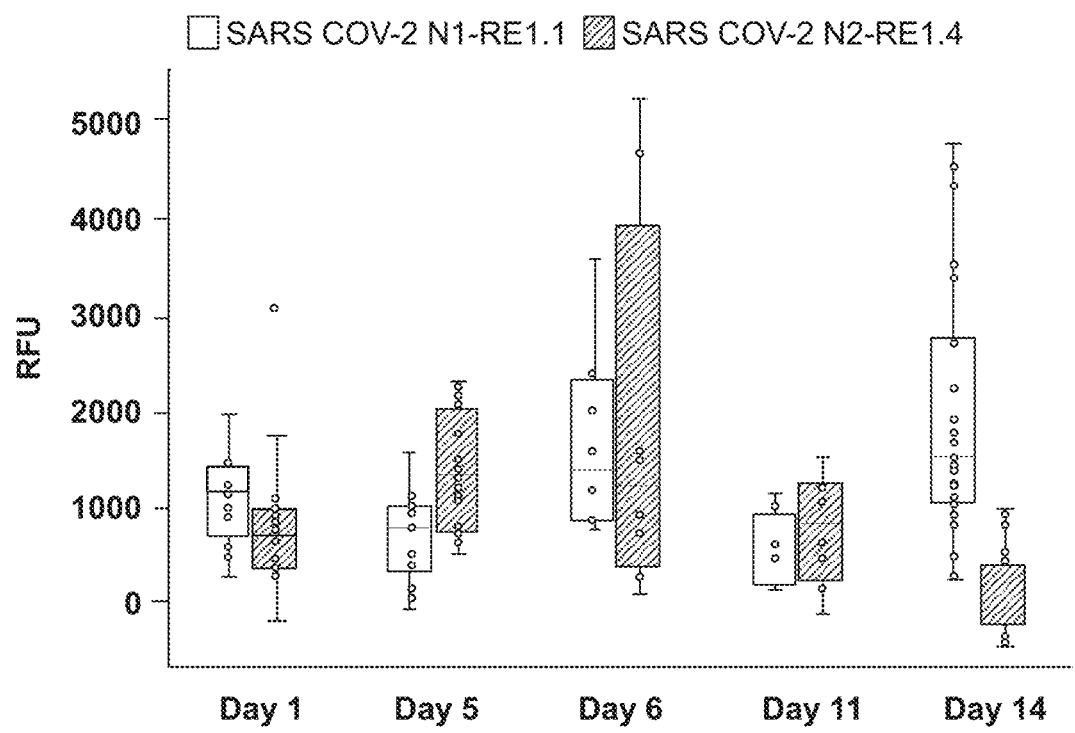
FIG. 36 shows a summary of threshold analysis for clinical matrix samples.

Results:

The data in Table 70 reveals a defined average with no drift in threshold values over the 5 repeat measurements. The analysis also revealed the presence of occasional outliers—e.g. day 19 for N2 and day 22 for N1 (FIG. 36), which shift the local average for these days. These outliers can be readily eliminated by adding a bead washing step in the above protocol to remove residual binding buffer.

Example 29

Optimization for Respiratory Syncytial Virus (RSV)

In continuation of the in silico analysis of RSV described in Example 16, primer and microarray testing was performed. Table 71 summarizes the results from an analytical sensitivity dilution series—purified human RSV-B gRNA (BEI) diluted to 1000, 100 and 10 genome copies/PCR reaction. The data demonstrates excellent specificity with no measurable signal detected above background for either of the two RSV-A probes tested in the array (HSV-A, RE1.1, 1.2). The data also demonstrate excellent sensitivity for detection of N1 and N2 above a threshold defined by the (0) genome copy control down to 10 copies/reaction.

TABLE 70

Summary of threshold analysis for clinical matrix samples

| Probe | | Day 1 | Day 5 | Day 6 | Day 11 | Day 14 | ALL |
|---|---|---|---|---|---|---|---|
| N1 | Threshold | 2258 | 2190 | 4783 | 1845 | 6021 | 4721 |
| | Average | 958 | 813 | 1739 | 674 | 2062 | 1434 |
| | Standard Deviation | 406 | 430 | 951 | 366 | 1237 | 1027 |
| | 95% CI | 759-1157 | 625-1002 | 1079-2398 | 420-927 | 1633-2490 | 1215-1654 |

TABLE 70-continued

Summary of threshold analysis for clinical matrix samples

| Probe | | Day 1 | Day 5 | Day 6 | Day 11 | Day 14 | ALL |
|---|---|---|---|---|---|---|---|
| N2 | Threshold | 2469 | 3292 | 8081 | 2662 | 1496 | 3950 |
| | Average | 846 | 1457 | 1949 | 880 | 227 | 870 |
| | Standard Deviation | 507 | 573 | 1916 | 557 | 397 | 962 |
| | 95% CI | 597-1094 | 1206-1709 | 622-3277 | 494-1266 | 89-364 | 664-1076 |

Example 30

Concurrent Microarray Analysis of Virus, Bacteria and Fungus

The method of detecting RNA virus comprises the following steps:

1) Recovery of viral RNA by capture of the virus from a fluid sample (analyte) by pipetting or centrifugation or binding of the pathogen to a solid phase such as an appropriate magnetic bead or column, followed by lysis of the captured pathogen and then in some cases additional purification of RNA from the virus by silica-based boom chemistry as routinely deployed in magnetic beads or columns.
2) RT-PCR of the viral RNA recovered, to generate PCR amplified cDNA amplicons that are further amplified using a suitable set of fluorescently labeled primers specific for the cDNA amplicons to obtain fluorescently labeled amplicons suitable for microarray hybridization.
3) Microarray hybridization of the resulting RT-PCR amplified DNA amplicons.
4) Analysis of the microarray hybridization patterns to detect the presence of viral analytes of interest.

TABLE 71

RSV specificity and sensitivity analysis

| | PCR machine | | | | | | | |
|---|---|---|---|---|---|---|---|---|
| | 2720 (Applied Biosystem) | | | | Veriti (Applied Biosystem) | | | |
| | HRSV (copies/reaction) | | | | HRSV (copies/reaction) | | | |
| Sample | 1000 Well 34 | 100 Well 35 | 10 Well 36 | NTC Well 40 | 1000 Well 66 | 100 Well 67 | 10 Well 68 | NTC Well 72 |
| 614D-SE-S1-RE1.4 | 40 | 78 | 47 | 148 | 4 | 109 | 15 | 130 |
| 614D-SE-S1-RE1.5 | 3102 | 2391 | 3710 | 2908 | 3466 | 2215 | 2018 | 3123 |
| 614D-SE-S1-RE1.7 | 2974 | 2466 | 2705 | 3233 | 3279 | 2417 | 2226 | 3176 |
| 614G-SE-S1-RE1.4 | 230 | −114 | 22 | 1 | −43 | −73 | 48 | 176 |
| 614G-SE-S1-RE1.5 | 2451 | 1890 | 2060 | 2328 | 3030 | 1605 | 1933 | 2419 |
| 614G-SE-S1-RE1.7 | 3380 | 2288 | 2185 | 2464 | 2595 | 2284 | 2215 | 2900 |
| 614U-SE-S1-RE1.1 | −59 | 12 | −50 | 176 | −45 | −45 | −47 | 89 |
| 614U-SE-S1-RE1.8 | 2625 | 1858 | 2225 | 2817 | 2672 | 1996 | 1911 | 2572 |
| 614U-SE-S1-RE1.9 | 2399 | 1254 | 1684 | 1325 | 1360 | 896 | 854 | 1152 |
| 62-Negcont-B | 76 | 113 | −41 | 229 | 180 | 97 | 168 | 227 |
| HRSV.A_RE 1.1 | 1889 | 519 | 1633 | 733 | 1673 | 8259 | 522 | 599 |
| HRSV.A_RE 1.2 | 4043 | 3541 | 1073 | 3375 | 1995 | 1032 | 522 | 830 |
| HRSV.B_RE 1.1 | 63637 | 63891 | 20038 | 1903 | 63641 | 49478 | 6709 | 858 |
| HRSV.B_RE 1.2 | 63582 | 56338 | 13683 | 1880 | 63564 | 42073 | 5470 | 1294 |
| HRSV.B_RE 1.3 | 63497 | 63732 | 38712 | 693 | 63404 | 54081 | 7533 | 582 |
| HRSV.B_RE 1.4 | 63512 | 63045 | 35071 | 836 | 63430 | 50738 | 4357 | 622 |
| InfA.7.univ-pubFwd | 1306 | 1313 | 1301 | 1586 | 683 | 1115 | 681 | 1241 |
| InfA.7.univ-pubRev | −154 | −133 | −235 | −25 | −199 | −76 | −81 | −30 |
| InfA.7.univ-RE1.1 | −230 | 44 | −32 | −138 | 687 | −56 | −52 | 127 |
| infA-AS-PR99526 | 1128 | 874 | 990 | 924 | 566 | 618 | 546 | 759 |
| infA-SE-PR99524 | 785 | 852 | 180 | 678 | 305 | 429 | 415 | 315 |
| infA-SE-PR99525 | 856 | 252 | 297 | 189 | 215 | 340 | 78 | 14 |
| InfB.8.univ-pub | −162 | −111 | 200 | 454 | −248 | 73 | −37 | 121 |
| infB-SE-PR99519 | 1123 | 338 | 1273 | 305 | 739 | 287 | 384 | 89 |
| infB-SE-PR99520 | 999 | 660 | 1048 | 626 | 776 | 491 | 586 | 442 |
| RNAse.P.Probe-pub1.1 | −209 | −210 | −197 | −100 | −125 | −159 | −122 | 794 |
| SARS.CoV1-N2-RE1.3 | 1497 | 1525 | 1392 | 1599 | 1534 | 921 | 993 | 1427 |
| SARS.CoV1-N2-RE1.6 | 2986 | 1649 | 1643 | 1930 | 2896 | 1253 | 1335 | 1461 |
| SARS.COV2-N1-pub | 19 | 85 | 42 | 215 | −142 | 117 | −3 | 153 |
| SARS.COV2-N1-RE1.1 | 979 | 579 | 810 | 1479 | 911 | 1155 | 546 | 1656 |
| SARS.CoV2-N2-RE1.12 | 2285 | 1645 | 1214 | 1146 | 2165 | 1031 | 2004 | 1067 |
| SARS.COV2-N2-RE1.4 | 1863 | 617 | 799 | 1000 | 947 | 504 | 385 | 98 |
| SARS.COV2-N3-RE1.1 | 1004 | 804 | 1046 | 1002 | 1008 | 573 | 556 | 488 |

The above method is extended to include DNA-containing pathogens including, DNA viruses, bacteria and fungus known to cause respiratory disease by accommodating capture and analysis of both RNA-containing and DNA-containing pathogens. Such a method comprises the following steps:
1) Use methods such as pipetting and centrifugation among others to capture concurrently, RNA viruses, DNA viruses, bacteria and fungus resident in the same clinical or environmental sample. Subsequent methods of lysis are then employed to enable concurrent lysis of all of the captured pathogens. Additional purification steps such as, silica-based boom chemistry as routinely deployed in magnetic beads or columns enables concurrent capture and purification of RNA and DNA from these pathogens.
2) Use of an appropriate panel of PCR primers enables reverse transcription of viral RNA to obtain cDNA followed by PCR amplification to concurrently amplify in the same reaction (single assay), cDNA and DNA from DNA viruses, bacteria and fungus to yield a set of amplicons that are further amplified using a suitable set of fluorescently labeled primers specific for each pathogen being queried to obtain fluorescently labeled amplicons suitable for microarray hybridization.
3) Concurrent microarray hybridization of the resulting fluorescent amplicons on the same microarray enables their analysis.
4). Analysis of the microarray hybridization patterns obtained is then used to concurrently detect in the same assay, presence of any or all of pathogens in a sample.

Conclusion

Rapid detection of respiratory disease-causing viruses including COVID-19 virus, other coronaviruses, Influenza A virus, Influenza B virus, RSV-A and RSV-B are crucial to controlling the COVID-19 pandemic. However, it is well known that there are other DNA containing respiratory disease-causing pathogens including DNA viruses like adenovirus and bacterial pathogens such as *Mycobacterium tuberculosis* and *Streptococcus pneumoniae*. The microarray-based detection methods described here are readily adaptable and extendable to detection of these DNA containing respiratory disease pathogens as well in a single assay. This is beneficial since it enables streamlined detection of COVID-19 virus concurrently with other respiratory disease pathogens.

Example 31

Clinical Validation of Influenza AB Analysis

Experiment 1: LoD studies in contrived clinical negative samples (NP-VTM, TriCore) were performed using inactivated flu virus (ATCC, InFA (H1NI), and InFB (Hong Kong)). Particle density in the ATCC samples was measured in infectious units via PFU assay (i.e. $CEID_{50}$/ml) which is approximately equal to particles/mL. In all cases, viral capture with Ceres beads was performed on the flu virus, followed by lysis and amplification of the lysate with the complete One Step RT-PCR master mix comprising the full N1, N2, N3, P, InFA, InFB multiplex described in previous reports. Hybridization was obtained in the 96-well format.

Protocol:
1. Dilutions of Inf A (H1N1) and Inf B (Hong Kong) were made in clinical matrix (VTM+negative clinical sample) as shown in Table 72.
2. Add 200 μL Ceres beads to 500 μL sample. Shake for 10 mins.
3. Place sample on magnetic stand to collect beads and remove supernatant.
4. All 200 μL PBS to sample and shake for 2 mins. Remove supernatant.
5. Add 100 μL lysis buffer to the sample. Shake for 2 mins.
6. Heat samples at 95° C. for 10 mins.
7. Place sample on magnetic stand to collect beads.
8. Transfer RNA from tube to PCR plate for storage until use.
9. PCR parameters: 55° C., 20 min (1 cycle); 94° C., 2 min (1 cycle); 94° C., 30 sec, 55° C., 30 sec, 68° C., 30 sec (40 cycles); 68° C., 7 min, (1 cycle); 4° C., ∞

TABLE 72

Protocol for clinical validation of Influenza A and Influenza B

| Dilution Factor | [Stock] ($CEID_{50}$/mL) | [Final] ($CEID_{50}$/mL) | Stock volume (μL) | Diluent (μL) | Total volume (μL) |
| --- | --- | --- | --- | --- | --- |
| Influenza A- H1N1 NR-2555 Lot 4771527 ($1.6 \times 10^8$ $CEID_{50}$/mL) | | | | | |
| 100.00 | $1.60 \times 10^8$ | $1.60 \times 10^6$ | 5 | 495 | 500 |
| 32.00 | $1.60 \times 10^6$ | $5.00 \times 10^4$ | 16 | 484 | 500 |
| 50.00 | $5.00 \times 10^4$ | 1000 | 116 | 5684 | 5800 |
| 1.33 | 1000 | 750 | 3375 | 1125 | 4500 |
| 1.50 | 750 | 500 | 2000 | 1000 | 3000 |
| 5.00 | 500 | 100 | 500 | 2000 | 2500 |
| Influenza B Hong Kong NR-41802 Lot 70020821 ($1.8 \times 10^7$ $CEID_{50}$/mL) | | | | | |
| 100.00 | $1.80 \times 10^7$ | $1.80 \times 10^5$ | 5 | 495 | 500 |
| 36.00 | $1.80 \times 10^5$ | 5000 | 14 | 486 | 500 |
| 50.00 | 5000 | 100 | 60 | 2940 | 3000 |
| 10.00 | 100 | 10 | 400 | 3600 | 4000 |
| 2.00 | 10 | 5 | 1500 | 1500 | 3000 |
| 5.00 | 5 | 1 | 500 | 2000 | 2500 |

Sample Analysis:

First, a clinical threshold was obtained using thirty-two (32) clinical negatives for the InF A and InF B probe content, using the formula;

Threshold (RFU)=3×(STV)+Mean

Figure 37A:
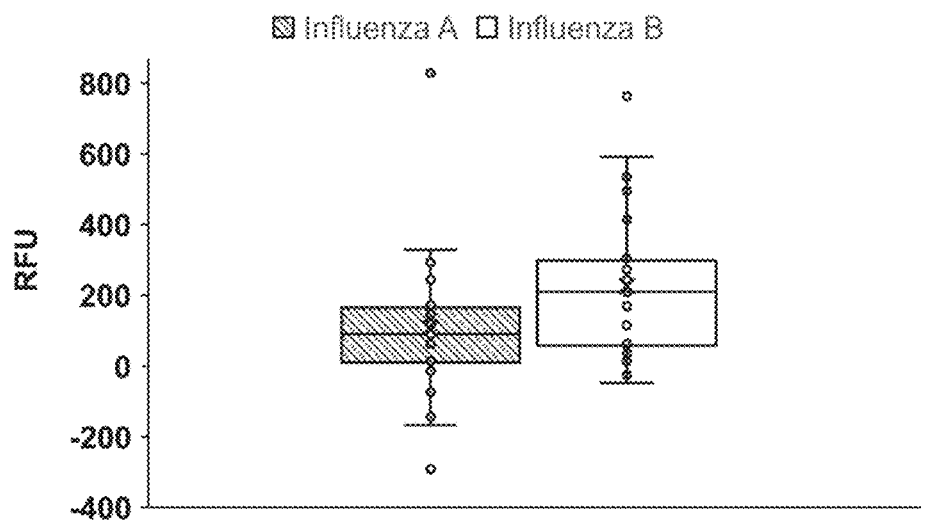
FIGS. 37A-37C show LoD determination in clinical validation for Influenza samples.

These data revealed low background values and as a result low thresholds (721 RFU for Inf A and 896 RFU for Inf B FIG. 37A).

Figure 37B:
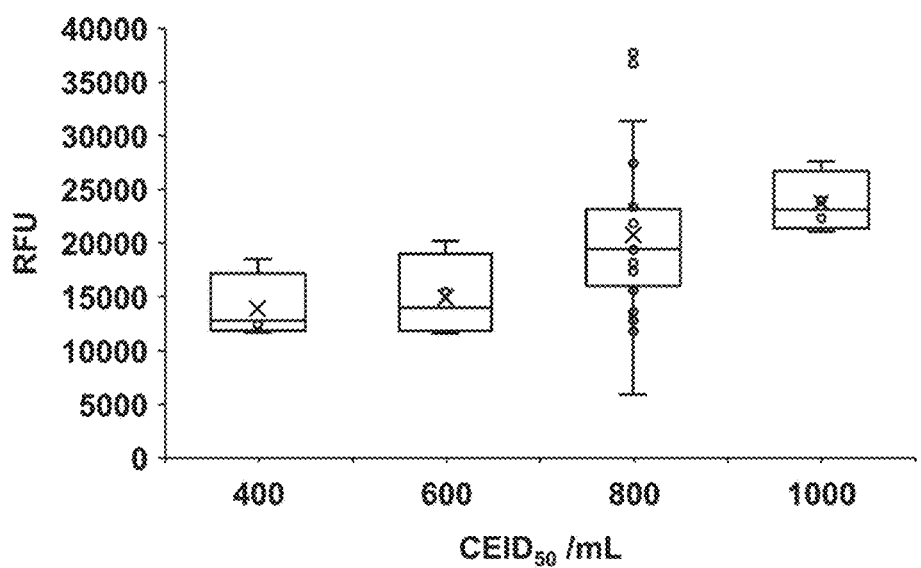
Figure 37C:
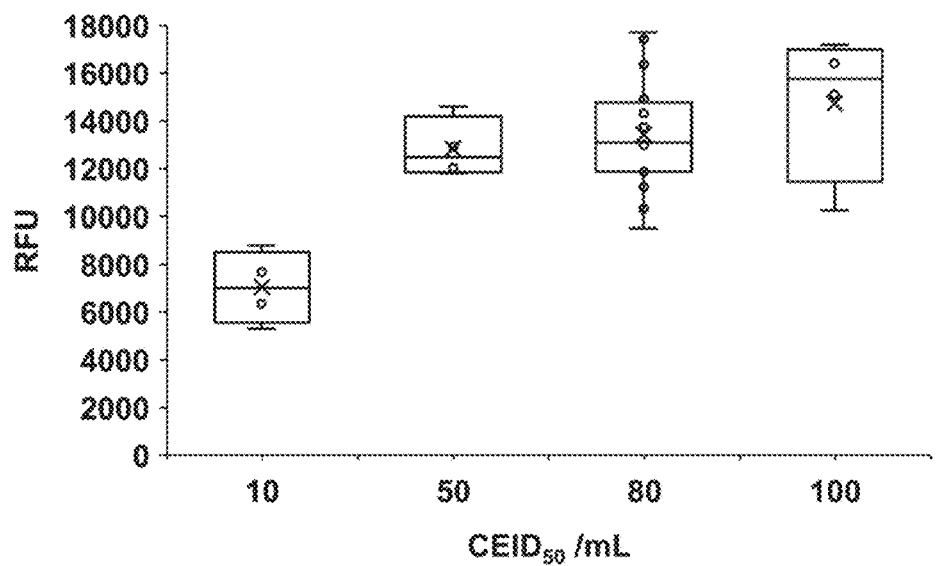

Next, a preliminary range-seeking study was performed on contrived InF A and InF B samples prepared on a single batch of pooled clinical negatives that revealed that the LoD would be in the approximate range of 1,000 $CEID_{50}$/ml for InF A and 100 $CEID_{50}$/ml for InF B (Inf A, LoD=100-1000 $CEID_{50}$; Inf B, LoD=1-10 $CEID_{50}$). Based on this preliminary analysis, a more detailed LoD determination was performed that showed that the LoD for InF A is less than 400 $CEID_{50}$/ml (FIG. 37B) and LoD for InfB is less than 10 $CEID_{50}$/ml (FIG. 37C).

Experiment 2: An extension of the above studies was performed at multiple data points closer to the LoD. Dilutions of Inf A (H1N1) and Inf B (Hong Kong) were made in clinical matrix (45 mL VTM+5 mL pooled negative clinical sample) as shown in Table 73 and the method performed as described above for Experiment 1.

TABLE 73

Protocol for clinical validation of Influenza A and Influenza B

| Dilution Factor | [Stock] ($CEID_{50}$/mL) | [Final] ($CEID_{50}$/mL) | Stock volume (µL) | Diluent (µL) | Total volume (µL) |
|---|---|---|---|---|---|
| Influenza A- HlN1 NR-2555 Lot 4771527 ($1.6 \times 10^8$ $CEID_{50}$/mL) | | | | | |
| 100.00 | $1.60 \times 10^6$ | $1.60 \times 10^6$ | 5 | 495 | 500 |
| 100.00 | $1.60 \times 10^5$ | 16000 | 5 | 495 | 500 |
| 16.00 | $5.00 \times 10^4$ | 1000 | 438 | 6563 | 7000 |
| 2.50 | 1000 | 400 | 4000 | 6000 | 10000 |
| 2.00 | 400 | 200 | 6500 | 6500 | 13000 |
| 2.00 | 200 | 100 | 1500 | 1500 | 3000 |
| Influenza B Hong Kong NR-41802 Lot 70020821 ($1.8 \times 10^7$ $CEID_{50}$/mL) | | | | | |
| 100.00 | $1.80 \times 10^7$ | $1.80 \times 10^5$ | 5 | 495 | 500 |
| 100.00 | $1.80 \times 10^5$ | 1800 | 5 | 495 | 500 |
| 18.00 | 1800 | 100 | 222 | 3778 | 4000 |
| 10.00 | 100 | 10 | 900 | 8100 | 9000 |
| 2.00 | 10 | 5 | 6000 | 6000 | 12000 |
| 5.00 | 5 | 1 | 600 | 2400 | 3000 |

Figure 38A:
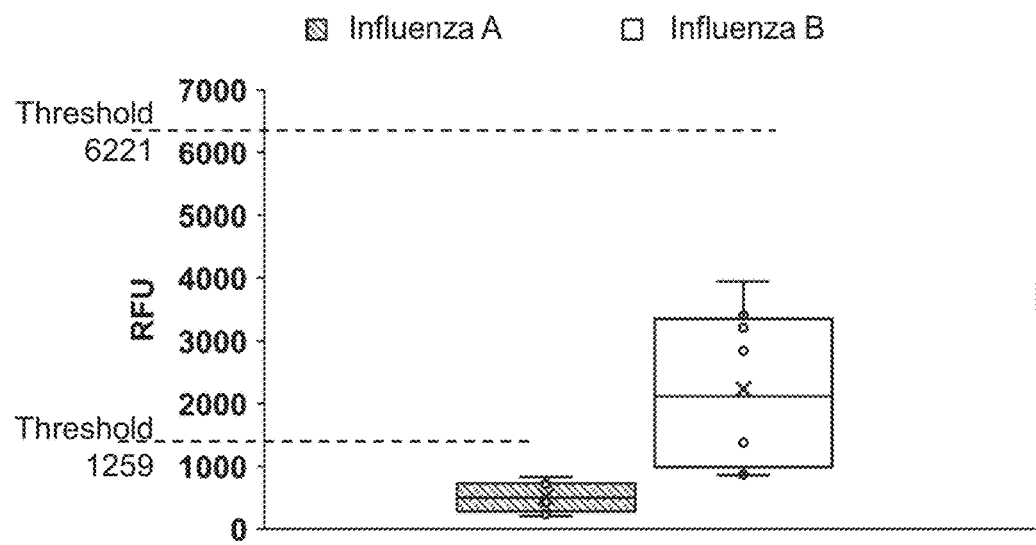
FIGS. 38A-38C show data from an extended clinical threshold analysis for Influenza samples.
Figure 38B:
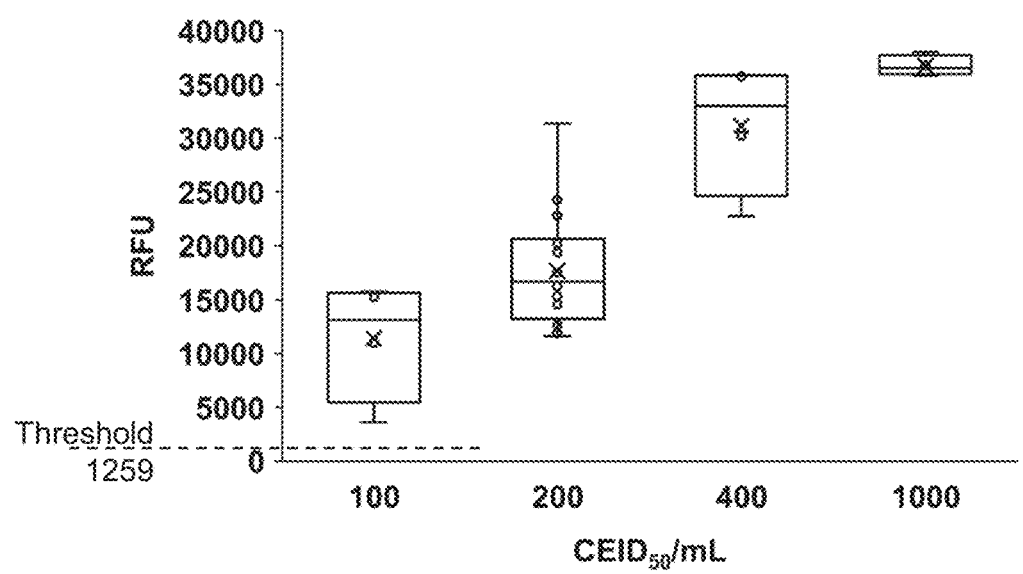
Figure 38C:
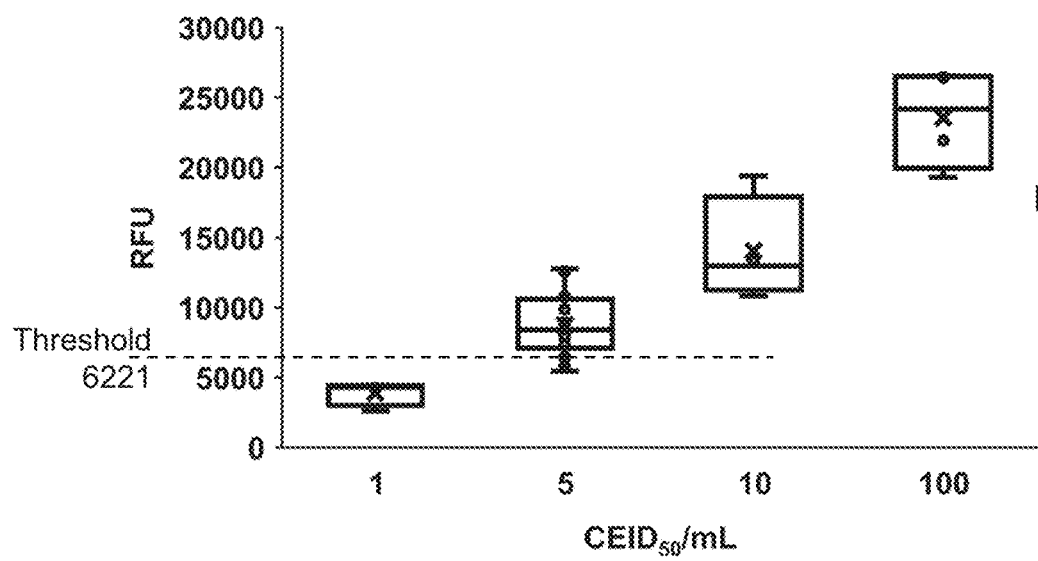

An extended clinical threshold was obtained by processing additional clinical negatives for the Inf A and Inf B probe content, using the formula used above. The extended data set revealed a statistically strong background mean and STD that is reproducible with a threshold value of 1259 RFU for Inf A and 6221 RFU for Inf B (FIG. 38A). Expanded range-seeking optimization on contrived influenza samples prepared on a single batch of pooled clinical negatives revealed that LoD for Inf A is less than 100 $CEID_{50}$/ml (FIG. 38B) and that the LoD for Inf B is less than 10 $CEID_{50}$/mL (FIG. 38C). A comparison of LoD obtained using influenza from various sources is shown in Table 74.

TABLE 74

Comparison of LoD values

| | Strain | LOD ($CEID_{50}$) | Company | Catalog # |
|---|---|---|---|---|
| BioFire RP2.1 | Inf. A H1N1 | 1000 | Zeptometrix | 0810036CF |
| | Inf A H1-2009 | 50 | Zeptometrix | 0810249CF |
| Analyte | Int A H3 | 10 | ATCC | VR-810 |
| | Inf B | 5 | Zeptometrix | 0810255CF |

Example 32

Mouthwash LoD on Clinical Samples

LoD studies were undertaken on QuikSal mouthwash negative clinical isolates. Briefly, three (3) oral rinse samples from healthy lab volunteers were pooled to generate a single 15 mL Cov-2 negative clinical sample. The pooled sample was then doped with gamma irradiated CoV-2 (BEI) ranging from 10,000 to 625 virus particles/mL (Table 75)

Protocol:
1. Add 100 µL beads to 500 µL sample. Shake for 10 mins at 1000 rpm.
2. Place sample on magnetic stand for 5 min to collect beads and remove supernatant.
3. All 200 µL PBS to sample and shake for 2 mins at 1000 rpm. Remove supernatant.
4. Add 100 µL lysis buffer to the sample. Shake for 2 mins at 1000 rpm.
5. Heat samples at 95° C. for 10 mins.
6. Place sample on magnetic stand to collect beads.
7. Transfer RNA from tube to PCR plate for storage at −20° C. until use.
8. PCR parameters: 55° C., 20 min (1 cycle); 94° C., 2 min (1 cycle); 94° C., 30 sec, 55° C., 30 sec, 68° C., 30 sec (40 cycles); 68° C., 7 min, (1 cycle); 4° C., ∞

TABLE 75

Protocol for clinical validation of Influenza A and Influenza B
Gamma irradiated cell lysate NR-52287 ($1.75 \times 10^9$ copies/mL)

| Dilution Factor | [Stock] (copies/mL) | [Final] (copies/mL) | Stock volume (µL) | Diluent (µL) | Total volume (µL) |
|---|---|---|---|---|---|
| 100.00 | $1.75 \times 10^9$ | $1.75 \times 10^7$ | 5 | 495 | 500 |
| 100.00 | $1.75 \times 10^7$ | $1.75 \times 10^5$ | 5 | 495 | 500 |

TABLE 75-continued

Protocol for clinical validation of Influenza
A and Influenza B
Gamma irradiated cell lysate NR-52287 (1.75 × 10⁹ copies/mL)

| Dilution Factor | [Stock] (copies/mL) | [Final] (copies/mL) | Stock volume (µL) | Diluent (µL) | Total volume (µL) |
|---|---|---|---|---|---|
| 17.50 | $1.75 \times 10^5$ | 10000 | 400 | 6600 | 7000 |
| 2.00 | 10000 | 5000 | 4000 | 4000 | 8000 |
| 5.00 | 5000 | 1000 | 5400 | 21600 | 27000 |
| 1.25 | 1000 | 800 | 15200 | 3800 | 19000 |
| 1.60 | 800 | 500 | 7500 | 4500 | 12000 |

Figure 39:
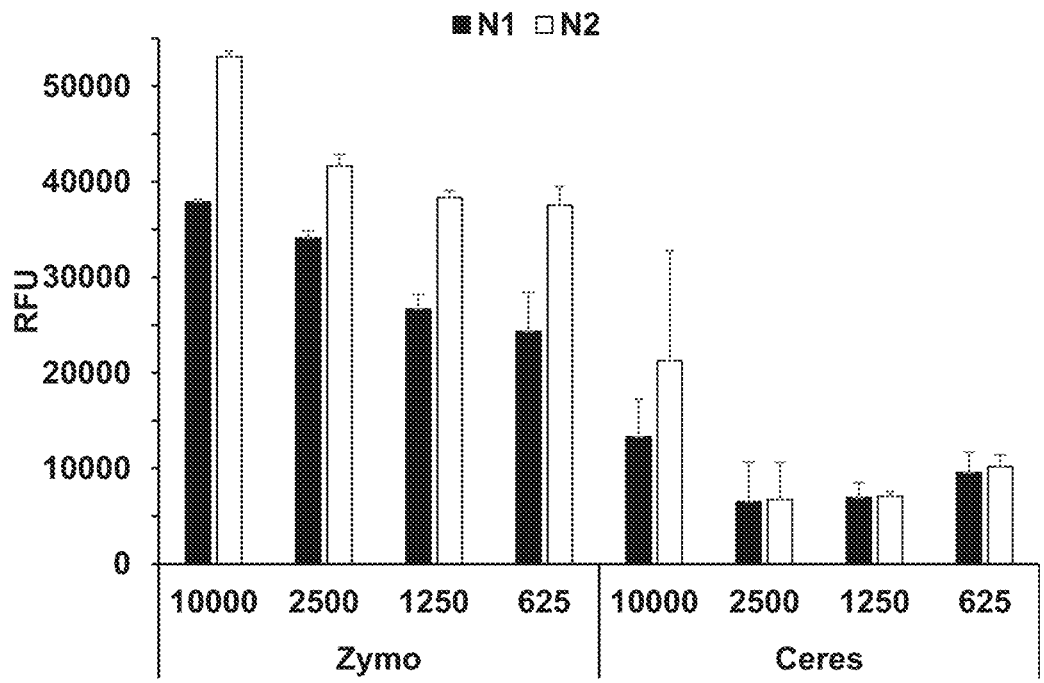
FIG. 39 shows a comparison of Zymo and Ceres processing of mouthwash clinical samples on LoD range analysis.

The summary of the range analysis (Zymo vs Ceres processing) is presented in FIG. 39. For Zymo magnetic bead-based RNA isolation from virally doped QuikSal negatives (FIG. 39, left panel) it can be seen that signal strength for both the N1 and N2 Cov-2 markers is >7 fold over the threshold across the entire viral density range tested. Based on that dose response, it appears that the LoD for the Zymo/One Step RT-PCR combination will be significantly lower than 625 virus copies/mL. In contrast, the preliminary range finding for Ceres magnetic bead-based viral capture on the same samples is at about 10-fold higher than the Zymo magnetic bead method (FIG. 39, right panel).

CoV-2 LoD Analysis

Figures 40A, 40B:
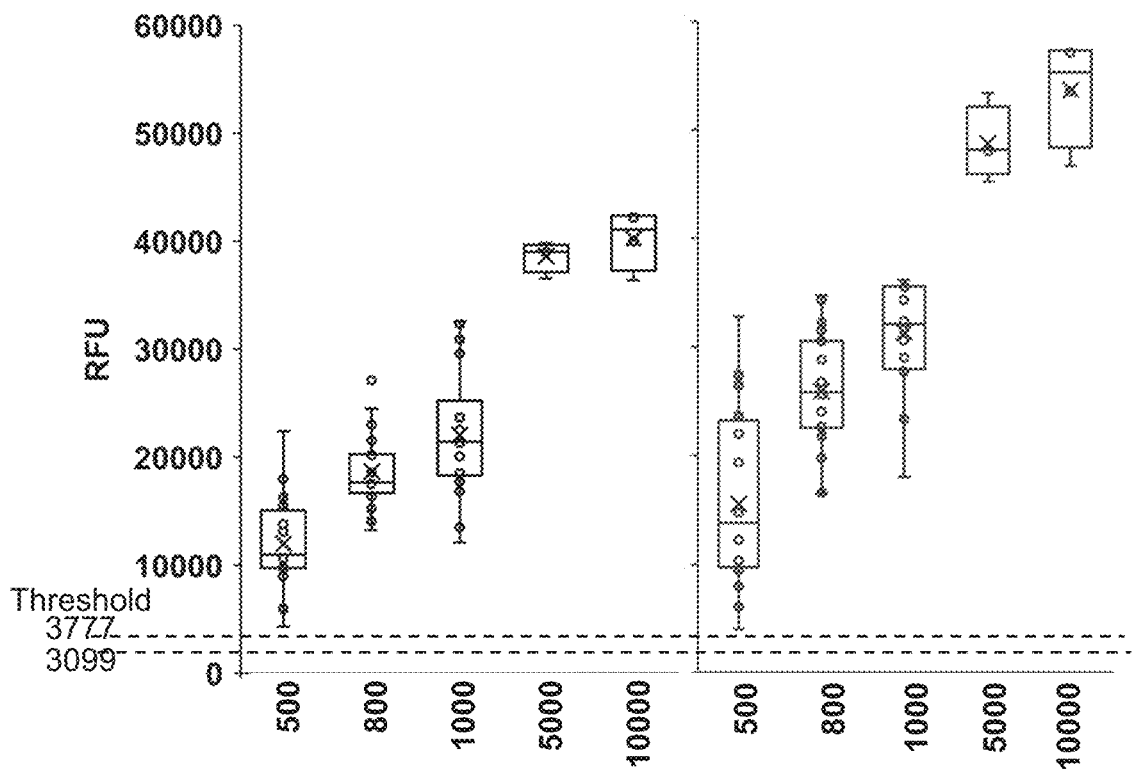
FIGS. 40A-40B show LoD analysis for SARS-CoV-2.

As discussed above, the LoD for both N1 and N2 SARS-CoV-2 probes was <1000 virus copies/mL. Using an expanded titration to include 500, 800, 1.000 copies/mL it is observed (FIGS. 40A and 40B) that LoD values for both N1 and N2 are less than a factor of 2 below 500 copies/mL. Thus, DETECTX-RV analysis for SARS CoV-2 may be expanded to additionally include concurrent detection/measurement of both influenza A and influenza B, without compromising LoD.

The following references are cited herein:
1. Li et al., (2020) J Med Virol.; 10.1002/jmv.25786. doi: 10.1002/jmv.25786
2. Feng et al., (2020) Jpn J Radiol.; 1-2. doi:10.1007/s11604-020-00967-9
3. Hu et al, (2003) J Clin Microbiol 41: 149-154. doi: 101128/jcm.41.1.149-154.2003

What is claimed:

1. A method for detecting at least two respiratory disease-causing coronaviruses in a sample, comprising:
obtaining a sample;
isolating total nucleic acids from the sample;
performing in tandem in a single assay:
a combined reverse transcription and a first PCR amplification reaction on the isolated total nucleic acids using at least two first primer pairs selective for the at least two respiratory disease-causing coronaviruses to generate at least two coronavirus specific cDNA amplicons; and
a second amplification using the at least two coronavirus specific cDNA amplicons as template and at least two fluorescent labeled second primer pairs selective for at least two target nucleotide sequences in the at least two coronavirus specific cDNA amplicons to generate at least two fluorescent labeled virus specific amplicons;
hybridizing the at least two fluorescent labeled coronavirus specific amplicons to a plurality of nucleic acid probes immobilized on a microarray support; wherein the plurality of probes comprise each of the nucleotide sequences of SEQ ID NOS: 45-66 and 85-97;
imaging the microarray to detect fluorescent signals corresponding to the at least two fluorescent labeled coronavirus specific amplicons, thereby detecting the at least two respiratory disease-causing coronaviruses in the sample.

2. The method of claim 1, further comprising, calculating an intensity of each of the fluorescent signals, said intensity correlating with the number of virus specific genomes in the sample.

3. The method of claim 1, wherein the respiratory disease-causing coronavirus is of a Severe Acute Respiratory Syndrome Coronavirus 2 (COVID-19 virus), a Respiratory Syncytial Virus, a Middle East Respiratory Syndrome coronavirus (MERS-COV), a Severe Acute Respiratory Syndrome Coronavirus (SARS-COV), a 229E Coronavirus, a OC43 Coronavirus, a NL63 Coronavirus, or a HKU1 Coronavirus.

4. The method of claim 1, wherein the at least two respiratory disease causing coronaviruses are COVID-19 and MERS-COV and said first primer pairs comprising SEQ ID NOS: 1 and 2 and SEQ ID NOS: 7 and 8 and the second primer pairs comprising SEQ ID NOS: 23 and 24 and SEQ ID NOS: 29 and 30.

5. The method of claim 1, wherein the sample is an individual sample or a pooled sample from a nasopharyngeal swab, a nasal swab, a mouth swab, a mouthwash, an aerosol, or a swab from a hard surface or a combination thereof.

6. A method for detecting a coronavirus 2019 disease (COVID-19) virus in a sample, comprising:
obtaining a sample;
isolating a total nucleic acid from the sample to obtain a test sample;
performing in tandem in a single assay:
a combined reverse transcription and a first PCR amplification reaction on the test sample using at least two first primer pairs selective for the COVID-19 virus and at least one non-COVID-19 virus to generate COVID-19 virus cDNA amplicons and at least one non-COVID-19 virus cDNA amplicon; and
a second amplification using the COVID-19 virus cDNA amplicons and the at least one non-COVID-19 virus cDNA amplicons as templates and at least two fluorescent labeled second primer pairs selective for a target nucleotide sequence in the COVID-19 virus cDNA and in the at least one non-COVID-19 cDNA to generate at least one fluorescent labeled COVID-19 virus amplicon and at least one fluorescent labeled non-COVID-19 virus amplicon;
hybridizing the at least one fluorescent labeled COVID-19 virus amplicon and the at least one fluorescent labeled non-COVID-19 virus amplicon to a plurality of nucleic acid probes immobilized on a microarray support; wherein the plurality of probes comprise each of the nucleotide sequences of SEQ ID NOS: 45-66 and 85-97;
washing the microarray at least once; and
imaging the microarray to detect fluorescent signals corresponding to the at least one fluorescent labeled COVID-19 virus amplicons, thereby detecting the COVID-19 in the sample.

7. The method of claim 6, wherein the non-COVID-19 virus is a Respiratory Syncytial Virus, a Middle East Respiratory Syndrome coronavirus (MERS-COV), a Severe Acute Respiratory Syndrome Coronavirus (SARSCOV), a 229E Coronavirus, a OC43 Coronavirus, a NL63 Coronavirus, or a HKU1 Coronavirus.

8. The method of claim 6, further comprising calculating an intensity of the fluorescent signal, said intensity correlating with the number of COVID-19 genomes in the sample.

9. The method of claim 6, wherein the sample is an individual sample or a pooled sample from a nasopharyngeal swab, a nasal swab, a mouth swab, a mouthwash, an aerosol, or a swab from a hard surface, or a combination thereof.

10. The method of claim 6, wherein the first primer pairs to amplify the COVID-19 virus RNA and the non-COVID-19 virus RNA are the nucleotide sequence pairs of SEQ ID NOS: 1 and 2 and SEQ ID NOS: 7 and 8, respectively, and the second primer pairs to prime the non-COVID-19 virus RNA and the non-COVID-19 virus RNA are the nucleotide sequence pairs of SEQ ID NOS: 23 and 24 and SEQ ID NOS: 29 and 30, respectively.

11. The method of claim 4, further comprising coronavirus nucleocapsis primers comprising SEQ ID NOS: 3 and 4 and SEQ ID NOS: 25 and 26.

12. The method of claim 4, further comprising coronavirus nucleocapsis primers comprising SEQ ID NOS: 5 and 6 and SEQ ID NOS: 27 and 28.

13. The method of claim 1, wherein the at least two respiratory disease-causing coronaviruses comprises human coronavirus 229E, wherein the primer pairs for human coronavirus 299E comprise SEQ ID NOS: 9 and 10 and SEQ ID NOS: 31 and 32.

14. The method of claim 1, wherein the at least two respiratory disease-causing coronaviruses comprises human coronavirus OC43, wherein the primer pairs for human coronavirus OC43 comprise SEQ ID NOS: 11 and 12 and said second primer comprising SEQ ID NOS: 33 and 34.

15. The method of claim 1, wherein the at least two respiratory disease-causing coronaviruses comprises human coronavirus NL63, wherein the primer pairs for human coronavirus NL63 comprise SEQ ID NOS: 13 and 14 and SEQ ID NOS: 35 and 36.

16. The method of claim 1, wherein the at least two respiratory disease-causing coronaviruses comprises human coronavirus HKU1, wherein the primer pairs for human coronavirus HKU1 comprise SEQ ID NOS: 15 and 16 and SEQ ID NOS: 37 and 38.

* * * * *